United States Patent
Yoshinaga et al.

(10) Patent No.: US 10,745,401 B2
(45) Date of Patent: *Aug. 18, 2020

(54) CONDENSED LACTAM DERIVATIVE

(71) Applicant: Sumitomo Dainippon Pharma Co., Ltd., Osaka (JP)

(72) Inventors: Hidefumi Yoshinaga, Osaka (JP); Yohei Ikuma, Ibaraki (JP); Junya Ikeda, Kashihara (JP); Satoshi Adachi, Osaka (JP); Harunobu Mitsunuma, Tokyo (JP); Yoshinori Aihara, Nishinomiya (JP); Jeremy Besnard, Eynsham (GB); Andrew Simon Bell, Deal (GB)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/786,053

(22) Filed: Feb. 10, 2020

(65) Prior Publication Data

US 2020/0172543 A1 Jun. 4, 2020

Related U.S. Application Data

(63) Continuation of application No. 16/637,335, filed as application No. PCT/JP2019/028577 on Jul. 22, 2019.

(30) Foreign Application Priority Data

Jul. 23, 2018 (JP) .................... 2018-138029

(51) Int. Cl.
| | | |
|---|---|---|
| *C07D 417/12* | (2006.01) | |
| *C07D 471/04* | (2006.01) | |
| *C07D 471/10* | (2006.01) | |
| *C07D 487/04* | (2006.01) | |
| *C07D 498/04* | (2006.01) | |

(52) U.S. Cl.
CPC ......... *C07D 471/04* (2013.01); *C07D 487/04* (2013.01)

(58) Field of Classification Search
CPC .. C07D 417/12; C07D 471/04; C07D 471/10; C07D 487/04; C07D 498/04
See application file for complete search history.

(56) References Cited

U.S. PATENT DOCUMENTS

| | | |
|---|---|---|
| 5,114,936 A | 5/1992 | Wettlaufer et al. |
| 5,141,930 A | 8/1992 | Nakao et al. |
| 5,532,240 A | 7/1996 | Nakao et al. |

OTHER PUBLICATIONS

International Search Report dated Oct. 8, 2019 in International (PCT) Application No. PCT/JP2019/028577.
Taylor et al., "Buspirone and Related Compounds as Alternative Anxiolytics", Neuropeptides, 1991, vol. 19, (Suppl.), pp. 15-19.
Schmidt et al., "The Role of 5-HT2A Receptors in Antipsychotic Activity", Life Sciences, 1995, vol. 56, No. 25, pp. 2209-2222.
Seeman et al., "Atypical Antipsychotics: Mechanism of Action", W. Can. J. Psychiatry, vol. 47, No. 1, Feb. 2002, pp. 29-40.

*Primary Examiner* — Bruck Kifle
(74) *Attorney, Agent, or Firm* — Wenderoth, Lind & Ponack, L.L.P.

(57) ABSTRACT

The present invention relates to a medicament for treating neuropsychiatric diseases, comprising a compound of Formula (1):

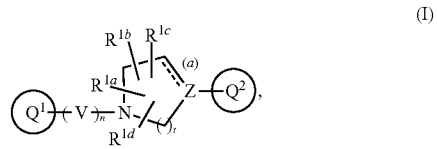

(I)

or a pharmaceutically acceptable salt thereof, as an active ingredient.

4 Claims, 1 Drawing Sheet

[Fig 1]
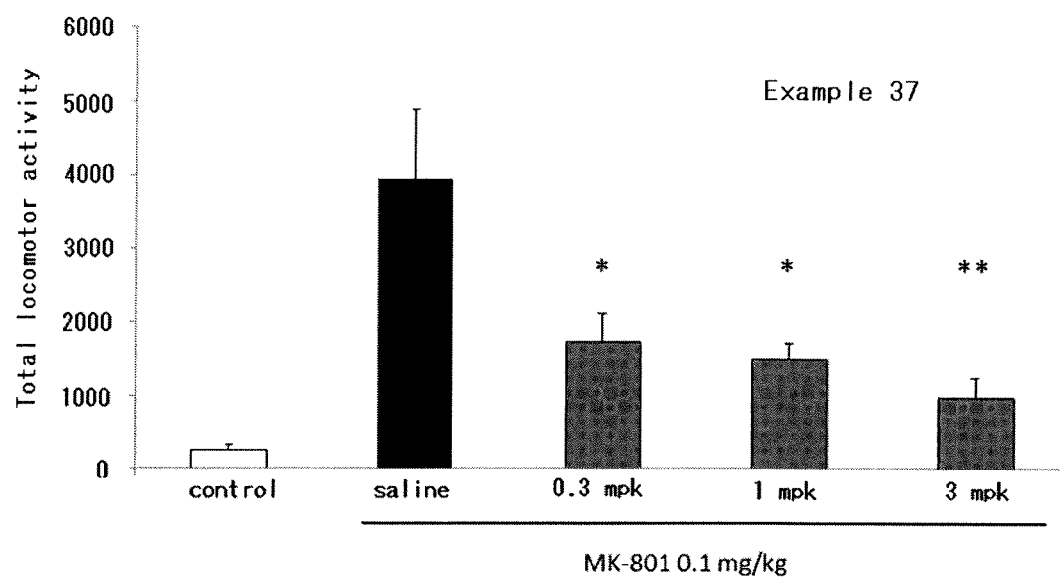
[Fig. 2]
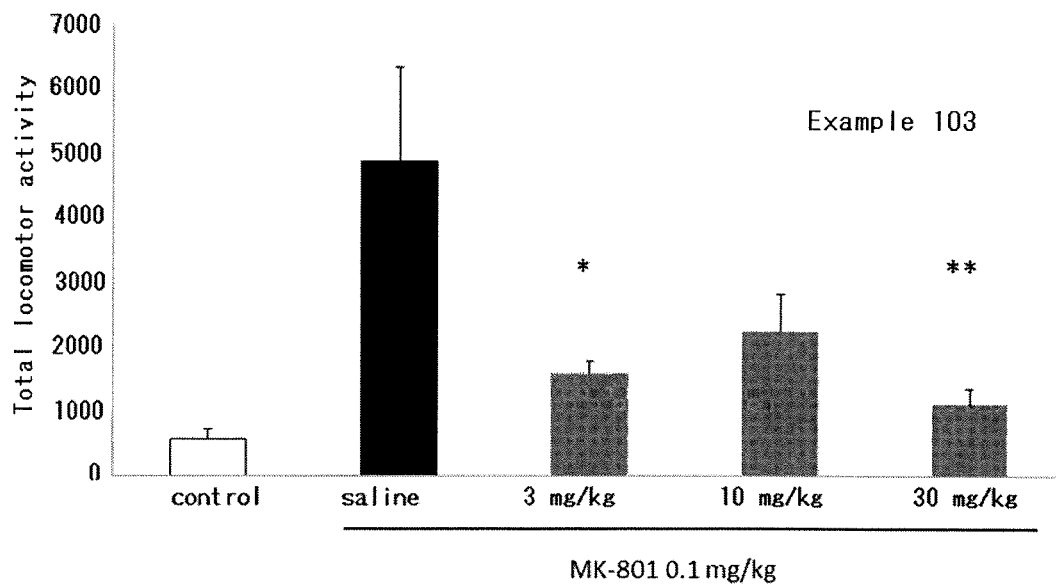

CONDENSED LACTAM DERIVATIVE

TECHNICAL FIELD

The present invention relates to a condensed lactam derivative having antagonist activity for serotonin 5-HT$_{2A}$ receptor and agonist activity for serotonin 5-HT$_{1A}$ receptor, or a pharmaceutically acceptable salt thereof, and a medicament for treating neuropsychiatric diseases comprising the same as an active ingredient.

BACKGROUND ART

Serotonin (5-hydroxytryptamine; hereinafter, also referred to as "5-HT") is known as one of main neurotransmitters in central nervous system, and it is also known that serotonin is involved in various brain functions such as emotional reaction and cognitive function.

5-HT$_{1A}$ receptor which is one of 5-HT receptor subtypes is a Gi/o protein-coupled receptor, and is expressed in cerebral cortex, hippocampus, raphe nucleus, amygdala, and the like. Compounds having agonist activity for 5-HT$_{1A}$ receptor includes, for example, tandospirone and buspirone. Tandospirone is used as a medicament for treating dysphoria and fear in neurosis, physical symptoms in psychosomatic diseases (autonomic dysregulation, essential hypertension, peptic ulcer), and dysphoria, anxiety, irritation, and sleep disorders. Buspirone is used as a medicament for treating generalized anxiety disorders (Non-Patent Literature 1).

5-HT$_{2A}$ receptor is a Gq/11 protein-coupled receptor, and is highly expressed in cerebral cortex, hippocampus, raphe nucleus, and the like. Drugs having antagonist activity for 5-HT$_{2A}$ receptor include antidepressant drugs, mianserin and mirtazapine. Atypical antipsychotic drugs which also have antagonist activity for 5-HT$_{2A}$ receptor are used as a medicament for treating schizophrenia, bipolar disorders, major depression, autistic spectrum disorder, and the like (Non-Patent Literature 2, Non-Patent Literature 3).

As described above, it is shown that agonists for 5-HT$_{1A}$ receptor and antagonists for 5-HT$_{2A}$ receptor are separately useful in the treatment of neuropsychiatric diseases, but no drugs having agonist activity for 5-HT$_{1A}$ receptor together with antagonist activity for 5-HT$_{2A}$ receptor in a selective and potent manner have been reported.

[Non Patent Literature 1] D. P. Taylor, Neuropeptides. 19 Suppl: 15-19 1991

[Non Patent Literature 2] P. Seeman, Can. J. Psychiatry. 47: 27-38, 2002

[Non Patent Literature 3] C. J. Schmidt, Life Science. 56 (25): 2209-2222, 1995

SUMMARY OF INVENTION

Problems to be Solved by the Invention

An object of the present invention is the provision of novel compounds which have antagonist activity for serotonin 5-HT$_{2A}$ receptor with agonist activity for serotonin 5-HT$_{1A}$ receptor, and are useful for a medicament for treating neuropsychiatric diseases.

Means of Solving the Problems

The present inventors have extensively studied to reach the above object, and then have found that a compound of Formula (1) as below, or a pharmaceutically acceptable salt thereof (hereinafter, also referred to as "the present compound") has antagonist activity for serotonin 5-HT$_{2A}$ receptor together with agonist activity for serotonin 5-HT$_{1A}$ receptor. Based upon the new findings, the present invention has been achieved.

The present invention is illustrated as follows.

[Item 1] A compound of Formula (1):

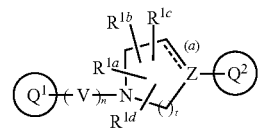

(1)

wherein V is CR$^A$R$^B$;

n is 1 or 2;

Z is nitrogen atom, carbon atom, or —CR$^J$—;

t is 1, 2, or 3;

the bond (a) accompanied with broken line is single bond or double bond;

R$^A$ and R$^B$ are each independent, where each symbol may be independently the same or different when each symbol exists plurally, and are hydrogen atom, C$_{1-6}$ alkyl, C$_{1-6}$ alkoxy, or C$_{3-10}$ cycloalkyl (wherein the alkyl, the alkoxy, and the cycloalkyl moieties may be each independent and optionally substituted with the same or different 1 to 3 halogen atoms);

R$^{1a}$, R$^{1b}$, R$^{1c}$, and R$^{1d}$ are each independently hydrogen atom, halogen atom, or C$_{1-6}$ alkyl optionally substituted with the same or different 1 to 3 halogen atoms;

Ring Q$^1$ is a group of the following Formula (2):

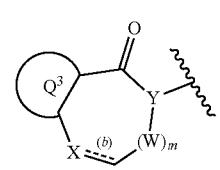

(2)

wherein Ring Q$^3$ is an optionally substituted 5- or 6-membered aromatic heterocyclic ring;

W is CR$^C$R$^D$;

m is 0 or 1;

X is —CR$^E$— or —CR$^F$R$^G$—;

Y is nitrogen atom or —CR$^H$—;

the bond (b) accompanied with broken line is single bond or double bond;

Ring Q$^2$ is a group of the following Formula (3a) or (3b):

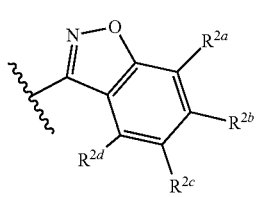

(3a)

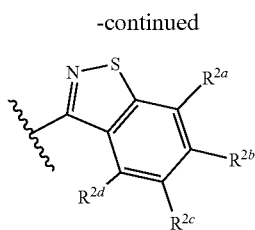

wherein $R^{2a}$, $R^{2b}$, $R^{2c}$, and $R^{2d}$ are each independently hydrogen atom, halogen atom, cyano, $C_{1-6}$ alkyl, $C_{1-6}$ alkoxy (wherein the alkyl and the alkoxy moieties may be each independent and optionally substituted with the same or different 1 to 3 halogen atoms), or amino optionally substituted with the same or different 1 or 2 $C_{1-6}$ alkyl;

$R^C$, $R^D$, $R^E$, $R^F$, $R^G$, $R^H$, and $R^J$ are each independently hydrogen atom, $C_{1-6}$ alkyl, $C_{1-6}$ alkoxy, or $C_{3-10}$ cycloalkyl (wherein the alkyl, the alkoxy, and the cycloalkyl moieties may be each independent and optionally substituted with the same or different 1 to 3 halogen atoms), provided that when $R^F$ and $R^G$ are $C_{1-6}$ alkyl, then these groups may combine together with the carbon atom to which they attach to form a 3- to 6-membered saturated carbocyclic ring;

provided that
(I) when Ring $Q^3$ is an optionally substituted 5-membered aromatic heterocyclic ring, then $R^{2a}$, $R^{2b}$, $R^{2c}$, and $R^{2d}$ are hydrogen atom;
(II) when Ring $Q^3$ is an optionally substituted 6-membered aromatic heterocyclic ring, then m is 0;
(III) when the bond (a) accompanied with broken line is double bond, then Z is carbon atom;
(IV) when the bond (b) accompanied with broken line is single bond, then X is —$CR^FR^G$—; and
(V) when the bond (b) accompanied with broken line is double bond, then X is —$CR^E$—, or a pharmaceutically acceptable salt thereof.

[Item 2] The compound according to Item 1, wherein Ring $Q^3$ is a 5- or 6-membered aromatic heterocyclic ring optionally substituted with the same or different 1 to 3 groups selected from the group consisting of hydrogen atom, halogen atom, cyano, $C_{1-6}$ alkyl, $C_{3-10}$ cycloalkyl (wherein the alkyl and the cycloalkyl moieties may be each independent and optionally substituted with the same or different 1 to 3 halogen atoms), and $C_{1-6}$ alkoxy (wherein the alkoxy moiety may be optionally substituted with the same or different 1 to 3 halogen atoms or 4- to 8-membered saturated heterocyclyl), or a pharmaceutically acceptable salt thereof.

[Item 3] The compound according to Item 1 or 2, wherein Formula (1) is Formula (1a):

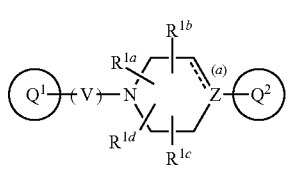

wherein $Q^1$, $Q^2$, V, Z, n, $R^{1a}$, $R^{1b}$, $R^{1c}$, $R^{1d}$, and the bond (a) accompanied with broken line are as defined in the above, or a pharmaceutically acceptable salt thereof.

[Item 4] The compound according to any one of Items 1 to 3, wherein $R^{1a}$, $R^{1b}$, $R^{1c}$, and $R^{1d}$ are hydrogen atom, or a pharmaceutically acceptable salt thereof.

[Item 5] The compound according to any one of Items 1 to 4, wherein both of $R^A$ and $R^B$ are hydrogen atom, or a pharmaceutically acceptable salt thereof.

[Item 6] The compound according to any one of Items 1 to 5, wherein n is 2, or a pharmaceutically acceptable salt thereof.

[Item 7] The compound according to any one of Items 1 to 6, wherein the bond (a) accompanied with broken line is single bond, or a pharmaceutically acceptable salt thereof.

[Item 8] The compound according to Item 1 or 2, wherein Formula (1) is represented by the following Formula (1b):

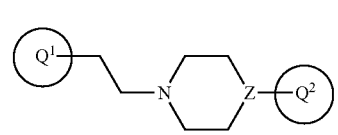

wherein $Q^1$, $Q^2$, and Z are as defined in the above, or a pharmaceutically acceptable salt thereof.

[Item 9] The compound according to any one of Items 1 to 8, wherein Z is nitrogen atom, or a pharmaceutically acceptable salt thereof.

[Item 10] The compound according to any one of Items 1 to 8, wherein Z is —CH—, or a pharmaceutically acceptable salt thereof.

[Item 11] The compound according to any one of Items 1 to 10, wherein Y is nitrogen atom, or a pharmaceutically acceptable salt thereof.

[Item 12] The compound according to any one of Items 1 to 11, wherein the bond (b) accompanied with broken line is single bond and X is —$CH_2$—, or a pharmaceutically acceptable salt thereof.

[Item 13] The compound according to any one of Items 1 to 12, wherein Ring $Q^1$ is any one of the following Formula (4a), (4b), (4c), (4d), (4e), or (4f):

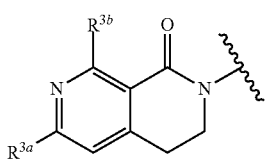

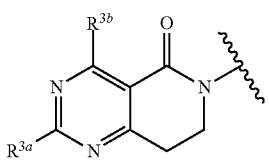

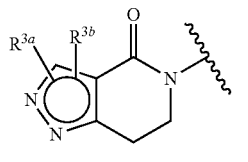

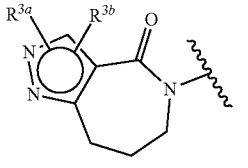

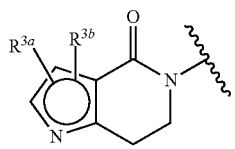
(4e)

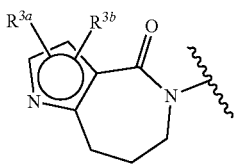
(4f)

wherein $R^{3a}$ and $R^{3b}$ are each independently hydrogen atom, halogen atom, cyano, $C_{1-6}$ alkyl, $C_{1-6}$ alkoxy (wherein the alkyl and the alkoxy moieties may be each independent and optionally substituted with the same or different 1 to 3 halogen atoms), or amino optionally substituted with the same or different 1 to 2 $C_{1-6}$ alkyl, or a pharmaceutically acceptable salt thereof.

[Item 14] The compound according to any one of Items 1 to 12, wherein Ring $Q^1$ is any one of the following Formula (5a), (5b), (5c), (5d), (5e), (5f), or (5g):

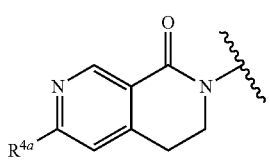
(5a)

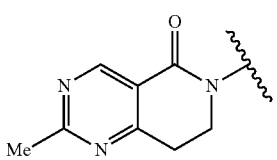
(5b)

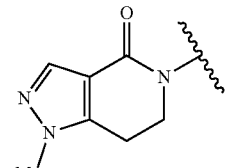
(5c)

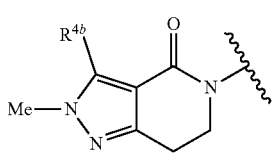
(5d)

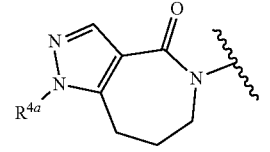
(5e)

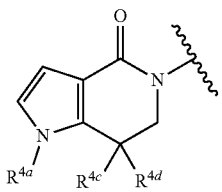
(5f)

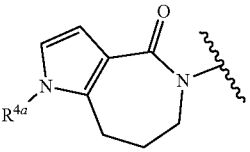
(5g)

wherein $R^{4a}$ is $C_{1-6}$ alkyl or $C_{1-6}$ alkoxy, $R^{4b}$ is hydrogen atom or $C_{1-6}$ alkyl, $R^{4c}$ and $R^{4d}$ are each independently hydrogen atom or $C_{1-6}$ alkyl, provided that when one of $R^{4c}$ or $R^{4d}$ is hydrogen atom, then the other is $C_{1-6}$ alkyl, or alternatively, $R^{4c}$ and $R^{4d}$ may combine together with the carbon atom to which they attach to form a 3- to 6-membered saturated carbocyclic ring, or a pharmaceutically acceptable salt thereof.

[Item 15] The compound according to any one of Items 1 to 14, wherein Ring $Q^2$ is a group of Formula (3a), or a pharmaceutically acceptable salt thereof.

[Item 16] The compound according to any one of Items 1 to 14, wherein Ring $Q^2$ is a group of Formula (3b), or a pharmaceutically acceptable salt thereof.

[Item 17] The compound according to any one of Items 1 to 16, wherein $R^{2a}$, $R^{2b}$, $R^{2c}$, and $R^{2d}$ are hydrogen atom, or a pharmaceutically acceptable salt thereof.

[Item 18] The compound according to Item 1, which is represented by any one of the following formulae:

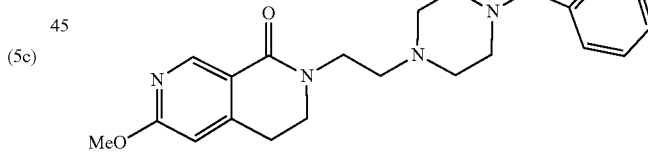

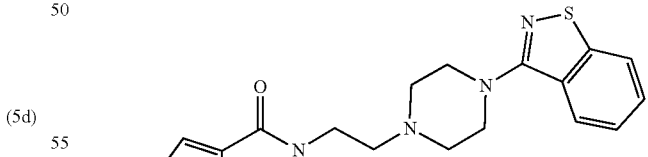

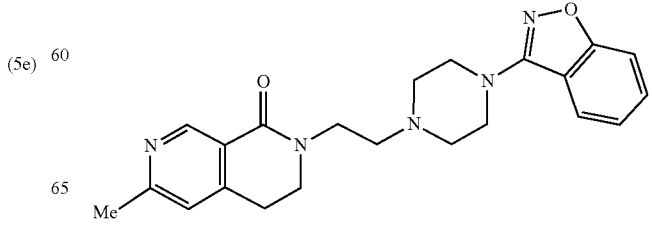

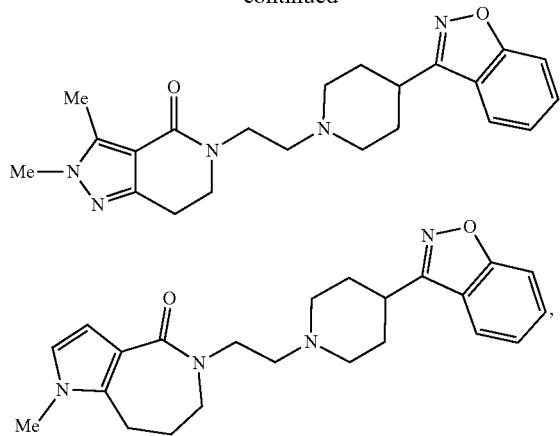

or a pharmaceutically acceptable salt thereof.

[Item 19] A drug comprising a compound according to any one of Items 1 to 18, or a pharmaceutically acceptable salt thereof, as an active ingredient.

[Item 20] A medicament for treating mental disease or central nervous system disease, comprising a compound according to any one of Items 1 to 18, or a pharmaceutically acceptable salt thereof, as an active ingredient.

[Item 21] The medicament according to Item 20, wherein the mental disease or central nervous system disease is organic, including symptomatic, mental disorders; mental and behavioural disorders due to psychoactive substance use; schizophrenia, schizotypal disorders, and delusional disorders; mood [affective] disorders; neurotic disorders, stress-related disorders, and somatoform disorders; nonorganic sleep disorders; sexual dysfunction, not caused by organic disorder or disease; pervasive developmental disorders; behavioural and emotional disorders with onset usually occurring in childhood and adolescence; extrapyramidal and movement disorders; other degenerative diseases of nervous system; or sleep disorders.

[Item 22] The medicament according to Item 20, wherein the mental disease or central nervous system disease is schizophrenia, positive symptoms of schizophrenia, negative symptoms of schizophrenia, bipolar disorders with psychotic features, depressive disorders with psychotic features, psychopathic symptoms associated with dementia, psychopathic symptoms associated with Alzheimer's disease, psychopathic symptoms associated with dementia with Lewy bodies, psychopathic symptoms associated with Parkinson's disease with dementia, psychopathic symptoms associated with Parkinson's disease, or irritation, agitation, or aggression associated with Alzheimer's disease.

[Item 23] The medicament according to Item 20, wherein the mental disease or central nervous system disease is schizophrenia, psychopathic symptoms associated with dementia, psychopathic symptoms associated with Alzheimer's disease, psychopathic symptoms associated with dementia with Lewy bodies, or irritation, agitation, or aggression associated with Alzheimer's disease.

[Item 24] A method for treating mental disease or central nervous system disease, comprising administering a therapeutically effective amount of a compound according to any one of Items 1 to 18, or a pharmaceutically acceptable salt thereof, to a patient in need thereof.

[Item 25] Use of a compound according to any one of Items 1 to 18, or a pharmaceutically acceptable salt thereof, in the manufacture of a medicament for treating mental disease or central nervous system disease.

[Item 26] A compound according to any one of Items 1 to 18, or a pharmaceutically acceptable salt thereof, for use in the treatment of mental disease or central nervous system disease.

[Item 27] A medicament for treating mental disease or central nervous system disease, comprising a compound according to any one of Items 1 to 18, or a pharmaceutically acceptable salt thereof, and at least one drug selected from the group consisting of antidepressant drugs, anxiolytic drugs, antischizophrenic agents, dopamine supplements, dopamine receptor agonists, antiparkinsonian drugs, antiepileptic drugs, analgesic drugs, hormone preparations, antimigraine drugs, adrenaline β receptor antagonists, antidementia drugs, drugs for treating mood disorders, antiemetic drugs, sleep-inducing drugs, and anticonvulsants.

[Item 28] A medicament for treating mental disease or central nervous system disease, comprising a compound according to any one of Items 1 to 18, or a pharmaceutically acceptable salt thereof, as an active ingredient, for combination use with at least one drug selected from the group consisting of antidepressant drugs, anxiolytic drugs, antischizophrenic agents, dopamine supplements, dopamine receptor agonists, antiparkinsonian drugs, antiepileptic drugs, analgesic drugs, hormone preparations, antimigraine drugs, adrenaline β receptor antagonists, antidementia drugs, drugs for treating mood disorders, antiemetic drugs, sleep-inducing drugs, and anticonvulsants.

Effect of the Invention

The present compound has antagonist activity for 5-HT$_{2A}$ receptor and agonist activity for 5-HT$_{1A}$ receptor. In a preferred embodiment, the present compound has a good metabolic stability, provides a long disappearance half-life ($T_{1/2}$) in human, and exhibits higher selectivities to these receptors than other GPCRs such as dopamine D$_2$ receptor (hereinafter, referred to as "D$_2$ receptor") and hERG channel. Thus, some preferred compounds of the present invention are useful as a medicament for treating neuropsychiatric diseases, which has a long persistence effect in human body and high safety.

BRIEF DESCRIPTION OF DRAWINGS

FIG. 1 shows the result of the compound of Example 37 in the inhibition test of MK-801-induced locomotor hyperactivity (Test 7).

FIG. 2 shows the result of the compound of Example 103 in the inhibition test of MK-801-induced locomotor hyperactivity (Test 7).

DESCRIPTION OF EMBODIMENTS

Hereinafter, the present invention is described in detail. In the description, the number of carbon atoms in the definition of "substituents" can indicates, for example, "C$_{1-6}$". The specific definition "C$_{1-6}$ alkyl" means an alkyl group having 1 to 6 carbon atoms.

The "halogen atom" used herein includes, for example, fluorine atom, chlorine atom, bromine atom, and iodine atom.

The "C$_{1-6}$ alkyl" used herein means a straight or branched chain saturated hydrocarbon group having 1 to 6 carbon atoms. Preferably, it is "C$_{1-4}$ alkyl". More preferably, it is "C$_{1-3}$ alkyl". The "C$_{1-3}$ alkyl" includes, for example, methyl, ethyl, propyl, and 1-methylethyl. The "$C_{1-4}$ alkyl" includes, for example, butyl, 1,1-dimethylethyl, 1-methylpropyl, and 2-methylpropyl, besides the above-listed examples of the "$C_{1-3}$ alkyl". The "$C_{1-6}$ alkyl" includes, for example, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, and hexyl, besides the above-listed examples of the "$C_{1-4}$ alkyl".

The "$C_{3-10}$ cycloalkyl" used herein means a cyclic saturated hydrocarbon group having 3 to 10 carbon atoms that includes those which have a partially-unsaturated bond and bridged structure. Preferably, it is "$C_{3-7}$ cycloalkyl". The "$C_{3-7}$ cycloalkyl" includes, for example, cyclopropyl, cyclobutyl, cyclopentyl, cyclohexyl, and cycloheptyl. The "$C_{3-10}$ cycloalkyl" includes, for example, cyclooctyl, cyclononyl, cyclodecyl, and adamantyl, besides the above-listed examples of the "$C_{3-7}$ cycloalkyl".

The "$C_{1-6}$ alkoxy" used herein means "$C_{1-6}$ alkyloxy" wherein the "$C_{1-6}$ alkyl" moiety is as defined in the above "$C_{1-6}$ alkyl". Preferably, it is "$C_{1-4}$ alkoxy". More preferably, it is "$C_{1-3}$ alkoxy". The "$C_{1-3}$ alkoxy" includes, for example, methoxy, ethoxy, propoxy, and 1-methylethoxy. The "$C_{1-4}$ alkoxy" includes, for example, butoxy, 1,1-dimethylethoxy, 1-methylpropoxy, and 2-methylpropoxy, besides the above-listed examples of the "$C_{1-3}$ alkyl". The "$C_{1-6}$ alkoxy" includes, for example, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, and hexyloxy, besides the above-listed examples of the "$C_{1-4}$ alkyl".

The "4- to 8-membered saturated heterocyclyl" used herein means a 4- to 8-membered saturated ring comprising 1 to 2 atoms independently selected from the group consisting of nitrogen atom, oxygen atom, and sulfur atom, as well as carbon atoms, that includes those which have a partially-unsaturated bond and bridged structure. The "4- to 8-membered saturated heterocyclyl" is preferably "4- to 6-membered monocyclic saturated heterocyclyl", and more preferably, "5- or 6-membered monocyclic saturated heterocyclyl". The "5- or 6-membered monocyclic saturated heterocyclyl" includes, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, tetrahydropyranyl. The "4- to 6-membered monocyclic saturated heterocyclyl" includes, for example, oxetanyl and azetidinyl, besides the above-listed examples of the "5- or 6-membered monocyclic saturated heterocyclic ring". The "4- to 8-membered saturated heterocyclic ring" includes, for example, azepinyl and oxepanyl, besides the above-listed examples of the "4- to 8-membered monocyclic saturated heterocyclic ring".

The "3- to 6-membered saturated carbocyclic ring" used herein means a cyclic saturated hydrocarbon having 3 to 6 carbon atoms that includes those which have a partially-unsaturated bond and bridged structure. The "3- to 6-membered saturated carbocyclic ring" is preferably "5- or 6-membered monocyclic saturated carbocyclic ring". The "5- or 6-membered monocyclic saturated carbocyclic ring" includes, for example, cyclopentane and cyclohexane. The "3- to 6-membered saturated carbocyclic ring" includes, for example, cyclopropane and cyclobutane, besides the above-listed examples of the "5- or 6-membered monocyclic saturated carbocyclic ring".

The "5- or 6-membered aromatic heterocyclic ring" used herein means a 5- or 6-membered monocyclic aromatic heterocyclic ring comprising 1 to 3 atoms independently selected from the group consisting of nitrogen atom, oxygen atom, and sulfur atom. Preferably, it includes pyrrole, imidazole, pyrazole, oxazole, isoxazole, pyridine, and pyrimidine. More preferably, it includes pyrrole, pyrazole, and pyridine. The "5- or 6-membered aromatic heterocyclic ring" includes, for example, pyrrole, furane, thiophene, imidazole, pyrazole, oxazole, isoxazole, thiazole, isothiazole, triazole, tetrazole, pyridine, pyridazine, pyrimidine, and pyrazine.

The "optionally substituted 5- or 6-membered aromatic heterocyclic ring" used herein is preferably a 5- or 6-membered aromatic heterocyclic ring, optionally substituted with the same or different 1 to 5 groups selected from the group consisting of:

(a) halogen atom, (b) hydroxy, (c) cyano, (d) $C_{1-6}$ alkyl, optionally substituted with the same or different 1 to 3 groups selected from the group consisting of halogen atom and $C_{1-6}$ alkoxy, (e) $C_{1-6}$ alkoxy, optionally substituted with the same or different 1 to 3 halogen atoms, and (f) amino, optionally substituted with the same or different 1 to 2 $C_{1-6}$ alkyl groups.

More preferably, it is a 5- or 6-membered aromatic heterocyclic ring, optionally substituted with the same or different 1 to 5 groups selected from the group consisting of $C_{1-6}$ alkyl optionally substituted with the same or different 1 to 3 groups selected from the group consisting of halogen atom and $C_{1-6}$ alkoxy; $C_{1-6}$ alkoxy optionally substituted with the same or different 1 to 3 halogen atoms; and halogen atom. Still more preferably, it is a 5- or 6-membered aromatic heterocyclic ring, optionally substituted with $C_{1-6}$ alkyl optionally substituted with 1 to 4 fluorine atoms or $C_{1-6}$ alkoxy optionally substituted with 1 to 4 fluorine atoms. Particularly preferably, it is a 5- or 6-membered aromatic heterocyclic ring, optionally substituted with $C_{1-6}$ alkyl or $C_{1-6}$ alkoxy.

Among the present compounds of Formula (1), preferable examples of n, t, Z, the bond (a) accompanied with broken line, $R^A$, $R^B$, $R^{1a}$, $R^{1b}$, $R^{1c}$, $R^{1d}$, $Q^3$, m, X, Y, the bond (b) accompanied with broken line, $Q^2$, $R^{2a}$, $R^{2b}$, $R^{2c}$, $R^{2d}$, $R^C$, $R^D$, $R^E$, $R^F$, $R^G$, $R^H$, and $R^J$ are illustrated below, but the scope of the present invention is not intended to be limited to the scope of those compounds illustrated below.

n is preferably 2.

One embodiment of Z is nitrogen atom. Another embodiment of Z is —CH—.

t is preferably 2.

The bond (a) accompanied with broken line is preferably single bond.

$R^A$ and $R^B$ are preferably hydrogen atom or $C_{1-6}$ alkyl. More preferably, they are hydrogen atom or $C_{1-3}$ alkyl. Still more preferably, they are hydrogen atom, methyl, or ethyl. Most preferably, they are hydrogen atom.

$R^{1a}$, $R^{1b}$, $R^{1c}$, and $R^{1d}$ are preferably hydrogen atom or $C_{1-6}$ alkyl. More preferably, they are hydrogen atom or $C_{1-3}$ alkyl. Still more preferably, they are hydrogen atom, methyl, or ethyl. Most preferably, they are hydrogen atom.

One embodiment of $Q^3$ is an optionally substituted 5-membered aromatic heterocyclic ring. Another embodiment of $Q^3$ is an optionally substituted 5-membered nitrogen-containing aromatic heterocyclic ring. Still another embodiment of $Q^3$ is a 5-membered nitrogen-containing aromatic heterocyclic ring, optionally substituted with the same or different 1 to 5 groups selected from the group consisting of $C_{1-6}$ alkyl optionally substituted with the same or different 1 to 3 halogen atoms or $C_{1-6}$ alkoxy; $C_{1-6}$ alkoxy optionally substituted with the same or different 1 to 3 halogen atoms; and halogen atom. Still another embodiment of $Q^3$ is a 5-membered nitrogen-containing aromatic heterocyclic ring optionally substituted with the same or different 1 to 2 groups selected from the group consisting of $C_{1-6}$ alkyl and $C_{1-6}$ alkoxy.

One embodiment of $Q^3$ is an optionally substituted 6-membered aromatic heterocyclic ring. Another embodiment of $Q^3$ is an optionally substituted 6-membered nitrogen-containing aromatic heterocyclic ring. Still another embodiment of $Q^3$ is a 6-membered nitrogen-containing aromatic heterocyclic ring optionally substituted with the same or different 1 to 5 groups selected from the group consisting of $C_{1-6}$ alkyl optionally substituted with the same or different 1 to 3 halogen atoms or $C_{1-6}$ alkoxy; $C_{1-6}$ alkoxy optionally substituted with the same or different 1 to 3 halogen atoms; and halogen atom. Still another embodiment of $Q^3$ is a 6-membered nitrogen-containing aromatic heterocyclic ring optionally substituted with the same or different 1 to 2 groups selected from the group consisting of $C_{1-6}$ alkyl and $C_{1-6}$ alkoxy.

One embodiment of m is 0. Another embodiment of m is 1.

Y is preferably nitrogen atom.

The bond (b) accompanied with broken line is preferably single bond.

One embodiment of $Q^2$ is Formula (3a). Another embodiment of $Q^2$ is Formula (3b).

$R^{2a}$, $R^{2b}$, $R^{2c}$, and $R^{2d}$ are preferably hydrogen atom or $C_1$-6 alkyl. More preferably, they are hydrogen atom or $C_{1-3}$ alkyl. Still more preferably, they are hydrogen atom, methyl, or ethyl. Most preferably, they are hydrogen atom.

$R^C$, $R^D$, $R^E$, $R^F$, $R^G$, $R^H$, and $R^J$ are preferably hydrogen atom or $C_{1-6}$ alkyl. More preferably, they are hydrogen atom or $C_{1-3}$ alkyl. Still more preferably, they are hydrogen atom, methyl, or ethyl. Most preferably, they are hydrogen atom.

One embodiment of the present compounds of Formula (1) includes the following embodiment (A).

(A)

A compound, wherein Formula (1) is Formula (1b), in which Z is —CH—,
Ring $Q^2$ is Formula (3a),
$R^{2a}$, $R^{2b}$, $R^{2c}$, and $R^{2d}$ are hydrogen atom,
Ring $Q^1$ is Formula (4c) or (4f), and
$R^{3a}$ and $R^{3b}$ are each independently hydrogen atom, $C_{1-6}$ alkyl, or $C_{1-6}$ alkoxy, or a pharmaceutically acceptable salt thereof.

Another embodiment of the present compounds of Formula (1) includes the following embodiment (B).

(B)

A compound, wherein Formula (1) is Formula (1b), in which Z is nitrogen atom,
Ring $Q^2$ is Formula (3a),
$R^{2a}$, $R^{2b}$, $R^{2c}$, and $R^{2d}$ are hydrogen atom,
Ring $Q^1$ is Formula (4a), and
$R^{3a}$ and $R^{3b}$ are each independently hydrogen atom, $C_{1-6}$ alkyl, or $C_{1-6}$ alkoxy, or a pharmaceutically acceptable salt thereof.

Another embodiment of the present compounds of Formula (1) includes the following embodiment (C).

(C)

A compound, wherein Formula (1) is Formula (1b), in which Z is nitrogen atom,
Ring $Q^2$ is Formula (3b),
$R^{2a}$, $R^{2b}$, $R^{2c}$, and $R^{2d}$ are hydrogen atom,
Ring $Q^1$ is Formula (4a) or (4c), and
$R^{3a}$ and $R^{3b}$ are each independently hydrogen atom, $C_{1-6}$ alkyl, or $C_{1-6}$ alkoxy, or a pharmaceutically acceptable salt thereof.

The compound of Formula (1) can exist as a tautomer thereof. Thus, the present compound also includes tautomers of the compound of Formula (1).

The compound of Formula (1) can have at least one chiral carbon atom. Thus, the present compound also includes a racemate of the compound of Formula (1) as well as optically active compounds thereof. When the compound of Formula (1) has two or more chiral carbon atoms, the compound can be a stereoisomeric form. Thus, the present compound also includes stereoisomers thereof and mixtures of stereoisomers.

In addition, the compound of Formula (1) in which any one or more $^1$H atoms are replaced by $^2$H(D) atoms (deuterium form) is also within the scope of the compound of Formula (1).

The compound of Formula (1) and a pharmaceutically acceptable salt thereof may also be in a form of hydrate and/or solvate, and thus, the present compound encompasses such hydrate and solvate such as ethanolate. In addition, the present compound also includes any embodiments of its crystal form.

The pharmaceutically acceptable salt of the compound of Formula (1), when the compound has an acidic group, includes, for example, alkali metal salts such as sodium salt and potassium salt; alkaline earth metal salts such as calcium salt and magnesium salt; inorganic metal salts such as zinc salt; and organic base salts such as triethylamine, triethanolamine, tri(hydroxymethyl)aminomethane, and amino acid.

The pharmaceutically acceptable salt of the compound of Formula (1), when the compound has a basic group, includes, for example, inorganic acid salts such as hydrochloride, hydrobromide, sulfate, phosphate, and nitrate; and organic acid salts such as acetate, propionate, succinate, lactate, tartrate, citrate, maleate, fumarate, malate, methanesulfonate, p-toluenesulfonate, benzenesulfonate, and ascorbate.

Hereinafter, the processes to prepare the present compound are explained along with examples, but the present invention should not be limited thereto.

Preparation Process

The compounds of the present invention can be prepared by means of the preparation processes mentioned below or those combined with known processes.

Each compound appearing in the following schemes may also be in its salt form, and such salts may include, for example, the corresponding salts exemplified as the salt of the compound of Formula (1). The reactions mentioned below are just examples, thus the compounds of the present invention may be prepared by other means based on the knowledge of a person skilled in organic synthesis.

If there is a functional group that needs to be protected in the preparation processes mentioned below, the functional group may be protected as appropriate and then deprotected after completing the reaction or the reaction sequences to obtain a desired compound, even though the use of any protecting groups is not specifically indicated.

The protecting group used herein includes, for example, general protecting groups described in T. W. Greene and P. G. M. Wuts, "*Protective Groups in Organic Synthesis*", 3rd Ed., John Wiley and Sons, inc., New York (1999); in more detail, it includes, for example, benzyloxycarbonyl, tert-butoxycarbonyl, acetyl, and benzyl, for amino group; and trialkylsilyl, acetyl, and benzyl, for hydroxy group.

The protection and deprotection can be carried out by conventional means in organic synthesis chemistry (for example, the methods described in T. W. Greene and P. G. M. Wuts, "*Protective Groups in Organic Synthesis*", 3rd Ed., John Wiley and Sons, inc., New York (1999)), or similar means to them.

Preparation Process 1

The compound of Formula (1) can be prepared, for example, by the following process.

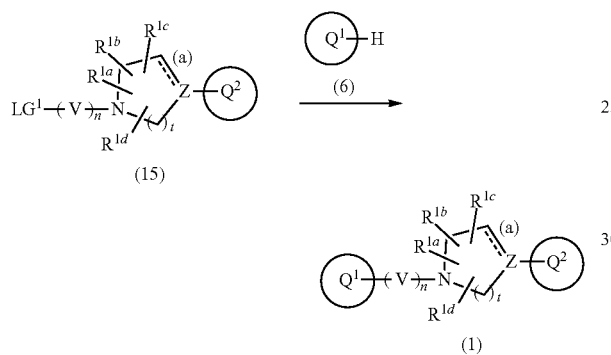

In the scheme, V, n, Z, t, the bond (a) accompanied with broken line, $R^{1a}$, $R^{1b}$, $R^{1c}$, $R^{1d}$, Ring $Q^1$, and Ring $Q^2$ are as defined in the above Item 1; $LG^1$ is a leaving group such as iodine, bromine, chlorine, and substituted sulfonyl (e.g., methanesulfonyl and p-toluenesulfonyl).

Compound (5) can be gotten as a marketed product or can be prepared according to a known synthetic method (for example, European Journal of Medicinal Chemistry 2002, 37(9), 721-730).

Compound (6) can be gotten as a marketed product or can be prepared according to a known synthetic method (for example, European Journal of Medicinal Chemistry 2012, 55, 58-66).

Compound (1) is prepared by reacting Compound (5) and Compound (6) in a suitable inert solvent in the presence of a suitable base. The reaction may be carried out in the presence of a suitable phase-transfer catalyst, as appropriate. The reaction temperature generally ranges from about −20° C. to the boiling point of the solvent used herein. The reaction time depends on the reaction condition such as the reaction temperature, the base, the starting materials, and the solvent used herein, and generally ranges from 10 minutes to 48 hours.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the phase-transfer catalyst used herein include tetrabutylammonium hydrogen sulfate.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), and 1,4-dioxane; lower alcohol solvents such as methanol, ethanol, and 2-propanol; aprotic polar solvents such as acetonitrile, acetone, methylethylketone, dimethylformamide, N-methyl-2-pyrrolidinone, and dimethylsulfoxide; and mixture solvents thereof.

Preparation Process 2

Among the compounds of Formula (1), the compound of Formula (1c) can be prepared, for example, by the following process.

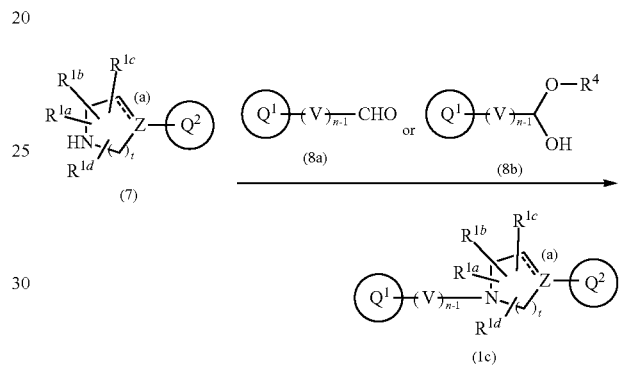

In the scheme, V, n, Z, t, the bond (a) accompanied with broken line, $R^{1a}$, $R^{1b}$, $R^{1c}$, $R^{1d}$, Ring $Q^1$, and Ring $Q^2$ are as defined in the above Item 1; and $R^4$ is optionally substituted $C_{1-6}$ alkyl.

Compound (7) can be gotten as a marketed product or can be prepared according to a known synthetic method (for example, Journal of Medicinal Chemistry 1985, 28(6), 761-769).

Compound (1c) is prepared by reacting Compound (7) and an aldehyde of Formula (8a) or a hemiacetal of Formula (8b) under reductive amination with a suitable reducing agent in a suitable inert solvent. The reaction may be carried out in the presence of a suitable base or acid, as appropriate. The reaction temperature generally ranges from about −20° C. to the boiling point of the solvent used herein. The reaction time depends on the reaction condition such as the reaction temperature, the reducing agent, the starting materials, and the solvent used herein, and generally ranges from 10 minutes to 48 hours.

Examples of the reducing agent used herein include complex hydride compounds such as sodium triacetoxyborohydride, lithium aluminum hydride, sodium borohydride, and sodium cyanoborohydride; and borane complexes such as borane-dimethyl sulfide complex and borane-tetrahydrofurane complex.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the acid used herein include organic acids such as acetic acid, trifluoroacetic acid, and methanesulfonic acid; and inorganic acids such as hydrochloric acid and sulfuric acid.

Examples of the inert solvent used herein include water; halogenated hydrocarbon solvents such as chloroform and dichloromethane; aromatic hydrocarbon solvents such as benzene and toluene; ether solvents such as 1,2-dimethoxyethane, tetrahydrofurane, and 1,4-dioxane; alcohol solvents such as methanol, ethanol, and 2-propanol; aprotic polar solvents such as acetonitrile, dimethylformamide, and N-methyl-2-pyrrolidinone; and mixture solvents thereof.

Preparation Process 3

The compound of Formula (5) can be prepared, for example, by the following process.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the phase-transfer catalyst used herein include tetrabutylammonium hydrogen sulfate.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), and 1,4-dioxane; lower alcohol solvents such as methanol, ethanol, and 2-propanol; aprotic

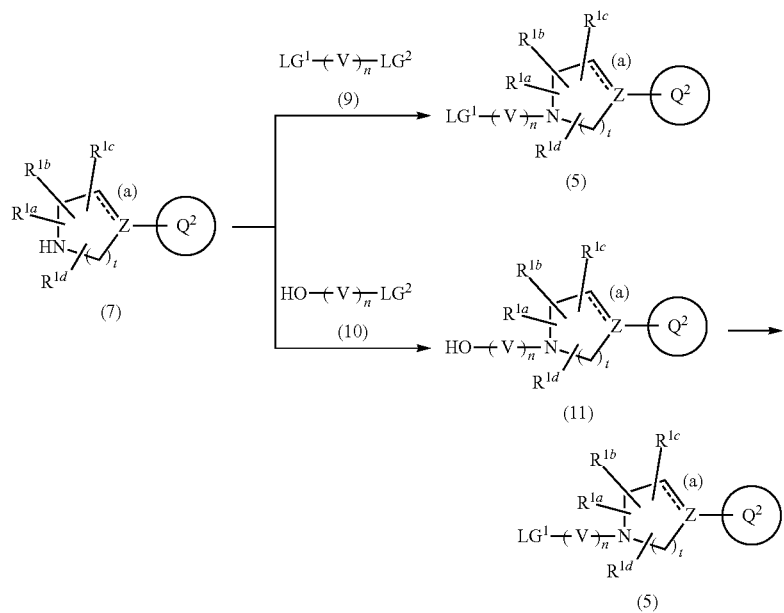

In the scheme, V, n, Z, t, the bond (a) accompanied with broken line, $R^{1a}$, $R^{1b}$, $R^{1c}$, $R^{1d}$, and Ring $Q^2$ are as defined in the above Item 1; $LG^1$ and $LG^2$ are a leaving group such as iodine, bromine, chlorine, and substituted sulfonyl (e.g., methanesulfonyl and p-toluenesulfonyl).

Compound (9) can be gotten as a marketed product or can be prepared according to a known synthetic method (for example, Organic Process Research & Development 2005, 9(6), 774-781).

Compound (10) can be gotten as a marketed product or can be prepared according to a known synthetic method (for example, Journal of the Chemical Society, Perkin Transactions 1 2001, 10, 1204-1211).

Compound (5) is prepared by reacting Compound (7) and an alkylating agent of Formula (9) in a suitable inert solvent. The reaction may be carried out in the presence of a suitable base and in the presence of a phase-transfer catalyst, as appropriate. The reaction temperature generally ranges from about −20° C. to the boiling point of the solvent used herein. The reaction time depends on the reaction condition such as the reaction temperature, the base used herein, the starting materials, and the solvent used herein, and generally ranges from 10 minutes to 48 hours.

polar solvents such as acetonitrile, acetone, methylethylketone, dimethylformamide, N-methyl-2-pyrrolidinone, and dimethylsulfoxide; and mixture solvents thereof.

Compound (5) is prepared by converting the hydroxyl group of Compound (11) into halogen atom or a substituted sulfonyloxy group such as p-toluenesulfonyloxy and methanesulfonyloxy in a suitable inert solvent according to conventional methods.

For example, Compound (5) wherein $LG^1$ is halogen atom is prepared by reacting Compound (11) and carbon tetrachloride or carbon tetrabromide in the presence of triphenylphosphine in a suitable inert solvent.

Compound (5) wherein $LG^1$ is substituted sulfonyloxy is prepared by reacting Compound (11) and p-toluenesulfonyl chloride or methanesulfonyl chloride, etc. in the presence of a suitable base in an inert solvent. The reaction temperature generally ranges from about −20° C. to the boiling point of the solvent used herein. The reaction time depends on the reaction condition such as the reaction temperature, the base used herein, the starting materials, and the solvent used herein, and generally ranges from 10 minutes to 48 hours.

Examples of the inert solvent used herein include halogenated hydrocarbon solvents such as chloroform and dichloromethane; ether solvents such as diethyl ether, tetrahydrofurane, 1,4-dioxane, and 1,2-dimethoxyethane; aprotic polar solvents such as acetonitrile, dimethylformamide, N-methyl-2-pyrrolidone, and dimethylsulfoxide; and mixture solvents thereof.

Examples of the base used herein include organic bases such as triethylamine and pyridine; and inorganic bases such as potassium carbonate and sodium hydroxide.

Compound (5) wherein $LG^1$ is halogen atom is also prepared by reacting Compound (5) wherein $LG^1$ is substituted sulfonyloxy and lithium bromide or lithium chloride, etc. in a suitable inert solvent.

Compound (11) is prepared by reacting Compound (7) and an alkylating agent of Formula (10) in a suitable inert solvent. The reaction may be carried out in the presence of a suitable base and in the presence of a suitable phase-transfer catalyst, as appropriate. The reaction temperature generally ranges from about −20° C. to the boiling point of the solvent used herein. The reaction time depends on the reaction condition such as the reaction temperature, the base used herein, the starting materials, and the solvent used herein, and generally ranges from 10 minutes to 48 hours.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the phase-transfer catalyst used herein include tetrabutylammonium hydrogen sulfate.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), and 1,4-dioxane; lower alcohol solvents such as methanol, ethanol, and 2-propanol; aprotic polar solvents such as acetonitrile, acetone, methylethylketone, dimethylformamide, N-methyl-2-pyrrolidinone, and dimethylsulfoxide; and mixture solvents thereof.

Preparation Process 4

Among the compounds of Formula (7), the compound of Formula (7a) can be prepared, for example, by the following process.

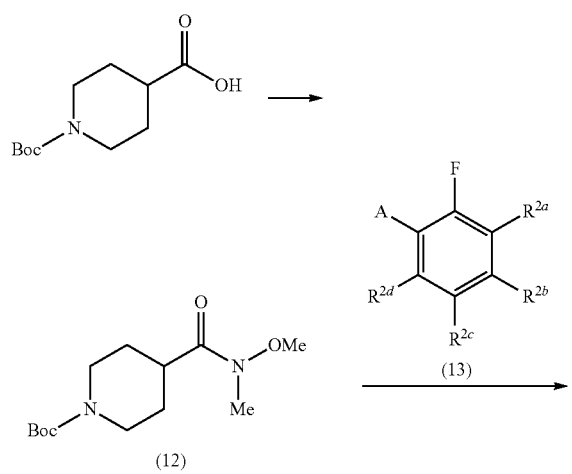

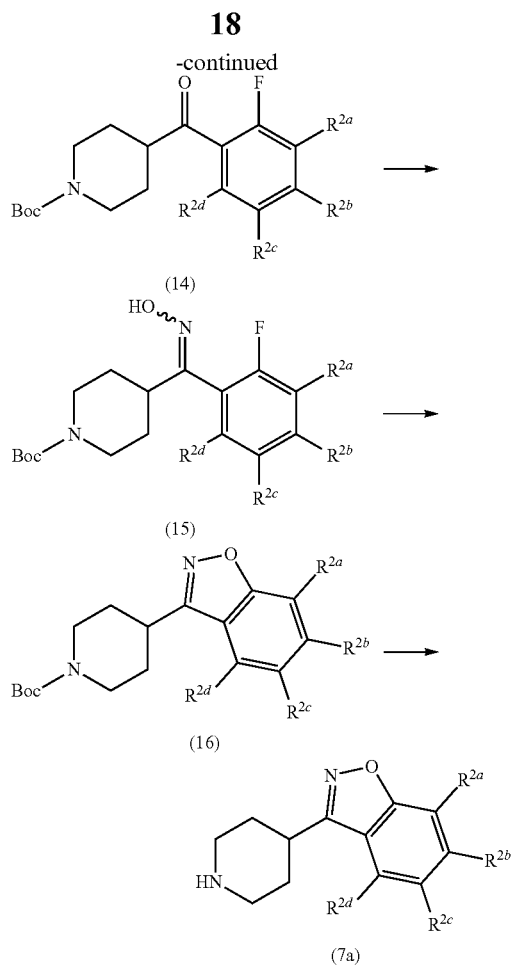

In the scheme, $R^{2a}$, $R^{2b}$, $R^{2c}$, and $R^{2d}$ are as defined in the above Item 1; and A is halogen atom such as iodine, bromine, and chlorine.

Compound (13) can be gotten as a marketed product or can be prepared according to a known synthetic method (for example, Chemical Communications 2016, 52(5), 958-961).

Compound (7a) is prepared by treating Compound (16) with a suitable acid in a suitable inert solvent. The reaction temperature generally ranges from −20° C. to the boiling point of the solvent used herein. The reaction time depends on the reaction condition such as the reaction temperature, the acid used herein, the starting materials, and the solvent used herein, and generally ranges from 10 minutes to 48 hours.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane, 1,4-dioxane, and 1,2-dimethoxyethane; lower alcohol solvents such as methanol, ethanol, and 2-propanol; aprotic polar solvents such as acetonitrile, dimethylformamide, N-methyl-2-pyrrolidinone, and dimethylsulfoxide; and mixture solvents thereof.

Examples of the acid used herein include inorganic acids such as hydrochloric acid and sulfuric acid and organic acids such as trifluoroacetic acid.

Compound (16) is prepared by treating Compound (15) with a suitable base in a suitable inert solvent. The reaction temperature generally ranges from about −20° C. to the boiling point of the solvent used herein. The reaction time depends on the reaction condition such as the reaction temperature, the base used herein, the starting materials, and the solvent used herein, and generally ranges from 10 minutes to 48 hours.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), and 1,4-dioxane; lower alcohol solvents such as methanol, ethanol, and 2-propanol; aprotic polar solvents such as acetonitrile, acetone, methylethylketone, dimethylformamide, N-methyl-2-pyrrolidinone, and dimethylsulfoxide; and mixture solvents thereof.

Compound (15) is prepared by reacting Compound (14) and hydroxylamine or a salt thereof in a suitable inert solvent, and if necessary, in the presence of a suitable base. The reaction temperature generally ranges from about $-20°$ C. to the boiling point of the solvent used herein. The reaction time depends on the reaction condition such as the reaction temperature, the base used herein, the starting materials, and the solvent used herein, and generally ranges from 10 minutes to 48 hours.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; metallic alkoxides such as sodium methoxide, and potassium tert-butoxide; and sodium acetate.

Examples of the inert solvent used herein include aromatic hydrocarbon solvents such as benzene and toluene; ether solvents such as diethyl ether, tetrahydrofurane (THF), and 1,4-dioxane; lower alcohol solvents such as methanol, ethanol, and 2-propanol; aprotic polar solvents such as dimethylformamide and N-methyl-2-pyrrolidinone; water; and mixture solvents thereof.

Compound (14) is prepared by treating Compound (13) with organic lithium such as n-butyllithium in a suitable inert solvent to give a lithiated compound, followed by reaction with Compound (12). The reaction temperature generally ranges from about $-78°$ C. to the boiling point of the solvent used herein. The reaction time depends on the reaction condition such as the reaction temperature, the reagent used herein, the starting materials, and the solvent used herein, and generally ranges from 10 minutes to 48 hours.

Examples of the inert solvent used herein include aromatic hydrocarbon solvents such as benzene and toluene; ether solvents such as diethyl ether, tetrahydrofurane (THF), and 1,4-dioxane; and mixture solvents thereof.

Compound (12) is prepared by reacting 1-(tert-butoxycarbonyl)piperidine-4-carboxylic acid and N,O-dimethylhydroxyamine or a hydrochloride salt thereof in the presence of a suitable condensing agent in a suitable inert solvent. The reaction may be carried out in the presence of a suitable base, as appropriate. The reaction temperature generally ranges from about $-20°$ C. to the boiling point of the solvent used herein. The reaction time depends on the reaction condition such as the reaction temperature, the condensing agent used herein, the starting materials, and the solvent used herein, and generally ranges from 10 minutes to 48 hours.

Compound (12) is also prepared by reacting N,O-dimethylhydroxyamine or a salt thereof and an acid halide or acid anhydride compound derived from 1-(tert-butoxycarbonyl)piperidine-4-carboxylic acid in the presence of a suitable base in a suitable inert solvent. The reaction temperature generally ranges from about $-20°$ C. to the boiling point of the solvent used herein. The reaction time depends on the reaction condition such as the reaction temperature, the condensing agent used herein, the starting materials, and the solvent used herein, and generally ranges from 10 minutes to 48 hours.

Examples of the condensing agent used herein include dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonyldiamide (DPPA), N,N-carbonyldiimidazole (CDI), and benzotriazol-1-yl-N,N,N',N'-tetramethyluronium hexafluorophosphate (HBTU). The reaction can be carried out by addition of an additive such as N-hydroxysuccinimide (HOSu), 1-hydroxybenzotriazole (HOBt), and 3-hydroxy-4-oxo-3,4-dihydro-1,2,3-benzotriazine (HOOBt), as appropriate.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), and 1,4-dioxane; aprotic polar solvents such as acetonitrile, acetone, methylethylketone, dimethylformamide, N-methyl-2-pyrrolidinone, and dimethylsulfoxide; basic solvents such as pyridine; and mixture solvents thereof.

Preparation Process 5

Among the compounds of Formula (7), the compound of Formula (7b) can be prepared, for example, by the following process.

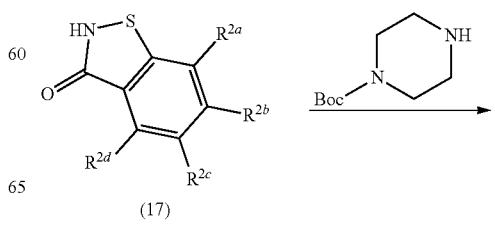

(17)

-continued

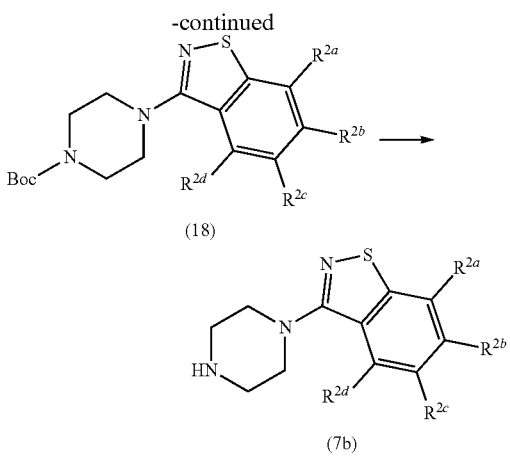

(18)

(7b)

In the scheme, $R^{2a}$, $R^{2b}$, $R^{2c}$, and $R^{2d}$ are as defined in the above Item 1.

Compound (17) can be gotten as a marketed product or can be prepared according to a known synthetic method (for example, European Journal of Organic Chemistry 2018, 40, 5520-5523).

Compound (7b) is prepared by treating Compound (18) with a suitable acid in a suitable inert solvent. The reaction temperature generally ranges from −20° C. to the boiling point of the solvent used herein. The reaction time depends on the reaction condition such as the reaction temperature, the acid used herein, the starting materials, and the solvent used herein, and generally ranges from 10 minutes to 48 hours.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), 1,4-dioxane, and 1,2-dimethoxyethane; lower alcohol solvents such as methanol, ethanol, and 2-propanol; aprotic polar solvents such as acetonitrile, dimethylformamide, N-methyl-2-pyrrolidinone, and dimethylsulfoxide; and mixture solvents thereof.

Examples of the acid used herein include inorganic acids such as hydrochloric acid and sulfuric acid and organic acids such as trifluoroacetic acid.

Compound (18) is prepared by activating Compound (17) with a reagent including phosphoryl halide such as phosphoryl chloride, a sulfonylating agent such as methanesulfonyl chloride, and bromotri(pyrrolidin-1-yl)phosphonium hexafluorophosphate (V) in a suitable inert solvent, followed by reaction with tert-butylpiperazine-1-carboxylate in the presence of a suitable base. The reaction temperature generally ranges from about −20° C. to the boiling point of the solvent used herein. The reaction time depends on the reaction condition such as the reaction temperature, the reagent used herein, the starting materials, and the solvent used herein, and generally ranges from 10 minutes to 48 hours.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane, 1,4-dioxane, and 1,2-dimethoxyethane; aprotic polar solvents such as acetonitrile, dimethylformamide, N-methyl-2-pyrrolidinone, and dimethylsulfoxide; and mixture solvents thereof.

Preparation Process 6

Among the compounds of Formula (7), the compound of Formula (7c) can be prepared, for example, by the following process.

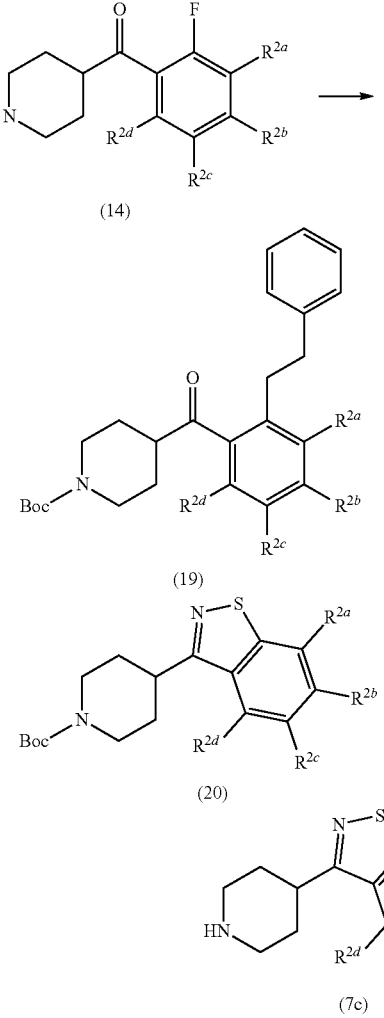

In the scheme, $R^{2a}$, $R^{2b}$, $R^{2c}$, and $R^{2d}$ are as defined in the above Item 1.

Compound (7c) is prepared by treating Compound (20) with a suitable acid in a suitable inert solvent. The reaction temperature generally ranges from −20° C. to the boiling point of the solvent used herein. The reaction time depends on the reaction condition such as the reaction temperature, the acid used herein, the starting materials, and the solvent used herein, and generally ranges from 10 minutes to 48 hours.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), 1,4-dioxane, and 1,2-dimethoxyethane; lower alcohol solvents such as methanol, ethanol, and 2-propanol; aprotic polar solvents such as acetonitrile, dimethylformamide, N-methyl-2-pyrrolidinone, and dimethylsulfoxide; and mixture solvents thereof.

Examples of the acid used herein include inorganic acids such as hydrochloric acid and sulfuric acid and organic acids such as trifluoroacetic acid.

Compound (20) is prepared by treating Compound (19) with sulfuryl chloride in a suitable inert solvent, followed by reaction with ammonia. The reaction temperature generally ranges from −20° C. to the boiling point of the solvent used herein. The reaction time depends on the reaction condition such as the reaction temperature, the starting materials, and the solvent used herein, and generally ranges from 10 minutes to 48 hours.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane, 1,4-dioxane, and 1,2-dimethoxyethane; lower alcohol solvents such as methanol, ethanol, and 2-propanol; and mixture solvents thereof.

Compound (19) is prepared by reacting Compound (14) and sodium sulfide in a suitable inert solvent, followed by treatment with benzyl halide such as benzyl bromide in the presence of a suitable base. Compound (19) is also prepared by reacting Compound (14) and benzyl mercaptan in the presence of a suitable base in a suitable inert solvent. The reaction temperature generally ranges from −20° C. to the boiling point of the solvent used herein. The reaction time depends on the reaction condition such as the reaction temperature, the reagent used herein, the starting materials, and the solvent used herein, and generally ranges from 10 minutes to 48 hours.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane, 1,4-dioxane, and 1,2-dimethoxyethane; aprotic polar solvents such as acetonitrile, dimethylformamide, N-methyl-2-pyrrolidinone, and dimethylsulfoxide; and mixture solvents thereof.

Preparation Process 7

The compound of Formula (8a) or (8b) can be prepared, for example, by the following process.

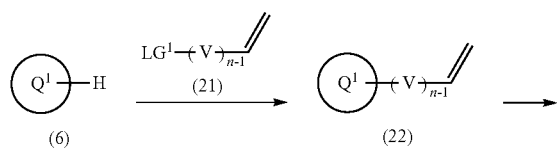

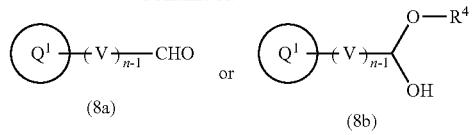

In the scheme, V, n, and Ring $Q^1$ are as defined in the above Item 1; $R^4$ is optionally substituted $C_{1-6}$ alkyl; and $LG^1$ is a leaving group such as iodine, bromine, chlorine, and substituted sulfonyl (e.g., methanesulfonyl and p-toluenesulfonyl).

Compound (21) can be gotten as a marketed product or can be prepared according to a known synthetic method (for example, Organic & Biomolecular Chemistry 2018, 16(41), 7753-7759).

Compound (8a) or Compound (8b) is prepared by reacting Compound (22) and a catalytic amount of osmium tetroxide in the presence of an oxidizing agent such as sodium periodate in a suitable inert solvent. The reaction temperature generally ranges from about −20° C. to the boiling point of the solvent used herein. The reaction time depends on the reaction condition such as the reaction temperature, the reagent used herein, the starting materials, and the solvent used herein, and generally ranges from 10 minutes to 48 hours.

Examples of the inert solvent used herein include aromatic hydrocarbon solvents such as benzene and toluene; ether solvents such as diethyl ether, tetrahydrofurane (THF) and 1,4-dioxane; aprotic polar solvents such as acetonitrile, acetone, dimethylformamide, and N-methyl-2-pyrrolidinone; water; and mixture solvents thereof.

Compound (22) is prepared by reacting Compound (6) and an alkylating agent of Formula (21) in the presence of a suitable base in a suitable inert solvent. The reaction temperature generally ranges from about −20° C. to the boiling point of the solvent used herein. The reaction time depends on the reaction condition such as the reaction temperature, the reagent used herein, the starting materials, and the solvent used herein, and generally ranges from 10 minutes to 48 hours.

Examples of the base used herein include organic bases such as triethylamine, diisopropylethylamine, and pyridine;

inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane, 1,4-dioxane, and 1,2-dimethoxyethane; aprotic polar solvents such as acetonitrile, dimethylformamide, N-methyl-2-pyrrolidinone, and dimethylsulfoxide; and mixture solvents thereof.

Preparation Process 8

Among the compounds of Formula (2), the compound of Formula (2a) can be prepared, for example, by the following process.

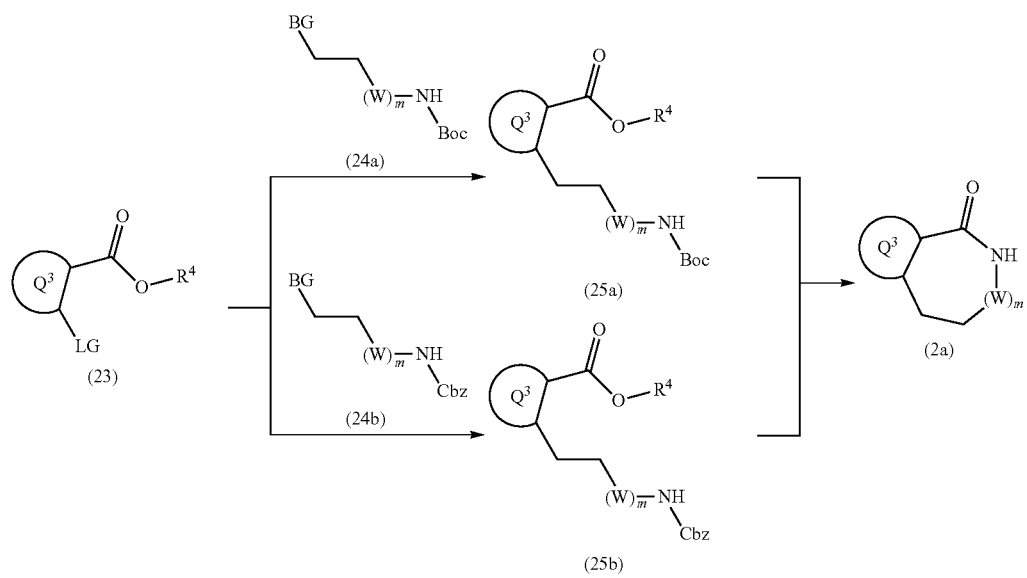

In the scheme, W, m, and Ring $Q^3$ are as defined in the above Item 1; $R^4$ is optionally substituted $C_{1-6}$ alkyl; LG is a leaving group such as iodine, bromine, chlorine, and substituted sulfonyl (e.g., trifluoromethanesulfonyl and p-toluenesulfonyl); and BG is boronic acid (—B(OH)$_2$), boronic acid ester (e.g., pinacol boronic acid ester), or trifluoroborate.

Compound (23) can be gotten as a marketed product or can be prepared according to a known synthetic method (for example, Journal of Medicinal Chemistry 2011, 54(2), 635-654).

Compound (24a) and (24b) can be gotten as a marketed product or can be prepared according to a known synthetic method (for example, Tetrahedron Letters 2004, 45(11), 2467-2471).

Compound (2a) is prepared by treating Compound (25a) with a suitable acid in a suitable inert solvent, followed by intramolecular cyclization in the presence of a suitable base, as appropriate. The reaction temperature generally ranges from −20° C. to the boiling point of the solvent used herein. The reaction time depends on the reaction condition such as the reaction temperature, the acid used herein, the starting materials, and the solvent used herein, and generally ranges from 10 minutes to 48 hours.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane, 1,4-dioxane, and 1,2-dimethoxyethane; lower alcohol solvents such as methanol, ethanol, and 2-propanol; aprotic polar solvents such as acetonitrile, dimethylformamide, N-methyl-2-pyrrolidinone, and dimethylsulfoxide; and mixture solvents thereof.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the acid used herein include inorganic acids such as hydrochloric acid and sulfuric acid and organic acids such as trifluoroacetic acid.

Compound (2a) is also prepared by hydrogenolysis of Compound (25b) in a suitable inert solvent under ordinary pressure or pressurized hydrogen atmosphere, followed by intramolecular cyclization in the presence of a suitable base, as appropriate. Examples of the catalyst used in the hydrogenolysis include palladium catalysts such as palladium-carbon and palladium hydroxide-carbon. The reaction temperature generally ranges from 0° C. to the boiling point of the solvent used herein. The reaction time depends on the reaction condition such as the reaction temperature, the catalyst used herein, the starting materials, and the solvent used herein, and generally ranges from 10 minutes to 48 hours.

Examples of the inert solvent used herein include ester solvents such as ethyl acetate; aromatic hydrocarbon solvents such as benzene and toluene; ether solvents such as diethyl ether, tetrahydrofurane (THF), 1,4-dioxane, and 1,2-dimethoxyethane; alcohol solvents such as methanol, ethanol, and 2-propanol; aprotic polar solvents such as dimethylformamide, N-methyl-2-pyrrolidinone, and dimethylsulfoxide; and mixture solvents thereof.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Compound (25a) is prepared by the coupling reaction of Compound (23) with Compound (24a) in the presence of a suitable transition-metal catalyst in a suitable inert solvent. The reaction may be carried out in the presence of a suitable ligand, a suitable base, and a suitable additive, as appropriate. The reaction temperature generally ranges from −10° C. to the boiling point of the solvent used herein. The reaction time depends on the reaction condition such as the reaction temperature, the transition-metal catalyst used herein, the starting materials, and the solvent used herein, and generally ranges from 10 minutes to 48 hours.

Examples of the transition-metal catalyst used herein include palladium (II) acetate, palladium (II) chloride, tris (dibenzylideneacetone)dipalladium (0), tetrakis(triphenylphosphine)palladium (0), bis(triphenylphosphine)palladium (II) chloride, dichlorobis(tri-O-tolylphosphine)palladium (II), bis(tri-tert-butylphosphine)palladium (0), and [1,1'-bis(diphenylphosphino)ferrocene]dichloropalladium (II).

Examples of the ligand used herein include triphenylphosphine, tri-O-tolylphosphine, tri-tert-butylphosphine, tri-2-furylphosphine, tricyclohexylphosphine, triphenylarsine, 1,1'-bis(diphenylphosphino)ferrocene, 2-dicyclohexylphosphino-2',6'-dimethoxybiphenyl, and 2-dicyclohexylphosphino-2',4',6'-triisopropylbiphenyl.

Examples of the base used herein include organic bases such as triethylamine and diisopropylethylamine; and inorganic bases such as sodium carbonate, sodium bicarbonate, potassium carbonate, cesium carbonate, and potassium phosphate.

Examples of the additive used herein include inorganic salts such as lithium chloride, cesium fluoride, copper (I) iodide, and copper (I) bromide.

Examples of the inert solvent used herein include water; acetonitrile; halogenated hydrocarbon solvents such as chloroform and dichloromethane; aromatic hydrocarbon solvents such as benzene and toluene; ether solvents such as 1,2-dimethoxyethane, tetrahydrofurane, and 1,4-dioxane; alcohol solvents such as methanol, ethanol, and 2-propanol; aprotic polar solvents such as dimethylformamide and N-methyl-2-pyrrolidinone; and mixture solvents thereof.

Compound (25b) is prepared by the coupling reaction of Compound (23) with Compound (24b) in the presence of a suitable transition-metal catalyst in a suitable inert solvent. The reaction may be carried out in the presence of a suitable ligand, a suitable base, or a suitable additive, as appropriate. The reaction temperature generally ranges from −10° C. to the boiling point of the solvent used herein. The reaction time depends on the reaction condition such as the reaction temperature, the transition-metal catalyst used herein, the starting materials, and the solvent used herein, and generally ranges from 10 minutes to 48 hours.

Examples of the transition-metal catalyst used herein include palladium (II) acetate, palladium (II) chloride, tris (dibenzylideneacetone)dipalladium (0), tetrakis(triphenylphosphine)palladium (0), bis(triphenylphosphine)palladium (II) chloride, dichlorobis(tri-O-tolylphosphine)palladium (II), bis(tri-tert-butylphosphine)palladium (0), and [1,1'-bis(diphenylphosphino)ferrocene]dichloropalladium (II).

Examples of the ligand used herein include triphenylphosphine, tri-O-tolylphosphine, tri-tert-butylphosphine, tri-2-furylphosphine, tricyclohexylphosphine, triphenylarsine, 1,1'-bis(diphenylphosphino)ferrocene, 2-dicyclohexylphosphino-2',6'-dimethoxybiphenyl, and 2-dicyclohexylphosphino-2',4',6'-triisopropylbiphenyl.

Examples of the base used herein include organic bases such as triethylamine and diisopropylethylamine; and inorganic bases such as sodium carbonate, sodium bicarbonate, potassium carbonate, cesium carbonate, and potassium phosphate.

Examples of the additive used herein include inorganic salts such as lithium chloride, cesium fluoride, copper (I) iodide, and copper (I) bromide.

Examples of the inert solvent used herein include water; acetonitrile; halogenated hydrocarbon solvents such as chloroform and dichloromethane; aromatic hydrocarbon solvents such as benzene and toluene; ether solvents such as 1,2-dimethoxyethane, tetrahydrofurane, and 1,4-dioxane; alcohol solvents such as methanol, ethanol, and 2-propanol; aprotic polar solvents such as dimethylformamide and N-methyl-2-pyrrolidinone; and mixture solvents thereof.

Preparation Process 9

Among the compounds of Formula (2), the compound of Formula (2b) can be prepared, for example, by the following process.

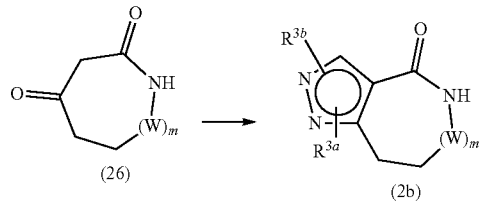

In the scheme, W and m are as defined in the above Item 1; and $R^{3a}$ and $R^{3b}$ are as defined in the above Item 13.

Compound (26) can be gotten as a marketed product or can be prepared according to a known synthetic method (for example, Organic Letters 2009, 11(10), 2133-2136).

Compound (2b) is prepared by reacting Compound (26) and alkylhydrazine such as hydrazine and methylhydrazine in a suitable inert solvent, and if necessary, in the presence of a suitable acid, followed by reaction with amide acetal such as dimethylformamide dimethyl acetal and dimethylacetamide dimethyl acetal. Alternatively, Compound (2b) is also prepared by reacting Compound (26) and amide acetal such as dimethylformamide dimethyl acetal and dimethylacetamide dimethyl acetal, followed by reaction with alkylhydrazine such as hydrazine and methylhydrazine. The reaction temperature generally ranges from about −20° C. to the boiling point of the solvent used herein. The reaction time depends on the reaction condition such as the reaction temperature, the reagent used herein, the starting materials, and the solvent used herein, and generally ranges from 10 minutes to 48 hours.

Examples of the inert solvent used herein include aromatic hydrocarbon solvents such as benzene and toluene; ether solvents such as diethyl ether, tetrahydrofurane, 1,4-dioxane, and 1,2-dimethoxyethane; lower alcohol solvents such as methanol, ethanol, and 2-propanol; aprotic polar solvents such as acetonitrile, dimethylformamide, N-methyl-2-pyrrolidinone, and dimethylsulfoxide; and mixture solvents thereof.

Examples of the acid used herein include organic acids such as acetic acid.

Preparation Process 10

Among the compounds of Formula (1), the compound of Formula (1d) can be prepared, for example, by the following process.

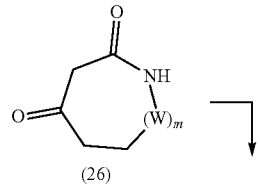

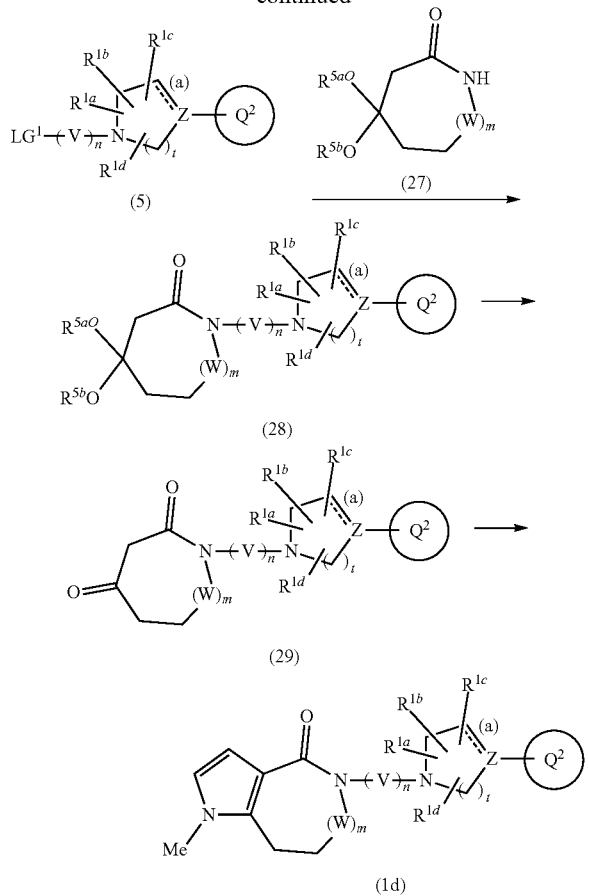

In the scheme, V, W, m, n, Z, t, the bond (a) accompanied with broken line, $R^{1a}$, $R^{1b}$, $R^{1c}$, $R^{1d}$, and Ring $Q^2$ are as defined in the above Item 1; $LG^1$ is a leaving group such as iodine, bromine, chlorine, and substituted sulfonyl (e.g., methanesulfonyl and p-toluenesulfonyl); and $R^{5a}$ and $R^{5b}$ are optionally substituted $C_{1-6}$ alkyl, or these groups may combine with each other to form a 5- to 7-membered cyclic acetal.

Compound (1d) is prepared by reacting Compound (29) and 2,2-dimethoxy-N-methylethan-1-amine in the presence of a suitable dehydrating agent and a suitable acid in a suitable inert solvent. The reaction temperature generally ranges from about −20° C. to the boiling point of the solvent used herein. The reaction time depends on the reaction condition such as the reaction temperature, the reagent used herein, the starting materials, and the solvent used herein, and generally ranges from 10 minutes to 48 hours.

Examples of the inert solvent used herein include aromatic hydrocarbon solvents such as benzene and toluene; ether solvents such as diethyl ether, tetrahydrofurane, 1,4-dioxane, and 1,2-dimethoxyethane; lower alcohol solvents such as methanol, ethanol, and 2-propanol; aprotic polar solvents such as acetonitrile, dimethylformamide, N-methyl-2-pyrrolidinone, and dimethylsulfoxide; and mixture solvents thereof.

Examples of the dehydrating agent used herein include magnesium sulfate and sodium sulfate.

Examples of the acid used herein include organic acids such as methanesulfonic acid and p-toluenesulfonic acid.

Compound (29) is prepared by treating Compound (28) with a suitable acid in a suitable inert solvent. The reaction temperature generally ranges from −20° C. to the boiling point of the solvent used herein. The reaction time depends on the reaction condition such as the reaction temperature, the acid used herein, the starting materials, and the solvent used herein, and generally ranges from 10 minutes to 48 hours.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane, 1,4-dioxane, and 1,2-dimethoxyethane; lower alcohol solvents such as methanol, ethanol, and 2-propanol; aprotic polar solvents such as acetone, acetonitrile, dimethylformamide, N-methyl-2-pyrrolidinone, and dimethylsulfoxide; and mixture solvents thereof.

Examples of the acid used herein include inorganic acids such as hydrochloric acid and sulfuric acid and organic acids such as trifluoroacetic acid.

Compound (28) is prepared by reacting Compound (5) and Compound (27) in the presence of a suitable base in a suitable inert solvent. The reaction may be carried out in the presence of a suitable phase-transfer catalyst, as appropriate. The reaction temperature generally ranges from about −20° C. to the boiling point of the solvent used herein. The reaction time depends on the reaction condition such as the reaction temperature, the base used herein, the starting materials, and the solvent used herein, and generally ranges from 10 minutes to 48 hours.

Examples of the base used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metallic alkoxides such as sodium methoxide and potassium tert-butoxide.

Examples of the phase-transfer catalyst used herein include tetrabutylammonium hydrogen sulfate.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), and 1,4-dioxane; lower alcohol solvents such as methanol, ethanol, and 2-propanol; aprotic polar solvents such as acetonitrile, acetone, methylethylketone, dimethylformamide, N-methyl-2-pyrrolidinone, and dimethylsulfoxide; and mixture solvents thereof.

Compound (27) is prepared by reacting Compound (26) and a suitable alcohol in the presence of a suitable acid in a suitable inert solvent. The reaction may be carried out under azeotropic dehydration with Dean-Stark apparatus, as appropriate. The reaction temperature generally ranges from about −20° C. to the boiling point of the solvent used herein. The reaction time depends on the reaction condition such as the reaction temperature, the base used herein, the starting materials, and the solvent used herein, and generally ranges from 10 minutes to 48 hours.

Examples of the inert solvent used herein include halogenated hydrocarbon solvents such as chloroform and dichloromethane; aromatic hydrocarbon solvents such as benzene and toluene; ether solvents such as diethyl ether, tetrahydrofurane (THF), and 1,4-dioxane; lower alcohol solvents such as methanol, ethanol, and 2-propanol; aprotic polar solvents such as acetonitrile, acetone, methylethylketone, dimethylformamide, N-methyl-2-pyrrolidinone, and dimethylsulfoxide; and mixture solvents thereof.

Examples of the acid used herein include organic acids such as methanesulfonic acid and p-toluenesulfonic acid.

Examples of the alcohol used herein include lower alcohol solvents such as methanol, ethanol, and ethane-1,2-diol.

The present compound having a desired functional group at a desired position can be prepared by suitably combining the above preparation processes. The isolation and purification of each intermediate or product in the above preparation processes can be carried out by conventional methods in organic synthesis, for example, by suitably combining filtration, extraction, washing, drying, concentration, crystallization, various chromatography, etc. Or, some intermediates may be sometimes used in the next step without purification.

Some starting compounds or intermediates in the above preparation processes can exist in a salt form such as hydrochloride depending on reaction conditions, etc., but can be used as it is or in a free form thereof. When starting compounds or intermediates that are in a salt form need to be used or obtained as a free form thereof, they can be transformed to free forms thereof by dissolving or suspending them in an appropriate solvent and neutralizing the solution or suspension with a base such as aqueous sodium bicarbonate.

Some of the compound of Formula (1) or a pharmaceutically acceptable salt thereof can exist as isomers such as tautomer (for example, keto-enol form), regioisomer, geometrical isomer, and optical isomer. The present invention encompasses every possible isomer including the above, and a mixture thereof which has various mixture proportions.

And, optical isomers thereof can be resolved by a known method such as chromatography with an optically-active column and fractional crystallization at a suitable step in the above-mentioned preparation processes. And, an optically-active starting material can also be used for starting materials.

In order to obtain the compound of Formula (1) as a salt thereof, when the product is a salt of the compound of Formula (1), the product should be directly purified; or when the product is in a free form of the compound of Formula (1), the product should be dissolved or suspended in an appropriate solvent and then an acid or a base should be added thereto to form a salt thereof.

The present compound has both agonist activity for $5-HT_{1A}$ receptor and antagonist activity for $5-HT_{2A}$ receptor with different mechanism from existing medicaments for treating mental diseases, and can provide a new option in medication for various mental diseases. Specifically, the present compound is beneficial for the treatment of mental diseases. The present compound is also beneficial for the treatment of central nervous system diseases.

The mental disease or central nervous system disease which is expected to be treated effectively includes, for example, F00-F09: organic, including symptomatic, mental disorders, F10-F19: mental and behavioural disorders due to psychoactive substance use, F20-F29: schizophrenia, schizotypal disorders, and delusional disorders, F30-F39: mood [affective] disorders, F40-F48: neurotic disorders, stress-related disorders, and somatoform disorders, F51: nonorganic sleep disorders, F52: sexual dysfunction, not caused by organic disorder or disease, F84: pervasive developmental disorders, F90-F98: behavioural and emotional disorders with onset usually occurring in childhood and adolescence, G20-G26: extrapyramidal and movement disorders, G30-G32: other degenerative diseases of the nervous system, and G47: sleep disorders in International Classification of Diseases, 10th edition (ICD-10).

F00-F09: Organic, including symptomatic, mental disorders includes, for example, dementia in Alzheimer's disease, vascular dementia, dementia with Lewy bodies, dementia in Parkinson's disease, mental disorders due to other diseases such as brain damage, and other mental disorders due to brain dysfunction and to physical disease.

F10-F19: Mental and behavioural disorders due to psychoactive substance use include, for example, delirium tremens, psychotic disorder, and amnestic syndrome, due to various substance use.

F20-F29: Schizophrenia, schizotypal disorders, and delusional disorders include, for example, paranoid schizophrenia, simple schizophrenia, and delusional disorders.

F30-F39: Mood [affective] disorders include, for example, manic episode, bipolar affective disorder, and depressive episode.

F40-F48: Neurotic disorders, stress-related disorders, and somatoform disorders include, for example, phobic anxiety disorders, obsessive-compulsive disorder, and somatoform disorders.

F51: Nonorganic sleep disorders include, for example, nonorganic insomnia, sleepwalking, and nightmares.

F52: Sexual dysfunction, not caused by organic disorder or disease includes, for example, lack or loss of sexual desire and unspecified sexual dysfunction.

F84: Pervasive developmental disorders include, for example, autism and overactive disorder associated with mental retardation and stereotyped movements.

F90-F98: Hyperkinetic disorders behavioural and emotional disorders with onset usually occurring in childhood and adolescence include, for example, hyperkinetic disorders, conduct disorders, and mixed disorders of conduct and emotions.

G20-G26: Extrapyramidal and movement disorders include, for example, Parkinson's disease, secondary parkinsonism, dyskinesia, and spinocerebellar degeneration.

G30-G32: Other degenerative diseases of the nervous system include, for example, Alzheimer's disease, frontotemporal dementia, frontotemporal lobar degeneration, dementia with Lewy bodies, senile degeneration of brain, and progressive supranuclear palsy.

G47: Sleep disorders include, for example, disorders of initiating and maintaining sleep [insomnias], disorders of the sleep-wake schedule, and narcolepsy and cataplexy.

The present compound is also useful for treatment or prevention of relapse of various symptoms associated with these diseases such as psychopathic symptoms, disquiet, aggression, irritability and irascibility, sleep disorders, depressive symptoms, anxiety symptoms, and cognitive dysfunction.

The mental disease or central nervous system disease which is expected to be treated effectively preferably includes schizophrenia, positive symptoms of schizophrenia, negative symptoms of schizophrenia, bipolar disorders with psychotic features, depressive disorders with psychotic features, psychopathic symptoms associated with dementia, psychopathic symptoms associated with Alzheimer's disease, psychopathic symptoms associated with dementia with Lewy bodies, psychopathic symptoms associated with Parkinson's disease with dementia, psychopathic symptoms associated with Parkinson's disease, and irritation, agitation, or aggression associated with Alzheimer's disease. More preferably, it includes schizophrenia, psychopathic symptoms associated with dementia, psychopathic symptoms associated with Alzheimer's disease, psychopathic symptoms associated with dementia with Lewy bodies, and irritation, agitation, or aggression associated with Alzheimer's disease.

The present compound has a potent binding affinity to $5\text{-HT}_{1A}$ receptor and $5\text{-HT}_{2A}$ receptor (Test 1); i.e., agonist activity for $5\text{-HT}_{1A}$ receptor and antagonist activity for $5\text{-HT}_{2A}$ receptor. In a preferred embodiment, the binding affinity of the present compound to $5\text{-HT}_{1A}$ receptor and $5\text{-HT}_{2A}$ receptor is 100 or more times potent compared with that of $D_2$ receptor, thus the present compound can exert the pharmacological effect based on $5\text{-HT}_{1A}$ receptor agonism and $5\text{-HT}_{2A}$ receptor antagonism, without reaching the blood level causing side effects such as extrapyramidal symptom and hyperprolactinemia which are thought to be caused by $D_2$ receptor antagonistic action. That is, the concentration for expressing pharmacological effect is detached from that for expressing side effects.

In another preferred embodiment, the present compound is expected to have a very small effect for cardiovascular system because there is a big difference between the inhibitory concentration of hERG channel which is an express indicator of arrhythmia in long QT, and the express concentration of the expected pharmacological effect based on the $5\text{-HT}_{1A}$ receptor agonism and $5\text{-HT}_{2A}$ receptor antagonism (Test 5). That is, the concentration for expressing pharmacological effect is detached from that for expressing side effects.

The disappearance half-life (hereinafter, also referred to as "$T_{1/2}$") of a medicament is a factor for determining the frequency of administration to retain the effect. It is thought that plural administrations of a medicament having a short $T_{1/2}$ per day can cause forgetting to take a medication or unfinishing taking a medication, which can hinder a suitable medication. Furthermore, if the frequency of administration increases, it is concerned that the incidence rate of side effects can increase or the tolerability can decrease in association with high-dose administration. From the viewpoint mentioned above, if a medicament having a long $T_{1/2}$ is found out, the medicament is expected to be a long-acting medicament with little concern mentioned above, which can bring in liability relief of medicated patients.

In a preferred embodiment, the estimated human disappearance half-life (hereinafter, also referred to as "estimated human $T_{1/2}$") of the present compound is 8 hours or more (Test 4). That is, it is expected that the drug efficacy can be retained for a long period in human body, the medication adherence of medicated patients can be improved, and a high tolerability can be exhibited at the administration.

The present compound can be orally or parenterally administered. In the case of oral administration, the compound can be administered in conventionally-used dosage form. In the case of parenteral administration, the compound can be administered in topical administration form, injection form, transdermal form, nasal form, etc. The oral form or the rectal administration form include, for example, capsule, tablet, pill, powder, cachet, suppository, and liquid. The injection includes, for example, aseptic solution and suspension. The topical administration form includes, for example, cream, ointment, lotion, and transdermal formulation (e.g., normal patch and matrix).

The above-mentioned dosage forms can be prepared with a pharmaceutically acceptable excipient and additive in a conventional manner. The pharmaceutically acceptable excipient and additive include carrier, binder, flavor, buffer, thickener, colorant, stabilizing agent, emulsifier, dispersant, suspending agent, and preservative.

The pharmaceutically acceptable carrier includes, for example, magnesium carbonate, magnesium stearate, talc, sugar, lactose, pectin, dextrin, starch, gelatin, tragacanth, methylcellulose, sodium carboxymethylcellulose, low-melting-point wax, and cocoa butter. The capsule form can be prepared by filling a capsule with the present compound and a pharmaceutically acceptable carrier. The present compound can be put into a capsule with or without a pharmaceutically acceptable excipient. The cachet can also be prepared in a similar manner.

The injectable liquid form includes solution, suspension, and emulsion, for example, water solution, water-propylene glycol, etc. The liquid form may comprise water, and also it may be prepared in a solution of polyethylene glycol or/and propylene glycol. The liquid form suitable for oral administration may be prepared by adding the present compound to water and also adding colorant, flavor, stabilizing agent, sweetener, solubilizer, thickener, etc. thereto, as appropriate. Alternatively, the liquid form suitable for oral administration may be prepared by adding the present compound with a dispersant to water and rendering the liquid sticky. The thickener used herein includes, for example, pharmaceutically acceptable natural or synthetic gum, resin, methylcellulose, sodium carboxymethylcellulose, and a known suspending agent.

The dose of each compound can depend on patient's disease, age, body weight, gender, symptom, and the administration route, etc. In general, the present compound is administered to an adult (body weight: 50 kg) by 0.1 to 1000 mg/day, preferably 1 to 300 mg/day, once a day or in 2 to 3 doses. Or, it may be administered once in a few days to a few weeks.

In order to enhance the effect and/or reduce the side effects thereof, the present compound may be used in combination with another drug. Hereinafter, drugs with which the present compound may be used in combination are abbreviated as a "concomitant drug".

Examples of the concomitant drug used herein include antidepressant drugs, anxiolytic drugs, antischizophrenic agents, dopamine supplements, dopamine receptor agonist, antiparkinsonian drugs, antiepileptic drugs, analgesic drugs, hormone preparations, antimigraine agents, adrenaline β receptor antagonist, antidementia drugs, drugs for treating mood disorders, antiemetic drugs, sleep-inducing drugs, and anticonvulsants. The concomitant drug is preferably anxiolytic drugs such as selective serotonin reuptake inhibitor.

The administration interval of the present compound and its concomitant drug is not limited, i.e., the concomitant drug may be administered to a subject patient at the same time as the present compound or at a suitable interval. Or, the present compound and its concomitant drug can be formulated into a combination drug. The dose of the concomitant drug can be suitably determined based on the standard of the clinically-used dose thereof. The combination ratio of the present compound and its concomitant drug can be suitably determined based on its subject patient, administration route, disease, pathology, and combinations thereof. For example, when the subject patient is a human being, the concomitant drug may be used in 0.01 to 100 parts by weight per part of the present compound. For the purpose of reducing side effects, an antiemetic drug, a sleep-inducing drug, an anticonvulsant, etc. may be used in combination as a concomitant drug.

EXAMPLES

The present invention is explained in more detail in the following by referring to Reference examples, Examples, and Tests; however, the technical scope of the present invention is not limited thereto. The compound names used in Reference examples and Examples are not always based on IUPAC nomenclature system. Compounds were identified by proton nuclear magnetic resonance spectroscopy ($^{1}$H-NMR), LC-MS, and the like.

LC-MS was carried out with the following conditions. Retention time (R.T.) denotes the time when a peak of a mass spectrum appears in the LC-MS measurement.

Condition A

Analytical apparatus: Shimadzu LCMS-2020

Column: Phenomenex Kinetex 1.7 μm C18 (50 mm×2.10 mm)

Eluent: A: MeOH, B: 0.05% TFA/H$_2$O

Gradient condition:

0.0 min; A/B=30:70

0.0 to 1.90 min; A/B=99:1

1.91 to 3.00 min; A/B=30:70

Flow rate: 0.5 mL/min

Wavelength: 220 nm

Column temperature: 40° C.

Herein, the following abbreviations are used.

Me: methyl

DMF: N,N-dimethylformamide

THF: tetrahydrofuran tert-: tertiary

CDCl$_3$: deuterated chloroform

DMSO-d$_6$: deuterated dimethylsulfoxide

Proton nuclear magnetic resonance spectra were measured with FT-NMR spectrometer (300 MHz or 400 MHz, JEOL). The chemical shifts were shown in δ value (ppm). The signs used in NMR denote the following meanings; s is singlet, d is doublet, dd is double doublet, dt is double triplet, t is triplet, q is quartet, m is multiplet, br is broad, brs is broad singlet, and J is the coupling constant.

Example 1

7-{2-[4-(1,2-Benzoisoxazol-3-yl)piperazin-1-yl]ethyl}-6,7-dihydro-1,7-naphthyridin-8(5H)-one

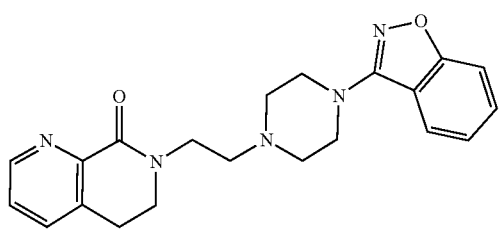 [SMILES: O=C1c2ncccc2CCN1CCN1CCN(c2noc3ccccc23)CC1]

To a solution of 6,7-dihydro-1,7-naphthyridin-8(5H)-one (240 mg) in toluene (5.0 mL) were added the compound of Reference example 1 (452 mg), potassium hydroxide (136 mg), and tetrabutylammonium bromide (172 mg) at room temperature. After stirring at reflux temperature for 1.5 hours, saturated aqueous ammonium chloride was added to the reaction mixture at room temperature, and the reaction mixture was extracted with ethyl acetate. The organic layer was dried over anhydrous sodium sulfate, filtered, and concentrated under reduced pressure. The residue was purified by silica gel column chromatography (chloroform/methanol) to obtain the titled compound (377 mg).

$^1$H-NMR (400 MHz, CDCl$_3$) δ: 2.71 (6H, m), 3.03 (2H, t, J=6.6 Hz), 3.55 (4H, t, J=6.6 Hz), 3.68 (2H, t, J=6.6 Hz), 3.78 (2H, t, J=6.3 Hz), 7.19 (1H, m), 7.31 (1H, dd, J=7.7, 4.8 Hz), 7.41-7.50 (2H, m), 7.52-7.56 (1H, m), 7.66 (1H, d, J=8.0 Hz), 8.67 (1H, dd, J=4.6, 1.7 Hz).

Example 2

2-{2-[4-(1,2-Benzoisothiazol-3-yl)piperazin-1-yl]ethyl}-6-methoxy-3,4-dihydro-2,7-naphthyridin-1(2H)-one

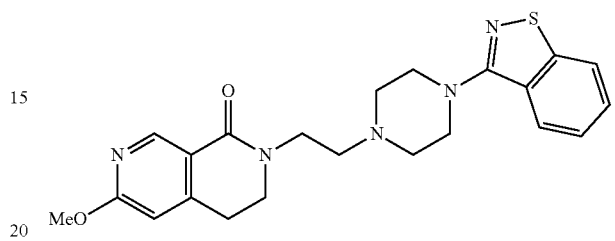

To a solution of the compound of Reference example 10 (99.0 mg) in toluene (3.7 mL) were added the compound of Reference example 2 (164 mg), potassium hydroxide (46.8 mg), and tetrabutylammonium bromide (59.1 mg) at room temperature. After stirring at reflux temperature for 15 hours, water was added to the reaction mixture at room temperature, and the reaction mixture was extracted with ethyl acetate. The organic layer was dried over anhydrous sodium sulfate, filtered, and concentrated under reduced pressure. The residue was purified by silica gel column chromatography (chloroform/methanol), and recrystallized with 2-propanol to yield the titled compound (160 mg).

$^1$H-NMR (400 MHz, CDCl$_3$) δ: 2.70 (2H, t, J=6.4 Hz), 2.75 (4H, t, J=4.8 Hz), 2.93 (2H, t, J=6.4 Hz), 3.51 (4H, t, J=4.8 Hz), 3.62 (2H, t, J=6.4 Hz), 3.71 (2H, t, J=6.4 Hz), 3.95 (3H, s), 6.49 (1H, s), 7.31-7.36 (1H, m), 7.42-7.47 (1H, m), 7.77-7.80 (1H, m), 7.86-7.89 (1H, m), 8.80 (1H, s).

Example 3

2-{2-[4-(1,2-Benzoisoxazol-3-yl)piperazin-1-yl]ethyl}-6-methyl-3,4-dihydro-2,7-naphthyridin-1(2H)-one

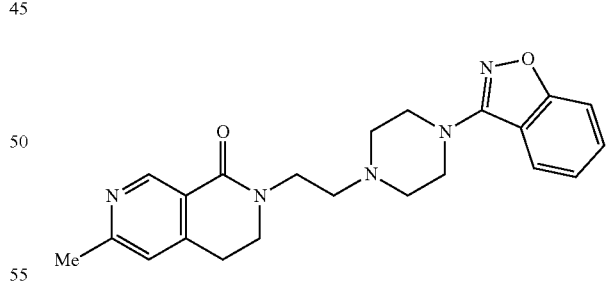

To a solution of the compound of Reference example 19 (684 mg) in toluene (8.4 mL) were added the compound of Reference example 1 (1.18 g), potassium hydroxide (355 mg), and tetrabutylammonium bromide (449 mg) at room temperature. After stirring for 2 hours at reflux temperature, brine was added to the reaction mixture at room temperature, and the reaction mixture was extracted with chloroform. The organic layer was dried over anhydrous sodium sulfate, filtered, and concentrated under reduced pressure. The residue was purified by silica gel column chromatography (chloroform/methanol) to obtain the titled compound (1.20 g).

¹H-NMR (400 MHz, CDCl₃) δ: 2.56 (3H, s), 2.65-2.85 (6H, m), 2.96 (2H, t, J=6.7 Hz), 3.60-3.66 (4H, m), 3.65 (2H, t, J=6.7 Hz), 3.70-3.85 (2H, m), 6.97 (1H, s), 7.21 (1H, dd, J=7.3, 7.3 Hz), 7.42-7.49 (2H, m), 7.65 (1H, d, J=7.9 Hz), 9.05 (1H, s).

Examples 4 to 21

According to the method of Example 3, the compounds of Examples 4 to 21 were prepared from the corresponding Reference example compounds.

| Example | Chemical structure | Instrumental analyses data |
|---|---|---|
| 4 | 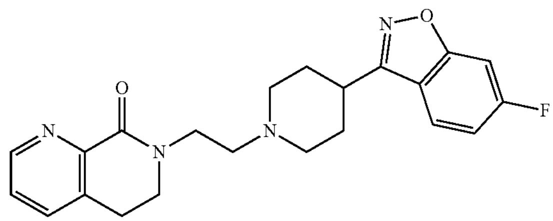 [SMILES: O=C1c2ncccc2CCN1CCN1CCC(c2noc3cc(F)ccc23)CC1] | ¹H-NMR (300 MHz, CDCl₃) δ: 1.93-2.14 (4H, m), 2.20-2.34 (2H, m), 2.72 (2H, t, J = 6.3 Hz), 3.00-3.19 (5H, m), 3.71 (2H, t, J = 6.5 Hz), 3.79 (2H, t, J = 6.3 Hz), 7.05 (1H, td, J = 8.9, 2.2 Hz), 7.22 (1H, d, J = 2.2 Hz), 7.34 (1H, dd, J = 7.7, 4.6 Hz), 7.57 (1H, d, J = 7.7 Hz), 7.65 (1H, dd, J = 8.7, 5.0 Hz), 8.71 (1H, d, J = 4.8 Hz). |
| 5 | 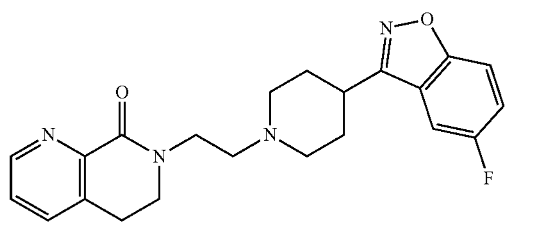 [SMILES: O=C1c2ncccc2CCN1CCN1CCC(c2noc3ccc(F)cc23)CC1] | ¹H-NMR (300 MHz, CDCl₃) δ: 1.95-2.13 (4H, m), 2.26 (2H, td, J = 11.7, 2.4 Hz), 2.72 (2H, t, J = 6.2 Hz), 2.95-3.19 (5H, m), 3.71 (2H, t, J = 6.4 Hz), 3.79 (2H, t, J = 6.2 Hz), 7.29-7.39 (4H, m), 7.46-7.62 (2H, m), 8.71 (1H, dd, J = 4.2, 1.2 Hz). |
| 6 | 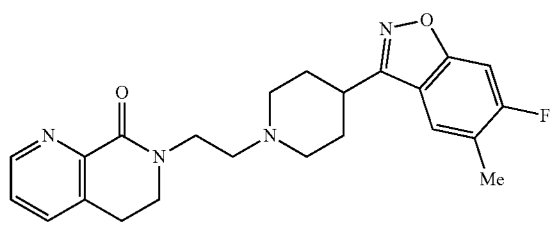 [SMILES: Cc1cc2c(C3CCN(CCN4CCc5cccnc5C4=O)CC3)noc2cc1F] | ¹H-NMR (300 MHz, CDCl₃) δ: 1.91-2.14 (4H, m), 2.25 (2H, td, J = 11.4, 3.0 Hz), 2.36 (3H, d, J = 2.4 Hz), 2.72 (2H, t, J = 6.5 Hz), 2.96-3.19 (5H, m), 3.71 (2H, t, J = 6.3 Hz), 3.79 (2H, t, J = 6.3 Hz), 7.19 (1H, d, J = 9.2 Hz), 7.33 (1H, dd, J = 7.6, 4.7 Hz), 7.47 (1H, d, J = 7.0 Hz), 7.57 (1H, d, J = 7.7 Hz), 8.70 (1H, dd, J = 4.8, 1.5 Hz). |
| 7 | 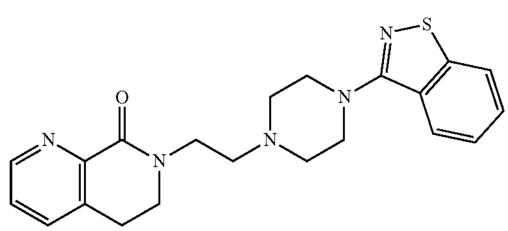 [SMILES: O=C1c2ncccc2CCN1CCN1CCN(c2nsc3ccccc23)CC1] | ¹H-NMR (400 MHz, CDCl₃) δ: 2.70-2.79 (6H, m), 3.03 (2H, t, J = 6.6 Hz), 3.50 (4H, t, J = 4.9 Hz), 3.69 (2H, t, J = 6.6 Hz), 3.78 (2H, t, J = 6.3 Hz), 7.29-7.36 (2H, m), 7.41-7.47 (1H, m), 7.51-7.55 (1H, m), 7.78 (1H, d, J = 8.0 Hz), 7.88 (1H, d, J = 8.0 Hz), 8.67 (1H, dd, J = 4.6, 1.7 Hz). |
| 8 | 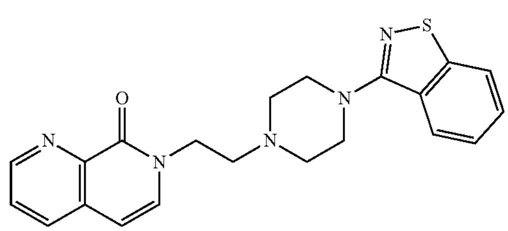 [SMILES: O=c1c2ncccc2ccn1CCN1CCN(c2nsc3ccccc23)CC1] | ¹H-NMR (400 MHz, CDCl₃) 2.74 (4H, t, J = 4.9 Hz), 2.85 (2H, t, J = 6.1 Hz), 3.50 (4H, t, J = 4.8 Hz), 4.20 (2H, t, J = 6.1 Hz), 6.40 (1H, d, J = 7.3 Hz), 7.25 (1H, d, J = 7.3 Hz), 7.30-7.35 (1H, m), 7.44-7.49 (1H, m), 7.54 (1H, dd, J = 8.2, 4.3 Hz), 7.80 (1H, d, J = 8.0 Hz), 7.86-7.90 (2H, m), 8.88 (1H, dd, J = 4.4, 1.5 Hz). |

-continued

| Example | Chemical structure | Instrumental analyses data |
|---|---|---|
| 9 | 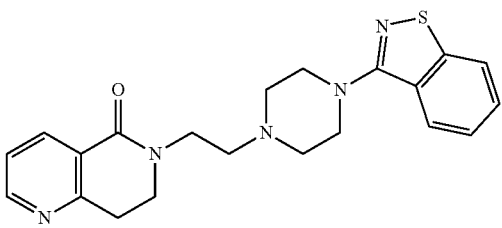 [SMILES: O=C1c2cccnc2CCN1CCN1CCN(c2nsc3ccccc23)CC1] | $^1$H-NMR (400 MHz, CDCl$_3$) δ: 2.71 (2H, t, J = 6.5 Hz), 2.75 (4H, t, J = 4.8 Hz), 3.19 (2H, t, J = 6.7 Hz), 3.52 (4H, t, J = 4.9 Hz), 3.70-3.78 (4H, m), 7.28 (1H, dd, J = 7.8, 4.9 Hz), 7.33 (1H, dd, J = 7.3, 7.3 Hz), 7.44 (1H, dd, J = 7.2, 7.2 Hz), 7.79 (1H, d, J = 8.0 Hz), 7.88 (1H, d, J = 8.3 Hz), 8.31 (1H, dd, J = 7.8, 1.7 Hz), 8.58 (1H, dd, J = 4.9, 1.7 Hz). |
| 10 | 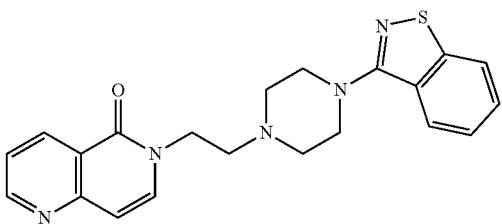 [SMILES: O=c1c2cccnc2ccn1CCN1CCN(c2nsc3ccccc23)CC1] | $^1$H-NMR (400 MHz, CDCl$_3$) δ: 2.75 (4H, t, J = 4.9 Hz), 2.81 (2H, t, J = 6.3 Hz), 3.52 (4H, t, J = 4.9 Hz), 4.15 (2H, t, J = 6.3 Hz), 6.74 (1H, d, J = 7.6 Hz), 7.30-7.35 (1H, m), 7.35-7.40 (2H, m), 7.41-7.47 (1H, m), 7.78 (1H, d, J = 8.0 Hz), 7.86 (1H, d, J = 8.3 Hz), 8.66 (1H, dd, J = 8.0, 1.7 Hz), 8.88 (1H, dd, J = 4.6, 1.7 Hz). |
| 11 | 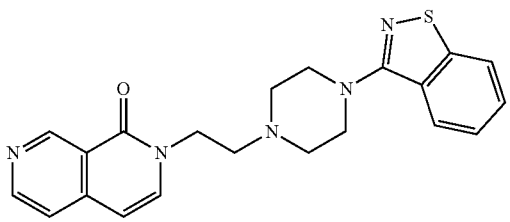 | $^1$H-NMR (400 MHz, CDCl$_3$) δ: 2.75 (4H, t, J = 4.9 Hz), 2.82 (2H, t, J = 6.2 Hz), 3.51 (4H, t, J = 4.9 Hz), 4.14 (2H, t, J = 6.2 Hz), 6.41 (1H, d, J = 7.3 Hz), 7.30-7.36 (3H, m), 7.42-7.47 (1H, m), 7.79 (1H, d, J = 8.3 Hz), 7.87 (1H, d, J = 8.0 Hz), 8.69 (1H, d, J = 5.4 Hz), 9.60 (1H, d, J = 0.7 Hz). |
| 12 | 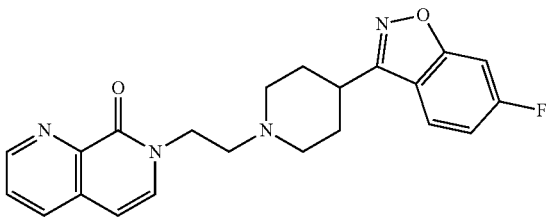 [SMILES: O=c1c2ncccc2ccn1CCN1CCC(c2noc3cc(F)ccc23)CC1] | $^1$H-NMR (400 MHz, CDCl$_3$) δ: 1.92-2.10 (4H, m), 2.29 (2H, td, J = 11.5, 2.9 Hz), 2.80 (2H, t, J = 6.2 Hz), 2.99-3.10 (3H, m), 4.19 (2H, t, J = 6.2 Hz), 6.41 (1H, d, J = 7.3 Hz), 7.03 (1H, ddd, J = 8.9, 8.9, 2.2 Hz), 7.20-7.24 (2H, m), 7.52 (1H, dd, J = 8.0, 4.4 Hz), 7.62 (1H, dd, J = 8.5, 5.1 Hz), 7.86 (1H, dd, J = 8.0, 1.7 Hz), 8.86 (1H, dd, J = 4.4, 1.5 Hz). |
| 13 | 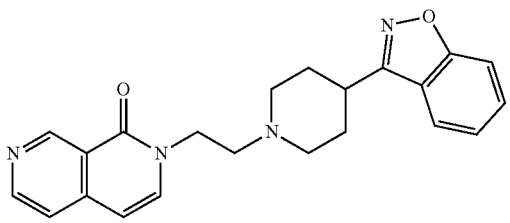 [SMILES: O=c1c2cnccc2ccn1CCN1CCC(c2noc3ccccc23)CC1] | $^1$H-NMR (300 MHz, CDCl$_3$) δ: 1.94-2.20 (4H, m), 2.28 (2H, td, J = 11.3, 3.1 Hz), 2.70 (2H, t, J = 6.5 Hz), 2.95-3.20 (5H, m), 3.64-3.78 (4H, m), 7.14 (1H, d, J = 5.0 Hz), 7.27-7.32 (1H, m), 7.49-7.63 (2H, m), 7.70 (1H, d, J = 7.9 Hz), 8.62 (1H, d, J = 5.0 Hz), 9.21 (1H, s). |

| Example | Chemical structure | Instrumental analyses data |
|---|---|---|
| 14 | 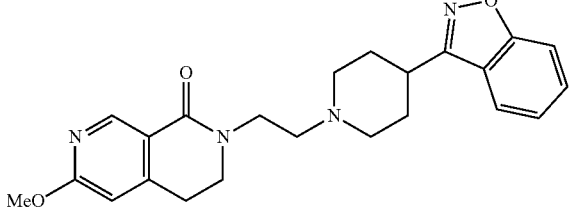 | ¹H-NMR (400 MHz, CDCl₃) δ: 1.86-2.10 (4H, m), 2.18-2.24 (2H, m), 2.62 (2H, t, J = 6.4 Hz), 2.88 (2H, t, J = 6.4 Hz), 2.99-3.11 (4H, m), 3.57 (2H, t, J = 6.4 Hz), 3.65 (2H, t, J = 6.4 Hz), 3.91 (3H, s), 6.46 (1H, s), 7.19-7.24 (1H, m), 7.44-7.50 (2H, m), 7.64 (1H, d, J = 7.8 Hz), 8.75 (1H, s). |
| 15 | 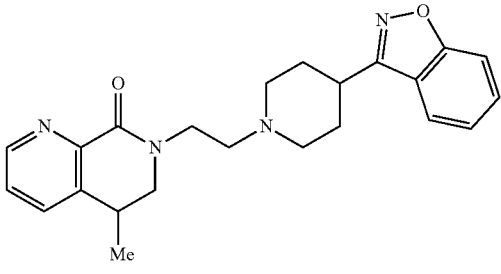 [SMILES: CC1CN(CCN2CCC(c3noc4ccccc34)CC2)C(=O)c2ncccc21] | ¹H-NMR (400 MHz, CDCl₃) δ: 1.32 (3H, d, J = 7.1 Hz), 1.90-2.07 (4H, m), 2.16-2.28 (2H, m), 2.65 (2H, t, J = 6.4 Hz), 2.97-3.16 (4H, m), 3.40 (1H, d, J = 12.4, 6.4 Hz), 3.60-3.82 (3H, m), 7.18-7.23 (1H, m), 7.29 (1H, dd, J = 8.0, 4.8 Hz), 7.42-7.54 (3H, m), 7.64 (1H, d, J = 8.0 Hz), 8.63 (1H, dd, J = 4.6, 0.9 Hz). |
| 16 | 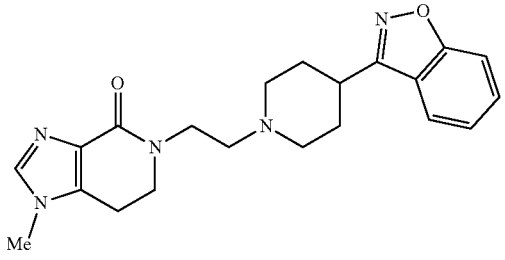 [SMILES: Cn1cnc2c1CCN(CCN1CCC(c3noc4ccccc34)CC1)C2=O] | ¹H-NMR (400 MHz, CDCl₃) δ: 1.97-2.16 (4H, m), 2.17-2.32 (2H, m), 2.65 (2H, t, J = 6.4 Hz), 2.87 (2H, t, J = 7.1 Hz), 3.00-3.23 (3H, m), 3.61 (3H, s), 3.67 (2H, t, J = 6.2 Hz), 3.77 (2H, t, J = 6.9 Hz), 7.25-7.34 (1H, m), 7.43 (1H, s), 7.49-7.61 (2H, m), 7.72 (1H, d, J = 8.1 Hz). |
| 17 | 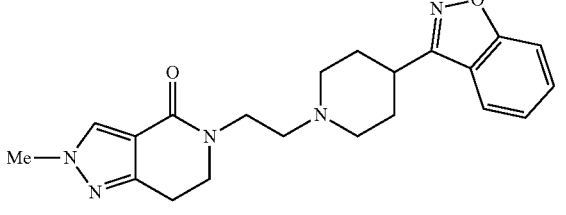 | ¹H-NMR (400 MHz, CDCl₃) δ: 2.04-2.15 (4H, m), 2.22-2.36 (2H, m), 2.60-2.72 (2H, m), 2.95 (2H, t, J = 6.7 Hz), 3.06-3.20 (3H, m), 3.64-3.74 (4H, m), 3.90 (3H, s), 7.27-7.32 (1H, m), 7.51-7.58 (2H, m), 7.72-7.77 (2H, m). |
| 18 | 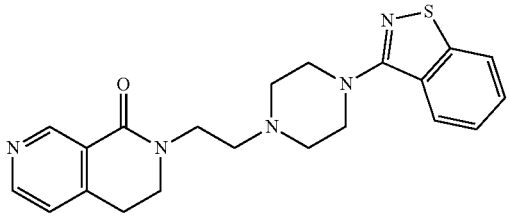 [SMILES: O=C1c2cnccc2CCN1CCN1CCN(c2nsc3ccccc23)CC1] | ¹H-NMR (400 MHz, CDCl₃) δ: 2.74 (2H, t, J = 6.4 Hz), 2.77 (4H, t, J = 4.8 Hz), 3.02 (2H, t, J = 6.6 Hz), 3.53 (4H, t, J = 4.8 Hz), 3.70 (2H, t, J = 6.6 Hz), 3.75 (2H, t, J = 6.4 Hz), 7.13 (1H, d, J = 5.0 Hz), 7.33-7.38 (1H, m), 7.44-7.49 (1H, m), 7.81 (1H, d, J = 8.3 Hz), 7.90 (1H, d, J = 8.3 Hz), 8.61 (1H, d, J = 5.0 Hz), 9.20 (1H, s). |

| Example | Chemical structure | Instrumental analyses data |
|---|---|---|
| 19 | 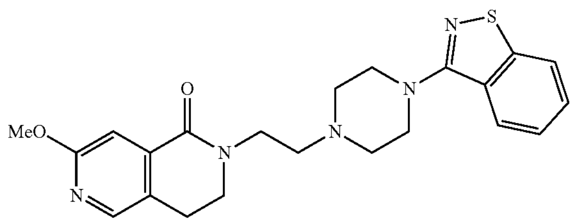 [SMILES: COc1cc2c(cn1)CCN(CCN1CCN(c3nsc4ccccc34)CC1)C2=O] | $^1$H-NMR (400 MHz, CDCl$_3$) δ: 2.69-2.81 (6H, m), 2.94 (2H, t, J = 6.6 Hz), 3.50-3.57 (4H, m), 3.66 (2H, t, J = 6.6 Hz), 3.75 (2H, t, J = 6.4 Hz), 3.94 (3H, s), 7.33-7.39 (1H, m), 7.44-7.49 (1H, m), 7.81 (1H, d, J = 8.3 Hz), 7.90 (1H, d, J = 8.3 Hz), 8.07 (1H, s). |
| 20 | 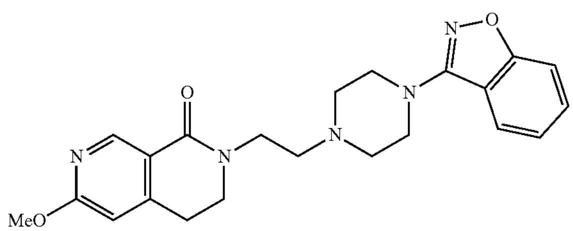 | $^1$H-NMR (400 MHz, CDCl$_3$) δ: 2.67 (2H, t, J = 6.6 Hz), 2.72 (4H, t, J = 5.0 Hz), 2.92 (2H, t, J = 6.6 Hz), 3.53 (4H, t, J = 5.0 Hz), 3.60 (2H, t, J = 6.4 Hz), 3.70 (2H, t, J = 6.4 Hz), 3.95 (3H, s), 6.50 (1H, s), 7.17-7.22 (1H, m), 7.41-7.49 (2H, m), 7.66 (1H, d, J = 8.3 Hz), 8.79 (1H, s). |
| 21 | 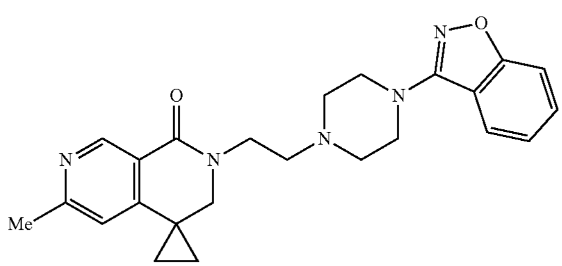 [SMILES: Cc1cc2c(cn1)C(=O)N(CCN1CCN(c3noc4ccccc34)CC1)CC21CC1] | $^1$H-NMR (400 MHz, CDCl$_3$) δ: 1.07 (2H, t, J = 6.0 Hz), 1.13 (2H, t, J = 6.0 Hz), 2.54 (3H, s), 2.67-2.73 (6H, m), 3.45 (2H, s), 3.54 (4H, t, J = 4.8 Hz), 3.70 (2H, t, J = 6.2 Hz), 6.57 (1H, s), 7.19-7.23 (1H, m), 7.43-7.49 (2H, m), 7.67 (1H, d, J = 7.8 Hz), 9.09 (1H, s). |

Example 22

7-{2-[4-(1,2-Benzoisoxazol-3-yl)piperidin-1-yl]ethyl}-6,7-dihydro-1,7-naphthyridin-8(5H)-one

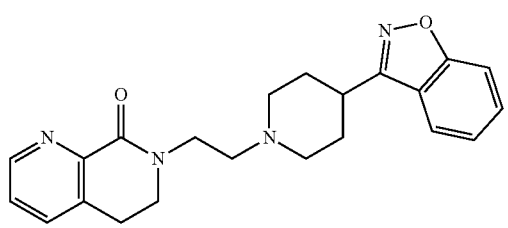 [SMILES: O=C1c2ncccc2CCN1CCN1CCC(c2noc3ccccc23)CC1]

To a solution of 3-(piperidin-4-yl)benzo[d]isoxazole (1.44 g) in dichloromethane (20 mL) were added the compound of Reference example 22 (1.58 g) and sodium triacetoxyborohydride (1.96 g), and the reaction mixture was stirred at room temperature for 2 hours. To the reaction mixture was added saturated aqueous sodium bicarbonate, and the reaction mixture was extracted with chloroform, dried over anhydrous sodium sulfate, filtered, and concentrated. The concentrated residue was purified by silica gel column chromatography (chloroform/methanol) to obtain the titled compound (2.30 g).

$^1$H-NMR (300 MHz, CDCl$_3$) δ: 1.96-2.16 (4H, m), 2.27 (2H, td, J=11.4, 2.9 Hz), 2.72 (2H, t, J=6.3 Hz), 3.00-3.17 (5H, m), 3.72 (2H, t, J=6.6 Hz), 3.79 (2H, t, J=6.3 Hz), 7.28-7.37 (2H, m), 7.49-7.60 (3H, m), 7.69-7.74 (1H, m), 8.70 (1H, dd, J=4.7, 1.6 Hz).

Examples 23 to 31

According to the method of Example 22, the compounds of Examples 23 to 31 were prepared from the corresponding Reference example compounds.

| Example | Chemical structure | Instrumental analyses data |
| --- | --- | --- |
| 23 | 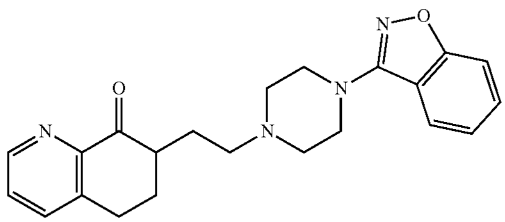 [SMILES: O=C1c2ncccc2CCC1CCN1CCN(c2noc3ccccc23)CC1] | ¹H-NMR (400 MHz, CDCl₃) δ: 1.76 (1H, td, J = 13.8, 6.9 Hz), 1.88-1.98 (1H, m), 2.16-2.27 (2H, m), 2.51 (2H, t, J = 7.3 Hz), 2.59-2.73 (5H, m), 2.93-3.06 (2H, m), 3.41-3.54 (4H, m), 7.14 (1H, ddd, J = 7.3, 1.4 Hz), 7.30 (1H, dd, J = 7.8, 4.6 Hz), 7.35-7.43 (2H, m), 7.57 (1H, d, J = 6.9 Hz), 7.62 (1H, d, J = 7.8 Hz), 8.62 (1H, d, J = 4.0 Hz). |
| 24 | 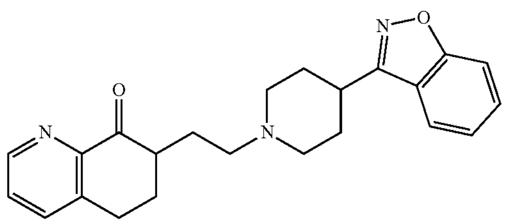 | ¹H-NMR (300 MHz, CDCl₃) δ: 1.16-1.38 (2H, m), 1.90-2.70 (8H, m), 2.72-3.59 (8H, m), 7.21-7.36 (2H, m), 7.39 (1H, dd, J = 7.6, 4.7 Hz), 7.50-7.60 (2H, m), 7.65 (1H, d, J = 7.7 Hz), 8.70 (1H, d, J = 4.2 Hz). |
| 25 | 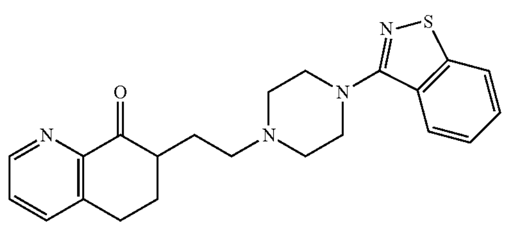 [SMILES: O=C1c2ncccc2CCC1CCN1CCN(c2nsc3ccccc23)CC1] | ¹H-NMR (400 MHz, CDCl₃) δ: 1.70-1.82 (2H, m), 1.89-1.99 (1H, m), 2.21-2.30 (2H, m), 2.55-2.76 (7H, m), 2.94-3.09 (2H, m), 3.42-3.56 (4H, m) 7.30 (2H, ddd, J =11.6, 4.0, 4.0 Hz), 7.39 (1H, dd, J = 4.0, 4.0 Hz), 7.58 (1H, d, J = 6.9 Hz), 7.74 (1H, d, J = 8.3 Hz), 7.83 (1H, d, J = 8.3 Hz), 8.61-8.65 (1H, m). |
| 26 | 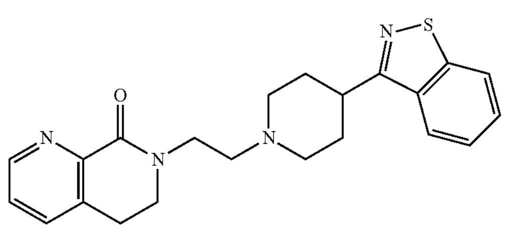 [SMILES: O=C1c2ncccc2CCN1CCN1CCC(c2nsc3ccccc23)CC1] | ¹H-NMR (400 MHz, CDCl₃) δ: 1.97-2.10 (4H, m), 2.19-2.31 (2H, m), 2.71 (2H, t, J = 6.2 Hz), 3.03 (2H, t, J =6.6 Hz), 3.07-3.14 (2H, m), 3.17-3.28 (1H, m), 3.72 (2H, t, J = 6.7 Hz), 3.75 (2H, t, J = 6.3 Hz), 7.30 (1H, dd, J = 7.7, 4.8 Hz), 7.37-7.42 (1H, m), 7.46-7.51 (1H, m), 7.51-7.56 (1H, m), 7.90 (1H, d, J =8.0 Hz), 7.96 (1H, d, J = 8.0 Hz), 8.66 (1H, dd, J = 4.6, 1.5 Hz). |
| 27 | 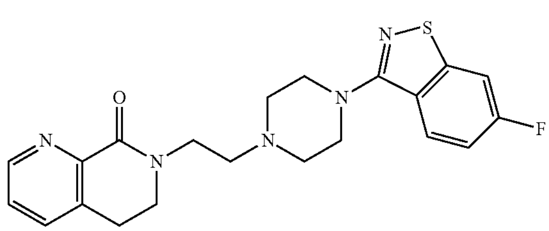 [SMILES: O=C1c2ncccc2CCN1CCN1CCN(c2nsc3cc(F)ccc23)CC1] | LC-MS: R.T. = 1.32 min ObsMS = 412 [M + 1] |
| 28 | 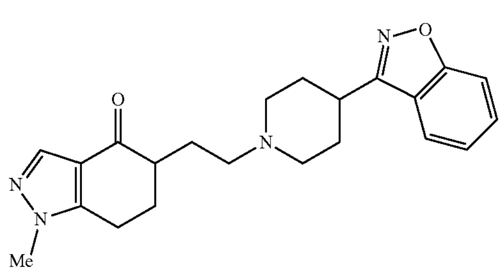 [SMILES: Cn1ncc2c1CCC(CCN1CCC(c3noc4ccccc34)CC1)C2=O] | ¹H-NMR (400 MHz, CDCl₃) δ: 1.63-1.70 (1H, m), 1.94-2.27 (8H, m), 2.28-2.36 (1H, m), 2.44-2.58 (3H, m), 2.76-2.94 (2H, m), 3.05-3.16 (3H, m), 3.82 (3H, s), 7.27-7.31 (1H, m), 7.50-7.58 (2H, m), 7.75 (1H, d, J = 7.8 Hz), 7.86 (1H, s). |

| Example | Chemical structure | Instrumental analyses data |
|---|---|---|
| 29 | 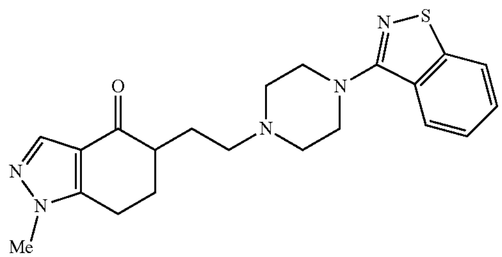 [SMILES: Cn1ncc2c1CCC(CCN1CCN(c3nsc4ccccc34)CC1)C2=O] | ¹H-NMR (400 MHz, CDCl₃) δ: 1.61-1.69 (1H, m), 1.95-2.06 (1H, m), 2.17-2.28 (1H, m), 2.28-2.37 (1H, m), 2.46-2.55 (2H, m), 2.57 (2H, t, J = 7.3 Hz), 2.71 (4H, t, J = 4.4 Hz), 2.77-2.95 (2H, m), 3.55 (4H, t, 3 = 4.8 Hz), 3.82 (3H, s), 7.33-7.38 (1H, m), 7.44-7.49 (1H, m), 7.81 (1H, d, J = 8.3 Hz), 7.86 (1H, s), 7.91 (1H, d, J = 8.3 Hz). |
| 30 | 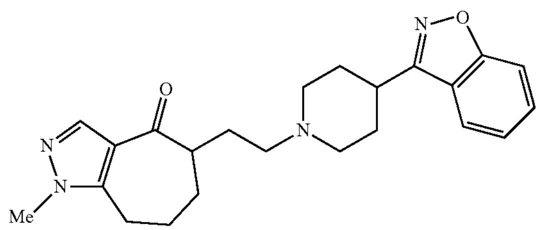 [SMILES: Cn1ncc2c1CCCC(CCN1CCC(c3noc4ccccc34)CC1)C2=O] | ¹H-NMR (400 MHz, CDCl₃) δ: 1.67-1.77 (2H, m), 1.97-2.22 (10H, in), 2.41-2.53 (2H, m), 2.65-2.73 (1H, In), 2.85-2.92 (2H, m), 3.05-3.13 (3H, m), 3.81 (3H, s), 7.27-7.31 (1H, 7.50-7.58 (2H, in), 7.75 (1H, d, J = 8.3 Hz), 7.89 (1H, s). |
| 31 | 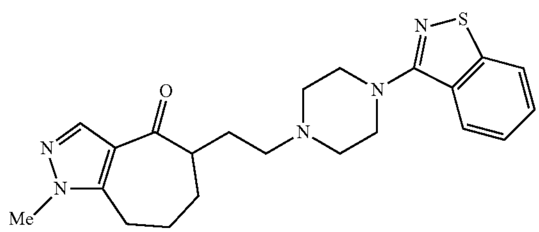 [SMILES: Cn1ncc2c1CCCC(CCN1CCN(c3nsc4ccccc34)CC1)C2=O] | ¹H-NMR (400 MHz, CDCl₃) δ: 1.67-1.78 (2H, in), 1.97-2.11 (3H, m), 2.11-2.22 (1H, m), 2.44-2.57 (2H, in), 2.65-2.75 (5H, in), 2.85-2.92 (2H, m), 3.54 (4H, t, J = 5.0 Hz), 3.80 (3H, s), 7.33-7.38 (1H, in), 7.44-7.49 (1H, m), 7.81 (1H, d, J = 7.8 Hz), 7.89-7.92 (2H, m). |

Example 32

5-{2-[4-(1,2-Benzoisoxazol-3-yl)piperazin-1-yl]ethyl}-3-methyl-6,7-dihydro[1,2]oxazolo[4,5-c]pyridin-4(5H)-one

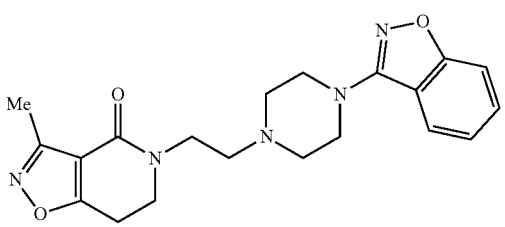 [SMILES: Cc1noc2c1C(=O)N(CCN1CCN(c3noc4ccccc34)CC1)CC2]

A mixture of the compound of Reference example 1 (40.0 mg), 3-methyl-6,7-dihydro[1,2]oxazolo[4,5-c]pyridin-4(5H)-one (22.9 mg), cesium carbonate (98.0 mg), potassium iodide (12.0 mg), and acetonitrile (2.0 mL) was stirred at 150° C. for 2 hours under microwave irradiation. The reaction mixture was filtered, and the filtrate was concentrated under reduced pressure. The residue was purified by amino silica gel column chromatography (hexane/ethyl acetate), and further purified by preparative thin-layer chromatography (chloroform/methanol) to obtain the titled compound (10.0 mg).

¹H-NMR (400 MHz, CDCl₃) δ: 2.50 (3H, s), 2.66 (2H, t, J=6.6 Hz), 2.73 (4H, t, J=5.0 Hz), 3.09 (2H, t, J=7.1 Hz), 3.56 (4H, t, J=4.8 Hz), 3.66 (2H, t, J=6.6 Hz), 3.78 (2H, t, J=7.1 Hz), 7.20-7.25 (1H, m), 7.43-7.51 (2H, m), 7.68 (1H, d, J=7.8 Hz).

Examples 33 to 34

According to the method of Example 32, the compounds of Examples 33 to 34 were prepared from the corresponding Reference example compounds.

| Example | Chemical structure | Instrumental analyses data |
|---|---|---|
| 33 | 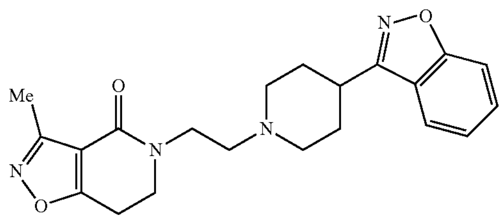 [SMILES: Cc1noc2c1C(=O)N(CCN1CCC(c3noc4ccccc34)CC1)CC2] | ¹H-NMR (400 MHz, CDCl₃) δ: 2.02-2.16 (4H, m), 2.23-2.34 (2H, m), 2.50 (3H, s), 2.65 (2H, t, J = 6.6 Hz), 3.05-3.17 (5H, m), 3.65 (2H, t, J = 6.4 Hz), 3.79 (2H, t, J = 7.1 Hz), 7.27-7.32 (1H, m), 7.51-7.59 (2H, m), 7.71 (1H, d, J = 8.3 Hz). |
| 34 | 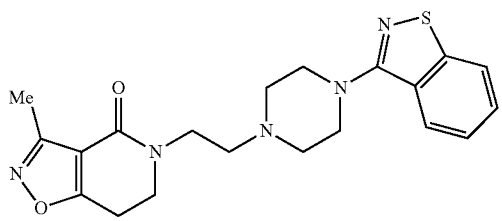 [SMILES: Cc1noc2c1C(=O)N(CCN1CCN(c3nsc4ccccc34)CC1)CC2] | ¹H-NMR (400 MHz, CDCl₃) δ: 2.50 (3H, s), 2.68 (2H, t, J = 6.4 Hz), 2.76 (4H, t, J = 4.8 Hz), 3.08 (2H, t, J = 7.1 Hz), 3.54 (4H, t, J = 4.8 Hz), 3.66 (2H, t, J = 6.4 Hz), 3.79 (2H, t, J = 7.1 Hz), 7.36 (1H, dd, J = 8.3, 8.3 Hz), 7.47 (1H, dd, J = 8.3, 8.3 Hz), 7.82 (1H, d, J = 8.3 Hz), 7.90 (1H, d, J = 8.3 Hz). |

Example 35

5-{2-[4-(1,2-Benzoisoxazol-3-yl)piperidin-1-yl]ethyl}-2-methyl-6,7-dihydro[1,3]oxazolo[5,4-c]pyridin-4(5H)-one

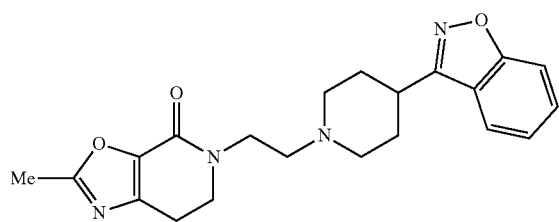 [SMILES: Cc1nc2c(o1)C(=O)N(CCN1CCC(c3noc4ccccc34)CC1)CC2]

To a suspension of 55% sodium hydride (34.4 mg) in N,N-dimethylformamide (1.0 mL) was added the compound of Reference example 26 (100 mg). After stirring for 30 minutes at room temperature, the compound of Reference example 3 (209 mg) and potassium iodide (54.6 mg) were added thereto, and the reaction mixture was stirred at room temperature for 18 hours. To the reaction mixture was added water, and the reaction mixture was extracted with chloroform, dried over anhydrous magnesium sulfate, filtered, and concentrated. The concentrated residue was purified by silica gel column chromatography (chloroform/methanol), and further purified by amino silica gel column chromatography (hexane/ethyl acetate) to obtain the titled compound (160 mg).

¹H-NMR (400 MHz, CDCl₃) δ: 1.97-2.11 (4H, m), 2.19-2.28 (2H, m), 2.52 (3H, s), 2.61 (2H, t, J=6.4 Hz), 2.88 (2H, t, J=7.1 Hz), 3.03-3.13 (3H, m), 3.62 (2H, t, J=6.4 Hz), 3.72 (2H, t, J=7.1 Hz), 7.24-7.29 (1H, m), 7.48-7.56 (2H, m), 7.70 (1H, d, J=7.8 Hz).

Example 36

5-{2-[4-(1,2-Benzoisothiazol-3-yl)piperazin-1-yl]ethyl}-2-methyl-2,5,6,7-tetrahydro-4H-pyrazolo[4,3-c]pyridin-4-one

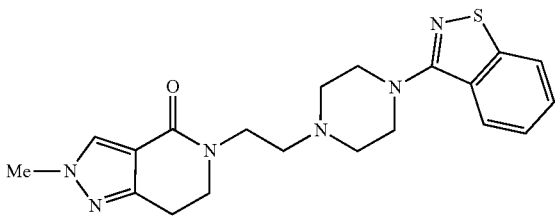 [SMILES: Cn1cc2c(n1)CCN(CCN1CCN(c3nsc4ccccc34)CC1)C2=O]

To a suspension of 55% sodium hydride (61.9 mg) in N,N-dimethylformamide (8.0 mL) was added the compound of Reference example 13 (156 mg). After the mixture was stirred at room temperature for 30 minutes, the compound of Reference example 2 (349 mg) and potassium iodide (86.0 mg) were added thereto, and the mixture was stirred at 50° C. for 16 hours. Water was added to the reaction mixture, and the reaction mixture was extracted with chloroform, dried over anhydrous sodium sulfate, filtered, and concentrated. The concentrated residue was purified by silica gel column chromatography (chloroform/methanol) to obtain the titled compound (205 mg).

¹H-NMR (400 MHz, CDCl₃) δ: 2.77 (2H, t, J=6.6 Hz), 2.85-2.87 (4H, br m), 2.95 (2H, t, J=6.4 Hz), 3.59-3.60 (4H, m), 3.66-3.73 (4H, m), 3.89 (3H, s), 7.36 (1H, ddd, J=8.3, 8.3, 0.8 Hz), 7.47 (1H, ddd, J=8.3, 8.3, 0.8 Hz), 7.75 (1H, s), 7.81 (1H, d, J=8.3 Hz), 7.89 (1H, d, J=8.3 Hz).

Example 37

5-{2-[4-(1,2-Benzoisoxazol-3-yl)piperidin-1-yl]ethyl}-2,3-dimethyl-2,5,6,7-tetrahydro-4H-pyrazolo[4,3-c]pyridin-4-one

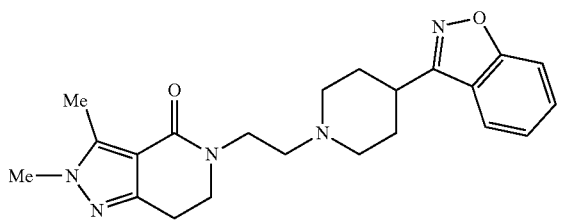 [SMILES: Cc1c2c(nn1C)CCN(CCN1CCC(c3noc4ccccc34)CC1)C2=O]

To a suspension of 55% sodium hydride (23.2 mg) in N,N-dimethylformamide (1.6 mL) was added the compound of Reference example 38 (80.0 mg) under ice temperature. After stirring at room temperature for 30 minutes, the compound of Reference example 3 (141 mg) and potassium iodide (40.2 mg) were added thereto, and the reaction mixture was stirred at 50° C. for 15 hours. Water was added to the reaction mixture, and the mixture was extracted with chloroform, dried over anhydrous sodium sulfate, filtered, and concentrated. The concentrated residue was purified by silica gel column chromatography (chloroform/methanol), and further purified by amino silica gel column chromatography (ethyl acetate/methanol) to obtain the titled compound (87.0 mg).

$^1$H-NMR (400 MHz, CDCl$_3$) δ: 2.04-2.10 (4H, m), 2.22-2.29 (2H, m), 2.53 (3H, s), 2.64 (2H, t, J=6.9 Hz), 2.89 (2H, t, J=6.6 Hz), 3.04-3.16 (3H, m), 3.61-3.67 (4H, m), 3.75 (3H, s), 7.26-7.29 (1H, m), 7.50-7.57 (2H, m), 7.73 (1H, d, J=7.8 Hz).

Examples 38 to 87

According to the method of Example 37, the compounds of Examples 38 to 87 were prepared from the corresponding Reference example compounds.

| Example | Chemical structure | Instrumental analyses data |
| --- | --- | --- |
| 38 | 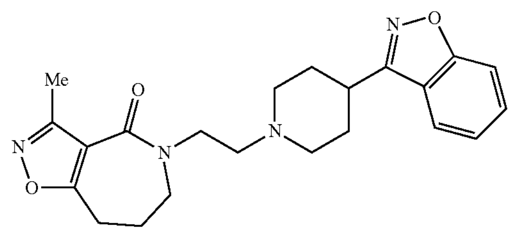 [SMILES: Cc1noc2c1C(=O)N(CCN1CCC(c3noc4ccccc34)CC1)CCC2] | $^1$H-NMR (400 MHz, CDCl$_3$) δ: 2.00-2.31 (8H, m), 2.49 (3H, s), 2.63 (2H, t, J = 6.4 Hz), 3.05 (2H, t, J = 7.1 Hz), 3.07-3.15 (3H, m), 3.52 (2H, t, J = 4.6 Hz), 3.69 (2H, t, J = 6.4 Hz), 7.27-7.32 (1H, m), 7.51-7.59 (2H, m), 7.71 (1H, d, J = 7.8 Hz). |
| 39 | 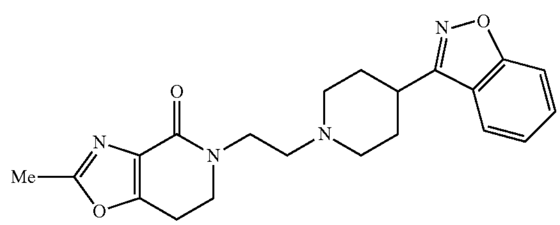 [SMILES: Cc1nc2c(o1)CCN(CCN1CCC(c3noc4ccccc34)CC1)C2=O] | $^1$H-NMR (400 MHz, CDCl$_3$) δ: 1.93-2.07 (4H, m), 2.17 (2H, td, J = 11.5, 2.9 Hz), 2.43 (3H, s), 2.57 (2H, t, J = 6.4 Hz), 2.94 (2H, t, J = 7.1 Hz), 2.99-3.04 (3H, m), 3.58 (2H, t, J = 6.4 Hz), 3.71 (2H, t, J = 7.1 Hz), 7.22 (2H, dq, J = 9.2, 2.4 Hz), 7.48 (2H, tdd, J = 10.2, 5.4, 3.1 Hz), 7.65 (1H, dd, J = 6.9, 0.9 Hz). |
| 40 | 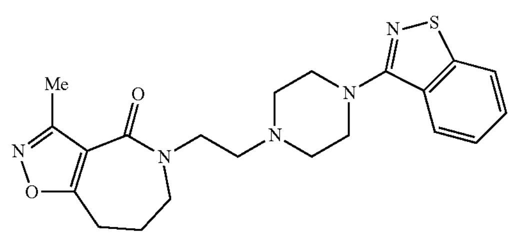 [SMILES: Cc1noc2c1C(=O)N(CCN1CCN(c3nsc4ccccc34)CC1)CCC2] | $^1$H-NMR (400 MHz, CDCl$_3$) δ: 2.15-2.24 (2H, m), 2.49 (3H, s), 2.67 (2H, t, J = 6.6 Hz), 2.76 (4H, t, J = 4.8 Hz), 3.04 (2H, t, J = 7.1 Hz), 3.49-3.58 (6H, m), 3.71 (2H, t, J = 6.4 Hz), 7.36 (1H, dd, J = 7.6, 7.6 Hz), 7.47 (1H, dd, J = 7.6, 7.6 Hz), 7.82 (1H, d, J = 8.3 Hz), 7.90 (1H, d, J = 8.3 Hz). |
| 41 | 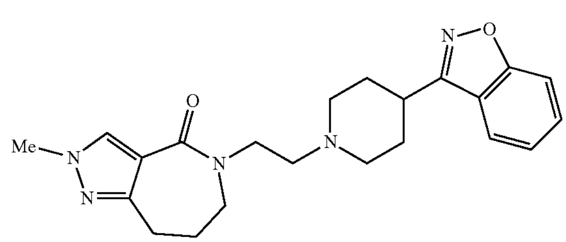 [SMILES: Cn1cc2c(n1)CCCN(CCN1CCC(c3noc4ccccc34)CC1)C2=O] | $^1$H-NMR (400 MHz, CDCl$_3$) δ: 2.03-2.17 (6H, m), 2.22-2.31 (2H, m), 2.63 (2H, t, J = 6.9 Hz), 2.94 (2H, t, J= 6.9 Hz), 3.06-3.16 (3H, m), 3.48-3.52 (2H, m), 3.69 (2H, t, J = 6.9 Hz), 3.86 (3H, s), 7.26-7.30 (1H, m), 7.50-7.58 (2H, m), 7.72 (1H, d, J = 7.8 Hz), 7.86 (1H, s). |

| Example | Chemical structure | Instrumental analyses data |
|---|---|---|
| 42 | 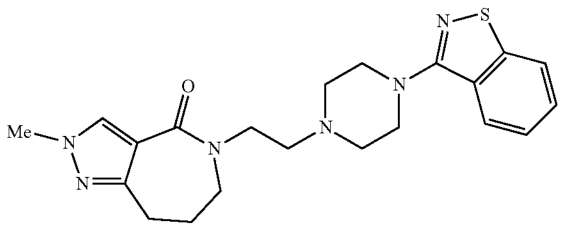 [SMILES: Cn1cc2c(n1)CCCN(CCN1CCN(c3nsc4ccccc34)CC1)C2=O] | $^1$H-NMR (400 MHz, CDCl$_3$) δ: 2.09-2.17 (2H, m), 2.68 (2H, t, J = 6.9 Hz), 2.76 (4H, t, J = 4.8 Hz), 2.94 (2H, t, J = 6.9 Hz), 3.48-3.52 (2H, m), 3.54 (4H, t, J = 4.8 Hz), 3.71 (2H, t, J = 6.6 Hz), 3.86 (3H, s), 7.33-7.38 (1H, m), 7.44-7.49 (1H, m), 7.81 (1H, d, J = 8.3 Hz), 7.87 (1H, s), 7.90 (1H, d, J = 8.3 Hz). |
| 43 | 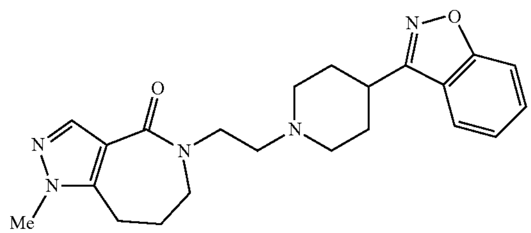 [SMILES: Cn1ncc2c1CCCN(CCN1CCC(c3noc4ccccc34)CC1)C2=O] | $^1$H-NMR (400 MHz, CDCl$_3$) δ: 2.00-2.14 (4H, m), 2.17-2.31 (4H, m), 2.63 (2H, t, J = 6.6 Hz), 2.84 (2H, t, J = 6.9 Hz), 3.05-3.15 (3H, m), 3.51 (2H, t, J = 4.8 Hz), 3.70 (2H, t, 3 = 6.6 Hz), 3.78 (3H, s), 7.27-7.31 (1H, m), 7.51-7.58 (2H, m), 7.72 (1H, d, J = 8.3 Hz), 7.99 (1H, s). |
| 44 | 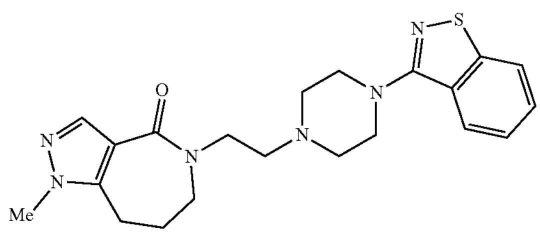 [SMILES: Cn1ncc2c1CCCN(CCN1CCN(c3nsc4ccccc34)CC1)C2=O] | $^1$H-NMR (400 MHz, CDCl$_3$) δ: 2.17-2.25 (2H, m), 2.68 (2H, t, J = 6.4 Hz), 2.76 (4H, t, J = 5.0 Hz), 2.84 (2H, t, J = 6.9 Hz), 3.49-3.57 (6H, m), 3.72 (2H, t, J = 6.4 Hz), 3.78 (3H, s), 7.33-7.39 (1H, m), 7.45-7.49 (1H, m), 7.81 (1H, d, 7.8 Hz), 7.90 (1H, d, Hz), 7.98 (1H, s). |
| 45 | 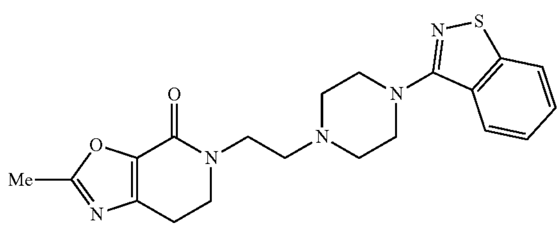 [SMILES: Cc1nc2c(o1)C(=O)N(CCN1CCN(c3nsc4ccccc34)CC1)CC2] | $^1$H-NMR (400 MHz, CDCl$_3$) δ: 2.54 (3H, s), 2.67 (2H, t, J = 6.6 Hz), 2.75 (4H, t, J = 4.8 Hz), 2.90 (2H, dd, J = 9.4, 4.8 Hz), 3.54 (4H, t, J = 4.8 Hz), 3.66 (2H, t, J = 6.4 Hz), 3.74 (2H, t, J = 7.1 Hz), 7. 7.36 (1H, ddd, J = 8.3, 8.3, 0.9 Hz), 7.47 (1H, ddd, J = 8.3, 8.3, 0.9 Hz), 7.81 (1H, dd, J = 8.3, 0.9 Hz), 7.90 (1H, dd, J = 8.3, 0.9 Hz). |
| 46 | 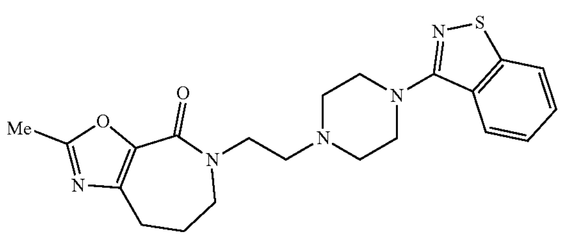 [SMILES: Cc1nc2c(o1)C(=O)N(CCN1CCN(c3nsc4ccccc34)CC1)CCC2] | $^1$H-NMR (400 MHz, CDCl$_3$) δ: 2.07-2.13 (2H, m), 2.48 (3H, s), 2.65 (2H, t, J = 6.4 Hz), 2.71-2.75 (4H, m), 2.80 (2H, t, J = 6.9 Hz), 3.49-3.52 (6H, m), 3.71 (2H, t, J = 6.4 Hz), 7.33 (1H, dd, J = 8.3, 8.3 Hz), 7.43-7.47 (1H, m), 7.79 (1H, d, J = 8.3 Hz), 7.88 (1H, d, J = 8.3 Hz). |
| 47 | 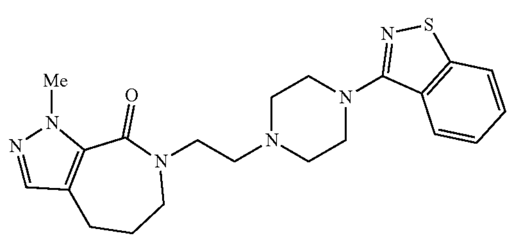 [SMILES: Cn1ncc2c1C(=O)N(CCN1CCN(c3nsc4ccccc34)CC1)CCC2] | $^1$H-NMR (400 MHz, CDCl$_3$) δ: 2.03-2.13 (2H, m), 2.70 (2H, t, J = 6.5 Hz), 2.74-2.81 (6H, m), 3.42 (2H, t, J = 5.6 Hz), 3.55 (4H, t, 3 = 4.8 Hz), 3.73 (2H, t, J = 6.6 Hz), 4.09 (3H, s), 7.28 (1H, s), 7.36 (1H, dd, J = 7.6, 7.6 Hz), 7.47 (1H, dd, J = 7.6, 7.6 Hz), 7.81 (1H, d, J = 8.0 Hz), 7.90 (1H, d, J = 8.0 Hz). |

-continued

| Example | Chemical structure | Instrumental analyses data |
|---|---|---|
| 48 | 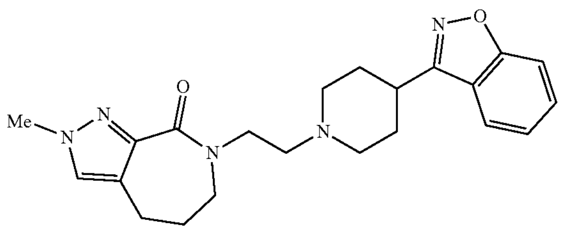 [SMILES: Cn1cc2c(n1)C(=O)N(CCN1CCC(c3noc4ccccc34)CC1)CCC2] | ¹H-NMR (400 MHz, CDCl₃) δ: 1.99-2.13 (6H, m), 2.21-2.30 (2H, m), 2.67 (2H, t, J = 6.5 Hz), 2.75 (2H, t, J = 7.3 Hz), 3.04-3.17 (3H, m), 3.44 (2H, t, J = 5.5 Hz), 3.73 (2H, t, J = 6.6 Hz), 3.93 (3H, s), 7.17 (1H, s), 7.29 (1H, d, J = 8.0 Hz), 7.50-7.58 (2H, m), 7.72 (1H, d, J = 8.0 Hz). |
| 49 | 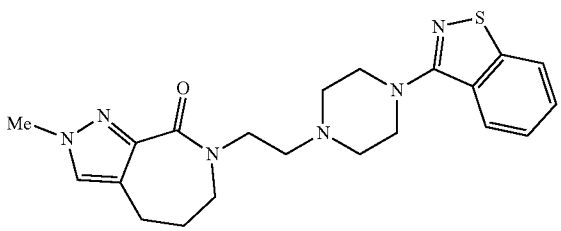 | ¹H-NMR (400 MHz, CDCl₃) δ: 2.01-2.10 (2H, m), 2.68-2.81 (8H, m), 3.44 (2H, t, J = 5.7 Hz), 3.54 (4H, t, J = 4.8 Hz), 3.75 (2H, t, J = 6.5 Hz), 3.92 (3H, s), 7.17 (1H, s), 7.36 (1H, dd, J = 7.4, 7.4 Hz), 7.47 (1H, dd, J = 7.4, 7.4 Hz), 7.81 (1H, d, J = 8.3 Hz), 7.90 (1H, d, J = 8.3 Hz). |
| 50 | 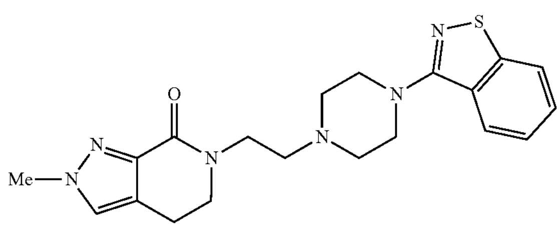 [SMILES: Cn1cc2c(n1)C(=O)N(CCN1CCN(c3nsc4ccccc34)CC1)CC2] | ¹H-NMR (400 MHz, CDCl₃) δ: 2.71 (2H, t, J = 6.5 Hz), 2.75 (4H, t, J = 4.8 Hz), 2.82 (2H, t, J = 6.6 Hz), 3.53 (4H, t, J = 4.5 Hz), 3.66 (2H, t, J = 6.6 Hz), 3.73 (2H, t, J = 6.3 Hz), 3.94 (3H, s), 7.17 (1H, s), 7.36 (1H, dd, J = 7.6, 7.6 Hz), 7.46 (1H, dd, J = 7.6, 7.6 Hz), 7.80 (1H, d, J = 8.0 Hz), 7.90 (1H, d, J = 8.0 Hz). |
| 51 | 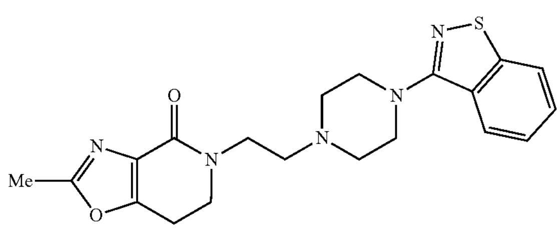 [SMILES: Cc1nc2c(o1)CCN(CCN1CCN(c3nsc4ccccc34)CC1)C2=O] | ¹H-NMR (400 MHz, CDCl₃) δ: 2.42 (3H, s), 2.60 (2H, t, J = 6.4 Hz), 2.67 (4H, t, J = 4.8 Hz), 2.93 (2H, t, J = 7.1 Hz), 3.43-3.47 (4H, m), 3.60 (2H, t, J = 6.4 Hz), 3.71 (2H, t, J = 7.1 Hz), 7.26-7.30 (1H, m), 7.37-7.41 (1H, m), 7.73 (1H, d, J = 8.3 Hz), 7.82 (1H, d, J = 7.8 Hz). |
| 52 | 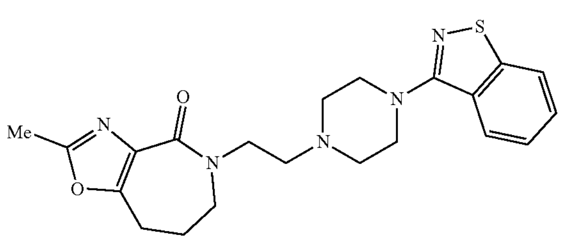 [SMILES: Cc1nc2c(o1)CCCN(CCN1CCN(c3nsc4ccccc34)CC1)C2=O] | ¹H-NMR (400 MHz, CDCl₃) δ: 2.06-2.12 (2H, m), 2.37 (3H, s), 2.60 (2H, t, J = 6.4 Hz), 2.65-2.69 (4H, m), 2.83 (2H, t, J = 6.9 Hz), 3.43-3.47 (6H, m), 3.66 (2H, t, J = 6.2 Hz), 7.27-7.31 (1H, m), 7.37-7.41 (1H, m), 7.73 (1H, d, J = 7.8 Hz), 7.83 (1H, d, J = 8.3 Hz). |
| 53 | 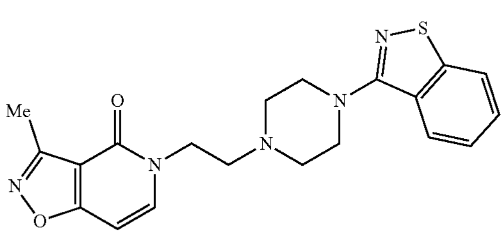 [SMILES: Cc1noc2ccn(CCN3CCN(c4nsc5ccccc45)CC3)c(=O)c12] | ¹H-NMR (400 MHz, CDCl₃) δ: 2.64 (3H, s), 2.76-2.80 (6H, m), 3.53 (4H, t, J = 4.9 Hz), 4.14-4.15 (2H, m), 6.50 (1H, d, J = 7.3 Hz), 7.36 (1H, ddd, J = 8.1, 8.3, 0.9 Hz), 7.45-7.48 (2H, m), 7.82 (1H, dd, J = 8.1, 0.9 Hz), 7.89 (1H, d, J = 8.3 Hz). |

-continued

| Example | Chemical structure | Instrumental analyses data |
|---|---|---|
| 54 | 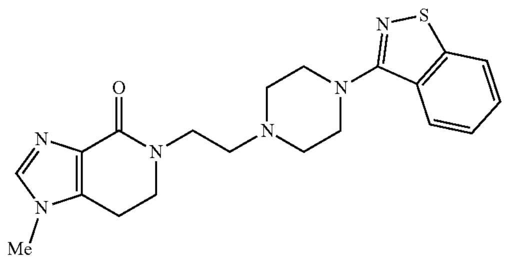 [SMILES: Cn1cnc2c1CCN(CCN1CCN(c3nsc4ccccc34)CC1)C2=O] | ¹H-NMR (400 MHz, CDCl₃) δ: 2.66-2.80 (6H, m), 2.87 (2H, t, J = 7.1 Hz), 3.47-3.64 (7H, m), 3.69 (2H, t, J = 6.4 Hz), 3.76 (2H, t, J = 6.9 Hz), 7.32-7.39 (1H, m), 7.40-7.50 (2H, m), 7.80 (1H, d, J = 8.3 Hz), 7.90 (1H, d, J = 8.4 Hz). |
| 55 | 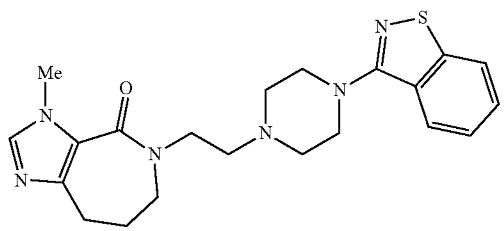 [SMILES: Cn1cnc2c1C(=O)N(CCN1CCN(c3nsc4ccccc34)CC1)CCC2] | ¹H-NMR (400 MHz, CDCl₃) δ: 2.08-2.16 (2H, m), 2.68 (2H, t, J = 6.6 Hz), 2.77 (4H, t, J = 4.8 Hz), 2.96 (2H, t, J = 7.3 Hz), 3.46-3.52 (2H, m), 3.55 (4H, t, J = 4.8 Hz), 3.72 (2H, t, J = 6.6 Hz), 3.87 (3H, s), 7.36 (1H, dd, J = 7.6, 7.6 Hz), 7.42-7.51 (2H, m), 7.81 (1H, d, J = 8.3 Hz), 7.90 (1H, d, J = 8.3 Hz). |
| 56 | 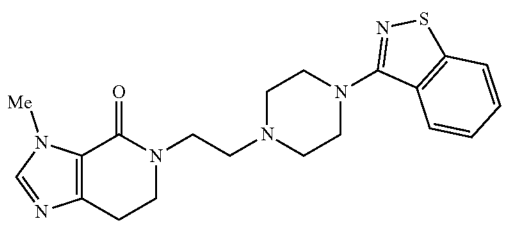 [SMILES: Cn1cnc2c1C(=O)N(CCN1CCN(c3nsc4ccccc34)CC1)CC2] | ¹H-NMR (400 MHz, CDCl₃) δ: 2.67 (2H, t, J = 6.5 Hz), 2.77 (4H, t, J = 5.0 Hz), 2.93 (2H, t, J = 7.2 Hz), 3.54 (4H, t, J = 4.8 Hz), 3.60-3.70 (4H, m), 3.91 (3H, s), 7.35 (1H, ddd, J = 8.0, 8.0, 1.2 Hz), 7.40 (1H, s), 7.46 (1H, ddd, J = 8.0, 8.0, 1.2 Hz), 7.80 (1H, d, J = 8.3 Hz), 7.89 (1H, d, J = 8.3 Hz). |
| 57 | 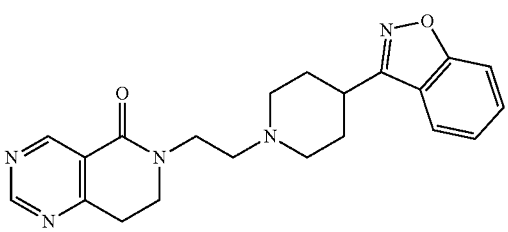 [SMILES: O=C1c2cncnc2CCN1CCN1CCC(c2noc3ccccc23)CC1] | ¹H-NMR (400 MHz, CDCl₃) δ: 2.01-2.25 (4H, m), 2.28 (2H, td, J = 11.8, 2.4 Hz), 2.70 (2H, t, J = 6.4 Hz), 3.06-3.17 (3H, m), 3.20 (2H, t, J = 6.6 Hz), 3.75 (2H, t, J = 6.5 Hz), 3.79 (2H, t, J = 6.9 Hz), 7.27-7.33 (1H, m), 7.50-7.60 (2H, m), 7.70 (1H, d, J = 8.3 Hz), 9.20 (1H, s), 9.25 (1H, s). |
| 58 | 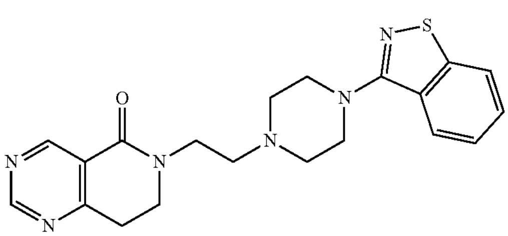 [SMILES: O=C1c2cncnc2CCN1CCN1CCN(c2nsc3ccccc23)CC1] | ¹H-NMR (400 MHz, CDCl₃) δ: 2.67-2.84 (6H, m), 3.20 (2H, t, J = 6.9 Hz), 3.48-3.66 (4H, m), 3.73-3.83 (4H, m), 7.32-7.40 (1H, m), 7.43-7.51 (1H, m), 7.81 (1H, d, J = 8.0 Hz), 7.89 (1H, d, J = 8.0 Hz), 9.19 (1H, s), 9.25 (1H, s). |
| 59 | 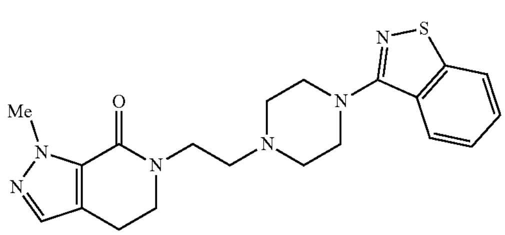 [SMILES: Cn1ncc2c1C(=O)N(CCN1CCN(c3nsc4ccccc34)CC1)CC2] | ¹H-NMR (400 MHz, CDCl₃) δ: 2.69 (2H, t, J = 6.6 Hz), 2.77 (4H, t, J = 4.8 Hz), 2.82 (2H, t, J = 6.6 Hz), 3.54 (4H, t, J = 4.8 Hz), 3.64-3.71 (4H, m), 4.18 (3H, s), 7.29 (1H, s), 7.32-7.39 (1H, m), 7.43-7.50 (1H, m), 7.81 (1H, d, J = 8.3 Hz), 7.90 (1H, d, J = 7.8 Hz). |

-continued

| Example | Chemical structure | Instrumental analyses data |
|---|---|---|
| 60 | 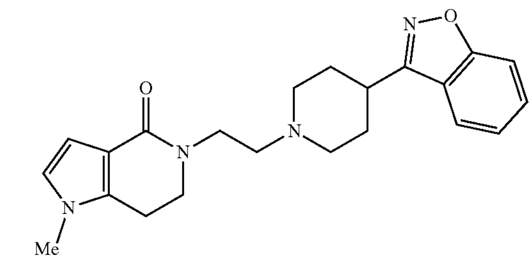 [SMILES: Cn1ccc2c1CCN(CCN1CCC(c3noc4ccccc34)CC1)C2=O] | $^1$H-NMR (400 MHz, CDCl$_3$) δ: 2.00-2.14 (4H, m), 2.20-2.32 (2H, m), 2.64 (2H, t, N-0 J = 6.9 Hz), 2.83 (2H, t, J = 6.9 Hz), 3.05-3.18 (3H, m), 3.55 (3H, s), 3.61-3.75 (4H, m), 6.52 (1H, d, J = 3.2 Hz), 6.54 (1H, d, J = 3.2 Hz), 7.33 (1H, dd, J = 7.6, 7.6 Hz), 7.25-7.32 (1H, m), 7.49-7.59 (2H, m), 7.74 (1H, d, J = 7.8 Hz). |
| 61 | 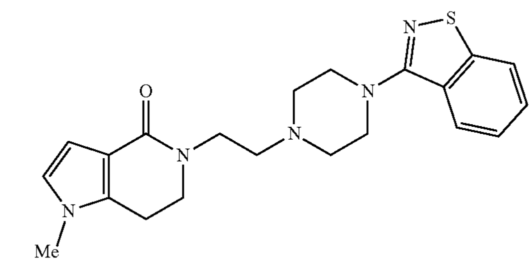 | $^1$H-NMR (400 MHz, CDCl$_3$) δ: 2.66 (2H, t, J = 6.6 Hz), 2.74 (4H, t, J = 5.0 Hz), 2.81 (2H, t, J = 6.9 Hz), 3.48-3.55 (7H, m), 3.62-3.70 (4H, m), 6.49 (1H, d, J = 2.8 Hz), 6.51 (1H, d, J = 3.2 Hz), 7.33 (1H, dd, J = 7.6, 7.6 Hz), 7.44 (1H, dd, J = 7.6, 7.6 Hz), 7.79 (1H, d, J = 8.3 Hz), 7.89 (1H, d, J = 7.8 Hz). |
| 62 | 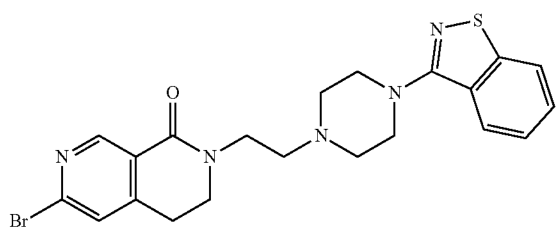 [SMILES: O=C1c2cnc(Br)cc2CCN1CCN1CCN(c2nsc3ccccc23)CC1] | $^1$H-NMR (400 MHz, CDCl$_3$) δ: 2.71 (2H, t, J = 6.4 Hz), 2.72-2.75 (4H, m), 2.98 (2H, t, J = 6.6 Hz), 3.49-3.53 (4H, m), 3.67 (2H, t, J = 6.4 Hz), 3.72 (2H, t, J = 6.4 Hz), 7.32-7.36 (1H, m), 7.34 (1H, s), 7.43-7.47 (1H, m) 7.79 (1H, d, J = 8.3 Hz) 7.88 (1H, d, J = 8.3 Hz) 8.92 (1H, s). |
| 63 | 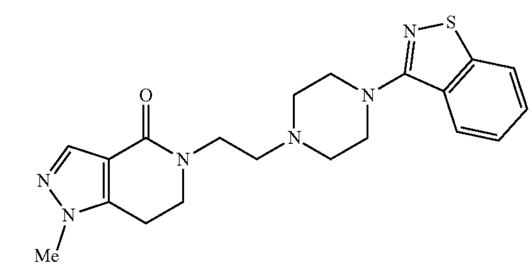 | $^1$H-NMR (400 MHz, CDCl$_3$) δ: 2.68 (2H, t, J = 6.4 Hz), 2.76 (4H, t, J = 4.8 Hz), 2.92 (2H, t, J = 6.9 Hz), 3.53 (4H, t, J = 4.8 Hz), 3.68 (2H, t, J = 6.6 Hz), 3.73 (2H, t, J = 6.9 Hz), 3.81 (3H, s), 7.36 (1H, ddd, J = 7.8, 7.6, 0.9 Hz), 7.47 (1H, ddd, J = 7.8, 7.6, 0.9 Hz), 7.81 (1H, d, J = 7.6 Hz), 7.84 (1H, s), 7.90 (1H, d, J = 7.8 Hz). |
| 64 | 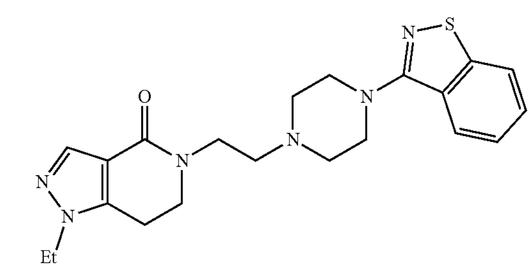 [SMILES: CCn1ncc2c1CCN(CCN1CCN(c3nsc4ccccc34)CC1)C2=O] | $^1$H-NMR (400 MHz, CDCl$_3$) δ: 1.45 (3H, t, J = 7.1 Hz), 2.69 (2H, t, J = 6.6 Hz), 2.76 (4H, t, J = 4.8 Hz), 2.93 (2H, t, J = 6.9 Hz), 3.54 (4H, t, J = 5.0 Hz), 3.71 (4H, dt, J = 23.2, 6.8 Hz), 4.10 (2H, q, J = 7.3 Hz), 7.36 (1H, ddd, J = 7.8, 7.8, 0.8 Hz), 7.47 (1H, ddd, J = 7.8, 7.8 0.8 Hz), 7.81 (1H, d, J = 7.8 Hz), 7.86 (1H, s), 7.90 (1H, d, J = 7.8 Hz). |
| 65 | 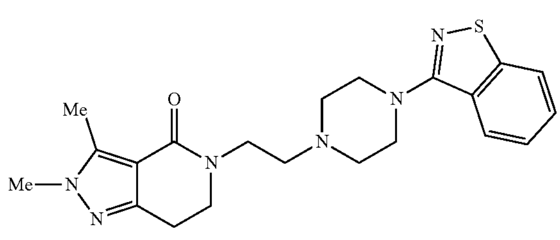 | $^1$H-NMR (400 MHz, CDCl$_3$) δ: 2.46 (3H, s), 2.62 (2H, t, J = 6.9 Hz), 2.68-2.73 (4H, m), 2.82 (2H, t, J = 6.9 Hz), 3.44-3.50 (4H, m), 3.56-3.62 (4H, m), 3.68 (3H, s), 7.27-7.31 (1H, m), 7.38-7.42 (1H, m), 7.74 (1H, d, J = 8.3 Hz), 7.83 (1H, d, J = 8.3 Hz). |

-continued

| Example | Chemical structure | Instrumental analyses data |
|---|---|---|
| 66 | 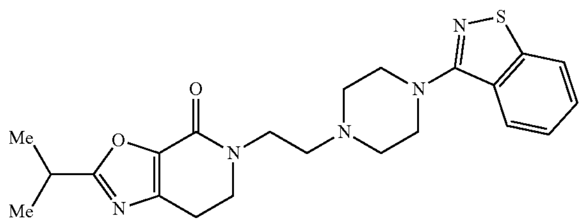 | $^1$H-NMR (400 MHz, CDCl$_3$) δ: 1.39 (6H, d, J = 6.9 Hz), 2.68 (2H, t, J = 6.4 Hz), 2.75 (4H, t, J = 4.8 Hz), 2.91 (2H, t, J = 6.4 Hz), 3.12-3.19 (1H, m), 3.54 (4H, t, J = 4.8 Hz), 3.66 (2H, t, J = 6.4 Hz), 3.74 (2H, t, J = 7.3 Hz), 7.36 (1H, ddd, J = 8.3, 8.3, 0.9 Hz), 7.47 (1H, ddd, J = 8.3, 8.3, 0.9 Hz), 7.81 (1H, d, J = 8.3 Hz), 7.90 (1H, dd, J = 8.3, 0.9 Hz). |
| 67 | 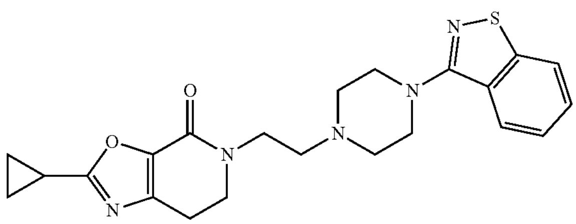 [SMILES: O=C1c2oc(C3CC3)nc2CCN1CCN1CCN(c2nsc3ccccc23)CC1] | $^1$H-NMR (400 MHz, CDCl$_3$) δ: 1.09-1.26 (4H, m), 2.12-2.14 (1H, m), 2.67 (2H, t, J = 6.4 Hz), 2.75 (4H, t, J = 4.8 Hz), 2.86 (2H, t, J = 7.1 Hz), 3.54 (4H, t, J = 4.8 Hz), 3.65 (2H, t, J = 6.4 Hz), 3.72 (2H, t, J = 7.1 Hz), 7.36 (1H, ddd, J = 8.3, 8.3, 0.9 Hz), 7.47 (1H, ddd, J = 8.3, 8.3, 0.9 Hz), 7.81 (1H, d, J = 8.3 Hz), 7.90 (1H, d, J = 8.3 Hz). |
| 68 | 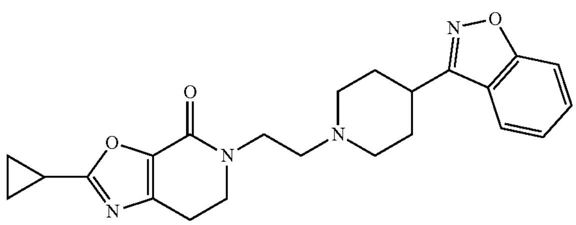 [SMILES: O=C1c2oc(C3CC3)nc2CCN1CCN1CCC(c2noc3ccccc23)CC1] | $^1$H-NMR (400 MHz, CDCl$_3$) δ: 1.09-1.25 (4H, m), 2.04-2.17 (5H, m), 2.26 (2H, td, J = 10.9, 3.2 Hz), 2.63 (2H, t, J = 6.4 Hz), 2.87 (2H, t, J = 7.3 Hz), 3.07-3.11 (3H, m), 3.64 (2H, t, J = 6.6 Hz), 3.72 (2H, t, J = 7.3 Hz), 7.29 (1H, ddd, J = 8.0, 7.8, 0.9 Hz), 7.51-7.58 (2H, m), 7.72 (1H, d, J = 7.8 Hz). |
| 69 | 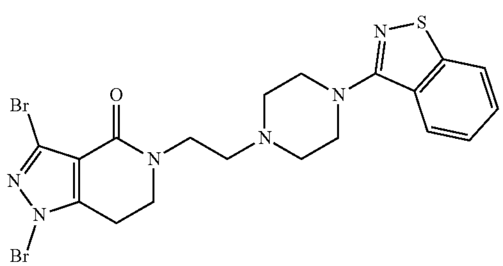 [SMILES: O=C1c2c(Br)nn(Br)c2CCN1CCN1CCN(c2nsc3ccccc23)CC1] | $^1$H-NMR (400 MHz, CDCl$_3$) δ: 2.66 (2H, t, J = 6.4 Hz), 2.73 (4H, t, J = 4.8 Hz), 2.91 (2H, t, J = 6.6 Hz), 3.50 (4H, t, J = 4.8 Hz), 3.64 (2H, t, J = 6.4 Hz), 3.71 (2H, t, J = 6.6 Hz), 3.76 (3H, s), 7.34 (1H, ddd, J = 8.3, 7.6, 0.9 Hz), 7.45 (1H, ddd, J = 7.6, 7.6, 0.9 Hz), 7.79 (1H, dd, J = 7.6, 0.9 Hz), 7.88 (1H, dd, J = 8.3, 0.9 Hz). |
| 70 | 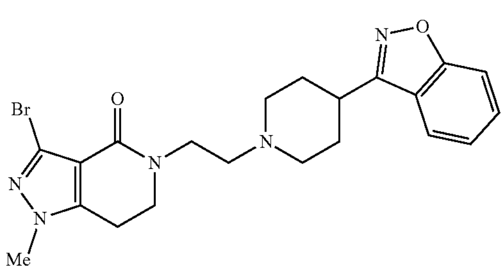 [SMILES: Cn1nc(Br)c2c1CCN(CCN1CCC(c3noc4ccccc34)CC1)C2=O] | $^1$H-NMR (400 MHz, CDCl$_3$) δ: 1.94-2.07 (4H, m), 2.19 (2H, td, J = 11.6, 2.6 Hz), 2.57 (2H, t, J = 6.4 Hz), 2.86 (2H, t, J = 6.6 Hz), 2.97-3.07 (3H, m), 3.58 (2H, t, J = 6.4 Hz), 3.66 (2H, t, J = 6.6 Hz), 3.72 (3H, s), 7.23 (1H, dt, J = 8.3, 3.2 Hz), 7.44-7.52 (2H, m), 7.65 (1H, d, J = 8.3 Hz). |

| Example | Chemical structure | Instrumental analyses data |
|---|---|---|
| 71 | 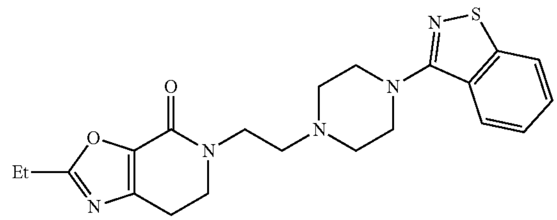 [SMILES: CCc1nc2c(o1)C(=O)N(CCN1CCN(c3nsc4ccccc34)CC1)CC2] | ¹H-NMR (400 MHz, CDCl₃) δ: 1.37 (3H, t, J = 8.9 Hz), 2.68 (2H, t, J = 6.4 Hz), 2.75 (4H, t, J = 5.0 Hz), 2.86-2.90 (4H, m), 3.54 (4H, t, J = 4.8 Hz), 3.66 (2H, t, J = 6.4 Hz), 3.74 (2H, t, J = 7.3 Hz), 7.36 (1H, dd, J = 8.3, 8.3 Hz), 7.47 (1H, dd, J = 8.3, 8.3 Hz), 7.81 (1H, d, J = 8.3 Hz), 7.90 (1H, d, J = 8.3 Hz). |
| 72 | 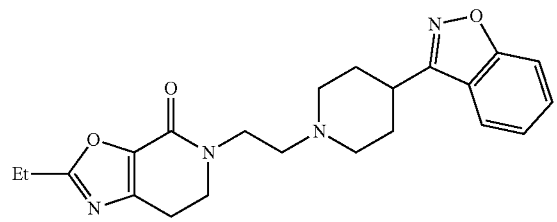 [SMILES: CCc1nc2c(o1)C(=O)N(CCN1CCC(c3noc4ccccc34)CC1)CC2] | ¹H-NMR (400 MHz, CDCl₃) δ: 1.38 (3H, t, J = 7.6 Hz), 2.04-2.11 (4H, m), 2.27 (2H, td, J = 10.9, 2.9 Hz), 2.64 (2H, t, J = 6.4 Hz), 2.87-2.90 (4H, m), 3.08-3.11 (3H, m), 3.65 (2H, t, J = 6.4 Hz), 3.75 (2H, t, J = 7.1 Hz), 7.29 (1H, m), 7.52-7.56 (2H, m), 7.72 (1H, d, J = 8.0 Hz). |
| 73 | 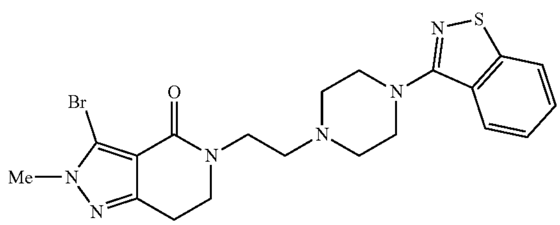 | ¹H-NMR (400 MHz, CDCl₃) δ: 2.00-2.14 (4H, brm), 2.20-2.32 (2H, br m), 2.58-2.60 (2H, br m), 2.92 (2H, t, J = 6.6 Hz), 3.02-3.08 (2H, m), 3.65 (4H, t, J = 6.4 Hz), 3.85 (3H, s), 7.26-7.29 (1H, m), 7.49-7.55 (2H, m), 7.71 (1H, d, J = 8.3 Hz). |
| 74 | 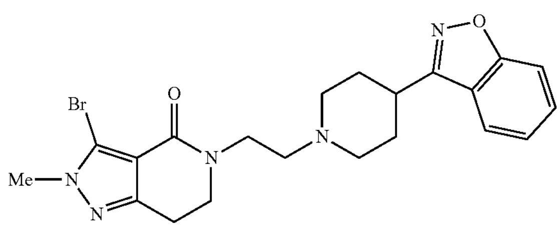 | ¹H-NMR (400 MHz, CDCl₃) δ: 2.67 (2H, t, J = 6.6 Hz), 2.73-2.77 (4H, s), 2.92 (2H, t, J = 6.7 Hz), 3.49-3.53 (4H, m), 3.63-3.68 (4H, m), 3.84 (3H, s), 7.33 (1H, dd, J = 8.0, 7.1 Hz), 7.44 (1H, dd, J = 8.0, 7.1 Hz), 7.79 (1H, t, J = 7.1 Hz), 7.88 (1H, d, J = 8.0 Hz). |
| 75 | 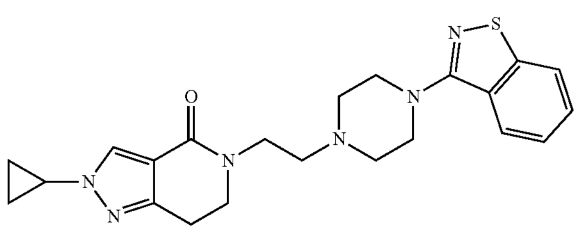 [SMILES: O=C1c2cn(C3CC3)nc2CCN1CCN1CCN(c2nsc3ccccc23)CC1] | ¹H-NMR (400 MHz, CDCl₃) δ: 1.02-1.14 (4H, m), 2.68 (2H, t, J = 6.6 Hz), 2.76 (4H, t, J = 4.8 Hz), 2.91-2.97 (2H, m), 3.54 (4H, t, J = 4.8 Hz), 3.58-3.60 (1H, m), 3.68 (4H, td, J = 6.8, 3.1 Hz), 7.35 (1H, ddd, J = 8.3, 8.3, 0.9 Hz), 7.47 (1H, ddd, J = 8.3, 8.3, 0.9 Hz), 7.81 (1H, d, J = 8.3 Hz), 7.83 (1H, s), 7.90 (1H, d, J = 8.3 Hz). |
| 76 | 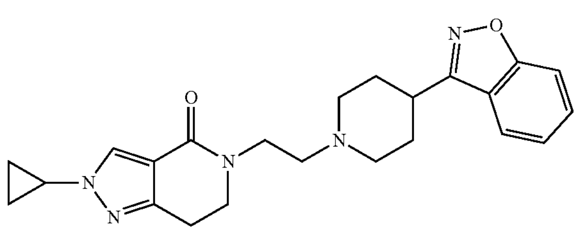 [SMILES: O=C1c2cn(C3CC3)nc2CCN1CCN1CCC(c2noc3ccccc23)CC1] | ¹H-NMR (400 MHz, CDCl₃) δ: 1.02-1.14 (4H, m), 2.01-2.10 (4H, m), 2.24-2.28 (2H, m), 2.64 (2H, t, J = 6.6 Hz), 2.94 (2H, t, J = 6.6 Hz), 3.07-3.12 (3H, m), 3.56-3.62 (1H, m), 3.66-3.68 (4H, m), 7.28 (1H, ddd, J = 8.4, 8.0, 1.0 Hz), 7.51-7.57 (2H, m), 7.73 (1H, d, J = 8.4 Hz), 7.83 (1H, s). |

| Example | Chemical structure | Instrumental analyses data |
|---|---|---|
| 77 | 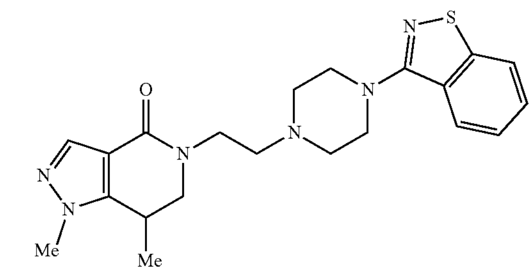 [SMILES: CC1CN(CCN2CCN(c3nsc4ccccc34)CC2)C(=O)c2cnn(C)c21] | $^1$H-NMR (400 MHz, CDCl$_3$) δ: 1.33 (3H, d, J = 6.9 Hz), 2.69 (2H, td, J = 6.3, 3.8 Hz), 2.76 (4H, t, J = 4.4 Hz), 3.07-3.10 (1H, m), 3.42-3.52 (6H, m), 3.83 (3H, s), 3.87-3.93 (2H, m), 7.36 (1H, dd, J = 8.0, 7.6 Hz), 7.47 (1H, dd, J = 8.3, 8.3 Hz), 7.81-7.82 (2H, m), 7.90 (1H, d, J = 8.3 Hz). |
| 78 | 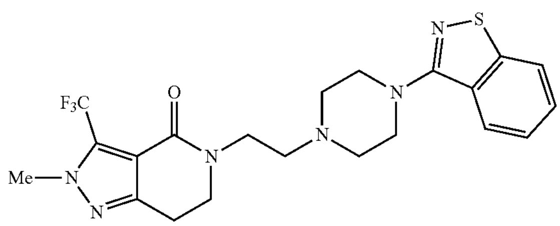 | $^1$H-NMR (400 MHz, CDCl$_3$) δ: 2.69 (2H, t, J = 6.6 Hz), 2.76 (4H, t, J = 4.8 Hz), 2.94 (2H, t, J = 6.6 Hz), 3.53 (4H, t, J = 4.8 Hz), 3.70 (4H, q, J = 26.6 Hz), 4.03 (3H, d, J = 1.4 Hz), 7.36 (1H, dd, J = 7.8, 7.8 Hz), 7.47 (1H, dd, J = 7.8, 7.8 Hz), 7.81 (1H, d, 3 = 7.8 Hz), 7.90 (1H, d, J = 7.8 Hz). |
| 79 | 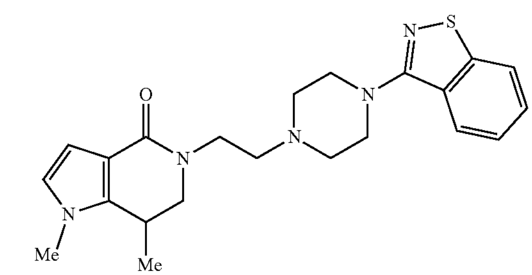 [SMILES: CC1CN(CCN2CCN(c3nsc4ccccc34)CC2)C(=O)c2ccn(C)c21] | $^1$H-NMR (400 MHz, CDCl$_3$) δ: 1.27 (4H, d, J = 6.9 Hz), 2.67-2.69 (2H, m), 2.76 (4H, t, J = 4.8 Hz), 2.95-2.98 (1H, m), 3.34 (1H, dd, J = 12.4, 1.8 Hz), 3.42-3.49 (1H, m), 3.54 (4H, t, J = 5.0 Hz), 3.57 (3H, s), 3.87-3.94 (2H, m), 6.50-6.51 (2H, m), 7.36 (1H, ddd, J = 8.0, 8.0, 0.9 Hz), 7.46 (1H, ddd, J = 8.0, 8.0, 0.9 Hz), 7.81 (1H, dd, J = 8.0, 0.9 Hz) 7.90 (1H, dd, J = 8.0, 0.9 Hz). |
| 80 | 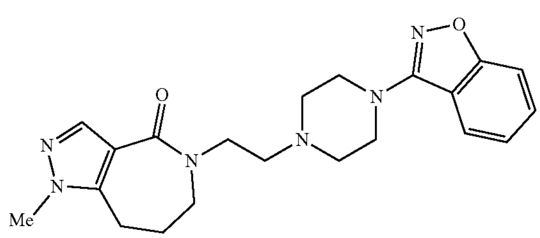 | $^1$H-NMR (400 MHz, CDCl$_3$) δ: 2.16-2.24 (2H, m), 2.65 (2H, t, J = 6.6 Hz), 2.73 (4H, t, J = 5.0 Hz), 2.84 (2H, t, J = 6.9 Hz), 3.50 (2H, t, J = 4.6 Hz), 3.56 (4H, t, J = 5.0 Hz), 3.71 (2H, t, J = 6.6 Hz), 3.77 (3H, s), 7.19-7.24 (1H, m), 7.43-7.51 (2H, m), 7.69 (1H, d, J = 8.3 Hz), 7.98 (1H, s). |
| 81 | 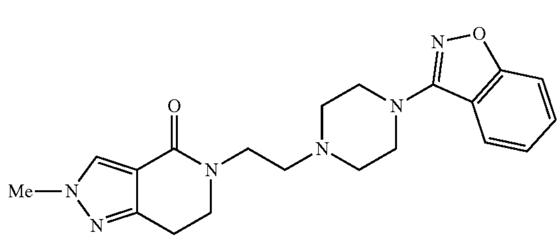 [SMILES: Cn1cc2c(n1)CCN(CCN1CCN(c3noc4ccccc34)CC1)C2=O] | $^1$H-NMR (400 MHz, CDCl$_3$) δ: 2.66 (2H, t, J = 6.6 Hz), 2.74 (4H, t, J = 5.0 Hz), 2.94 (2H, t, J = 6.4 Hz), 3.56 (4H, t, J = 5.0 Hz), 3.67 (4H, q, J = 6.3 Hz), 3.89 (3H, s), 7.21 (1H, ddd, J = 8.0, 7.8, 1.2 Hz), 7.45-7.47 (2H, m), 7.68 (1H, d, J = 7.8 Hz), 7.74 (1H, s). |

-continued

| Example | Chemical structure | Instrumental analyses data |
|---|---|---|
| 82 | 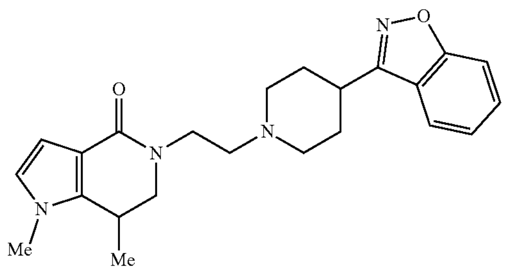 [SMILES: CC1CN(CCN2CCC(c3noc4ccccc34)CC2)C(=O)c2ccn(C)c21] | ¹H-NMR (400 MHz, CDCl₃) δ: 1.27 (411, d, J = 4.8 Hz), 2.06-2.10 (4H, m), 2.24-2.28 (2H, m), 2.64-2.66 (2H, m), 2.95-2.98 (1H, m), 3.09-3.13 (3H, m), 3.35 (1H, dt, J = 12.4, 1.8 Hz), 3.46 (1H, dt, J = 17.4, 5.0 Hz), 3.57 (3H, s), 3.82-3.96 (2H, m), 6.51 (2H, m), 7.28 (1H, dd, J = 8.0, 7.8 Hz), 7.51-7.57 (2H, m), 7.74 (1H, d, J = 7.8 Hz). |
| 83 | 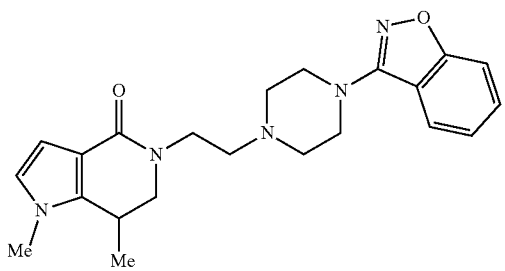 | ¹H-NMR (400 MHz, CDCl₃) δ: 1.27 (3H, d, J = 10.0 Hz), 2.66 (2H, dd, J = 10.3, 6.2 Hz), 2.74 (4H, t, J = 4.8 Hz), 2.97 (1H, t, J = 6.0 Hz), 3.31 (1H, dd, J = 12.4, 1.8 Hz), 3.47 (1H, dd, J = 13.8, 6.9 Hz), 3.57 (3H, s), 3.86-3.93 (2H, m), 6.50-6.51 (2H, m), 7.21 (1H, ddd, J = 8.0, 7.8, 1.2 Hz), 7.45-7.48 (2H, m), 7.69 (1H, d, J = 8.0 Hz). |
| 84 | 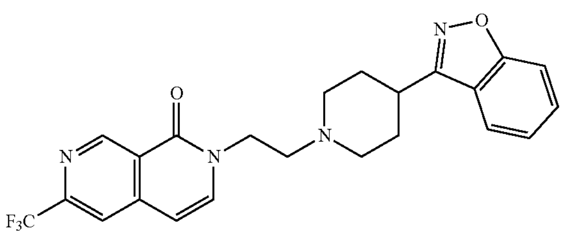 [SMILES: O=c1c2cnc(C(F)(F)F)cc2ccn1CCN1CCC(c2noc3ccccc23)CC1] | ¹H-NMR (400 MHz, CDCl₃) δ: 1.97-2.14 (4H, m), 2.29-2.38 (2H, m), 2.80 (2H, t, J = 6.2 Hz), 3.01-3.14 (3H, m), 4.17 (2H, t, J = 6.2 Hz), 6.53 (1H, d, J = 7.3 Hz), 7.27-7.31 (1H, m), 7.49 (1H, d, J = 7.3 Hz), 7.51-7.58 (2H, m), 7.69 (1H, d, J = 8.3 Hz), 7.75 (1H, s), 9.67 (1H, s). |
| 85 | 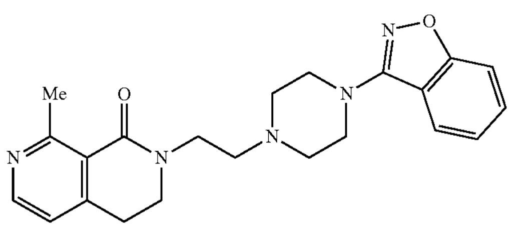 [SMILES: Cc1nccc2c1C(=O)N(CCN1CCN(c3noc4ccccc34)CC1)CC2] | ¹H-NMR (400 MHz, CDCl₃) δ: 2.68 (2H, t, J = 6.4 Hz). 2.73 (4H, t, J = 4.8 Hz), 2.88 (3H, s), 2.93 (2H, t, J = 6.4 Hz) 3.54 (4H, t, J = 4.8 Hz) 3.58 (2H, t, J = 6.8 Hz) 3.71 (2H, t, J = 6.4 Hz) 6.96 (1H, d, J = 5.0 Hz), 7.18-7.22 (1H, m), 7.42-7.48 (2H, m), 7.66 (1H, d, J = 7.3 Hz), 8.42 (1H, d, 3 = 5.0 Hz). |
| 86 | 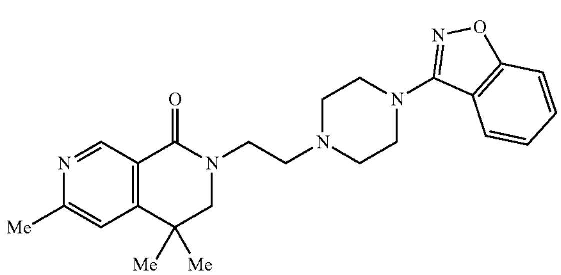 [SMILES: Cc1cc2c(cn1)C(=O)N(CCN1CCN(c3noc4ccccc34)CC1)CC2(C)C] | ¹H-NMR (400 MHz, CDCl₃) δ: 1.35 (6H, s), 2.61 (3H, s), 2.71-2.74 (6H, m), 3.40 (2H, s), 3.56 (4H, t, 3= 4.8 Hz), 3.73 (2H, t, J = 6.4 Hz), 7.05 (1H, s), 7.22 (1H, ddd, J = 8.0, 8.0, 1.2 Hz), 7.45-7.49 (2H, m), 7.69 (1H, d, J = 8.0 Hz), 9.09 (1H, s). |

| Example | Chemical structure | Instrumental analyses data |
|---|---|---|
| 87 | 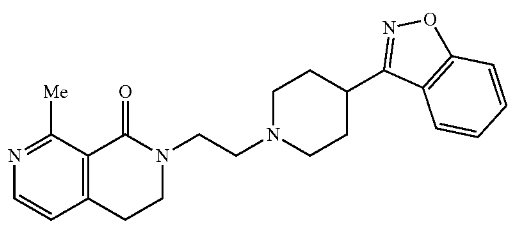 [SMILES: Cc1nccc2c1C(=O)N(CCN1CCC(c3noc4ccccc34)CC1)CC2] | ¹H-NMR (400 MHz, CDCl₃) δ: 2.06-2.21 (4H, m), 2.30-2.45 (2H, m), 2.70-2.80 (2H, m), 2.91 (3H, s), 2.96 (2H, t, J = 6.4 Hz), 3.10-3.22 (3H, m), 3.62 (2H, t, J = 6.4 Hz), 3.76 (2H, t, J = 6.1 Hz), 6.99 (1H, d, J = 4.9 Hz), 7.27-7.31 (1H, m), 7.51-7.58 (2H, m), 7.72 (1H, d, J = 7.9 Hz), 8.45 (1H, d, J = 4.9 Hz). |

Example 88

6-{2-[4-(1,2-Benzoisoxazol-3-yl)piperidin-1-yl]ethyl}-2-methyl-7,8-dihydropyrido[4,3-d]pyrimidin-5(6H)-one A mixture of the compound of Reference example 3 (852 mg), the compound of Reference example 42 (500 mg), 55% sodium hydride (134 mg), and N,N-dimethylformamide (15 mL) was stirred at 60° C. for 3.5 hours. Water (5.0 mL) was added to the reaction mixture, and the reaction mixture was extracted with chloroform/methanol (90/10), dried over anhydrous sodium sulfate, filtered, and concentrated. The resulting N,N-dimethylformamide was azeotroped with toluene, and the residue was purified by silica gel column chromatography (ethyl acetate), and recrystallized with ethanol (12 mL) to obtain the titled compound (710 mg).

¹H-NMR (400 MHz, CDCl₃) δ: 1.98-2.15 (4H, m), 2.23-2.31 (2H, m), 2.69 (2H, t, J=6.4 Hz), 2.78 (3H, s), 3.05-3.17 (5H, m), 3.70-3.79 (4H, m), 7.27-7.31 (1H, m), 7.50-7.59 (2H, m), 7.70 (1H, d, J=7.8 Hz), 9.15 (1H, s).

Examples 89 to 92

According to the method of Example 88, the compounds of Examples 89 to 92 were prepared from the corresponding Reference example compounds.

| Example | Chemical structure | Instrumental analyses data |
|---|---|---|
| 89 | 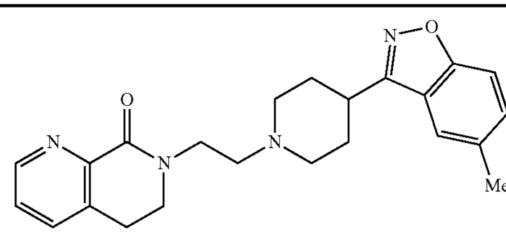 | ¹H-NMR (400 MHz, CDCl₃) δ: 1.96-2.12 (4H, m), 2.19-2.32 (2H, m), 2.46 (3H, s), 2.67-2.75 (2H, m), 2.97-3.17 (5H, m), 3.72 (2H, t, J = 6.6 Hz), 3.78 (2H, t, J = 6.3 Hz), 7.29-7.36 (2H, m), 7.39-7.47 (2H, m), 7.56 (1H, d, J = 7.8 Hz), 8.69 (1H, m). |
| 90 | 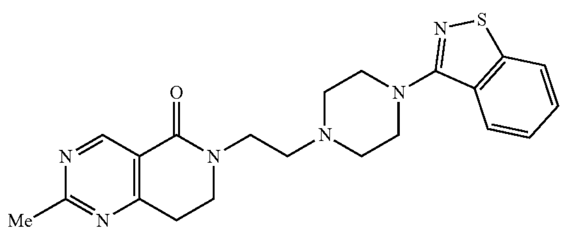 | ¹H-NMR (400 MHz, CDCl₃) δ: 2.71-2.81 (9H, m), 3.13 (2H, J = 6.9 Hz), 3.50-3.59 (4H, m), 3.72-3.79 (4H, m), 7.33-7.39 (1H, m), 7.44-7.49 (1H, m), 7.81 (1H, d, J = 7.8 Hz), 7.90 (1H, d, J = 8.3 Hz), 9.14 (1H, s). |
| 91 | 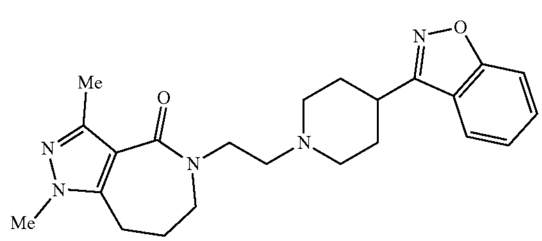 [SMILES: Cc1nn(C)c2c1C(=O)N(CCN1CCC(c3noc4ccccc34)CC1)CCC2] | ¹H-NMR (400 MHz, CDCl₃) δ: 2.00-2.19 (6H, m), 2.22-2.34 (2H, m), 2.44 (3H, s), 2.64 (2H, t, J = 6.7 Hz), 2.81 (2H, t, J = 7.3 Hz), 3.03-3.20 (3H, m), 3.41-3.45 (2H, m), 3.65-3.72 (5H, m), 7.25-7.29 (1H, m), 7.48-7.57 (2H, m), 7.70 (1H, d, J = 7.9 Hz). |

| Example | Chemical structure | Instrumental analyses data |
|---|---|---|
| 92 | (structure) | $^1$H-NMR (400 MHz, CDCl$_3$) δ: 2.10-2.16 (2H, m), 2.42 (3H, s), 2.64-2.75 (2H, m), 2.76-2.86 (6H, m), 3.42-3.47 (2H, m), 3.54-3.65 (4H, m), 3.68 (3H, s), 3.70-3.78 (2H, m), 7.18-7.22 (1H, m), 7.42-7.49 (2H, m), 7.65 (1H, d, J = 7.9 Hz). |

Example 93

6-{2-[4-(1,2-Benzoisothiazol-3-yl)piperazin-1-yl]ethyl}-2-ethyl-7,8-dihydropyrido[4,3-d]pyrimidin-5(6H)-one To a solution of the compound of Reference example 43 (100 mg) in dimethylsulfoxide (1.0 mL) were added potassium hydroxide (38.0 mg) and the compound of Reference example 2 (159 mg) sequentially, and the mixture was stirred at room temperature for 2 hours. The reaction mixture was purified by silica gel column chromatography (chloroform/methanol), and further purified by amino silica gel column chromatography (hexane/ethyl acetate) to obtain the titled compound (92.7 mg).

$^1$H-NMR (400 MHz, CDCl$_3$) δ: 1.38 (3H, t, J=7.7 Hz), 2.69-2.80 (6H, m), 3.01 (2H, q, J=7.0 Hz), 3.14 (2H, t, J=6.7 Hz), 3.54 (4H, t, J=4.8 Hz), 3.72-3.79 (4H, m), 7.33-7.38 (1H, m), 7.44-7.49 (1H, m), 7.81 (1H, dd, J=8.2, 0.9 Hz), 7.90 (1H, dd, J=8.0, 0.7 Hz), 9.17 (1H, s).

Examples 94 to 95

According to the method of Example 93, the compounds of Examples 94 to 95 were prepared from the corresponding Reference example compounds.

| Example | Chemical structure | Instrumental analyses data |
|---|---|---|
| 94 | (structure) | $^1$H-NMR (400 MHz, CDCl$_3$) δ: 1.10-1.16 (2H, m), 1.19-1.24 (2H, m), 2.23-2.32 (1H, m), 2.68-2.81 (6H, m), 3.08 (2H, t, J = 6.7 Hz), 3.50-3.57 (4H, m), 3.70-3.77 (4H, m), 7.33-7.39 (1H, m), 7.44-7.50 (1H, m), 7.81 (1H, d, J = 8.3 Hz), 7.90 (1H, d, J = 8.0 Hz), 9.05 (1H, s). |
| 95 | (structure) | $^1$H-NMR (400 MHz, CDCl$_3$) δ: 2.74 (4H, t, J = 4.8 Hz), 2.78-2.83 (5H, m), 3.51 (4H, t, J = 4.8 Hz), 4.13 (2H, t, J = 6.2 Hz), 6.56 (d, J = 7.8 Hz), 7.31-7.36 (1H, m), 7.42-7.47 (1H, m), 7.54 (1H, d, J = 7.3 Hz), 7.79 (1H, d, J = 8.3 Hz), 7.86 (1H, d, J = 8.3 Hz), 9.54 (1H, s). |

Example 96

6-{2-[4-(1,2-Benzoisoxazol-3-yl)piperidin-1-yl]ethyl}-1-methyl-1,4,5,6-tetrahydro-7H-pyrazolo[3,4-c]pyridin-7-one

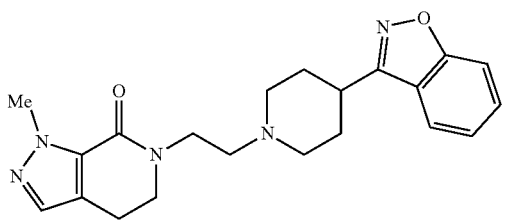 [SMILES: Cn1ncc2c1C(=O)N(CCN1CCC(c3noc4ccccc34)CC1)CC2]

To a suspension of the compound of Reference example 45 (100 mg) in dichloromethane (2.1 mL) was added N,N-diisopropylethylamine (0.110 mL), and the mixture was stirred at room temperature for 5 minutes. After the compound of Reference example 46 (38.3 mg) and acetic acid (0.0241 mL) were added to the mixture, sodium triacetoxyborohydride (89.0 mg) was added thereto, and the mixture was stirred at room temperature for 24 hours. Saturated aqueous sodium bicarbonate was added to the reaction mixture, and the mixture was extracted with chloroform, dried over anhydrous sodium sulfate, filtered, and concentrated. The concentrated residue was purified by silica gel column chromatography (chloroform/methanol) to obtain the titled compound (4.60 mg).

¹H-NMR (400 MHz, CDCl₃) δ: 2.01-2.15 (4H, m), 2.23-2.33 (2H, m), 2.66 (2H, t, J=6.9 Hz), 2.83 (2H, t, J=6.6 Hz), 3.05-3.16 (3H, m), 3.64-3.71 (4H, m), 4.18 (3H, s), 7.27-7.32 (2H, m), 7.51-7.59 (2H, m), 7.71 (1H, d, J=7.8 Hz).

Example 97

5-{2-[4-(1,2-Benzoisoxazol-3-yl)piperidin-1-yl]ethyl}-5,6,7,8-tetrahydropyrazolo[4,3-c]azepin-4(1H)-one

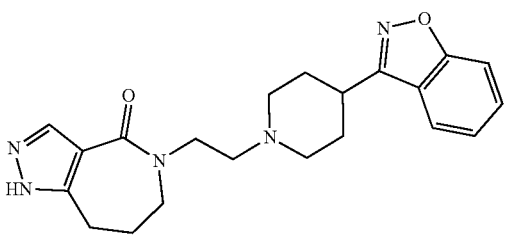 [SMILES: O=C1c2cn[nH]c2CCCN1CCN1CCC(c2noc3ccccc23)CC1]

A mixture of the compound of Reference example 47 (0.102 g), triethylamine (0.145 mL), N,N-dimethylformamide dimethyl acetal (0.0700 mL), and dichloromethane (5.0 mL) was stirred at room temperature for 60 hours. N,N-Dimethylformamide dimethyl acetal (0.100 mL) was added thereto, and the mixture was heated under reflux for 3 hours. Additional N,N-dimethylformamide dimethyl acetal (0.250 mL) was added thereto, and the mixture was heated under reflux for 2.5 hours. To the reaction mixture was added toluene (30 mL), and the mixture was concentrated under reduced pressure. To a solution of the concentrated residue in ethanol (10 mL) was added hydrazine monohydrate (14.3 mg). After heating under reflux for 24 hours, the reaction mixture was concentrated under reduced pressure, and the resulting residue was purified by preparative thin-layer chromatography (chloroform/methanol) to obtain the titled compound (13.0 mg).

¹H-NMR (400 MHz, CDCl₃) δ: 2.01-2.20 (6H, m), 2.22-2.34 (2H, m), 2.66 (2H, t, J=6.6 Hz), 2.99 (2H, t, J=6.9 Hz), 3.05-3.20 (3H, m), 3.52 (2H, t, J=4.8 Hz), 3.73 (2H, t, J=6.6 Hz), 7.26-7.31 (1H, m), 7.50-7.58 (2H, m), 7.70-7.73 (1H, m), 8.07 (1H, s).

Example 98

6-{2-[4-(1,2-Benzoisoxazol-3-yl)piperidin-1-yl]ethyl}-1,4,5,6-tetrahydro-7H-pyrazolo[3,4-c]pyridin-7-one

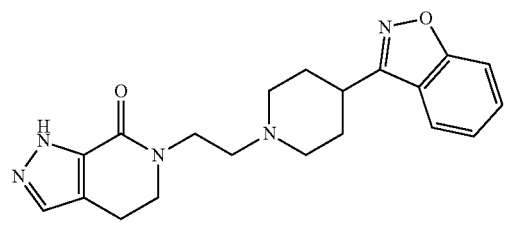 [SMILES: O=C1c2[nH]ncc2CCN1CCN1CCC(c2noc3ccccc23)CC1]

A solution of the compound of Reference example 50 (9.00 mg) in trifluoroacetic acid (1.0 mL) was heated under reflux for 2 hours. The reaction mixture was concentrated, and tetrahydrofuran (1.0 mL) and triethylamine (0.50 mL) were added thereto. After heating under reflux for 78 hours, the reaction mixture was concentrated, purified by silica gel column chromatography (chloroform/methanol), and further purified by preparative thin-layer column chromatography (chloroform/methanol) to obtain the titled compound (2.30 mg).

¹H-NMR (400 MHz, CDCl₃) δ: 2.03-2.16 (4H, m), 2.20-2.34 (2H, m), 2.62-2.73 (2H, m), 2.87 (2H, t, J=6.8 Hz), 3.03-3.19 (3H, m), 3.67-3.75 (4H, m), 7.27-7.31 (1H, m), 7.46 (1H, s), 7.51-7.58 (2H, m), 7.71 (1H, d, J=8.0 Hz).

Example 99

5-{2-[4-(1,2-Benzoisoxazol-3-yl)piperidin-1-yl]ethyl}-3-methyl-1,5,6,7-tetrahydro-4H-pyrazolo[4,3-c]pyridin-4-one

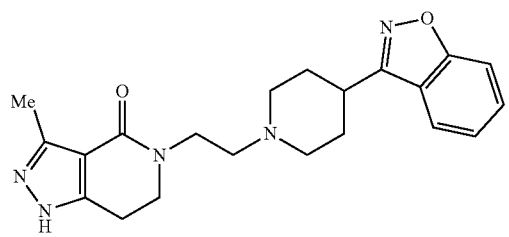 [SMILES: Cc1n[nH]c2c1C(=O)N(CCN1CCC(c3noc4ccccc34)CC1)CC2]

To the compound of Reference example 48 (103 mg) was added 48% hydrobromic acid (1.50 mL). After stirring at room temperature for 2 hours, 4 mol/L aqueous sodium hydroxide was added to the reaction mixture. The reaction mixture was adjusted to pH 7, and extracted with chloroform/methanol (4/1). The organic layer was dried over anhydrous sodium sulfate, filtered, and concentrated under reduced pressure. To a solution of the resulting concentrated residue (84.7 mg) in methylene chloride (1.2 mL) were added pyridine (0.0401 mL), magnesium chloride (23.6 mg), and acetic anhydride (0.0257 mL) at room temperature. After stirring at room temperature for 2 hours, saturated aqueous ammonium chloride was added to the reaction mixture, and the mixture was extracted with chloroform/methanol (4/1) The organic layer was dried over anhydrous sodium sulfate, filtered, and concentrated under reduced pressure. To a solution of the resulting concentrated residue (81.7 mg) in ethanol (0.71 mL) was added a solution of hydrazine (10.7 mg) in water (0.355 ml) at room temperature. After stirring at room temperature for 48 hours, water was added to the reaction mixture, and the mixture was extracted with chloroform. The organic layer was dried over anhydrous sodium sulfate, filtered, and concentrated under reduced pressure. The residue was purified by silica gel column chromatography (ethyl acetate/methanol) to obtain the titled compound (1.1 mg).

$^1$H-NMR (400 MHz, CDCl$_3$) δ: 2.01-2.14 (4H, m), 2.22-2.32 (2H, m), 2.55 (3H, s), 2.61-2.69 (2H, m), 2.92 (2H, t, J=6.9 Hz), 3.05-3.18 (2H, m), 3.66 (2H, t, J=6.9 Hz), 7.26-7.31 (1H, m), 7.48-7.57 (2H, m), 7.71 (1H, d, J=7.8 Hz).

Example 100

5-{2-[4-(1,2-Benzoisothiazol-3-yl)piperazin-1-yl]ethyl}-5,6,7,8-tetrahydroimidazo[4,5-c]azepin-4(3H)-one

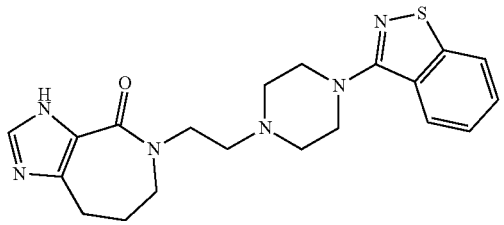 [SMILES: O=C1c2[nH]cnc2CCCN1CCN1CCN(c2nsc3ccccc23)CC1]

A mixture of the compound of Reference example 51 (401 mg), 20% palladium hydroxide on carbon (1.25 g), and methanol (4.5 mL) was stirred under hydrogen atmosphere (1 atm) at 60° C. for 1.5 hours. The reaction mixture was filtered, and the filtrate was concentrated under reduced pressure. A mixture of the resulting residue (283 mg), triethylamine (915 mg), and ethanol (4.5 mL) was stirred at 80° C. for 72 hours. After concentrated, the reaction mixture was purified by silica gel column chromatography (chloroform/methanol). To a solution of the resulting purified product (10.5 mg) in N,N-dimethylformamide (0.37 mL) was added 55% sodium hydride (2.98 mg) under ice temperature. After stirring under ice temperature for 30 minutes, the compound of Reference example 2 (11.0 mg) and potassium iodide (3.10 mg) were added thereto, and the mixture was stirred at room temperature for 12 hours. The reaction mixture was concentrated, and the residue was purified by silica gel column chromatography (chloroform/methanol). The obtained purified product was dissolved in dichloromethane (0.37 mL), and trifluoroacetic acid (0.37 mL) was added thereto. The mixture was stirred at room temperature for 1 hour, and concentrated. The reaction mixture was purified by reversed-phase liquid chromatography (water/acetonitrile) to obtain the titled compound (0.87 mg).

$^1$H-NMR (400 MHz, CDCl$_3$) δ: 2.11-2.18 (2H, m), 2.63-2.84 (6H, m), 2.95 (2H, t, J=6.6 Hz), 3.40-3.62 (6H, m), 3.73 (2H, t, J=6.4 Hz), 7.36 (1H, dd, J=7.1, 7.1 Hz), 7.47 (1H, dd, J=7.6, 7.6 Hz), 7.64 (1H, s), 7.81 (1H, d, J=8.3 Hz), 7.90 (1H, d, J=8.3 Hz).

Example 101

5-{2-[4-(1,2-Benzoisoxazol-3-yl)piperidin-1-yl]ethyl}-1-methyl-5,6,7,8-tetrahydroimidazo[4,5-c]azepin-4(1H)-one

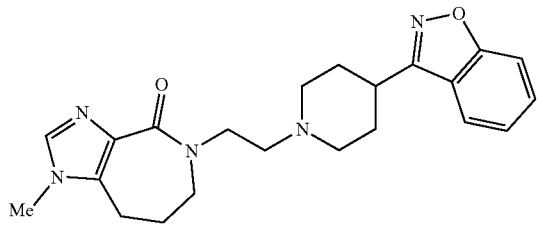 [SMILES: Cn1cnc2c1CCCN(CCN1CCC(c3noc4ccccc34)CC1)C2=O]

A mixture of the compound of Reference example 51 (697 mg), 20% palladium hydroxide on carbon (3310 mg), and methanol (7.9 mL) was stirred under hydrogen atmosphere (1 atm) at 60° C. for 1.5 hours. The reaction mixture was filtered, and concentrated under reduced pressure. A mixture of the resulting residue (492 mg), triethylamine (2.18 mL), and ethanol (7.9 mL) was heated under reflux for 72 hours. The reaction mixture was concentrated, and the residue was purified by silica gel column chromatography (chloroform/methanol). The resulting purified product (5.9 mg) was dissolved in dichloromethane (0.42 mL), and trifluoroacetic acid (0.42 mL) were added thereto. The mixture was stirred at room temperature for 3 hours. After the reaction mixture was concentrated, the residue was dissolved in N,N-dimethylformamide (0.42 mL), and 8 mol/L aqueous potassium hydroxide (2.88 μL) and methyl iodide (3.27 mg) were added thereto at 0° C. The mixture was stirred at 0° C. for 3 hours, and concentrated. To a solution of the resulting residue (3.47 mg) in N,N-dimethylformamide (0.21 mL) was added 55% sodium hydride (1.68 mg) under ice temperature. After stirring under ice temperature for 30 minutes, the compound of Reference example 3 (5.84 mg) and potassium iodide (1.74 mg) were added thereto, and the mixture was stirred at room temperature for 12 hours. The reaction mixture was concentrated, and the residue was purified by silica gel column chromatography (chloroform/methanol) to obtain the titled compound (0.64 mg).

$^1$H-NMR (400 MHz, CDCl$_3$) δ: 2.00-2.14 (2H, m), 2.20-2.34 (4H, m), 2.63 (2H, t, J=6.6 Hz), 3.05-3.19 (2H, m), 3.33-3.45 (2H, m), 3.54-3.74 (6H, m), 3.92 (3H, s), 7.26-7.32 (1H, m), 7.41 (1H, s), 7.49-7.59 (2H, m), 7.73 (1H, d, J=8.3 Hz).

Example 102

7-{2-[4-(1,2-Benzoisothiazol-3-yl)piperazin-1-yl]ethyl}-8-oxo-5,6,7,8-tetrahydro-2,7-naphthyridine-3-carbonitrile

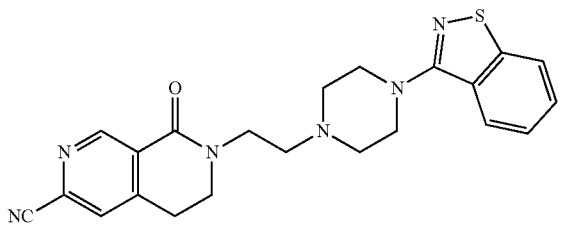 [SMILES: N#Cc1cc2c(cn1)C(=O)N(CCN1CCN(c3nsc4ccccc34)CC1)CC2]

To a solution of the compound of Reference example 62 (24.0 mg) in N,N-dimethylformamide (0.25 mL) were added zinc cyanide (25.1 mg) and tetrakis(triphenylphosphine)palladium (11.7 mg) at room temperature. After stirring at 100° C. for 1.5 hours, to the reaction mixture was added saturated aqueous ammonium chloride, and the mixture was extracted with chloroform. The organic layer was dried over sodium sulfate, filtered, and then concentrated under reduced pressure. The residue was purified by silica gel column chromatography (chloroform/methanol) to obtain the titled compound (9.5 mg).

1H-NMR (400 MHz, CDCl$_3$) δ: 2.66-2.71 (6H, m), 3.01 (2H, t, J=6.6 Hz), 3.44-3.48 (4H, m), 3.65-3.74 (4H, m), 7.29 (1H, dd, J=8.0, 7.1 Hz), 7.40 (1H, dd, J=8.0, 7.1 Hz), 7.49 (1H, s), 7.74 (1H, d, J=8.0 Hz), 7.82 (1H, d, J=8.0 Hz), 9.19 (1H, s).

Example 103

5-{2-[4-(1,2-Benzoisoxazol-3-yl)piperidin-1-yl]ethyl}-1-methyl-5,6,7,8-tetrahydropyrrolo[3,2-c]azepin-4(1H)-one

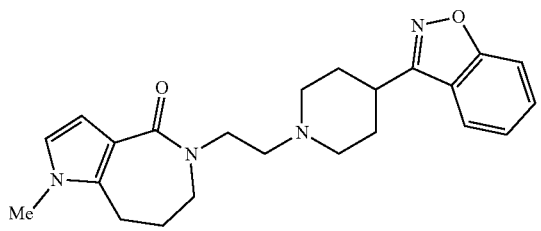

To a solution of the compound of Reference example 47 (75.0 mg) in N-methylpyrrolidone (0.53 mL) were added 2,2-dimethoxy-N-methylethan-1-amine (251 mg), methanesulfonic acid (27.4 μL), and magnesium sulfate (152 mg), and the mixture was stirred at 110° C. for 1 hour. The mixture was stirred at 150° C. for 2 hours, and 10% aqueous sodium hydroxide was added thereto to adjust pH to 9 or above. The mixture was extracted with chloroform. The combined organic layer was dried over anhydrous sodium sulfate, filtered, and concentrated. To the residue was added ethyl acetate/hexane (2/1), and the mixture was washed with water. The combined aqueous layer was extracted with ethyl acetate/hexane (2/1). The combined organic layer was dried over anhydrous sodium sulfate, filtered, and concentrated. The concentrated residue was purified by amino silica gel column chromatography (hexane/ethyl acetate). To the resulting solid was added ethyl acetate (0.91 mL). After confirming that all solid were dissolved at 70° C., the mixture was gradually cooled to room temperature. After confirming that a solid was precipitated, the mixture was stirred under ice temperature for 2 hours, and the solid was collected by filtration. The solid was washed with ethyl acetate cooled to 0° C., and dried under reduced pressure to obtain the titled compound (46.0 mg).

1H-NMR (400 MHz, CDCl$_3$) δ: 1.98-2.18 (6H, m), 2.18-2.29 (2H, m), 2.61 (2H, t, J=6.7 Hz), 2.77 (2H, t, J=7.0 Hz), 3.01-3.14 (3H, m), 3.43-3.51 (5H, m), 3.69 (2H, t, J=6.7 Hz), 6.54 (1H, d, J=2.4 Hz), 6.67 (1H, d, J=2.4 Hz), 7.24-7.30 (1H, m), 7.47-7.56 (2H, m), 7.71 (1H, d, J=7.9 Hz).

Examples 104

2-{2-[4-(1,2-Benzoisothiazol-3-yl)piperazin-1-yl]ethyl}-6-ethyl-3,4-dihydro-2,7-naphthyridin-1(2H)-one

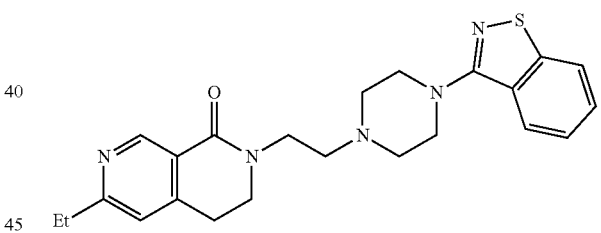

To a solution of the compound of Example 62 (114 mg) in tetrahydrofuran (6.0 mL) were added 1.1 mol/L aqueous diethylzinc-hexane (0.329 mL), and [1,1'-bis(diphenylphosphino)ferrocene]dichloropalladium (II), dichloromethane adduct (17.7 mg) at room temperature. After stirring at 70° C. for 2 hours, water was added to the reaction mixture, and the mixture was extracted with chloroform. The organic layer was dried over sodium sulfate, filtered, and concentrated under reduced pressure. The residue was purified by silica gel column chromatography (ethyl acetate/methanol) to obtain the titled compound (62.3 mg).

1H-NMR (400 MHz, CDCl$_3$) δ: 1.24 (3H, t, J=7.6 Hz), 2.66 (3H, t, J=6.4 Hz), 2.67-2.71 (4H, m), 2.77 (2H, q, J=7.6 Hz), 2.90 (2H, t, J=6.6 Hz), 3.44-3.47 (4H, m), 3.60 (2H, t, J=6.6 Hz), 3.67 (2H, t, J=6.6 Hz), 6.91 (1H, s), 7.28 (1H, dd, J=8.3, 8.3 Hz), 7.39 (1H, dd, J=8.3, 8.3 Hz), 7.73 (1H, d, J=8.3 Hz), 7.83 (1H, d, J=8.3 Hz), 9.04 (1H, s).

Example 105

5-{2-[4-(1,2-Benzoisothiazol-3-yl)piperazin-1-yl]ethyl}-1,3-dimethyl-1,5,6,7-tetrahydro-4H-pyrazolo[4,3-c]pyridin-4-one

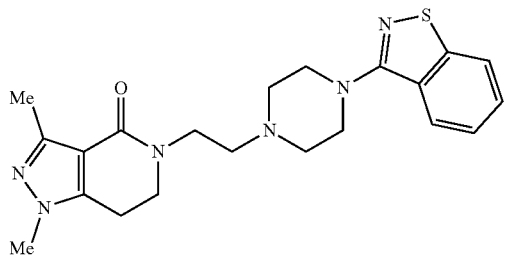 [SMILES: Cc1nn(C)c2c1C(=O)N(CCN1CCN(c3nsc4ccccc34)CC1)CC2]

To a solution of the compound of Example 69 (62.0 mg) in N,N-dimethylformamide (0.50 mL) were added potassium carbonate (54.1 mg), trimethylboroxine (0.0500 mL), and tetrakis(triphenylphosphine)palladium (15.1 mg) at room temperature. After stirring at 150° C. under microwave irradiation, the reaction mixture was filtered through Celite, and the filtrate was concentrated under reduced pressure. The residue was purified by reversed-phase liquid chromatography (acetonitrile/water, including 0.05% trifluoroacetic acid) to obtain the titled compound (12.3 mg).
$^1$H-NMR (400 MHz, CDCl$_3$) δ: 2.44 (3H, s), 2.65 (2H, t, J=6.6 Hz), 2.74 (4H, t, J=5.0 Hz), 2.85 (2H, t, J=6.9 Hz), 3.51 (4H, t, J=5.0 Hz), 3.63 (2H, t, J=6.6 Hz), 3.68 (2H, d J=6.9 Hz), 3.70 (3H, s), 7.31-7.35 (1H, ddd, J=8.3, 7.8 0.9 Hz), 7.44 (1H, ddd, J=7.8, 7.8, 0.9 Hz), 7.79 (1H, d, J=7.8 Hz), 7.88 (1H, d, J=8.3 Hz).

Example 106

5-{2-[4-(1,2-Benzoisothiazol-3-yl)piperazin-1-yl]ethyl}-3-methoxy-2-methyl-2,5,6,7-tetrahydro-4H-pyrazolo[4,3-c]pyridin-4-one

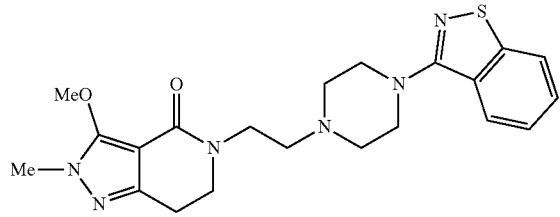 [SMILES: COc1c2c(nn1C)CCN(CCN1CCN(c3nsc4ccccc34)CC1)C2=O]

To a solution of the compound of Example 73 (14.0 mg) in methanol (1.0 mL) was added sodium methoxide (15.9 mg) at room temperature. After stirring at 120° C. for 5 hours, the reaction mixture was concentrated under reduced pressure. The residue was purified by silica gel column chromatography (chloroform/methanol) to obtain the titled compound (2.1 mg).
$^1$H-NMR (400 MHz, CDCl$_3$) δ: 2.67 (2H, t, J=6.6 Hz), 2.76 (4H, t, J=4.8 Hz), 2.83 (2H, t, J=6.6 Hz), 3.54 (4H, t, J=4.8 Hz), 3.61 (3H, s), 3.62 (2H, t, J=6.6 Hz), 3.67 (2H, t, J=6.6 Hz), 4.34 (3H, s), 7.35 (1H, dd, J=7.6, 7.6 Hz), 7.46 (1H, dd, J=7.6, 7.6 Hz), 7.81 (1H, d, J=7.6 Hz), 7.90 (1H, d, J=7.6 Hz).

Example 107

2-{2-[4-(1,2-Benzoisothiazol-3-yl)piperazin-1-yl]ethyl}-6-[($^2$H$_3$)methyloxy] (4,4-$^2$H$_2$)-3,4-dihydro-2,7-naphthyridin-1(2H)-one

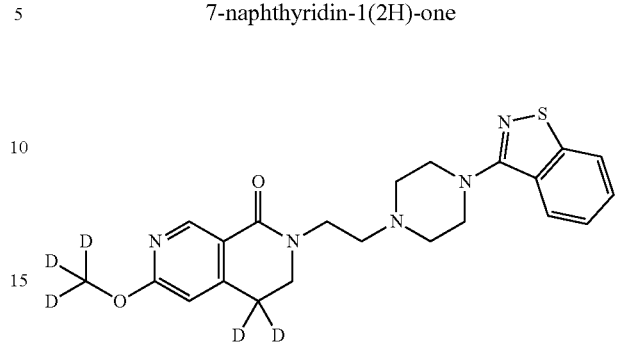

To a solution of the compound of Example 62 (60.0 mg) in deuteromethanol (0.50 mL) was added 55% sodium hydride (16.6 mg) under ice temperature. After stirring at 80° C. for 4 hours, water was added to the reaction mixture, and the mixture was extracted with chloroform. The organic layer was dried over sodium sulfate, filtered, and concentrated under reduced pressure. The residue was purified by silica gel column chromatography (chloroform/methanol) to obtain the titled compound (32.2 mg).
$^1$H-NMR (400 MHz, CDCl$_3$) δ: 2.70 (2H, t, J=6.4 Hz), 2.75 (4H, t, J=4.8 Hz), 3.51 (4H, t, J=4.8 Hz), 3.60 (2H, s), 3.71 (2H, t, J=6.4 Hz), 6.49 (1H, s), 7.33 (1H, 1H, dd, J=8.3, 8.3 Hz), 7.44 (1H, dd, J=8.3, 8.3 Hz), 7.78 (1H, d, J=8.3 Hz), 7.88 (1H, d, J=8.3 Hz), 8.79 (1H, s).

Example 108

2-{2-[4-(1,2-Benzoisothiazol-3-yl)piperazin-1-yl]ethyl}-6-methyl-3,4-dihydro-2,7-naphthyridin-1(2H)-one

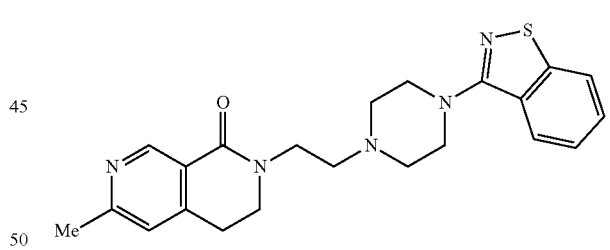

To a solution of the compound of Example 62 (84.0 mg) in 1,2-dimethoxyethane (1.6 mL) were added potassium carbonate (98.0 mg), trimethylboroxine (0.0820 mL), and tetrakis(triphenylphosphine)palladium (41.1 mg) at room temperature. After stirring at 100° C. for 3 hours under microwave irradiation, the reaction mixture was filtered through Celite, and the filtrate was concentrated under reduced pressure. The residue was purified by silica gel column chromatography (ethyl acetate/methanol) to obtain the titled compound (7.0 mg).
$^1$H-NMR (400 MHz, CDCl$_3$) δ: 2.56 (3H, s), 2.71 (2H, t, J=6.6 Hz), 2.75 (4H, t, J=4.8 Hz), 2.94 (2H, t, J=6.6 Hz), 3.51 (4H, t, J=4.8 Hz), 3.65 (2H, t, J=6.6 Hz), 3.72 (2H, t, J=6.6 Hz), 6.96 (1H, s), 7.32-7.36 (1H, m), 7.43-7.47 (1H, m), 7.79 (1H, d, J=8.3 Hz), 7.88 (1H, d, J=8.3 Hz), 9.06 (1H, s).

Example 109

5-{2-[4-(1,2-Benzoisoxazol-3-yl)piperazin-1-yl]ethyl}-1-methyl-5,6,7,8-tetrahydropyrrolo[3,2-c]azepin-4 (H)-one

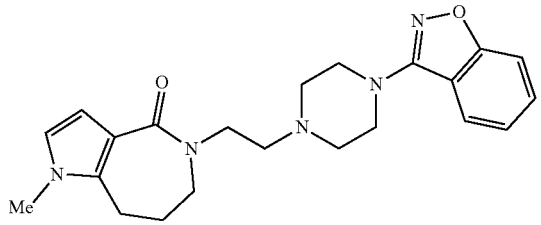 [SMILES: Cn1ccc2c1CCCN(CCN1CCN(c3noc4ccccc34)CC1)C2=O]

The compound of Reference example 49 (0.790 g), sodium sulfate (8.00 g), and p-toluenesulfonic acid monohydrate (0.422 g) were dissolved in 2,2-dimethoxy-N-methylethanamine (25 mL), and the mixture was stirred at 150° C. for 12 hours. The reaction mixture was filtered through Celite, and washed with chloroform. To the filtrate was added saturated aqueous sodium bicarbonate, and the mixture was extracted with chloroform. The organic layer was dried over sodium sulfate, and concentrated. The residue was purified by silica gel column chromatography (chloroform/methanol), and subjected to reverse-phase purification to obtain the titled compound (0.161 g).

$^1$H-NMR (400 MHz, CDCl$_3$) δ: 2.15-2.16 (2H, m), 2.66 (2H, t, J=6.6 Hz), 2.74 (4H, t, J=5.0 Hz), 2.79 (2H, t, J=6.9 Hz), 3.48-3.49 (2H, m), 3.50 (3H, s), 3.56 (4H, t, J=5.0 Hz), 3.72 (2H, t, J=6.6 Hz), 6.56 (1H, d, J=3.2 Hz), 6.68 (1H, d, J=2.8 Hz), 7.21 (1H, ddd, J=8.3, 8.0, 0.9 Hz), 7.43-7.48 (2H, m), 7.69 (1H, d, J=8.3 Hz).

Example 110

2-{2-[4-(1,2-Benzoisothiazol-3-yl)piperazin-1-yl]ethyl}-6-(trifluoromethyl)-3,4-dihydro-2,7-naphthyridin-1(2H)-one

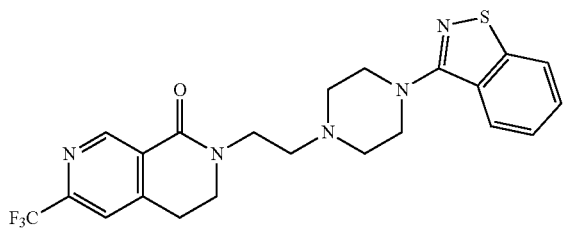 [SMILES: O=C1c2cnc(C(F)(F)F)cc2CCN1CCN1CCN(c2nsc3ccccc23)CC1]

To a mixture of the compound of Reference example 53 (70.0 mg), the compound of Reference example 52 (86.0 mg), triethylamine (0.082 mL), and dichloromethane (2.0 mL) was added sodium triacetoxyborohydride (78.0 mg), and the mixture was stirred at room temperature for an hour. To the reaction mixture was added saturated aqueous sodium bicarbonate, and the mixture was extracted with chloroform. The mixture was dried over anhydrous sodium sulfate, filtered, and concentrated. The concentrated residue was purified by silica gel column chromatography (hexane/ethyl acetate) to obtain the titled compound (2.20 mg).

$^1$H-NMR (400 MHz, CDCl$_3$) δ: 2.72-2.81 (6H, m), 3.11 (2H, t, J=6.4 Hz), 3.53 (4H, t, J=4.6 Hz), 3.72-3.81 (4H, m), 7.36 (1H, dd, J=7.3, 7.3 Hz), 7.47 (1H, dd, J=7.6, 7.6 Hz), 7.54 (1H, s), 7.81 (1H, d, J=8.3 Hz), 7.90 (1H, d, J=8.3 Hz), 9.29 (1H, s).

Example 111

2-{2-[4-(1,2-Benzoisothiazol-3-yl)piperazin-1-yl]ethyl}-6-[(oxetan-3-yl)oxy]-3,4-dihydro-2,7-naphthyridin-1(2H)-one

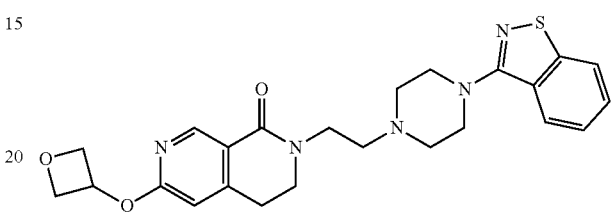

To oxetan-3-ol (83.0 mg) in N,N-dimethylformamide (0.21 mL) was added 55% sodium hydride (36.9 mg) under ice temperature. After stirring at room temperature for 15 minutes, the compound of Example 62 (50.0 mg) was added to the reaction mixture. After stirring at 80° C. for an hour, water was added to the reaction mixture, and the mixture was extracted with chloroform. The organic layer was dried over sodium sulfate, filtered, and concentrated under reduced pressure. The residue was purified by silica gel column chromatography (ethyl acetate/methanol) to obtain the titled compound (11.4 mg).

$^1$H-NMR (400 MHz, CDCl$_3$) δ: 2.72 (2H, t, J=6.6 Hz), 2.77 (4H, t, J=4.6 Hz), 2.96 (2H, t, J=6.6 Hz), 3.53 (4H, t, J=4.6 Hz), 3.64 (2H, t, J=6.6 Hz), 3.73 (2H, t, J=6.6 Hz), 4.71 (2H, dd, J=8.0, 5.3 Hz), 5.00 (2H, t, J=7.3 Hz), 5.63-5.69 (1H, m), 6.58 (1H, s), 7.36 (1H, dd, J=8.3, 8.3 Hz), 7.47 (1H, ddd, J=8.3, 8.3, 0.9 Hz), 7.81 (1H, d, J=8.3 Hz), 7.90 (1H, d, J=8.3 Hz), 8.71 (1H, s).

Example 112

5-{2-[4-(1,2-Benzoisothiazol-3-yl)piperazin-1-yl]ethyl}-2-fluoro-1-methyl-1,5,6,7-tetrahydro-4H-pyrrolo[3,2-c]pyridin-4-one

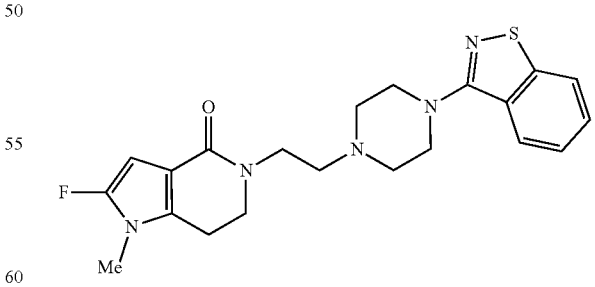

To a solution of the compound of Example 61 (286 mg) in methanol (3.6 mL) was added fumaric acid (84.0 mg), and the mixture was stirred at room temperature for 2 hours. The precipitated solid was filtered to obtain a solid (300 mg). A mixture of the resulting solid (300 mg), N-fluorobenzenesulfonimide (370 mg), and acetonitrile (2.9 mL) was stirred at room temperature for 1.5 hours. The reaction mixture was concentrated, and the resulting residue was purified by silica gel column chromatography (chloroform/methanol), and further purified by preparative thin-layer chromatography (chloroform/methanol) to obtain the titled compound (3.7 mg).

$^1$H-NMR (400 MHz, CDCl$_3$) δ: 2.67 (2H, t, J=6.6 Hz), 2.72-2.79 (6H, m), 3.41 (3H, s), 3.54 (4H, t, J=4.8 Hz), 3.61-3.74 (4H, m), 5.86 (1H, d, J=4.1 Hz), 7.36 (1H, dd, J=7.6, 7.6 Hz), 7.47 (1H, dd, J=7.3, 7.3 Hz), 7.81 (1H, d, J=7.8 Hz), 7.90 (1H, d, J=8.3 Hz).

Example 113

2-{2-[4-(1,2-Benzoisoxazol-3-yl)piperazin-1-yl]ethyl}-6-methyl-2,7-naphthyridin-1(2H)-one

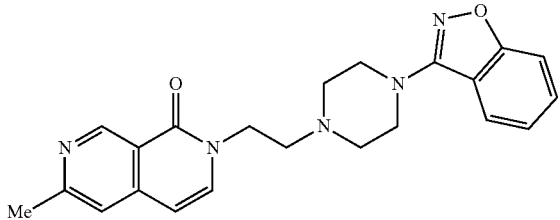

To a solution of the compound of Example 3 (104 mg) in 1,4-dioxane (1.0 mL) was added 2,3-dichloro-5,6-dicyano-p-benzoquinone (60.3 mg). After stirring at 100° C. for an hour, saturated aqueous sodium bicarbonate was added to the reaction mixture. The mixture was filtered, extracted with chloroform, dried over anhydrous sodium sulfate, filtered, and concentrated. The residue was purified by silica gel column chromatography (chloroform/methanol), and further purified by amino silica gel column chromatography (ethyl acetate/methanol) to obtain the titled compound (10.5 mg).

$^1$H-NMR (400 MHz, CDCl$_3$) δ: 2.64 (3H, s), 2.73 (4H, t, J=4.9 Hz), 2.81 (2H, t, J=6.4 Hz), 3.54 (4H, t, J=4.9 Hz), 4.13 (2H, t, J=6.4 Hz), 6.34 (1H, d, J=7.3 Hz), 7.16 (1H, s), 7.17-7.22 (1H, m), 7.27 (1H, d, J=7.3 Hz), 7.41-7.50 (2H, m), 7.64 (1H, d, J=7.9 Hz), 9.49 (1H, s).

Example 114

6-{2-[4-(1,2-Benzoisoxazol-3-yl)piperidin-1-yl]ethyl}-2,4-dimethylpyrido[4,3-d]pyrimidin-5(6H)-one

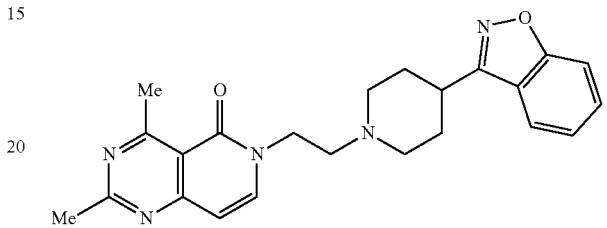

According to a similar method to Example 1, the titled compound was prepared from the compound of Reference example 3 and 2,4-dimethyl-pyrido[4,3-d]pyrimidin-5(6H)-one.

$^1$H-NMR (400 MHz, CDCl$_3$) δ: 1.95-2.08 (4H, m), 2.25-2.35 (2H, m), 2.69 (3H, s), 2.72 (2H, t, J=6.1 Hz), 2.98 (3H, s), 2.99-3.10 (3H, m), 4.05 (2H, t, J=6.4 Hz), 6.48 (1H, d, J=7.3 Hz), 7.20-7.25 (1H, m), 7.44-7.52 (3H, m), 7.63 (1H, d, J=7.9 Hz).

Examples 115 to 139

According to the method of Example 3, the compounds of Examples 115 to 139 were prepared from the corresponding Reference example compounds.

| Example | Chemical structure | Instrumental analyses data |
|---|---|---|
| 115 | 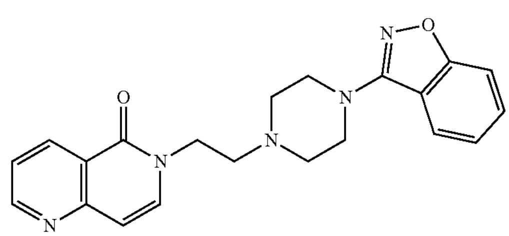 | $^1$H-NMR (400 MHz, CDCl$_3$) δ: 2.73 (4H, t, J = 5.0 Hz), 2.80 (2H, t, J = 6.4 Hz), 3.54 (4H, t, J = 5.0 Hz), 4.15 (2H, t, J = 6.4 Hz), 6.74 (1H, d, J = 7.8 Hz), 7.16-7.21 (1H, m), 7.33-7.48 (4H, m), 7.65 (1H, d, J = 8.3 Hz), 8.66 (1H, dd, J = 7.8, 1.8 Hz), 8.88 (1H, dd, J = 4.4, 1.6 Hz). |
| 116 | 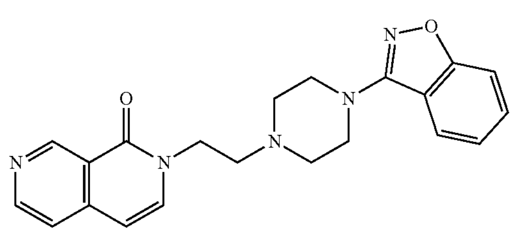 [SMILES: O=c1c2cnccc2ccn1CCN1CCN(c2noc3ccccc23)CC1] | $^1$H-NMR (400 MHz, CDCl$_3$) δ: 2.72 (4H, t, J = 4.8 Hz), 2.80 (2H, t, J = 6.2 Hz), 3.53 (4H, t, J = 4.6 Hz), 4.13 (2H, t, J = 6.2 Hz), 6.41 (1H, d, J = 7.3 Hz), 7.19 (1H, t, J = 7.3 Hz), 7.28-7.34 (2H, m), 7.39-7.50 (2H, m), 7.64 (1H, d, J = 7.8 Hz), 8.69 (1H, d, J = 5.6 Hz), 9.59 (1H, s). |

-continued

| Example | Chemical structure | Instrumental analyses data |
|---|---|---|
| 117 | 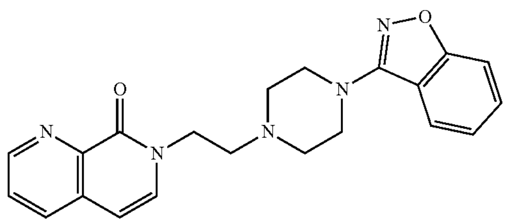 | ¹H-NMR (400 MHz, CDCl₃) δ: 2.71 (4H, t, J = 5.0 Hz), 2.83 (2H, t, J = 6.2 Hz), 3.52 (4H, t, J = 4.9 Hz), 4.19 (2H, t, J = 6.2 Hz), 6.40 (1H, d, J = 7.3 Hz), 7.16-7.23 (2H, m), 7.40-7.48 (2H, m), 7.52 (1H, dd, J = 8.0, 4.4 Hz), 7.65 (1H, d, J = 8.0 Hz), 7.85 (1H, dd, J = 8.2, 1.6 Hz), 8.85 (1H, dd, J = 4.3, 1.6 Hz). |
| 118 | 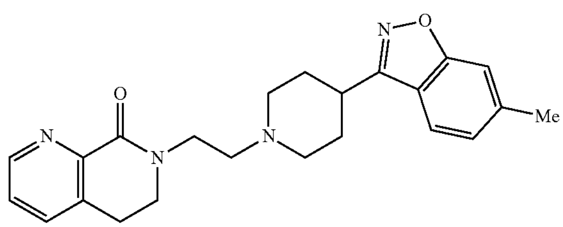 [SMILES: Cc1ccc2c(C3CCN(CCN4CCc5cccnc5C4=O)CC3)noc2c1] | ¹H-NMR (400 MHz, CDCl₃) δ: 1.93-2.11 (4H, m), 2.17-2.27 (2H, m), 2.46 (3H, s), 2.68 (2H, t, J = 6.3 Hz), 2.99-3.13 (5H, m), 3.68 (2H, t, J = 6.6 Hz), 3.74 (2H, t, J = 6.3 Hz), 7.06 (1H, d, J = 8.0 Hz), 7.28-7.33 (2H, m), 7.53 (2H, d, J = 7.8 Hz), 8.66 (1H, dd, J = 4.8, 1.6 Hz). |
| 119 | 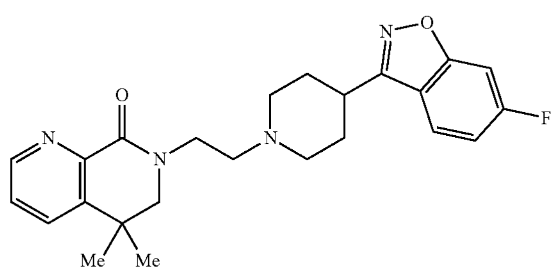 [SMILES: CC1(C)CN(CCN2CCC(c3noc4cc(F)ccc34)CC2)C(=O)c2ncccc21] | LC — MS: R.T. = 1.33 min, ObsMS = 423 [M + 1] |
| 120 | 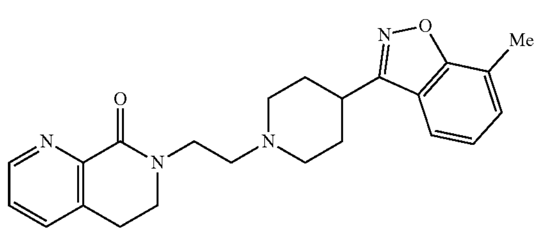 [SMILES: Cc1cccc2c(C3CCN(CCN4CCc5cccnc5C4=O)CC3)noc12] | ¹H-NMR (400 MHz, CDCl₃) δ: 1.96-2.13 (4H, m), 2.26 (2H, td, J = 11.2, 3.3 Hz), 2.55 (3H, s), 2.72 (2H, t, J = 6.3 Hz), 3.01-3.18 (5H, m), 3.72 (2H, t, J = 6.6 Hz), 3.78 (2H, t, J = 6.3 Hz), 7.17 (1H, dd, J = 7.5, 7.5 Hz), 7.27-7.37 (2H, m), 7.49-7.59 (2H, m), 8.70 (1H, dd, J = 4.6, 1.7 Hz). |
| 121 | 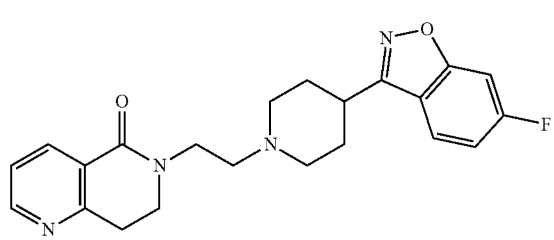 [SMILES: O=C1c2cccnc2CCN1CCN1CCC(c2noc3cc(F)ccc23)CC1] | ¹H-NMR (400 MHz, CDCl₃) δ: 1.93-2.12 (4H, m), 2.19-2.31 (2H, m), 2.68 (2H, t, J = 6.6 Hz), 2.99-3.16 (3H, m), 3.20 (2H, t, J = 7.0 Hz), 3.72 (4H, t, J = 6.6 Hz), 7.02 (1H, ddd, J = 8.8, 8.8, 2.2 Hz), 7.22 (1H, dd, J = 9.5, 2.9 Hz), 7.29 (1H, dd, J = 7.7, 4.8 Hz), 7.62 (1H, dd, J = 8.1, 5.1 Hz), 8.31 (1H, dd, J = 7.7, 1.8 Hz), 8.58 (1H, dd, J = 5.1, 1.5 Hz). |

-continued

| Example | Chemical structure | Instrumental analyses data |
|---|---|---|
| 122 | 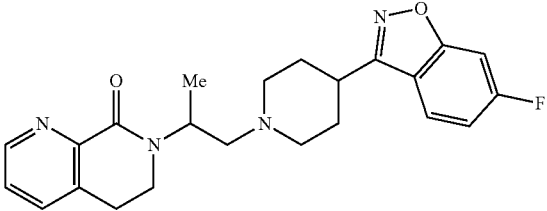 [SMILES: CC(CN1CCC(c2noc3cc(F)ccc23)CC1)N1CCc2cccnc2C1=O] | LC — MS: R.T. = 1.30 min, ObsMS = 409 [M + 1] |
| 123 | 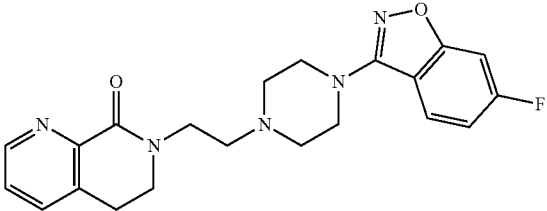 [SMILES: O=C1c2ncccc2CCN1CCN1CCN(c2noc3cc(F)ccc23)CC1] | LC — MS: R.T. = 1.38 min, ObsMS = 396 [M + 1] |
| 124 | 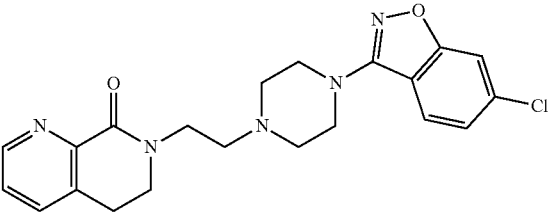 [SMILES: O=C1c2ncccc2CCN1CCN1CCN(c2noc3cc(Cl)ccc23)CC1] | LC — MS: R.T. = 1.33 min, ObsMS = 412 [M + 1] |
| 125 | 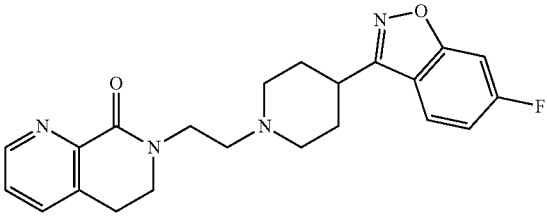 [SMILES: O=C1c2ncccc2CCN1CCN1CCC(c2noc3cc(F)ccc23)CC1] | $^1$H-NMR (400 MHz, CDCl$_3$) δ: 1.93-2.13 (4H, m), 2.20-2.32 (2H, m), 2.72 (2H, t, J = 6.3 Hz), 3.00-3.17 (5H, m), 3.71 (2H, t, J = 6.5 Hz), 3.79 (2H, t, J = 6.2 Hz), 7.05 (1H, ddd, J = 8.9, 8.9, 2.2 Hz), 7.21-7.26 1H, m), 7.34 (1H, dd, J = 7.7, 4.6 Hz), 7.55-7.59 (1H, m), 7.65 (1H, dd, J = 8.7, 5.0 Hz), 8.70 (1H, dd, J = 4.7, 1.6 Hz). |
| 126 | 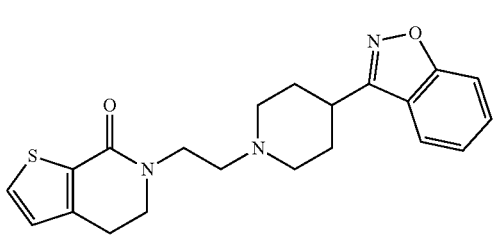 | $^1$H-NMR (400 MHz, CDCl$_3$) δ: 2.00-2.15 (4H, m), 2.22-2.31 (2H, m), 2.67 (2H, t, J = 6.7 Hz), 2.94 (2H, t, J = 7.0 Hz), 3.05-3.18 (3H, m), 3.66-3.74 (4H, m), 6.91 (1H, d, J = 5.1 Hz), 7.26-7.31 (1H, m), 7.45 (1H, d, J = 4.9 Hz), 7.50-7.58 (2H, m), 7.72 (1H, dd, J = 7.9, 0.9 Hz). |
| 127 | 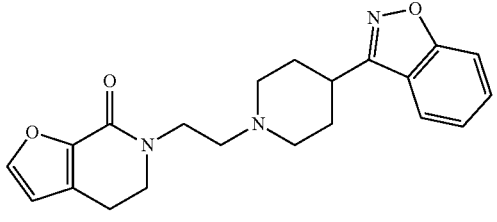 [SMILES: O=C1c2sccc2CCN1CCN1CCC(c2noc3ccccc23)CC1] | $^1$H-NMR (400 MHz, CDCl$_3$) δ: 1.98-2.10 (4H, m), 2.17-2.33 (2H, m), 2.59-2.66 (2H, m), 2.75 (2H, t, J = 6.9 Hz), 2.99-3.13 (3H, m), 3.58-3.67 (4H, m), 6.30 (1H, d, J = 1.8 Hz), 7.20-7.25 (1H, m), 7.43 (1H, d, J = 1.8 Hz), 7.44-7.51 (2H, m), 7.67 (1H, d, J = 8.3 Hz). |

-continued

| Example | Chemical structure | Instrumental analyses data |
|---|---|---|
| 128 | 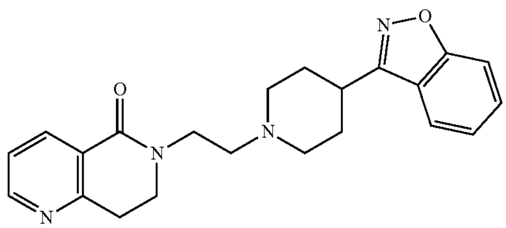 [SMILES: O=C1c2cccnc2CCN1CCN1CCC(c2noc3ccccc23)CC1] | ¹H-NMR (400 MHz, CDCl₃) δ: 2.03-2.14 (4H, m), 2.28 (2H, td, J = 11.0, 3.7 Hz), 2.69 (2H, t, J = 6.6 Hz), 3.06-3.17 (3H, m), 3.22 (2H, t, J = 6.9 Hz), 3.72-3.78 (4H, m), 7.27-7.33 (2H, m), 7.50-7.58 (2H, m), 7.71 (1H, d, J = 7.8 Hz), 8.34 (1H, dd, J = 7.8, 1.8 Hz), 8.60 (1H, dd, J = 4.8, 1.6 Hz). |
| 129 | 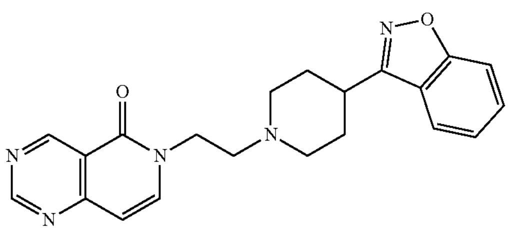 [SMILES: O=c1c2cncnc2ccn1CCN1CCC(c2noc3ccccc23)CC1] | ¹H-NMR (400 MHz, CDCl₃) δ: 1.98-2.15 (4H, m), 2.33 (2H, td, J = 11.2, 3.1 Hz), 2.79 (2H, t, J = 6.0 Hz), 3.02-3.15 (3H, m), 4.15 (2H, t, J = 6.0 Hz), 6.68 (1H, d, J = 7.3 Hz), 7.27-7.32 (1H, m), 7.51-7.59 (2H, m), 7.61 (1H, d, J = 7.3 Hz), 7.68-7.71 (1H, m), 9.35 (1H, s), 9.66 (1H, s). |
| 130 | 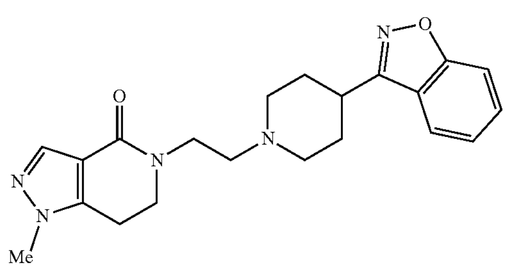 [SMILES: Cn1ncc2c1CCN(CCN1CCC(c3noc4ccccc34)CC1)C2=O] | ¹H-NMR (400 MHz, CDCl₃) δ: 2.00-2.16 (4H, m), 2.27 (2H, td, J = 11.6, 3.4 Hz), 2.65 (2H, t, J = 6.6 Hz), 2.93 (2H, t, J = 7.0 Hz), 3.04-3.16 (3H, m), 3.66 (2H, t, J = 6.6 Hz), 3.74 (2H, t, J = 7.0 Hz), 3.82 (3H, s), 7.27-7.32 (1H, m), 7.50-7.59 (2H, m), 7.72 (1H, d, J = 8.1 Hz), 7.85 (1H, s). |
| 131 | 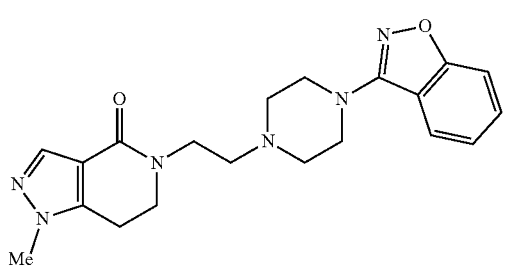 | ¹H-NMR (400 MHz, CDCl₃) δ: 2.66 (2H, t, J = 6.2 Hz), 2.73 (4H, t, J = 4.8 Hz), 2.92 (2H, t, J = 6.6 Hz), 3.56 (4H, t, J = 5.1 Hz), 3.64-3.75 (4H, m), 3.81 (3H, s), 7.18-7.25 (1H, m), 7.42-7.52 (2H, m), 7.69 (1H, d, J = 8.1 Hz), 7.84 (1H, s). |
| 132 | 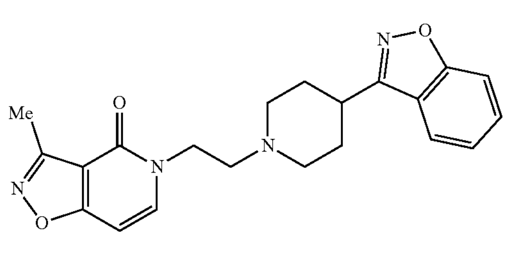 [SMILES: Cc1noc2ccn(CCN3CCC(c4noc5ccccc45)CC3)c(=O)c12] | ¹H-NMR (400 MHz, CDCl₃) δ: 2.06-2.22 (4H, m), 2.38-2.50 (2H, m), 2.65 (3H, s), 2.83 (2H, t, J = 6.2 Hz), 3.07-3.22 (3H, m), 4.20 (2H, t, J = 6.2 Hz), 6.54 (1H, d, J = 7.3 Hz), 7.29-7.33 (1H, m), 7.51 (1H, d, J = 7.3 Hz), 7.53-7.60 (2H, m), 7.72 (1H, d, J = 7.8 Hz). |

-continued

| Example | Chemical structure | Instrumental analyses data |
|---|---|---|
| 133 | 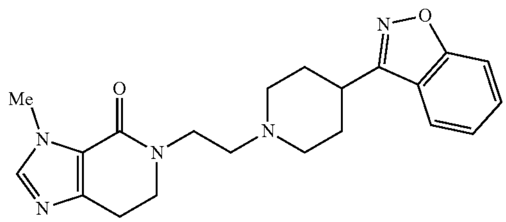 | ¹H-NMR (400 MHz, CDCl₃) δ: 2.03-2.14 (2H, m), 2.20-2.34 (2H, m), 2.59-2.68 (2H, m), 2.87-2.99 (4H, m), 3.04-3.22 (2H, m), 3.55-3.77 (5H, m), 3.92 (3H, s), 7.27-7.32 (1H, m), 7.39-7.46 (2H, m), 7.49-7.59 (1H, m), 7.72 (1H, d, J = 7.9 Hz). |
| 134 | 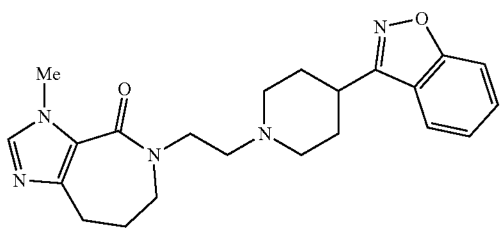 [SMILES: Cn1cnc2c1C(=O)N(CCN1CCC(c3noc4ccccc34)CC1)CCC2] | ¹H-NMR (400 MHz, CDCl₃) δ: 2.04-2.15 (4H, m), 2.23-2.35 (2H, m), 2.59-2.67 (2H, m), 2.97 (2H, t, J = 7.2 Hz), 3.04-3.17 (3H, m), 3.50 (2H, t, J = 7.9 Hz), 3.65 (2H, t, J = 5.5 Hz), 3.70 (2H, t, J = 6.8 Hz), 3.87 (3H, s), 7.28-7.32 (1H, m), 7.42-7.46 (1H, m), 7.51-7.59 (2H, m), 7.71-7.76 (1H, m). |
| 135 | 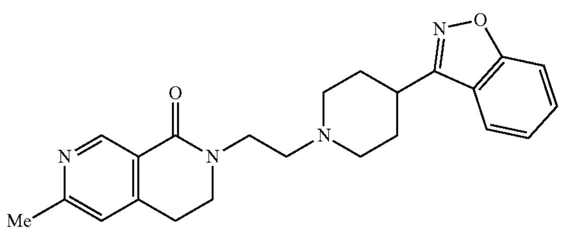 | ¹H-NMR (400 MHz, CDCl₃) δ: 1.99-2.16 (4H, m), 2.23-2.32 (2H, m), 2.59 (3H, s), 2.69 (2H, t, J = 6.6 Hz), 2.97 (2H, t, 6.4 Hz), 3.05-3.16 H, m), 3.67 (2H, t, J = 6.6 Hz), 3.73 (2H, t, J = 6.6 Hz), 7.00 (1H, s), 7.27-7.31 (1H, m), 7.50-7.59 (2H, m), 7.71 (1H, d, J = 7.8 Hz), 9.09 (1H, s). |
| 136 | 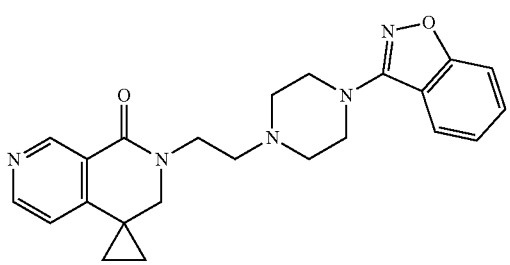 [SMILES: O=C1c2cnccc2C2(CC2)CN1CCN1CCN(c2noc3ccccc23)CC1] | ¹H-NMR (400 MHz, CDCl₃) δ: 1.06-1.16 (4H, m), 2.66-2.74 (6H, m), 3.47 (2H, s), 3.53 (4H, t, J = 5.0 Hz), 3.70 (2H, t, J = 6.2 Hz), 6.71 (1H, d, J = 5.5 Hz), 7.17-7.23 (1H, m), 7.41-7.49 (2H, m), 7.66 (1H, d, J = 8.3 Hz), 8.56 (1H, d, J = 5.5 Hz), 9.19 (1H, s). |
| 137 | 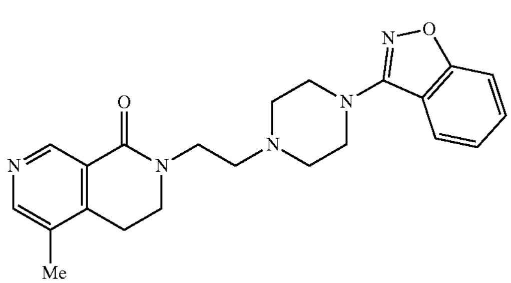 [SMILES: Cc1cncc2c1CCN(CCN1CCC(c3noc4ccccc34)CC1)C2=O] | ¹H-NMR (400 MHz, CDCl₃) δ: 2.22 (3H, s), 2.62-2.71 (6H, m), 2.87 (2H, t, J = 6.4 Hz), 3.49 (4H, t, J = 5.2 Hz), 3.60 (2H, t, J = 6.7 Hz), 3.67 (2H, t, J = 6.4 Hz), 7.12-7.17 (1H, m), 7.35-7.44 (2H, m), 7.61 (1H, d, J = 7.9 Hz), 8.40 (1H, s), 9.00 (1H, s). |

| Example | Chemical structure | Instrumental analyses data |
|---|---|---|
| 138 | (structure) | $^1$H-NMR (400 MHz, CDCl$_3$) δ: 1.91-2.09 (4H, m), 2.16-2.26 (5H, m), 2.63 (2H, t, J = 6.4 Hz), 2.87 (2H, t, J = 6.7 Hz), 2.97-3.10 (3H, m), 3.59-3.69 (4H, m), 7.19-7.25 (1H, m), 7.43-7.51 (2H, m), 7.64 (1H, d, J = 7.9 Hz), 8.41 (1H, s), 9.01 (1H, s). |
| 139 | (structure) | $^1$H-NMR (400 MHz, CDCl$_3$) δ: 1.92-2.08 (4H, m), 2.16-2.26 (2H, m), 2.58-2.65 (5H, m), 2.80 (3H, s), 2.98-3.09 (5H, m), 3.60 (2H, t, J = 6.7 Hz), 3.64 (2H, t, J = 6.4 Hz), 7.20-7.24 (1H, m), 7.43-7.52 (2H, m), 7.63 (1H, d, J = 7.9 Hz). |

Examples 140 to 152

According to the method of Example 22, the compounds of Examples 140 to 152 were prepared from the corresponding Reference example compounds.

| Example | Chemical structure | Instrumental analyses data |
|---|---|---|
| 140 | (structure) | $^1$H-NMR (300 MHz, CDCl$_3$) δ: 1.95-2.14 (4H, m), 2.21-2.32 (2H, m), 2.72 (2H, t, J = 6.3 Hz), 3.01-3.18 (5H, m), 3.71 (2H, t, J = 6.6 Hz), 3.79 (2H, t, J = 6.4 Hz), 7.18-7.26 (2H, m), 7.34 (1H, dd, J = 7.6, 4.7 Hz), 7.45-7.50 (1H, m), 7.57 (1H, dd, J = 7.8, 1.2 Hz), 8.70 (1H, dd, J = 4.8, 1.7 Hz). |
| 141 | (structure) | $^1$H-NMR (300 MHz, CDCl$_3$) δ: 1.90-2.16 (4H, m), 2.20-2.32 (2H, m), 2.72 (2H, t, J = 6.2 Hz), 3.00-3.22 (5H, m), 3.69-3.81 (4H, m), 6.94 (1H, dd, J = 9.4, 7.6 Hz), 7.30-7.37 (2H, m), 7.44-7.53 (1H, m), 7.54-7.59 (1H, m), 8.70 (1H, dd, J = 4.7, 1.7 Hz). |
| 142 | (structure) | $^1$H-NMR (300 MHz, CDCl$_3$) δ: 1.88-2.09 (4H, m), 2.16-2.28 (2H, m), 2.67 (2H, t, J = 6.2 Hz), 2.91-3.02 (3H, m), 3.02-3.11 (2H, m), 3.65 (2H, t, J = 6.6 Hz), 3.73 (2H, t, J = 6.2 Hz), 3.80 (3H, s), 6.96 (1H, d, J = 2.2 Hz), 7.09 (1H, dd, J = 8.8, 2.2 Hz), 7.27 (1H, dd, J = 7.7, 4.8 Hz), 7.38 (1H, d, J = 9.5 Hz), 7.50 (1H, dd, J = 8.1, 1.5 Hz), 8.63 (1H, dd, J = 5.1, 1.5 Hz). |

-continued

| Example | Chemical structure | Instrumental analyses data |
|---|---|---|
| 143 | 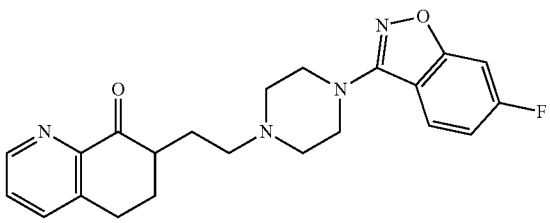 [SMILES: O=C1c2ncccc2CCC1CCN1CCN(c2noc3cc(F)ccc23)CC1] | LC - MS : R.T. = 1.15 min, ObsMS = 395 [M + 1] |
| 144 | 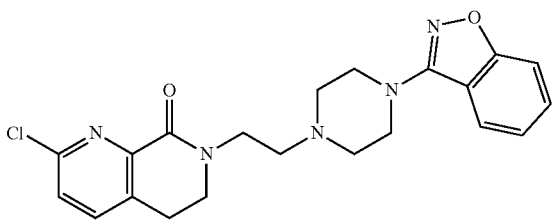 [SMILES: O=C1c2nc(Cl)ccc2CCN1CCN1CCN(c2noc3ccccc23)CC1] | $^1$H-NMR (400 MHz, CDCl$_3$) δ: 2.70-2.90 (6H, m), 3.04 (2H, t, J = 5.7 Hz), 3.55-3.65 (4H, m), 3.70 (2H, t, J = 6.4 Hz), 3.78-3.85 (2H, m), 7.19-7.23 (1H, m), 7.36 (1H, d, J = 8.3 Hz), 7.42-7.48 (2H, m), 7.52 (1H, d, J = 8.3 Hz), 7.65 (1H, d, J = 8.3 Hz). |
| 145 | 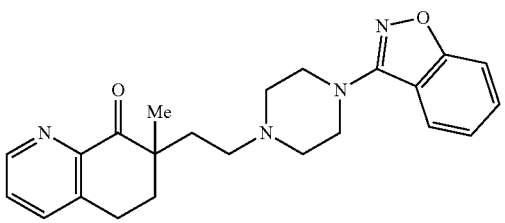 [SMILES: CC1(CCN2CCN(c3noc4ccccc34)CC2)CCc2cccnc2C1=O] | $^1$H-NMR (400 MHz, CDCl$_3$) δ: 1.22 (3H, s), 1.68-1.77 (1H, m), 1.89-1.97 (1H, m), 2.01-2.16 (2H, m), 2.33-2.46 (2H, m), 2.47-2.62 (4H, m), 2.98 (2H, t, J = 6.4 Hz), 3.31-3.50 (4H, m), 7.11-7.16 (1H, m), 7.29 (1H, dd, J = 8.0, 4.4 Hz), 7.34-7.43 (2H, m), 7.55 (1H, dd, J = 7.8, 0.9 Hz), 7.60 (1H, d, J = 8.3 Hz), 8.63 (1H, dd, J = 4.1, 1.4 Hz). |
| 146 | 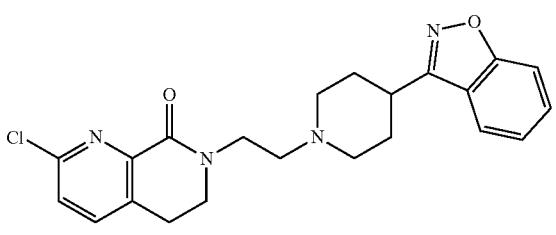 | $^1$H-NMR (400 MHz, CDCl$_3$) δ: 2.01-2.19 (4H, m), 2.23-2.45 (1H, m), 2.71-2.85 (2H, m), 3.03 (2H, t, J = 6.6 Hz), 3.10-3.23 (4H, m), 3.72 (2H, t, J = 6.6 Hz), 3.77-3.87 (2H, m), 7.26-7.31 (1H, m), 7.36 (1H, d, J = 8.3 Hz), 7.49-7.57 (3H, m), 7.72 (1H, d, J = 7.8 Hz). |
| 147 | 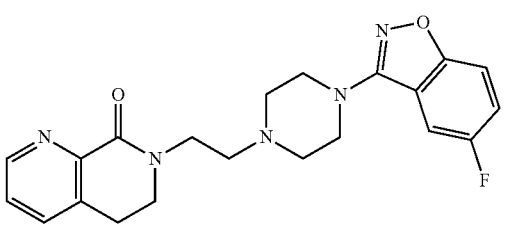 | $^1$H-NMR (400 MHz, CDCl$_3$) δ: 2.68-2.75 (6H, m), 3.03 (2H, t, J = 6.5 Hz), 3.44-3.53 (4H, m), 3.68 (2H, t, J = 6.6 Hz), 3.78 (2H, t, J = 6.3 Hz), 7.18-7.24 (1H, m), 7.28-7.34 (2H, m), 7.37 (1H, dd, J = 9.0, 4.1 Hz), 7.52-7.56 (1H, m), 8.68 (1H, dd, J = 5.0, 1.1 Hz). |
| 148 | 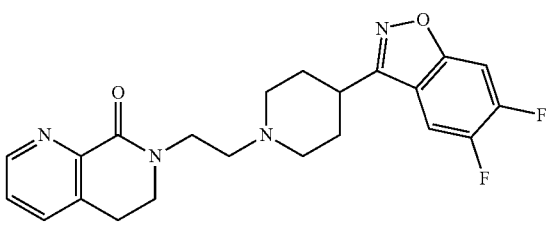 [SMILES: O=C1c2ncccc2CCN1CCN1CCC(c2noc3cc(F)c(F)cc23)CC1] | $^1$H-NMR (400 MHz, CDCl$_3$) δ: 1.88-2.01 (2H, m), 2.03-2.11 (2H, m), 2.18-2.27 (2H, m), 2.69 (2H, t, J = 6.2 Hz), 3.03 (2H, t, J = 6.6 Hz), 3.05-3.16 (3H, m), 3.70 (2H, t, J = 6.6 Hz), 3.75 (2H, t, J = 6.2 Hz), 6.85 (1H, ddd, J = 8.8, 8.8, 2.5 Hz), 7.17 (1H, ddd, J = 9.1, 9.1, 3.6 Hz), 7.31 (1H, dd, J = 7.6, 4.6 Hz), 7.52-7.56 (1H, m), 8.67 (1H, dd, J = 5.0, 1.1 Hz). |

-continued

| Example | Chemical structure | Instrumental analyses data |
|---|---|---|
| 149 | 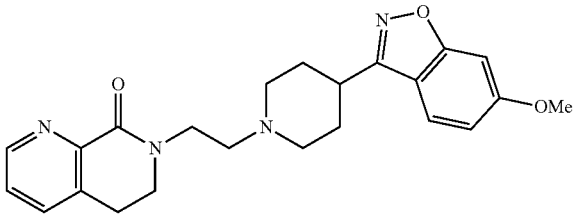 [SMILES: COc1ccc2c(C3CCN(CCN4CCc5cccnc5C4=O)CC3)noc2c1] | ¹H-NMR (400 MHz, CDCl₃) δ: 1.93-2.09 (4H, m), 2.18-t, J = 6.3 Hz), 2.95-3.06 (3H, m), 3.06-3.13 (2H, m), 3.69 (2H, t, J = 6.6 Hz), 3.76 (2H, t, J = 6.3 Hz), 3.86 (3H, s), 6.86 6.96 (1H, d, J = 2.2 Hz), 7.31 (1H, dd, J = 7.7, 4.8 Hz), 7.51 (1H, d, J = 8.8 Hz), 7.53-7.57 (1H, m), 8.68 (1H, dd, J = 5.0, 1.3 Hz). |
| 150 | 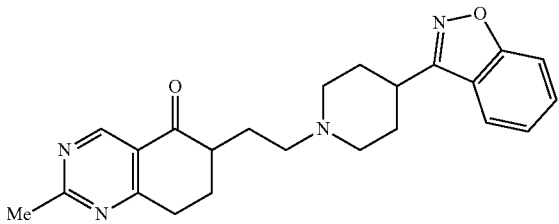 [SMILES: Cc1ncc2c(n1)CCC(CCN1CCC(c3noc4ccccc34)CC1)C2=O] | ¹H-NMR (400 MHz, CDCl₃) δ: 1.58-1.70 (1H, m), 1.82-1.94 (1H, m), 1.94-2.05 (4H, m), 2.09-2.23 (3H, m), 2.23-2.32 (1H, m), 2.49 (2H, t, J = 6.8 Hz), 2.55-2.65 (1H, m), 2.71 (3H, s), 2.96-3.08 (5H, m), 7.20-7.24 (1H, m), 7.43-7.51 (2H, m), 7.65 (1H, dd, J = 8.0, 1.0 Hz), 9.05 (1H, s). |
| 151 | 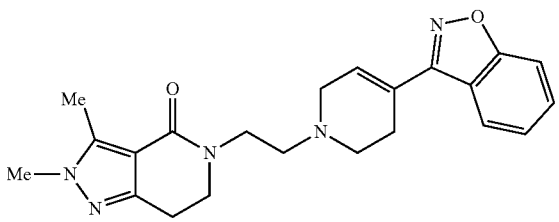 [SMILES: Cc1c2c(nn1C)CCN(CCN1CC=C(c3noc4ccccc34)CC1)C2=O] | ¹H-NMR (400 MHz, CD₃OD) δ: 2.50 (3H, s), 2.73-2.82 (4H, m), 2.85-2.92 (4H, m), 3.40-3.44 (2H, m), 3.66-3.77 (7H, m), 6.82-6.87 (1H, m), 7.37-7.42 (1H, m), 7.58-7.65 (2H, m), 8.01 (1H, d, J = 7.8 Hz). |
| 152 | 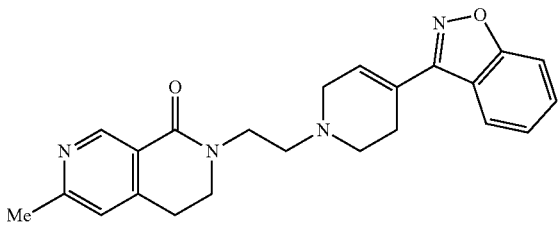 | ¹H-NMR (400 MHz, CD₃OD) δ: 2.55 (3H, s), 2.75-2.86 (4H, m), 2.91 (2H, t, J = 5.7 Hz), 3.06 (2H, t, J = 6.6 Hz), 3.41-3.46 (2H, m), 3.72 (2H, t, J = 6.6 Hz), 3.82 (2H, t, J = 6.6 Hz), 6.82-6.87 (1H, m), 7.23 (1H, s), 7.36-7.42 (1H, m), 7.58-7.65 (2H, m), 8.01 (1H, d, J = 8.2 Hz), 8.86 (1H, s). |

Example 153

6-{2-[4-(1,2-Benzoisoxazol-3-yl)piperazin-1-yl]ethyl}-7,8-dihydro-1,6-naphthyridin-5(6H)-one

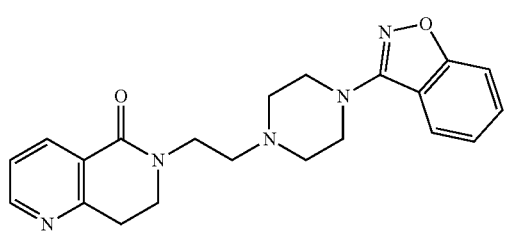

According to the method of Example 32, the titled compound was prepared from the corresponding Reference examples.

LC-MS: R.T.=1.22 min, ObsMS=379 [M+1]

Examples 154 to 175

According to the method of Example 37, the compounds of Examples 154 to 175 were prepared from the corresponding Reference example compounds.

| Example | Chemical structure | Instrumental analyses data |
|---|---|---|
| 154 | 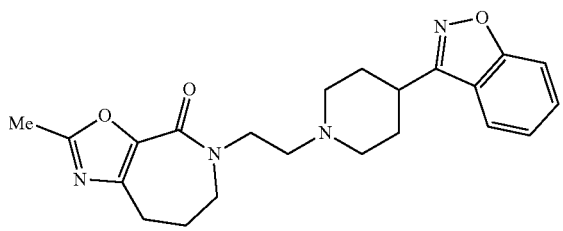 [SMILES: Cc1nc2c(o1)C(=O)N(CCN1CCC(c3noc4ccccc34)CC1)CCC2] | ¹H-NMR (400 MHz, CDCl₃) δ: 1.92-2.10 (6H, m), 2.15-2.24 (2H, m), 2.43 (3H, s), 2.56 (2H, t, J = 6.5 Hz), 2.76 (2H, t, J = 6.7 Hz), 2.98-3.07 (3H, m), 3.46 (2H, t, J = 6.5 Hz), 7.20-7.24 (1H, m), 7.43-7.51 (2H, m), 7.62-7.66 (1H, m). |
| 155 | 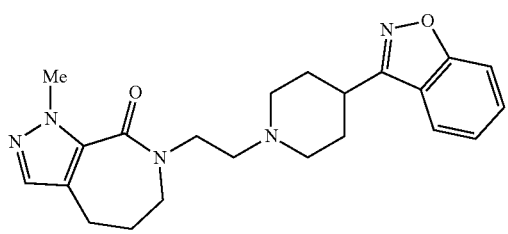 | ¹H-NMR (400 MHz, CDCl₃) δ: 2.01-2.16 (6H, m), 2.23-2.34 (2H, m), 2.66 (2H, t, J = 6.7 Hz), 2.78 (2H, t, J = 7.4 Hz), 3.06-3.18 (3H, m), 3.42 (2H, t, J = 5.6 Hz), 3.72 (2H, t, J = 6.7 Hz), 4.10 (3H, s), 7.27-7.32 (2H, m), 7.50-7.59 (2H, m), 7.71 (1H, d, J = 8.0 Hz). |
| 156 | 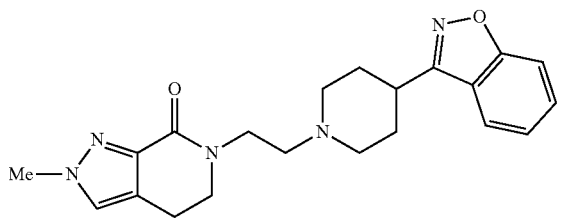 [SMILES: Cn1cc2c(n1)C(=O)N(CCN1CCC(c3noc4ccccc34)CC1)CC2] | ¹H-NMR (400 MHz, CDCl₃) δ: 1.99-2.14 (4H, m), 2.21-2.31 (2H, m), 2.67 (2H, t, J = 6.5 Hz), 2.82 (2H, t, J = 6.6 Hz), 3.04-3.16 (3H, m), 3.67 (2H, t, J = 6.6 Hz), 3.71 (2H, t, J = 6.5 Hz), 3.95 (3H, s) 7.17 (1H, s), 7.29 (1H, d, J = 7.8 Hz), 7.50-7.58 (2H, m), 7.72 (1H, d, J = 7.8 Hz). |
| 157 | 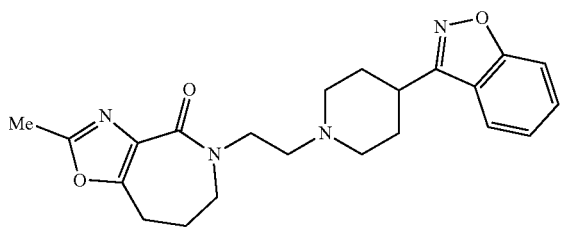 [SMILES: Cc1nc2c(o1)CCCN(CCN1CCC(c3noc4ccccc34)CC1)C2=O] | ¹H-NMR (400 MHz, CDCl₃) δ: 1.91-2.13 (6H, m), 2.14-2.24 (2H, m), 2.38 (3H, s), 2.57 (2H, t, J = 6.5 Hz), 2.84 (2H, t, J = 7.1 Hz), 2.96-3.09 (3H, m), 3.46 (2H, t, J = 4.6 Hz), 3.65 (2H, t, J = 6.3 Hz), 7.20-7.24 (1H, m), 7.43-7.51 (2H, m), 7.63-7.67 (1H, m). |
| 158 | 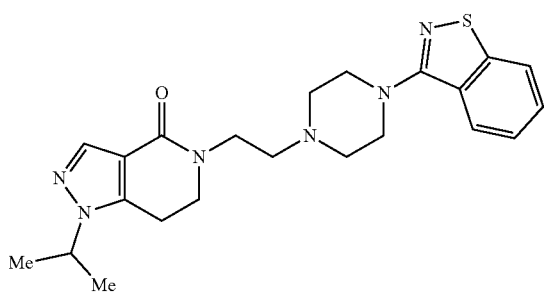 [SMILES: CC(C)n1ncc2c1CCN(CCN1CCN(c3nsc4ccccc34)CC1)C2=O] | ¹H-NMR (400 MHz, CDCl₃) δ: 1.51 (6H, d, J = 6.9 Hz), 2.68 (2H, t, J = 6.6 Hz), 2.76 (4H, t, J = 4.8 Hz), 2.94 (2H, t, J = 6.9 Hz), 3.54 (4H, t, J = 5.0 Hz), 3.68 (2H, t, J = 6.4 Hz), 3.73 (2H, t, J = 6.9 Hz), 4.35-4.44 (1H, m), 7.34-7.39 (1H, m), 7.45-7.50 (1H, m), 7.81 (1H, d, J = 8.3 Hz), 7.88 (1H, s), 7.91 (1H, d, J = 8.3 Hz). |
| 159 | 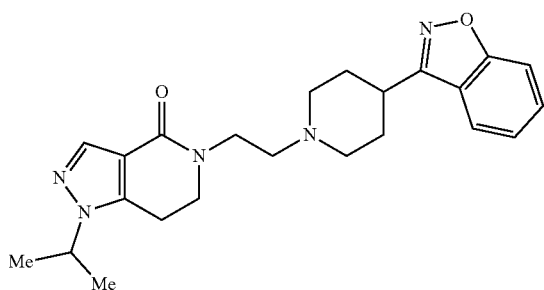 [SMILES: CC(C)n1ncc2c1CCN(CCN1CCC(c3noc4ccccc34)CC1)C2=O] | ¹H-NMR (400 MHz, CDCl₃) δ: 1.52 (6H, d, J = 6.9 Hz), 2.00-2.14 (4H, m), 2.22-2.30 (2H, m), 2.64 (2H, t, J = 6.6 Hz), 2.95 (2H, t, J = 6.9 Hz), 3.05-3.17 (3H, m), 3.66 (2H, t, J = 6.4 Hz), 3.73 (2H, t, J = 6.9 Hz), 4.36-4.46 (1H, m), 7.27-7.32 (1H, m), 7.51-7.58 (2H, m), 7.71-7.75 (1H, m), 7.88 (1H, s). |

| Example | Chemical structure | Instrumental analyses data |
|---|---|---|
| 160 | 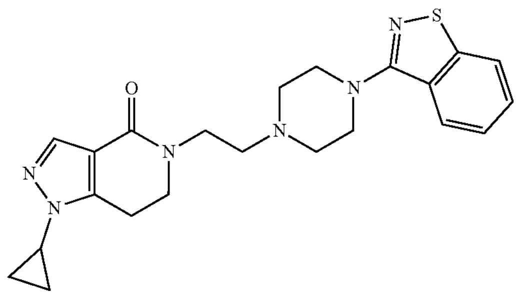 | ¹H-NMR (400 MHz, CDCl₃) δ: 1.03-1.20 (4H, m), 2.68 (2H, t, J = 6.6 Hz), 2.76 (4H, t, J = 4.8 Hz), 3.02 (2H, t, J = 6.9 Hz), 3.36-3.43 (1H, m), 3.54 (4H, t, J = 5.0 Hz), 3.67 (2H, t, J = 6.4 Hz), 3.73 (2H, t, J = 6.9 Hz), 7.34-7.38 (1H, m), 7.45-7.49 (1H, m), 7.79 (1H, s), 7.80-7.83 (1H, m), 7.89-7.92 (1H, m). |
| 161 | 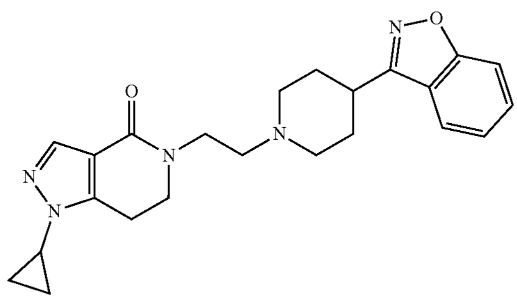 [SMILES: O=C1c2cnn(C3CC3)c2CCN1CCN1CCC(c2noc3ccccc23)CC1] | ¹H-NMR (400 MHz, CDCl₃) δ: 1.04-1.21 (4H, m), 2.02-2.14 (4H, m), 2.22-2.31 (2H, m), 2.64 (2H, t, J = 6.4 Hz), 3.03 (2H, t, J = 6.9 Hz), 3.06-3.16 (3H, m), 3.37-3.43 (1H, m), 3.66 (2H, t, J = 6.6 Hz), 3.73 (2H, t, J = 6.9 Hz), 7.27-7.31 (1H, m), 7.51-7.58 (2H, m), 7.71-7.74 (1H, m), 7.80 (1H, s). |
| 162 | 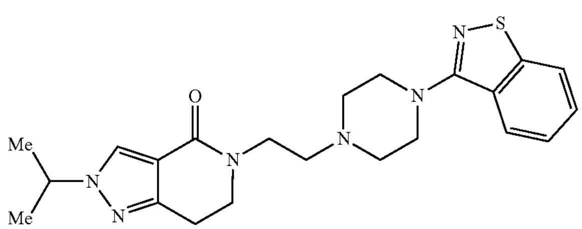 [SMILES: CC(C)n1cc2c(n1)CCN(CCN1CCN(c3nsc4ccccc34)CC1)C2=O] | ¹H-NMR (400 MHz, CDCl₃) δ: 1.51 (6H, d, J = 6.9 Hz), 2.68 (2H, t, J = 6.6 Hz), 2.76 (4H, t, J = 4.8 Hz), 2.96 (2H, t, J = 6.6 Hz), 3.54 (4H, t, J = 4.8 Hz), 3.69 (4H, t, J = 6.6 Hz), 4.42-4.51 (1H, m), 7.35 (1H, dd, J = 7.6, 7.6 Hz), 7.46 (1H, dd, J = 7.6, 7.6 Hz), 7.81 (1H, d, J = 8.3 Hz), 7.83 (1H, s), 7.90 (1H, d, J = 8.3 Hz). |
| 163 | 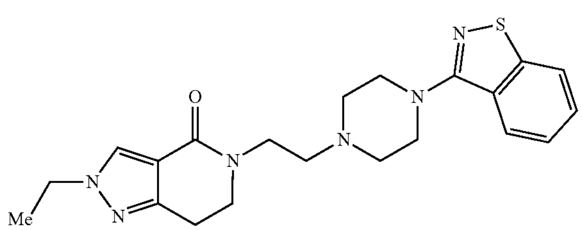 [SMILES: CCn1cc2c(n1)CCN(CCN1CCN(c3nsc4ccccc34)CC1)C2=O] | ¹H-NMR (400 MHz, CDCl₃) δ: 1.50 (3H, t, J = 7.3 Hz), 2.68 (2H, t, J = 6.6 Hz), 2.77 (4H, t, J = 4.8 Hz), 2.95 (2H, t, J = 6.9 Hz), 3.54 (4H, t, J = 4.8 Hz), 3.69 (4H, t, J = 6.6 Hz), 4.16 (2H, q, J = 7.3 Hz), 7.33-7.38 (1H, m), 7.44-7.49 (1H, m), 7.78-7.83 (2H, m), 7.89-7.92 (1H, m). |
| 164 | 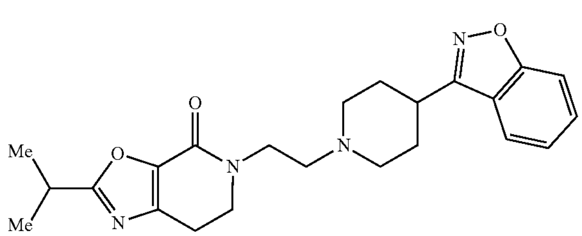 [SMILES: CC(C)c1nc2c(o1)C(=O)N(CCN1CCC(c3noc4ccccc34)CC1)CC2] | ¹H-NMR (400 MHz, CDCl₃) δ: 1.39 (6H, d, J = 6.9 Hz), 2.00-2.14 (4H, m), 2.21-2.31 (2H, m), 2.64 (2H, t, J = 6.4 Hz), 2.91 (2H, t, J = 7.1 Hz), 3.04-3.22 (4H, m), 3.65 (2H, t, J = 6.4 Hz), 3.75 (2H, t, J = 7.1 Hz), 7.26-7.31 (1H, m), 7.51-7.59 (2H, m), 7.72 (1H, d, J = 8.3 Hz). |

| Example | Chemical structure | Instrumental analyses data |
|---|---|---|
| 165 | 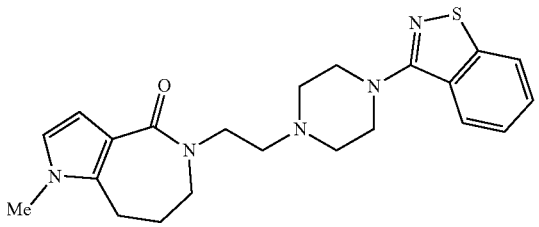 [SMILES: Cn1ccc2c1CCCN(CCN1CCN(c3nsc4ccccc34)CC1)C2=O] | $^1$H-NMR (400 MHz, CDCl$_3$) δ: 2.12-2.20 (2H, m), 2.68 (2H, t, J = 6.9 Hz), 2.74-2.81 (6H, m), 3.47-3.52 (5H, m), 3.54 (4H, t, J = 4.8 Hz), 3.72 (2H, t, J = 6.6 Hz), 6.56 (1H, d, J = 2.8 Hz), 6.68 (1H, d, J = 3.2 Hz), 7.35 (1H, dd, J = 7.1 Hz), 7.47 (1H, dd, J = 7.6, 7.6 Hz), 7.80 (1H, d, J = 8.3 Hz), 7.90 (1H, d, J = 8.3 Hz). |
| 166 | 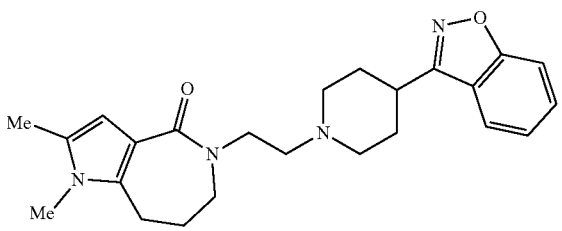 [SMILES: Cc1cc2c(n1C)CCCN(CCN1CCC(c3noc4ccccc34)CC1)C2=O] | $^1$H-NMR (400 MHz, CDCl$_3$) δ: 2.03-2.18 (6H, m), 2.20 (3H, s), 2.22-2.32 (2H, m), 2.58-2.68 (2H, m), 2.77 (2H, t, J = 6.9 Hz), 3.03-3.16 (3H, m), 3.36 (3H, s), 3.48 (2H, t, J = 4.6 Hz), 3.71 (2H, t, J = 6.6 Hz), 6.43 (1H, d, J = 0.9 Hz), 7.27-7.31 (1H, m), 7.50-7.58 (2H, m), 7.74 (1H, d, J = 7.8 Hz). |
| 167 | 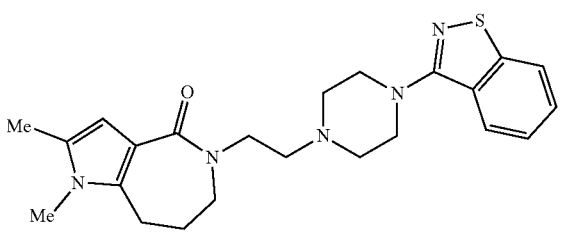 [SMILES: Cc1cc2c(n1C)CCCN(CCN1CCN(c3nsc4ccccc34)CC1)C2=O] | $^1$H-NMR (400 MHz, CDCl$_3$) δ: 2.11-2.19 (2H, m), 2.20 (3H, s), 2.67 (2H, t, J = 6.6 Hz), 2.73-2.80 (6H, m), 3.36 (3H, s), 3.48 (2H, t, J = 4.4 Hz), 3.51-3.57 (4H, m), 3.72 (2H, t, J = 6.9 Hz), 6.42 (1H, s), 7.35 (1H, dd, J = 7.6, 7.6 Hz), 7.46 (1H, dd, J = 7.6, 7.6 Hz), 7.80 (1H, d, J = 8.3 Hz), 7.90 (1H, d, J = 8.3 Hz). |
| 168 | 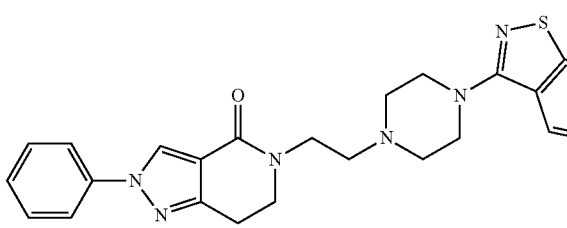 | $^1$H-NMR (400 MHz, CDCl$_3$) δ: 2.71 (2H, t, J = 6.6 Hz), 2.78 (4H, t, J = 5.0 Hz), 3.06 (2H, t, J = 6.6 Hz), 3.55 (4H, t, J = 4.8 Hz), 3.70-3.79 (4H, m), 7.30-7.38 (2H, m), 7.44-7.50 (3H, m), 7.65-7.69 (2H, m), 7.81 (1H, d, J = 7.8 Hz), 7.91 (1H, d, J = 8.3 Hz), 8.31 (1H, s). |
| 169 | 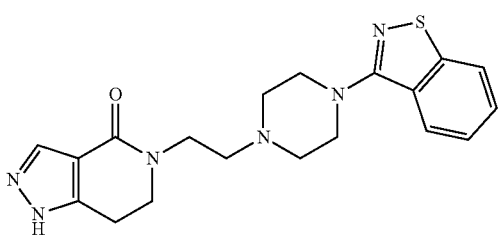 | $^1$H-NMR (400 MHz, CDCl$_3$) δ: 2.73 (4H, t, J = 4.8 Hz), 2.87-2.97 (4H, m), 3.51-3.64 (6H, m), 4.28 (2H, t, J = 6.4 Hz), 5.84 (1H, s), 7.33-7.38 (1H, m), 7.44-7.49 (1H, m), 7.81 (1H, d, J = 7.8 Hz), 7.89 (1H, d, J = 8.3 Hz), 7.94 (1H, s). |
| 170 | 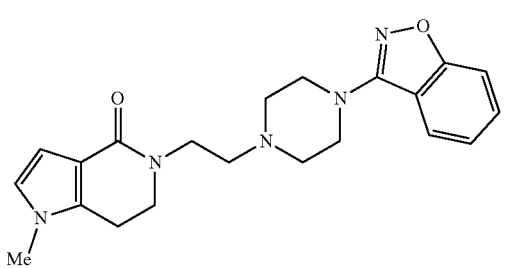 [SMILES: Cn1ccc2c1CCN(CCN1CCN(c3noc4ccccc34)CC1)C2=O] | $^1$H-NMR (400 MHz, CDCl$_3$) δ: 2.66 (2H, t, J = 6.6 Hz), 2.73 (4H, t, J = 5.0 Hz), 2.83 (2H, t, J = 6.9 Hz), 3.52-3.59 (7H, m), 3.63-3.71 (4H, m), 6.50-6.55 (2H, m), 7.18-7.25 (1H, m), 7.42-7.53 (2H, m), 7.69 (1H, d, J = 7.8 Hz). |

| Example | Chemical structure | Instrumental analyses data |
|---|---|---|
| 171 | 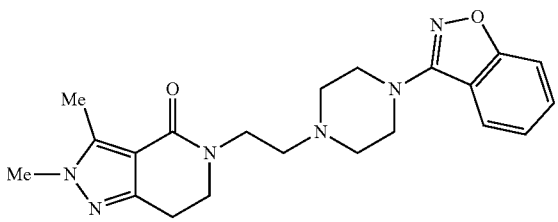 | ¹H-NMR (400 MHz, CDCl₃) δ: 2.51 (3H, s), 2.63 (2H, t, J = 6.7 Hz), 2.71 (4H, t, J = 5.2 Hz), 2.87 (2H, t, J = 6.7 Hz), 3.54 (4H, t, J = 5.2 Hz), 3.58-3.67 (4H, m), 3.73 (3H, s), 7.16-7.22 (1H, m), 7.40-7.49 (2H, m), 7.66 (1H, d, J = 7.9 Hz). |
| 172 | 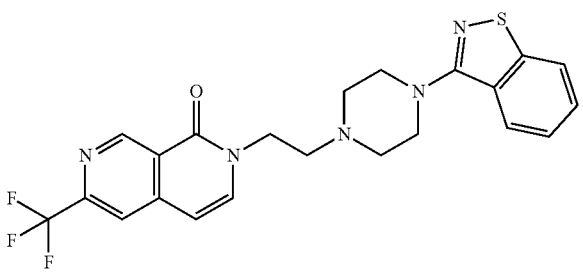 | ¹H-NMR (400 MHz, CDCl₃) δ: 2.76 (4H, t, J = 4.8 Hz), 2.85 (2H, t, J = 6.0 Hz), 3.52 (4H, t, J = 4.8 Hz), 4.18 (2H, t, J = 6.0 Hz), 6.52 (1H, d, J = 7.3 Hz), 7.33-7.38 (1H, m), 7.44-7.50 (2H, m), 7.75 (1H, s), 7.81 (1H, d, J = 7.3 Hz), 7.88 (1H, d, J = 8.3 Hz), 9.67 (1H, s). |
| 173 | 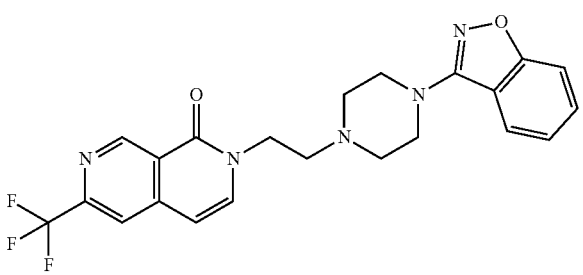 [SMILES: O=c1c2cnc(C(F)(F)F)cc2ccn1CCN1CCN(c2nsc3ccccc23)CC1] | ¹H-NMR (400 MHz, CDCl₃) δ: 2.74 (4H, t, J = 4.8 Hz), 2.83 (2H, t, J = 6.2 Hz), 3.54 (4H, t, J = 5.0 Hz), 4.18 (2H, t, J = 6.2 Hz), 6.52 (1H, d, J = 7.3 Hz), 7.19-7.24 (1H, m), 7.42-7.51 (3H, m), 7.66 (1H, d, J = 8.3 Hz), 7.75 (1H, s), 9.67 (1H, s). |
| 174 | 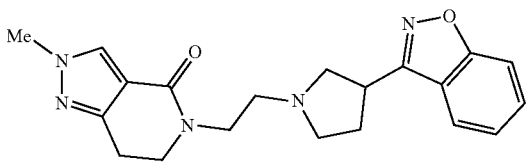 [SMILES: Cn1cc2c(n1)CCN(CCN1CCC(c3noc4ccccc34)C1)C2=O] | ¹H-NMR (400 MHz, CDCl₃) δ: 2.14-2.26 (1H, m), 2.33-2.43 (1H, m), 2.71-2.80 (3H, m), 2.92 (2H, t, J = 6.9 Hz), 2.95-3.09 (3H, m), 3.55-3.67 (3H, m), 3.74-3.86 (2H, m), 3.89 (3H, s), 7.08-7.13 (1H, m), 7.45-7.53 (2H, m), 7.72 (1H, s), 7.81 (1H, d, J = 8.3 Hz). |
| 175 | 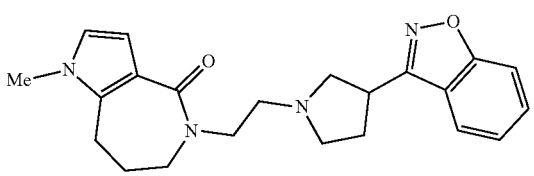 [SMILES: Cn1ccc2c1CCCN(CCN1CCC(c3noc4ccccc34)C1)C2=O] | ¹H-NMR (400 MHz, CDCl₃) δ: 2.05-2.14 (2H, m), 2.18-2.29 (1H, m), 2.35-2.46 (1H, m), 2.71-2.85 (4H, m), 2.96-3.04 (2H, m), 3.09-3.15 (1H, m), 3.45-3.49 (2H, m), 3.50 (3H, s), 3.58-3.68 (2H, m), 3.79-3.91 (2H, m), 6.57 (1H, d, J = 2.8 Hz), 6.69 (1H, d, J = 2.8 Hz), 7.11-7.16 (1H, m), 7.46-7.55 (2H, m), 7.83 (1H, d, J = 8.3 Hz). |

Examples 176 to 179

According to the method of Example 88, the compounds of Examples 176 to 179 were prepared from the corresponding Reference example compounds.

| Example | Chemical structure | Instrumental analyses data |
|---|---|---|
| 176 | 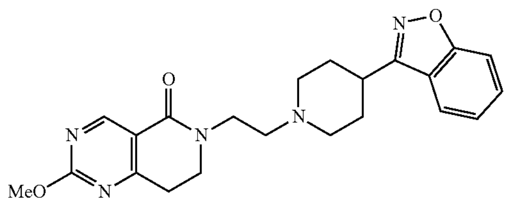 [SMILES: COc1ncc2c(n1)CCN(CCN1CCC(c3noc4ccccc34)CC1)C2=O] | $^1$H-NMR (400 MHz, CDCl$_3$) δ: 1.99-2.15 (4H, m), 2.28 (2H, t, J = 10.5 Hz), 2.68 (2H, t, J = 7.1 Hz), 3.06-3.16 (5H, m), 3.69-3.77 (4H, m), 4.07 (3H, s), 7.28-7.31 (1H, m), 7.51-7.59 (2H, m), 7.70 (1H, d, J = 7.8 Hz), 9.05 (1H, s). |
| 177 | 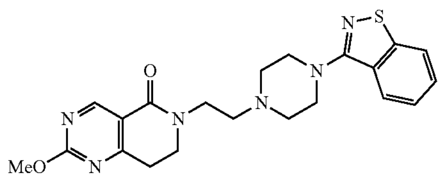 [SMILES: COc1ncc2c(n1)CCN(CCN1CCN(c3nsc4ccccc34)CC1)C2=O] | $^1$H-NMR (400 MHz, CDCl$_3$) δ: 2.72 (2H, t, J = 6.6 Hz), 2.77 (4H, t, J = 4.8 Hz), 3.09 (2H, t, J = 6.6 Hz), 3.53 (4H, t, J = 4.8 Hz), 3.73 (4H, t, J = 6.6 Hz), 4.07 (3H, s), 7.36 (1H, t, J = 7.6 Hz), 7.47 (1H, t, J = 7.6 Hz), 7.81 (1H, d, J = 7.8 Hz), 7.90 (1H, d, J = 8.3 Hz), 9.04 (1H, s). |
| 178 | 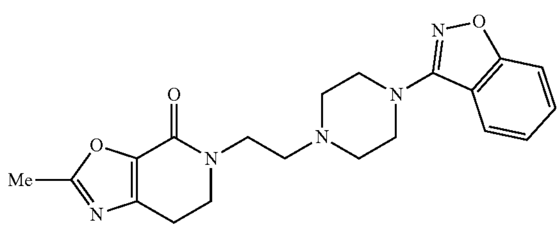 [SMILES: Cc1nc2c(o1)C(=O)N(CCN1CCN(c3noc4ccccc34)CC1)CC2] | $^1$H-NMR (400 MHz, CDCl$_3$) δ: 2.51 (3H, s), 2.63 (2H, dd, J = 8.0, 5.3 Hz), 2.70 (4H, t, J = 5.0 Hz), 2.87 (2H, t, J = 7.3 Hz), 3.53 (4H, t, J = 5.0 Hz), 3.63 (2H, t, J = 6.4 Hz), 3.70 (2H, t, J = 7.1 Hz), 7.17-7.22 (1H, m), 7.41-7.49 (2H, m), 7.66 (1H, d, J = 8.3 Hz). |
| 179 | 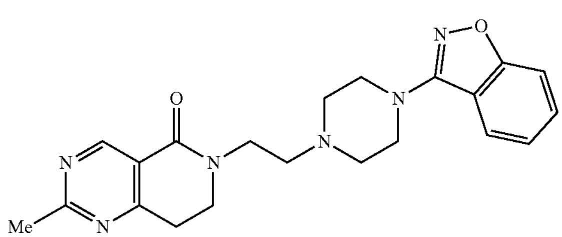 | $^1$H-NMR (400 MHz, CDCl$_3$) δ: 2.65-2.77 (9H, m), 3.11 (2H, t, J = 7.0 Hz), 3.50-3.59 (4H, m), 3.72 (4H, t, J = 6.7 Hz), 7.17-7.23 (1H, m), 7.41-7.50 (2H, m), 7.66 (1H, d, J = 7.9 Hz), 9.12 (1H, s). |

Examples 180 to 182

According to the method of Example 93, the compounds of Examples 180 to 182 were prepared from the corresponding Reference example compounds.

| Example | Chemical structure | Instrumental analyses data |
|---|---|---|
| 180 | 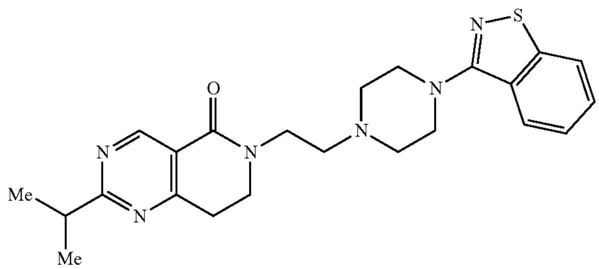 [SMILES: CC(C)c1ncc2c(n1)CCN(CCN1CCN(c3nsc4ccccc34)CC1)C2=O] | $^1$H-NMR (400 MHz, CDCl$_3$) δ: 1.36 (6H, d, J = 6.8 Hz), 2.70-2.82 (6H, m), 3.14 (2H, t, J = 6.7 Hz), 3.20-3.29 (1H, m), 3.48-3.60 (4H, m), 3.71-3.82 (4H, m), 7.36 (1H, dd, J = 8.2, 7.2 Hz), 7.47 (1H, dd, J = 8.0, 7.1 Hz), 7.81 (1H, d, J = 8.0 Hz), 7.90 (1H, d, J = 8.0 Hz), 9.17 (1H, s). |
| 181 | 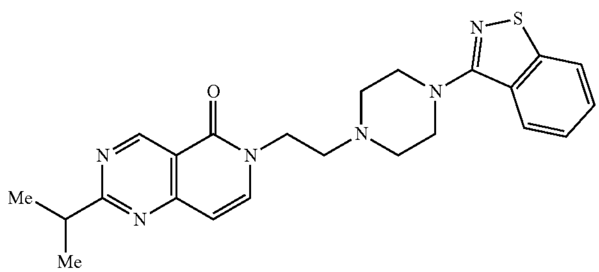 [SMILES: CC(C)c1ncc2c(=O)n(CCN3CCN(c4nsc5ccccc45)CC3)ccc2n1] | $^1$H-NMR (400 MHz, CDCl$_3$) δ: 1.40 (6H, d, J = 7.1 Hz), 2.76 (4H, t, J = 4.6 Hz), 2.82 (2H, t, J = 6.1 Hz), 3.26-3.36 (1H, m), 3.53 (4H, t, J = 4.6 Hz), 4.15 (2H, t, J = 6.1 Hz), 6.61 (1H, d, J = 7.3 Hz), 7.35 (1H, dd, J = 8.0, 7.1 Hz), 7.47 (1H, dd, J = 8.3, 7.1 Hz), 7.55 (1H, d, J = 7.6 Hz), 7.81 (1H, d, J = 8.3 Hz), 7.88 (1H, d, J = 8.3 Hz), 9.60 (1H, s). |
| 182 | 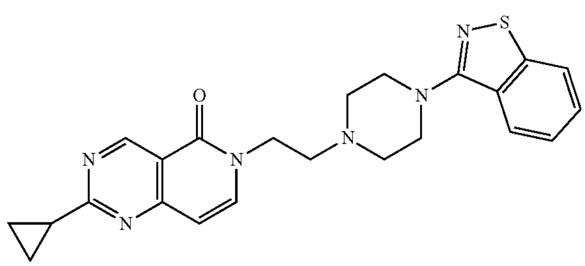 [SMILES: O=c1c2cnc(C3CC3)nc2ccn1CCN1CCN(c2nsc3ccccc23)CC1] | $^1$H-NMR (400 MHz, CDCl$_3$) δ: 1.11-1.21 (2H, m), 1.22-1.32 (2H, m), 2.30-2.38 (1H, m), 2.76 (4H, t, J = 4.8 Hz), 2.81 (2H, t, J = 6.0 Hz), 3.53 (4H, t, J = 4.6 Hz), 4.13 (2H, t, J = 6.0 Hz), 6.53 (1H, d, J = 7.6 Hz), 7.35 (1H, dd, J = 7.7, 7.7 7.88 (1H, d, J = 7.6 Hz), 9.47 (1H, s). |

Examples 183 to 185

According to the method of Example 108, the compounds of Examples 183 to 185 were prepared from the corresponding compound of Example 144 or Example 146.

| Example | Chemical structure | Instrumental analyses data |
|---|---|---|
| 183 | 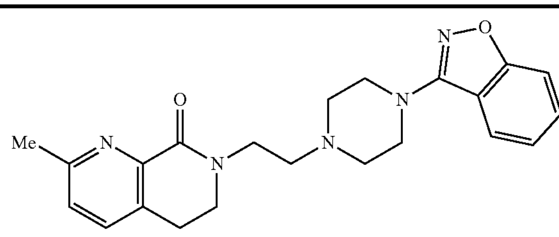 | $^1$H-NMR (400 MHz, CDCl$_3$) δ: 2.57 (3H, s), 2.64-2.77 (6H, m), 2.93 (2H, t, J = 6.4 Hz), 3.46-3.53 (4H, m), 3.60 (2H, t, J = 6.6 Hz), 3.73 (2H, t, J = 6.2 Hz), 7.12 (1H, d, J = 7.8 Hz), 7.28-7.39 (4H, m), 7.61 (1H, d, J = 8.3 Hz). |

-continued

| Example | Chemical structure | Instrumental analyses data |
|---|---|---|
| 184 | 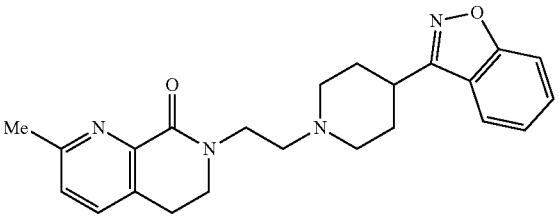 [SMILES: Cc1ccc2c(n1)C(=O)N(CCN1CCC(c3noc4ccccc34)CC1)CC2] | ¹H-NMR (400 MHz, CDCl₃) δ: 1.99-2.16 (4H, m), 2.24-2.34 (2H, m), 2.65 (3H, s), 2.74 (2H, t, J = 6.4 Hz), 3.01 (2H, t, J = 6.6 Hz), 3.05-3.19 (3H, m), 3.70 (2H, t, J = 6.6 Hz), 3.79 (2H, t, J = 6.4 Hz), 7.21 (1H, d, J = 7.8 Hz) 7.28-7.32 (1H, m) 7.45 (1H, d, J = 7.8 Hz), 7.51-7.59 (2H m), 7.71-7.74 (1H, m). |
| 185 | 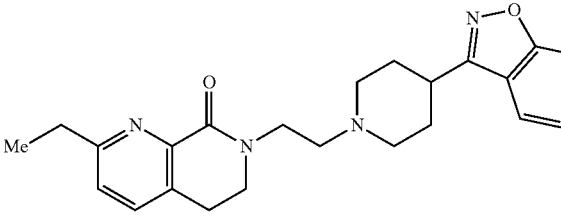 | ¹H-NMR (400 MHz, CDCl₃) δ: 1.32 (3H, t, J = 7.6 Hz), 1.99-2.14 (4H, m), 2.27 (2H, td, J = 11.3, 2.9 Hz), 2.72 (2H, t, J = 6.4 Hz), 2.94 (2H, q, J = 7.5 Hz), 3.01 (2H, t, J = 6.6 Hz), 3.04-3.17 (3H, N), 3.69 (2H, t, J = 6.6 Hz), 3.77 (2H, t, J = 6.4 Hz), 7.23 (1H, d, J = 7.8 Hz), 7.27-7.31 (1H, m), 7.48 (1H, d, J = 7.8 Hz), 7.51-7.58 (2H, m), 7.72 (1H, d, J = 7.8 Hz). |

Examples 186 to 187

According to the method of Example 106, the compounds of Examples 186 to 187 were prepared from the corresponding compound of Example 144 or Example 146.

| Example | Chemical structure | Instrumental analyses data |
|---|---|---|
| 186 | 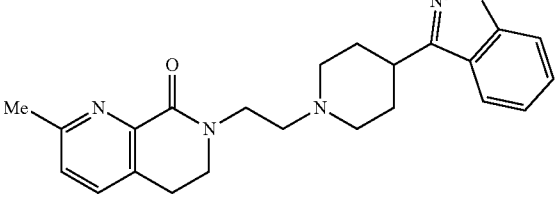 | ¹H-NMR (400 MHz, CDCl₃) δ: 2.70-2.80 (6H, m), 2.95 (2H, t, J = 6.6 Hz), 3.56 (4H, t, J = 4.8 Hz), 3.65 (2H, t, J = 6.6 Hz), 3.76 (2H, t, J = 6.4 Hz), 4.05 (3H, s), 6.81 (1H, d, J = 8.3 Hz), 7.22 (1H, dd, J = 7.3, 7.3 Hz), 7.41-7.51 (3H, m), 7.69 (1H, d, J = 7.8 Hz). |
| 187 | 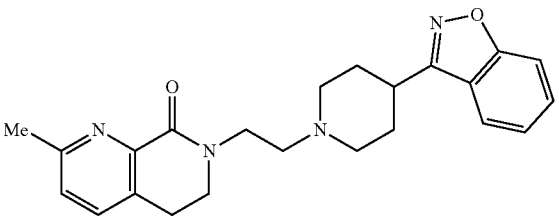 [SMILES: Cc1ccc2c(n1)C(=O)N(CCN1CCC(c3noc4ccccc34)CC1)CC2] | ¹H-NMR (400 MHz, CDCl₃) δ: 2.00-2.15 (4H, m), 2.24-2.33 (2H, m), 2.72 (2H, t, J = 6.4 Hz), 2.95 (2H, t, J = 6.6 Hz), 3.06-3.18 (3H, m), 3.67 (2H, t, J = 6.6 Hz), 3.75 (2H, t, J = 6.4 Hz), 4.05 (3H, s), 6.82 (1H, d, J = 8.3 Hz), 7.27-7.32 (1H, m), 7.44 (1H, d, J = 8.7 Hz), 7.51-7.59 (2H, m), 7.70-7.74 (1H, m). |

Example 188

7-{2-[4-(1,2-Benzoisoxazol-3-yl)piperidin-1-yl]ethyl}-2-fluoro-6,7-dihydro-1,7-naphthyridin-8(5H)-one

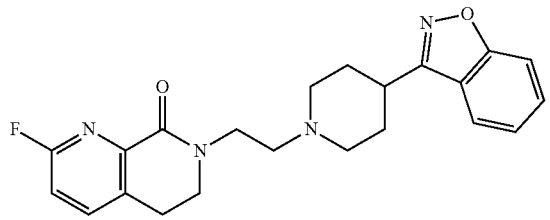 [SMILES: O=C1c2nc(F)ccc2CCN1CCN1CCC(c2noc3ccccc23)CC1]

To a solution of the compound of Example 146 (10.0 mg) in N,N-dimethylformamide (0.5 mL) was added cesium fluoride (18.5 mg). After stirring at 200° C. for 2 hours under microwave irradiation, water was added to the reaction mixture. The mixture was extracted with chloroform, and the combined organic layer was concentrated. The concentrated residue was purified by preparative thin-layer chromatography (chloroform/methanol) to obtain the titled compound (1.6 mg).

$^1$H-NMR (400 MHz, CDCl$_3$) δ: 1.99-2.16 (4H, m), 2.29 (2H, t, J=11.5 Hz), 2.73 (2H, t, J=6.2 Hz), 3.05 (2H, t, J=6.6 Hz), 3.09-3.18 (3H, m), 3.73 (2H, t, J=6.6 Hz), 3.78 (2H, t, J=6.2 Hz), 7.02 (1H, dd, J=8.3, 3.2 Hz), 7.28-7.33 (1H, m), 7.51-7.59 (2H, m), 7.66-7.74 (2H, m).

Example 189

5-{2-[4-(1,2-Benzoisoxazol-3-yl)piperidin-1-yl]ethyl}-1,5,6,7-tetrahydro-4H-pyrazolo[4,3-c]pyridin-4-one

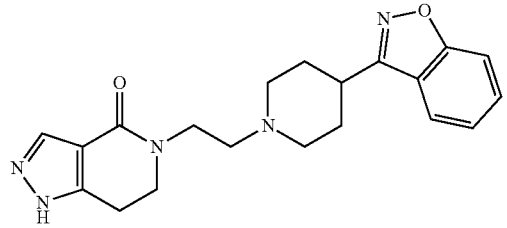 [SMILES: O=C1c2cn[nH]c2CCN1CCN1CCC(c2noc3ccccc23)CC1]

To a solution of the compound of Reference example 54 (210 mg) in tetrahydrofuran (6.0 mL) was added 5 mol/L hydrochloric acid (1.2 mL), and the mixture was stirred at room temperature for 6 hours. Then, saturated aqueous sodium bicarbonate was added to the reaction mixture, and the mixture was extracted with chloroform, dried over anhydrous sodium sulfate, filtered, and concentrated. The concentrated residue was purified by amino silica gel column chromatography (chloroform/methanol), and further purified by reversed-phase liquid chromatography (acetonitrile/water, including 0.05% trifluoroacetic acid) to obtain the titled compound (96.0 mg).

$^1$H-NMR (400 MHz, CDCl$_3$) δ: 1.99-2.12 (4H, m), 2.19-2.31 (2H, m), 2.65 (2H, t, J=6.6 Hz), 2.98 (2H, t, J=6.7 Hz), 3.04-3.18 (3H, m), 3.64-3.73 (4H, m), 7.24-7.28 (1H, m), 7.48-7.56 (2H, m), 7.69 (1H, d, J=8.0 Hz), 7.95 (1H, s).

Example 190

5-{2-[4-(1,2-Benzoisoxazol-3-yl)piperidin-1-yl]ethyl}-6,7-dihydro[1,3]oxazolo[4,5-c]pyridin-4(5H)-one

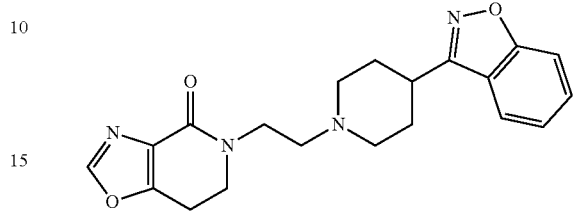

According to a similar method to Example 110 and Reference example 52, the titled compound was obtained from 3-(piperidin-4-yl)benzo[d]isoxazole hydrochloride.

$^1$H-NMR (400 MHz, CDCl$_3$) δ: 1.92-2.09 (4H, m), 2.14-2.24 (2H, m), 2.59 (2H, t, J=6.4 Hz), 2.98-3.09 (5H, m), 3.61 (2H, t, J=6.4 Hz), 3.76 (2H, t, J=7.3 Hz), 7.20-7.25 (1H, m), 7.44-7.52 (2H, m), 7.65 (1H, d, J=7.8 Hz), 7.77 (1H, s).

Example 191

5-{2-[4-(1,2-Benzoisoxazol-3-yl)piperidin-1-yl]ethyl}-6,7-dihydro[1,3]imidazolo[4,5-c]pyridin-4(5H)-one

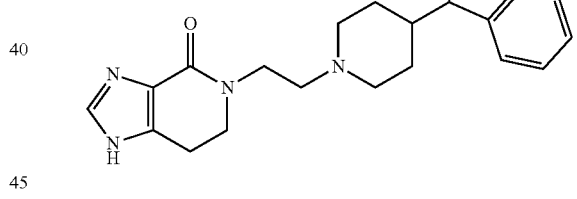

To a solution of 6,7-dihydro-3H-imidazo[4,5-c]pyridin-4(5H)-one (78.5 mg) in tetrahydrofuran (2.0 mL) was added di-tert-butyl dicarbonate (187 mg). After stirring at room temperature for 24 hours, the reaction mixture was concentrated, and the residue was purified by silica gel chromatography (chloroform/methanol). To a solution of the resulting solid (17.0 mg) and the compound of Reference example 3 (19.9 mg) in toluene (0.4 mL) were added tetrabutylammonium bromide (7.62 mg) and potassium hydroxide (6.03 mg), and the mixture was stirred at room temperature for 6 hours. Then, 4 mol/L hydrochloric acid-ethyl acetate (0.5 mL) was added thereto. After stirring at room temperature for 24 hours, the reaction mixture was purified by amino silica gel column chromatography and silica gel column chromatography (chloroform/methanol) to obtain the titled compound (14.4 mg).

$^1$H-NMR (300 MHz, CDCl$_3$) δ: 2.01-2.13 (4H, m), 2.25-2.37 (2H, m), 2.80 (2H, t, J=6.4 Hz), 2.94 (2H, t, J=7.0 Hz), 3.00-3.16 (3H, m), 3.61 (2H, td, J=7.1, 2.6 Hz), 4.44 (2H, t, J=6.3 Hz), 5.23 (1H, s), 7.26-7.32 (1H, m), 7.50-7.59 (2H, m), 7.63 (1H, s), 7.73 (1H, d, J=7.9 Hz).

Example 192

5-{2-[4-(1,2-Benzoisoxazol-3-yl)piperidin-1-yl]ethyl}-3-bromo-1,5,6,7-tetrahydro-4H-pyrazolo[4,3-c]pyridin-4-one

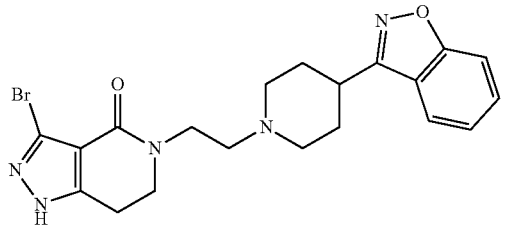 [SMILES: O=C1c2c(Br)n[nH]c2CCN1CCN1CCC(c2noc3ccccc23)CC1]

To a suspension of 55% sodium hydride (31.6 mg) in N,N-dimethylformamide (1.3 mL) was added 3-bromo-1-(4-methoxybenzyl)-6,7-dihydro-1H-pyrazolo[4,3-c]pyridin-4(5H)-one (177 mg) under ice temperature. After stirring under ice temperature for an hour, potassium iodide (43.7 mg) and the compound of Reference example 3 (146 mg) were added thereto, and the mixture was stirred at room temperature for 72 hours. Then, water (30 mL) was added to the reaction mixture, and the mixture was extracted with chloroform (30 mL×2), dried over anhydrous sodium sulfate, filtered, and concentrated. The concentrated residue was purified by silica gel column chromatography (ethyl acetate). To the resulting product was added trifluoroacetic acid (1.0 mL), and the mixture was stirred at 75° C. for 2 hours. Then, the reaction mixture was purified by amino silica gel column chromatography (chloroform/methanol) to obtain the titled compound (47.8 mg).

$^1$H-NMR (400 MHz, CDCl$_3$) δ: 1.99-2.14 (4H, m), 2.24-2.32 (2H, m), 2.68 (2H, t, J=6.4 Hz), 3.02 (2H, t, J=6.6 Hz), 3.06-3.14 (1H, m), 3.14-3.21 (2H, m), 3.65-3.73 (4H, m), 7.27-7.31 (1H, m), 7.50-7.58 (2H, m), 7.70 (1H, d, J=7.8 Hz).

Example 193

6-{2-[4-(1,2-Benzoisoxazol-3-yl)piperazin-1-yl]ethyl}-2-methylpyrido[4,3-d]pyrimidin-5(6H)-one

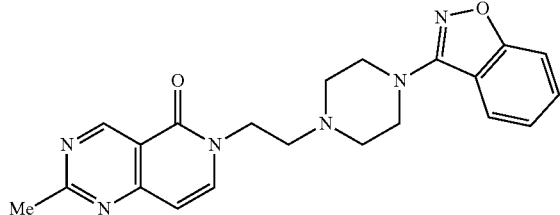

To a solution of the compound of Example 179 (100 mg) in 1,4-dioxane (0.7 mL) was added dimethyldioxirane (37.8 mg). After stirring at 100° C. for 2 hours, saturated aqueous sodium bicarbonate (30 mL) was added to the reaction mixture, and the mixture was extracted with chloroform (30 mL×2), dried over anhydrous sodium sulfate, filtered, and concentrated. The concentrated residue was purified by silica gel column chromatography (chloroform/methanol), and further purified by preparative thin-layer column chromatography (ethyl acetate/methanol) to obtain the titled compound (8.10 mg).

$^1$H-NMR (400 MHz, CDCl$_3$) δ: 2.67 (4H, t, J=4.9 Hz), 2.74 (2H, t, J=6.1 Hz), 2.77 (3H, s), 3.49 (4H, t, J=4.9 Hz), 4.08 (2H, t, J=6.1 Hz), 6.52 (1H, d, J=7.3 Hz), 7.12-7.17 (1H, m), 7.36-7.44 (2H, m), 7.47 (1H, d, J=7.3 Hz), 7.60 (1H, d, J=8.5 Hz), 9.49 (1H, s).

Example 194

6-{2-[4-(1,2-Benzoisoxazol-3-yl)piperidin-1-yl]ethyl}-2-methylpyrido[4,3-d]pyrimidin-5(6H)-one

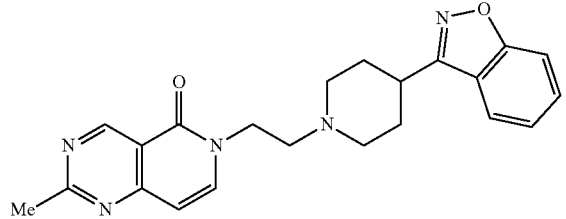 [SMILES: Cc1ncc2c(=O)n(CCN3CCC(c4noc5ccccc45)CC3)ccc2n1]

According to a similar method to Example 193, the titled compound was prepared from the compound of Example 150.

$^1$H-NMR (400 MHz, CDCl$_3$) δ: 1.91-2.08 (4H, m), 2.22-2.32 (2H, m), 2.71 (2H, t, J=6.1 Hz), 2.77 (3H, s), 2.95-3.08 (3H, m), 4.06 (2H, t, J=6.1 Hz), 6.52 (1H, d, J=7.3 Hz), 7.20-7.25 (1H, m), 7.44-7.52 (3H, m), 7.62 (1H, d, J=7.9 Hz), 9.49 (1H, s).

Reference Example 1

3-[4-(2-Chloroethyl)piperazin-1-yl]-1,2-benzoisoxazole

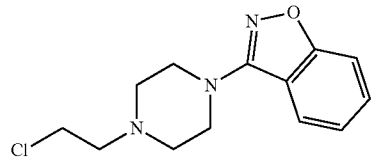 [SMILES: ClCCN1CCN(c2noc3ccccc23)CC1]

A mixture of 3-(piperazin-1-yl)benzo[d]isoxazole hydrochloride (5.44 g), potassium hydroxide (3.82 g), 1-bromo-2-chloroethane (9.41 mL), tetrahydrofuran (100 mL), and water (100 mL) was stirred at room temperature for 24 hours. Then, water was added to the reaction mixture, and the mixture was extracted with chloroform. The combined organic layer was dried over anhydrous sodium sulfate, filtered, and concentrated. The residue was purified by silica gel column chromatography (hexane/ethyl acetate) to obtain the titled compound (3.45 g).

$^1$H-NMR (400 MHz, CDCl$_3$) δ: 2.56-2.92 (6H, m), 3.42-3.76 (6H, m), 7.17-7.23 (1H, m), 7.42-7.50 (2H, m), 7.66 (1H, d, J=7.9 Hz).

Reference Example 2

3-[4-(2-Chloroethyl)piperazin-1-yl]-1,2-benzoisothiazole

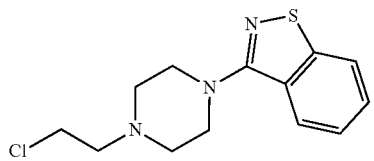 [SMILES: ClCCN1CCN(c2nsc3ccccc23)CC1]

To a mixture of 3-(piperazin-1-yl)benzo[d]isothiazole (25.0 g), potassium hydroxide (12.8 g), tetrahydrofuran (60 mL), and water (7.5 mL) was added 1-bromo-2-chloroethane (37.8 mL), and the mixture was stirred at room temperature for 72 hours. Then, water was added to the reaction mixture, and the mixture was extracted with chloroform. The combined organic layer was dried over anhydrous sodium sulfate, filtered, and concentrated. The residue was purified by silica gel column chromatography (hexane/ethyl acetate) to obtain the titled compound (22.3 g).

$^1$H-NMR (400 MHz, CDCl$_3$) δ: 2.76 (4H, t, J=5.0 Hz), 2.84 (2H, t, J=7.1 Hz), 3.58 (4H, t, J=4.8 Hz), 3.65 (2H, t, J=6.9 Hz), 7.33-7.39 (1H, m), 7.44-7.50 (1H, m), 7.79-7.83 (1H, m), 7.88-7.92 (1H, m).

Reference Example 3

3-[1-(2-Chloroethyl)piperidin-4-yl]-1,2-benzoisoxazole

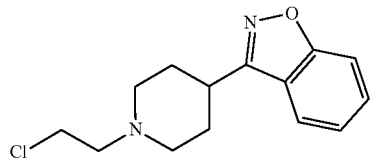 [SMILES: ClCCN1CCC(c2noc3ccccc23)CC1]

To a mixture of 3-(piperidin-4-yl)benzo[d]isoxazole hydrochloride (2.01 g), tetrahydrofuran (4.0 mL), water (2.4 mL) was added potassium hydroxide (1.42 g), and the mixture was stirred at room temperature for 30 minutes. Then, 1-bromo-2-chloroethane (2.79 mL) was added thereto, and the mixture was stirred at room temperature for 24 hours. Water was added to the reaction mixture, and the mixture was extracted with chloroform, dried over anhydrous sodium sulfate, filtered, and concentrated. The residue was purified by silica gel column chromatography (ethyl acetate/methanol) to obtain the titled compound (1.10 g).

$^1$H-NMR (400 MHz, CDCl$_3$) δ: 2.04-2.20 (4H, m), 2.27-2.36 (2H, m), 2.80 (2H, t, J=7.1 Hz), 3.04-3.15 (3H, m), 3.64 (2H, t, J=7.1 Hz), 7.27-7.32 (1H, m), 7.51-7.59 (2H, m), 7.74-7.78 (1H, m).

Reference Examples 4 to 5

According to the method of Reference example 3, the compounds of Reference examples 4 to 5 were prepared from the corresponding starting materials.

| Reference example | Chemical structure | Instrumental analyses data |
|---|---|---|
| 4 | (6-fluoro benzo[d]isoxazol-3-yl piperidine with N-(2-chloroethyl)) | $^1$H-NMR (400 MHz, CDCl$_3$) δ: 2.02-2.18 (4H, m), 2.24-2.39 (2H, m), 2.81 (2H, t, J = 6.9 Hz), 3.01-3.15 (3H, m), 3.64 (2H, t, J = 6.9 Hz), 7.06 (1H, ddd, J = 8.8, 8.8, 2.1 Hz), 7.25 (1H, dd, J = 8.9, 2.5 Hz), 7.70 (1H, dd, J = 8.5, 5.3 Hz). |
| 5 | (5-fluoro benzo[d]isoxazol-3-yl piperidine with N-(2-chloroethyl)) | $^1$H-NMR (400 MHz, CDCl$_3$) δ: 2.03-2.13 (4H, m), 2.25-2.37 (2H, m), 2.80 (2H, t, J = 7.2 Hz), 3.00-3.13 (3H, m), 3.63 (2H, t, J = 7.1 Hz), 7.28 (1H, ddd, J = 8.8, 8.8, 2.5 Hz), 7.38 (1H, dd, J = 7.8, 2.1 Hz), 7.51 (1H, dd, J = 8.7, 3.6 Hz). |

Reference Example 6

3-[1-(2-Chloroethyl)piperidin-4-yl]-6-fluoro-5-methyl-1,2-benzoisoxazole

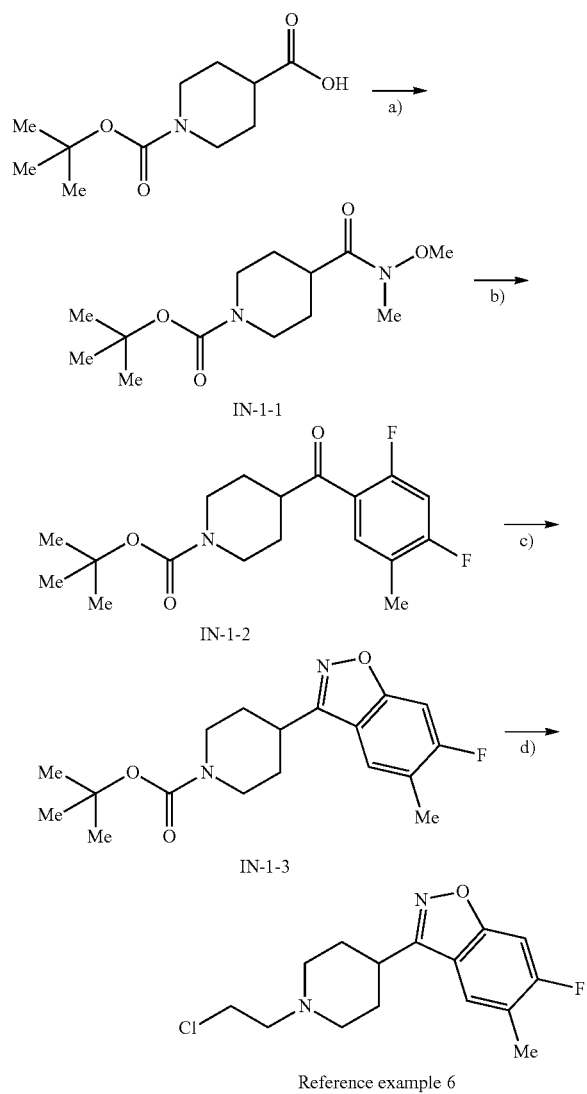

Reference example 6 a) Preparation of tert-butyl 4-[methoxy(methyl)carbamoyl]piperidine-1-carboxylate (Compound IN-1-1)

A mixture of 1-(tert-butoxycarbonyl)piperidine-4-carboxylic acid (5.00 g), N,O-dimethylhydroxyamine hydrochloride (3.19 g), N1-((ethylimino)methylene)-N3,N3-dimethylpropane-1,3-diamine hydrochloride (5.02 g), triethylamine (4.41 g), and N,N-dimethylformamide (100 mL) was stirred at room temperature for 1.5 hours. Then, saturated aqueous ammonium chloride was added to the reaction mixture, and the mixture was extracted with ethyl acetate. The combined organic layer was washed with saturated aqueous ammonium chloride for twice, saturated aqueous sodium bicarbonate and brine. The organic layer was dried over anhydrous sodium sulfate, filtered, and concentrated to obtain the titled compound (4.52 g).

$^1$H-NMR (400 MHz, CDCl$_3$) δ: 1.46 (9H, s), 1.63-1.76 (4H, m), 2.70-2.86 (3H, m), 3.19 (3H, s), 3.72 (3H, s), 4.03-4.24 (2H, m).

b) Preparation of tert-butyl 4-(2,4-difluoro-5-methylbenzoyl)piperidine-1-carboxylate (Compound IN-1-2)

To a solution of 1-bromo-2,4-difluoro-5-methylbenzene (2.28 g) in tetrahydrofuran (36 mL) was added dropwise 1.63 mol/L n-butyllithium/hexane (7.43 mL) at −78° C. over 3 minutes. After stirring at −78° C. for an hour, Compound IN-1-1 (1.50 g) was added thereto, and the mixture was stirred at −78° C. for 2.5 hours. Then, saturated aqueous ammonium chloride was added to the reaction mixture, and the mixture was extracted with ethyl acetate, dried over anhydrous sodium sulfate, filtered, and concentrated. The concentrated residue was purified by silica gel column chromatography (hexane/ethyl acetate) to obtain the titled compound (2.01 g).

$^1$H-NMR (400 MHz, CDCl$_3$) δ: 1.45 (9H, s), 1.59-1.69 (2H, m), 1.83-1.92 (2H, m), 6.80-6.87 (1H, m), 7.17-7.25 (1H, m).

c) Preparation of tert-butyl 4-(6-fluoro-5-methyl-1,2-benzoisoxazol-3-yl)piperidine-1-carboxylate (Compound IN-1-3)

A mixture of compound IN-1-2 (731 mg), hydroxylamine hydrochloride (599 mg), sodium acetate (707 mg), and ethanol (10 mL) was stirred at 60° C. for 4 hours. Then, water was added to the reaction mixture, and the mixture was extracted with ethyl acetate, washed with brine, dried over anhydrous sodium sulfate, filtered, and concentrated. The concentrated residue was purified by silica gel column chromatography (hexane/ethyl acetate). A mixture of the resulting product (335 mg), cesium carbonate (615 mg), and acetonitrile (9.0 mL) was stirred in a sealed tube at 130° C. for 3.5 hours. Then, the reaction mixture was filtered, concentrated, and purified by silica gel column chromatography (hexane/ethyl acetate) to obtain the titled compound (90.8 mg).

$^1$H-NMR (400 MHz, CDCl$_3$) δ: 1.87-1.99 (2H, m), 2.01-2.10 (2H, m), 2.38 (3H, d, J=1.7 Hz), 2.89-3.03 (2H, m), 3.16-3.26 (1H, m), 4.11-4.36 (2H, m), 7.21 (1H, d, J=9.0 Hz), 7.47 (1H, d, J=7.1 Hz).

d) Preparation of 3-[1-(2-chloroethyl)piperidin-4-yl]-6-fluoro-5-methyl-1,2-benzoisoxazole (Reference Example 6)

To a solution of compound IN-1-3 (131 mg) in dichloromethane (1.0 mL) was added 4 mol/L hydrochloric acid/ethyl acetate (1.0 mL), and the mixture was stirred at room temperature for 1.5 hours. Then, the reaction mixture was concentrated to obtain the solid (114 mg). A mixture of the resulting solid (114 mg), potassium carbonate (232 mg), 1-bromo-2-chloroethane (301 mg), tetrahydrofuran (1.7 mL), and water (0.42 mL) was stirred at room temperature overnight. Then, the reaction mixture was concentrated, and the residue was purified by silica gel column chromatography (hexane/ethyl acetate) to obtain the titled compound (41.8 mg).

$^1$H-NMR (300 MHz, CDCl$_3$) δ: 1.98-2.45 (9H, m), 2.76-2.88 (2H, m), 3.00-3.15 (3H, m), 3.58-3.75 (2H, m), 7.20 (1H, d, J=9.2 Hz), 7.52 (1H, d, J=7.0 Hz).

Reference Example 7

3-[1-(2-Chloroethyl)piperidin-4-yl]-5-methyl-, 2-benzoisoxazole

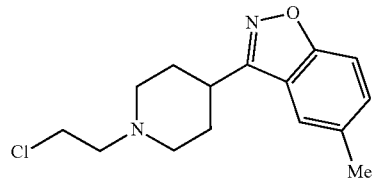 [SMILES: Cc1ccc2onc(C3CCN(CCCl)CC3)c2c1]

According to a similar method to Reference example 6, the titled compound was prepared from 1-fluoro-2-iodo-4-methylbenzene.

$^1$H-NMR (400 MHz, CDCl$_3$) δ: 1.97-2.25 (4H, m), 2.27-2.42 (2H, m), 2.45 (3H, s), 2.71-2.97 (2H, m), 2.99-3.22 (3H, m), 3.58-3.80 (2H, m), 7.24-7.27 (1H, m), 7.33 (1H, d, J=8.5 Hz), 7.43 (1H, d, J=8.3 Hz).

Reference Example 8

3-(Piperidin-4-yl)-1,2-benzoisothiazole

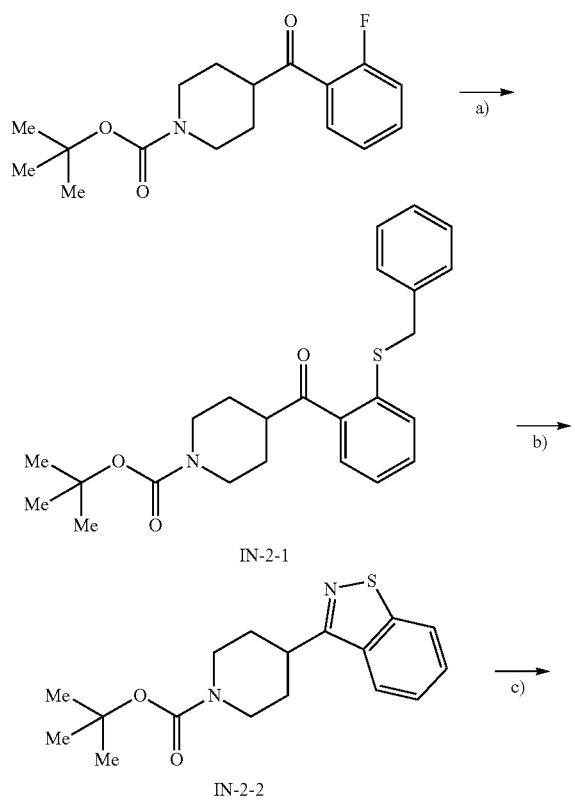

Reference example 8 a) Preparation of tert-butyl 4-[2-(benzylsulfanyl)benzoyl]piperidine-1-carboxylate (Compound IN-2-1)

To a solution of tert-butyl 4-(2-fluorobenzoyl)piperidine-1-carboxylate (664 mg) in dimethylsulfoxide (5.0 mL) was added anhydrous sodium sulfide (554 mg), and the mixture was stirred at 80° C. for 2 hours. Then, additional anhydrous sodium sulfide (560 mg) was added thereto, and the mixture was stirred at 110° C. for 3 hours. To the reaction mixture were added potassium carbonate (895 mg) and benzyl bromide (0.270 mL). After stirring at room temperature for 5 hours, saturated aqueous ammonium chloride was added to the reaction mixture, and the mixture was extracted with ethyl acetate, washed with saturated aqueous ammonium chloride and brine, dried over anhydrous sodium sulfate, filtered, and concentrated. The residue was purified by silica gel column chromatography (hexane/ethyl acetate) to obtain the titled compound (391 mg).

LC-MS: R.T.=2.12 min ObsMS=412 [M+1]

b) Preparation of tert-butyl 4-(1,2-benzoisothiazol-3-yl)piperidine-1-carboxylate (Compound IN-2-2)

To a solution of Compound IN-2-1 (391 mg) in dichloromethane (5.0 mL) was added sulfuryl chloride (0.081 mL) under ice temperature, and the mixture was stirred under ice temperature for an hour. Then, the reaction mixture was concentrated, and to a solution of the resulting residue in tetrahydrofuran (5.0 mL) was added 2 mol/L ammonia-ethanol (4.75 mL), and the mixture was stirred at room temperature for 2 hours. To the reaction mixture was added saturated aqueous sodium bicarbonate, and the mixture was extracted with ethyl acetate. After washed with brine, the mixture was dried over anhydrous sodium sulfate, filtered, and concentrated. The residue was purified by silica gel column chromatography (hexane/ethyl acetate) to obtain the titled compound (187 mg).

$^1$H-NMR (400 MHz, CDCl$_3$) δ: 1.46 (9H, s), 1.86-2.10 (4H, m), 2.85-3.04 (2H, m), 3.31-3.44 (1H, m), 4.15-4.35 (2H, m), 7.38-7.44 (1H, m), 7.47-7.53 (1H, m), 7.92 (1H, d, J=8.0 Hz), 7.97 (1H, d, J=8.0 Hz).

c) Preparation of 3-(piperidin-4-yl)-1,2-benzoisothiazole (Reference Example 8)

To a solution of Compound IN-2-2 (173 mg) in chloroform (5.0 mL) was added 4 mol/L hydrochloric acid-ethyl acetate (5.0 mL), and the mixture was stirred at room temperature for 15 minutes. Then, the reaction mixture was concentrated to obtain the titled compound (119 mg).

LC-MS: R.T.=1.28 min ObsMS=219 [M+1]

Reference Example 9

6-Fluoro-3-(piperazin-1-yl)-1,2-benzoisothiazole

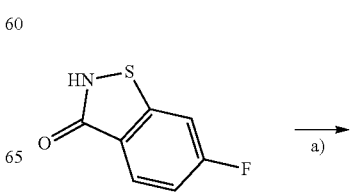

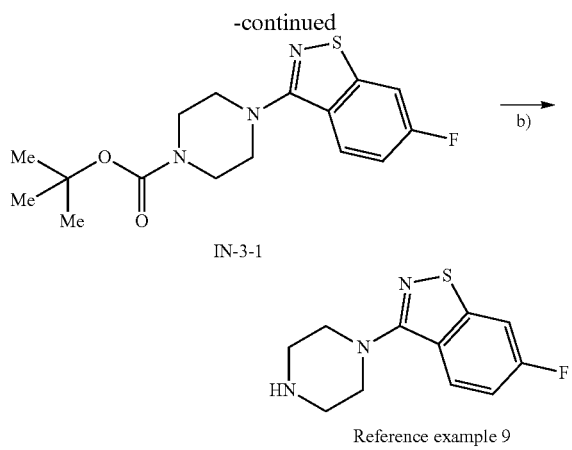

Reference example 9 a) Preparation of tert-butyl 4-(6-fluoro-1,2-benzo-isothiazol-3-yl)piperazine-1-carboxylate (Compound IN-3-1)

To a mixture of 6-fluorobenzo[d]isothiazol-3(2H)-one (2.00 g), triethylamine (8.22 mL), and 1,4-dioxane (59 mL) was added bromotri(pyrrolidin-1-yl)phosphonium hexafluorophosphate(V) (6.06 g). After stirring at room temperature for an hour, to the reaction mixture was added tert-butylpiperazine-1-carboxylate (6.61 g), and the reaction mixture was stirred at 80° C. for 48 hours. Then, water was added to the reaction mixture, and the mixture was extracted with chloroform, dried over anhydrous sodium sulfate, filtered, and concentrated. The residue was purified by silica gel column chromatography (hexane/ethyl acetate) to obtain the titled compound (0.260 g).
¹H-NMR (400 MHz, CDCl₃) δ: 1.50 (9H, s), 3.46 (4H, t, J=5.0 Hz), 3.65 (4H, t, J=5.0 Hz), 7.12 (1H, ddd, J=8.7, 8.7, 2.3 Hz), 7.47 (1H, dd, J=8.3, 2.3 Hz), 7.84 (1H, dd, J=8.9, 4.8 Hz).

b) Preparation of 6-fluoro-3-(piperazin-1-yl)-1,2-benzoisothiazole (Reference Example 9)

To a solution of Compound IN-3-1 (912 mg) in dichloromethane (6.8 mL) was added trifluoroacetic acid (6.8 mL), and the mixture was stirred at room temperature for 13 hours. Then, the reaction mixture was concentrated, saturated sodium bicarbonate was added thereto, and the mixture was extracted with chloroform, dried over anhydrous sodium sulfate, filtered, and concentrated to obtain the titled compound (639 mg).
¹H-NMR (400 MHz, CDCl₃) δ: 3.12 (4H, t, J=5.0 Hz), 3.50 (4H, t, J=4.8 Hz), 7.10 (1H, ddd, J=8.7, 8.7, 2.3 Hz), 7.46 (1H, dd, J=8.3, 1.8 Hz), 7.85 (1H, dd, J=8.9, 4.8 Hz).

Reference Example 10

6-Methoxy-3,4-dihydro-2,7-naphthyridin-1(2H)-one

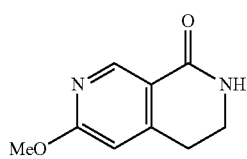

To a solution of 28% sodium methoxide-methanol (50.0 mL) was added 6-bromo-3,4-dihydro-2,7-naphthyridin-1(2H)-one (5.00 g) under room temperature. After stirring at 70° C. for 2 hours, to the reaction mixture was added saturated aqueous ammonium chloride at 0° C., and the mixture was extracted with chloroform. The organic layer was dried over sodium sulfate, filtered, and concentrated under reduced pressure to obtain the titled compound (3.68 g).
¹H-NMR (400 MHz, CDCl₃) δ: 2.92 (2H, t, J=6.4 Hz), 3.53 (2H, td, J=6.5, 3.1 Hz), 3.96 (3H, s), 6.06 (1H, br s), 6.53 (1H, d, J=0.9 Hz), 8.80 (1H, s).

Reference Example 11

5-Methyl-6,7-dihydro-1,7-naphthyridin-8(5H)-one

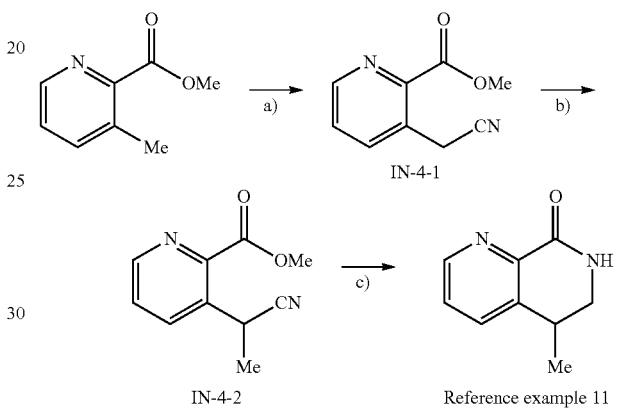

a) Preparation of methyl 3-(cyanomethyl)pyridine-2-carboxylate (Compound IN-4-1)

To a solution of methyl 3-methylpicolinate (1.00 g) in chloroform (27 mL) were added N-bromosuccinimide (1.53 g) and benzoyl peroxide (0.214 g) at room temperature. After stirring at 70° C. for 16 hours, saturated aqueous sodium thiosulfate was added to the reaction mixture, and the mixture was extracted with chloroform. The organic layer was dried over sodium sulfate, filtered, and concentrated under reduced pressure. The residue was purified by silica gel column chromatography (chloroform/methanol). To a solution of the resulting product (0.304 g) in N,N-dimethylformamide (3.3 mL) was added sodium cyanide (0.0712 g) at room temperature. After stirring at room temperature for 3 hours, water was added to the reaction mixture, and the mixture was extracted with chloroform. The organic layer was dried over anhydrous sodium sulfate, filtered, and concentrated under reduced pressure. The residue was purified by amino silica gel column chromatography (hexane/ethyl acetate) to obtain the titled compound (0.0440 g).
¹H-NMR (400 MHz, CDCl₃) δ: 4.01 (3H, s), 4.28 (2H, s), 7.55 (1H, dd, J=7.8, 4.6 Hz), 8.01 (1H, dd, J=7.8, 1.4 Hz), 8.73 (1H, dd, J=4.6, 1.4 Hz).

b) Preparation of methyl 3-(1-cyanoethyl)pyridine-2-carboxylate (Compound IN-4-2)

To a solution of Compound IN-4-1 (63.0 mg) in tetrahydrofuran (1.2 mL) was added 55% sodium hydride (15.6 mg) under ice temperature. After stirring at 0° C. for 30 minutes, a solution of methyl iodide (0.0291 mL) in tetrahydrofuran (0.30 mL) was added dropwise. After stirring at 0° C. for 30 minutes, the reaction mixture was concentrated under reduced pressure. To the residue was added water, and the mixture was extracted with chloroform. The organic layer was dried over sodium sulfate, filtered, and concentrated under reduced pressure. The residue was purified by silica gel column chromatography (hexane/ethyl acetate) to obtain the titled compound (35.0 mg).

$^1$H-NMR (400 MHz, CDCl$_3$) δ: 1.66 (3H, d, J=7.2 Hz), 4.00 (3H, s), 5.09 (1H, q, J=7.2 Hz), 7.55 (1H, dd, J=7.6, 4.4 Hz), 8.08 (1H, dd, J=7.6, 1.2 Hz), 8.70 (1H, dd, J=4.4, 1.2 Hz).

c) Preparation of 5-methyl-6,7-dihydro-1,7-naphthyridin-8(5H)-one (Reference Example 11)

To a solution of Compound IN-4-2 (35.0 mg) in ethanol (2.17 mL) was added raney nickel (15.8 mg) under ice temperature. After stirring under hydrogen atmosphere at 50° C. for 5 hours, the reaction mixture was filtered through Celite, and concentrated under reduced pressure. The residue was purified by silica gel column chromatography (chloroform/methanol) to obtain the titled compound (22.3 mg).

$^1$H-NMR (400 MHz, CDCl$_3$) δ: 1.32 (3H, d, J=7.2 Hz), 3.10-3.21 (1H, m), 3.26-3.32 (1H, m), 3.60-3.65 (1H, m), 7.34 (1H, dd, J=8.0, 4.8 Hz), 7.56-7.58 (1H, m), 7.80 (1H, br s), 8.64 (1H, dd, J=4.6, 1.4 Hz).

Reference Example 12

1-Methyl-1,5,6,7-tetrahydro-4H-imidazo[4,5-c]pyridin-4-one

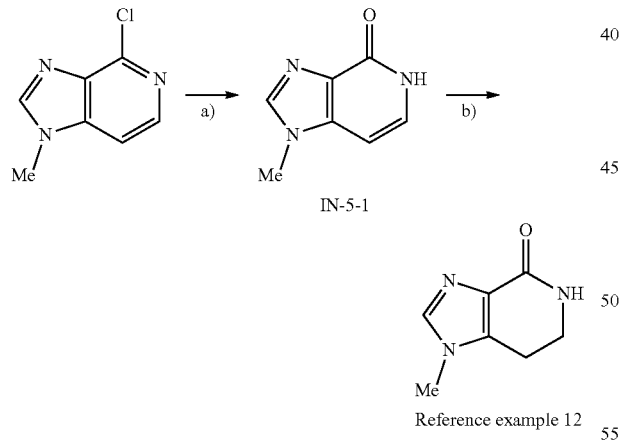

Reference example 12 a) Preparation of 1-methyl-1,5-dihydro-4H-imidazo[4,5-c]pyridin-4-one (Compound IN-5-1)

A mixture of 4-chloro-1-methyl-1H-imidazo[4,5-C]pyridine (100 mg) and formic acid (1.40 mL) was heated under reflux for 5 hours. Then, to the reaction mixture was added saturated aqueous sodium bicarbonate, and the mixture was extracted with ethyl acetate, dried over anhydrous sodium sulfate, filtered, and concentrated to obtain the titled compound (127 mg).

$^1$H-NMR (300 MHz, CD$_3$OD) δ: 4.03 (3H, s), 6.91 (1H, d, J=7.3 Hz), 7.55 (1H, d, J=7.3 Hz), 8.07 (1H, s), 9.20 (1H, s).

b) Preparation of 1-methyl-1,5,6,7-tetrahydro-4H-imidazo[4,5-c]pyridin-4-one (Reference Example 12)

A mixture of Compound IN-5-1 (0.106 g), 20% palladium hydroxide on carbon (1.25 g) and acetic acid (7.1 mL) was stirred under hydrogen atmosphere (1 atm) at 70° C. for 8 hours. Then, the reaction mixture was filtered, and the filtrate was concentrated under reduced pressure. The residue was purified by silica gel column chromatography (chloroform/methanol) to obtain the titled compound (13.9 mg).

$^1$H-NMR (300 MHz, CD$_3$OD) δ: 3.01-2.91 (2H, m), 3.74 (3H, s), 3.66-3.57 (2H, m), 7.97 (1H, s).

Reference Example 13

2-Methyl-2,5,6,7-tetrahydro-4H-pyrazolo[4,3-c]pyridin-4-one

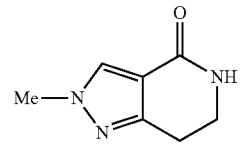 [SMILES: Cn1cc2c(n1)CCNC2=O]

To a mixture of piperidin-2,4-dione (19.0 g), acetic acid (1.01 g), and N,N-dimethylformamide (80 mL) was added methylhydrazine (7.74 g) at 0° C., and the mixture was stirred for 20 minutes. After stirring at room temperature for an hour, N,N-dimethylformamide dimethyl acetal (44.0 g) was added thereto. After stirring at 60° C. for 2 hours, the reaction mixture was cooled to room temperature, diethyl ether (100 mL) was added thereto, and the mixture was stirred at 0° C. for 30 minutes. The precipitated solid was collected by filtration to obtain the titled compound (14.4 g).

$^1$H-NMR (400 MHz, CDCl$_3$) δ: 2.91 (2H, t, J=6.6 Hz), 3.57 (2H, td, J=6.6, 2.6 Hz), 3.90 (3H, s), 5.85 (1H, s), 7.78 (1H, s).

Reference Example 14

2-Cyclopropyl-2,5,6,7-tetrahydro-4H-pyrazolo[4,3-c]pyridin-4-one

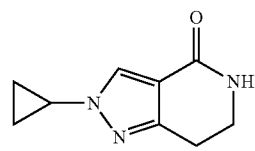 [SMILES: O=C1NCCc2nn(C3CC3)cc21]

According to a similar method to Reference example 13, the titled compound was purified by cyclopropylhydrazine monohydrochloride.

$^1$H-NMR (400 MHz, CDCl$_3$) δ: 1.03-1.15 (4H, m), 2.91 (2H, t, J=6.6 Hz), 3.55-3.60 (2H, m), 5.56 (1H, brs), 7.87 (1H, s).

Reference Example 15

1-Methyl-1,5,6,7-tetrahydro-4H-pyrazolo[4,3-c]pyridin-4-one

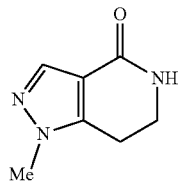

To a solution of piperidin-2,4-dione (500 mg) in ethanol (9.0 mL) was added N,N-dimethylformamide dimethylacetal (632 mg), and the mixture was heated under reflux for 2 hours. Then, methylhydrazine (224 mg) was added dropwise under ice temperature, and the mixture was stirred at room temperature for 2 hours. After stirring at 80° C. for an hour, diethyl ether (15 mL) was added thereto. The mixture was triturated, and the solid was collected by filtration to obtain the titled compound (565 mg).

$^1$H-NMR (400 MHz, CDCl$_3$) δ: 2.91 (2H, t, J=6.6 Hz), 3.63 (2H, td, J=6.8, 2.4 Hz), 3.84 (3H, s), 6.10 (1H, s), 7.87 (1H, s).

Reference Example 16

1,7-Dimethyl-1,5,6,7-tetrahydro-4H-pyrazolo[4,3-c]pyridin-4-one

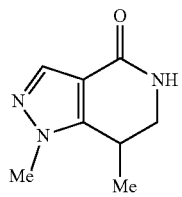

According to a similar method to Reference example 15, the titled compound was prepared from 5-methyl-2,4-piperadinedione.

$^1$H-NMR (400 MHz, CDCl$_3$) δ: 1.33 (3H, d, J=6.9 Hz), 3.06-3.14 (1H, m), 3.29 (1H, dq, J=12.5, 2.2 Hz), 3.79 (1H, dd, J=12.4, 5.0 Hz), 3.85 (3H, s), 5.29 (1H, brs), 7.86 (1H, s).

Reference Example 17

1-Methyl-5,6,7,8-tetrahydropyrazolo[4,3-c]azepin-4(1H)-one

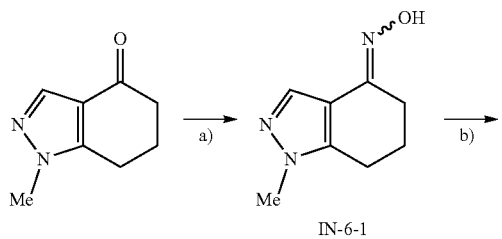

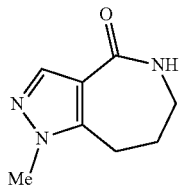

Reference example 17 a) Preparation of N-(1-methyl-1,5,6,7-tetrahydro-4H-indazol-4-ylidene)hydroxylamine (Compound IN-6-1)

A mixture of 1-methyl-6,7-dihydro-1H-indazol-4(5H)-one (855 mg), hydroxylamine hydrochloride (475 mg), sodium acetate (560 mg), and ethanol (28 mL) was stirred at 60° C. for 14 hours. Then, the reaction mixture was filtered, and concentrated. The concentrated residue was triturated with hexane:ethyl acetate (1:1), collected by filtration, and dried to obtain the titled compound (635 mg).

$^1$H-NMR (400 MHz, CDCl$_3$) δ: 2.00-2.08 (2H, m), 2.48 (2H, t, J=6.2 Hz), 2.73 (2H, t, J=6.2 Hz), 3.81 (3H, s), 8.19 (1H, s).

b) Preparation of 1-methyl-5,6,7,8-tetrahydropyrazolo[4,3-c]azepin-4(1H)-one (Reference Example 17)

To a mixture of Compound IN-6-1 (7.86 g), triethylamine (9.95 mL), and dichloromethane (95 mL) was added p-toluenesulfonyl chloride (10.4 g), and the mixture was heated under reflux for 30 minutes. Then, to the reaction mixture were added saturated aqueous sodium bicarbonate and water, and the mixture was extracted with chloroform, dried over anhydrous sodium sulfate, filtered, and concentrated. To the residue was added ethyl acetate (18 mL), and the mixture was heated to 80° C. After confirming that all solid was dissolved, the mixture was gradually cooled to room temperature, and hexane (18 mL) and ethyl acetate (3.0 mL) were added successively. After stirring at room temperature for an hour, the precipitated solid was collected by filtration, washed with hexane:ethyl acetate (2:3, 50 mL) and hexane (20 mL), and dried to obtain the solid (13.6 g). A mixture of the resulting solid (13.6 g) and trifluoroacetic acid (22.9 mL) was heated under reflux for 30 minutes. Then, the reaction mixture was concentrated, and purified by amino silica gel column chromatography (chloroform/methanol). To the resulting solid was added ethanol (60 mL). After stirring at 80° C. for an hour, and the mixture was gradually cooled to room temperature, stirred at 0° C. for an hour, and filtered. The resulting solid was washed with ethanol:hexane (1:1, 10 mL), and dried to obtain the titled compound (5.52 g).

$^1$H-NMR (400 MHz, CDCl$_3$) δ: 2.13-2.20 (2H, m), 2.91 (2H, t, J=6.4 Hz), 3.38 (2H, td, J=5.0, 5.0 Hz), 3.79 (3H, s), 6.10 (1H, brs), 7.99 (1H, s).

Reference Example 18

1,3-Dimethyl-5,6,7,8-tetrahydropyrazolo[4,3-c]azepin-4 (1H)-one

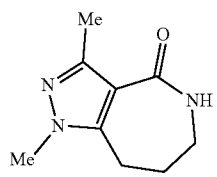 [SMILES: Cc1nn(C)c2c1C(=O)NCCC2]

According to a similar method to Reference example 17, the titled compound was obtained from 1,3-dimethyl-1,5,6,7-tetrahydro-4H-indazol-4-one.

$^1$H-NMR (400 MHz, CDCl$_3$) δ: 2.06-2.13 (2H, m), 2.44 (3H, s), 2.86 (2H, t, J=6.7 Hz), 3.26-3.33 (2H, m), 3.69 (3H, s), 6.18 (1H, brs).

Reference Example 19

6-Methyl-3,4-dihydro-2,7-naphthyridin-1(2H)-one

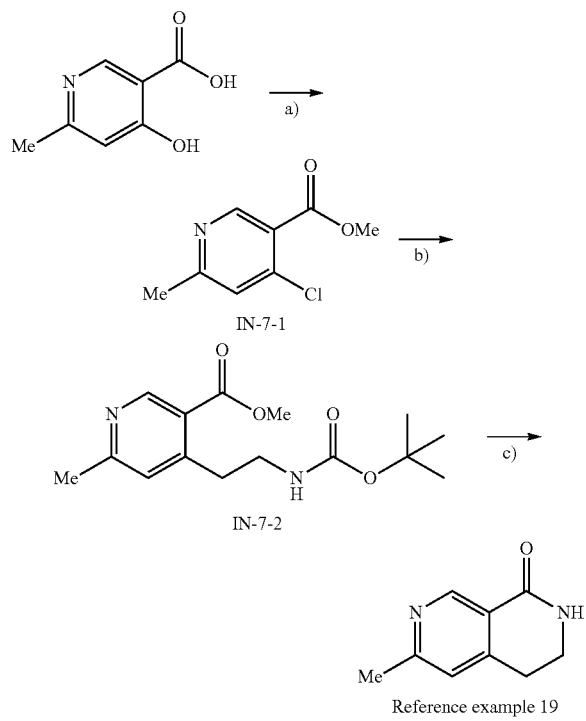

a) Preparation of methyl 4-chloro-6-methylpyridine-3-carboxylate (Compound IN-7-1)

To a solution of 4-hydroxy-6-methyl nicotinate (1.00 g) in toluene (6.5 mL) were added N,N-dimethylformamide (0.0200 mL), and then dropwise oxalyl chloride (3.00 mL) at room temperature. After stirring at room temperature for 3 hours, the reaction mixture was concentrated under reduced pressure. To the residue was added toluene (3.0 mL), and then methanol (10 mL) was added at 0° C. After stirring at room temperature for 30 minutes, the reaction mixture was concentrated under reduced pressure. To the residue was added saturated aqueous sodium bicarbonate, and the mixture was extracted with chloroform. The organic layer was dried over anhydrous sodium sulfate, filtered, and concentrated under reduced pressure to obtain the titled compound (1.20 g).

$^1$H-NMR (400 MHz, CDCl$_3$) δ: 2.57 (3H, s), 3.93 (3H, s), 7.27 (1H, s), 8.92 (1H, s).

b) Preparation of methyl 4-{2-[(tert-butoxycarbonyl)amino]ethyl}-6-methylpyridine-3-carboxylate (Compound IN-7-2)

To a mixture of Compound IN-7-1 (5.03 g) and toluene/water (3:1, 54 mL) were added potassium tert-butyl N-[2-(trifluoroboranuidyl)ethyl]carbamate (10.2 g), cesium carbonate (22.1 g), and 1,1'-bis(diphenylphosphino)ferrocene palladium dichloride dichloromethane adduct (1.98 g) at room temperature. After stirring under nitrogen atmosphere at 100° C. for 3 hours, to the reaction mixture were added water (55 mL) and ethyl acetate (30 mL). The mixture was filtered through Celite, and the filtrate was extracted with ethyl acetate. The organic layer was dried over anhydrous sodium sulfate, filtered, and concentrated under reduced pressure. The residue was purified by silica gel column chromatography (hexane/ethyl acetate) to obtain the titled compound (7.84 g).

$^1$H-NMR (400 MHz, CDCl$_3$) δ: 1.39 (9H, s), 2.57 (3H, s), 3.11-3.17 (2H, m), 3.36-3.42 (2H, m), 3.90 (3H, s), 7.08 (1H, s), 8.97 (1H, s).

c) Preparation of 6-methyl-3,4-dihydro-2,7-naphthyridin-1(2H)-one (Reference Example 19)

To a solution of Compound IN-7-2 (1.25 g) in ethyl acetate/methanol (1:1, 4.2 mL) was added 4 mol/L hydrochloric acid-ethyl acetate (21.2 mL, 85.0 mmol) at room temperature. After stirring at room temperature for 2 hours, the reaction mixture was concentrated under reduced pressure. The residue was dissolved in methanol (5.0 mL), and 28% sodium methoxide-methanol solution (3.27 g) was added thereto at room temperature. After stirring for 30 minutes at room temperature, the reaction mixture was concentrated under reduced pressure. To the residue was added 2 mol/L hydrochloric acid (10.0 ml), and the aqueous layer was washed with ethyl acetate. To the aqueous layer was added 1 mol/L aqueous sodium hydroxide for neutralization, and the mixture was extracted with chloroform/methanol (4:1). The organic layer was dried over sodium sulfate, filtered, and concentrated under reduced pressure. The residue was triturated with ethanol/hexane to obtain the titled compound (519 mg).

$^1$H-NMR (400 MHz, CDCl$_3$) δ: 2.60 (3H, s), 2.97 (2H, t, J=6.6 Hz), 3.59 (2H, td, J=6.6, 2.9 Hz), 6.36 (1H, s), 7.03 (1H, s), 9.08 (1H, s).

Reference Example 20

6'-Methyl-2',3'-dihydro-1'H-spir[cyclopropane-1,4'-[2,7]naphthyridine]-1'-one

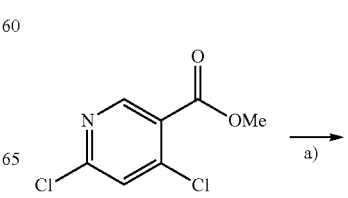

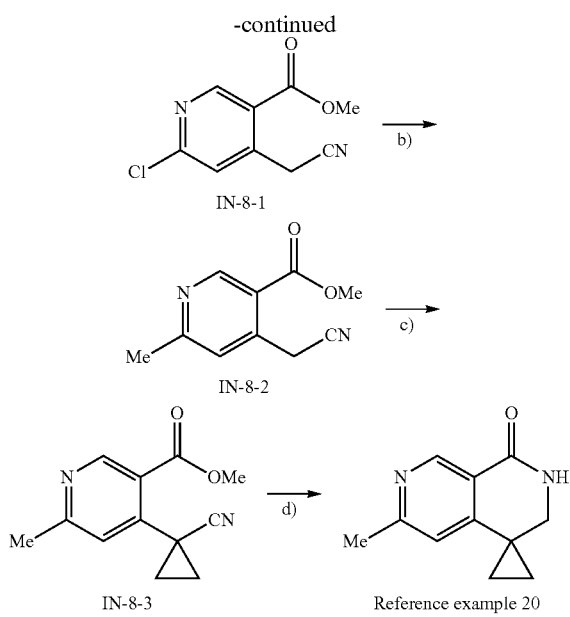

a) Preparation of methyl 6-chloro-4-(cyanomethyl)pyridine-3-carboxylate (Compound IN-8-1)

To a solution of methyl 4,6-dichloronicotinate (5.00 g) in N,N-dimethylformamide (49 mL) were added potassium carbonate (6.71 g) and tert-butyl cyanoacetate (3.77 g) at room temperature. After stirring at 100° C. for 2 hours, to the reaction mixture was added water (100 mL), and the mixture was neutralized with 2 mol/L hydrochloric acid (35 mL), and extracted with toluene (100 mL×4). After the organic layer was washed with 0.1 mol/L hydrochloric acid (50 mL), the mixture was dried over anhydrous sodium sulfate. The mixture was filtered, concentrated under reduced pressure until the solvent was reduced to 300 mL, and p-toluenesulfonic acid monohydrate (0.462 g) was added thereto. After stirring at 100° C. for an hour, to the reaction mixture was added saturated aqueous sodium bicarbonate, and the mixture was extracted with ethyl acetate. The organic layer was dried over anhydrous sodium sulfate, filtered, and concentrated under reduced pressure. The residue was purified by silica gel column chromatography (hexane/ethyl acetate) to obtain the titled compound (4.35 g).

$^1$H-NMR (400 MHz, CDCl$_3$) δ: 3.97 (3H, s), 4.28 (2H, s), 7.65 (1H, s), 9.02 (1H, s).

b) Preparation of methyl 4-(cyanomethyl)-6-methylpyridine-3-carboxylate (Compound IN-8-2)

To a solution of Compound IN-8-1 (2.55 g) in 1,2-dimethoxyethane (17 mL) were added potassium carbonate (2.51 g), trimethylboroxine (5.08 mL), tetrakis(triphenylphosphine)palladium (1.40 g) at room temperature. After stirring at 100° C. for 2 hours, to the reaction mixture was added water, and the mixture was extracted with ethyl acetate. The organic layer was dried over anhydrous sodium sulfate, filtered, and concentrated under reduced pressure. The residue was purified by silica gel column chromatography (hexane/ethyl acetate) to obtain the titled compound (465 mg).

$^1$H-NMR (400 MHz, CDCl$_3$) δ: 2.66 (3H, s), 3.95 (3H, s), 4.25 (2H, s), 7.44 (1H, s), 9.11 (1H, s).

c) Preparation of methyl 4-(1-cyanocyclopropyl)-6-methylpyridine-3-carboxylate (Compound IN-8-3)

To a solution of Compound IN-8-2 (101 mg) in acetonitrile (1.8 mL) were added 1,2-dibromoethane (0.0554 mL), and potassium carbonate (220 mg) at room temperature. After stirring at 70° C. for 48 hours, to the reaction mixture was added water, and the mixture was extracted with chloroform. The organic layer was dried over anhydrous sodium sulfate, filtered, and concentrated under reduced pressure. The residue was purified by silica gel column chromatography (hexane/ethyl acetate) to obtain the titled compound (67.1 mg).

$^1$H-NMR (400 MHz, CDCl$_3$) δ: 1.32 (2H, dd, J=7.8, 5.5 Hz), 1.76 (2H, t, J=3.7 Hz), 2.60 (3H, s), 3.99 (3H, s), 7.18 (1H, s), 9.05 (1H, s).

d) Preparation of 6'-methyl-2',3'-dihydro-1'H-spir[cyclopropane-1,4'-[2,7]naphthyridine]-1'-one (Reference Example 20)

To a solution of Compound IN-8-3 (61.0 mg) in ethanol (3.3 mL) was added 50% raney nickel-water suspension (0.17 mL) under ice temperature. After stirring under hydrogen atmosphere at room temperature for 2 hours, the reaction mixture was filtered through Celite, and concentrated under reduced pressure. The residue was purified by silica gel column chromatography (chloroform/methanol) to obtain the titled compound (35.4 mg).

$^1$H-NMR (400 MHz, CDCl$_3$) δ: 1.07 (2H, t, J=2.9 Hz), 1.12 (2H, t, J=2.9 Hz), 2.55 (3H, s), 3.39 (2H, d, J=2.7 Hz), 6.59 (1H, s), 7.40 (1H, brs), 9.06 (1H, s).

Reference Example 21

4,4,6-Trimethyl-3,4-dihydro-2,7-naphthyridin-1(2H)-one

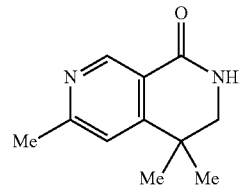 [SMILES: Cc1cc2c(cn1)C(=O)NCC2(C)C]

According to a similar method to Reference example 20, the titled compound was prepared using methyl iodide from Compound IN-8-2.

$^1$H-NMR (400 MHz, CDCl$_3$) δ: 1.36 (6H, s), 2.62 (3H, s), 3.34 (2H, d, J=0.8 Hz), 6.52 (1H, brs), 7.09 (1H, s), 9.09 (1H, s).

Reference Example 22

7-(2-Hydroxy-2-methoxyethyl)-6,7-dihydro-1,7-naphthyridin-8(5H)-one

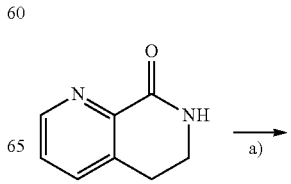

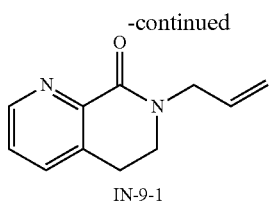

IN-9-1

↓ b)

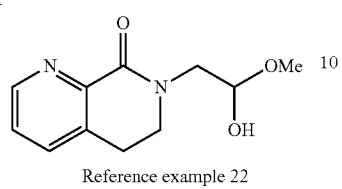

Reference example 22 a) Preparation of 7-(prop-2-en-1-yl)-6,7-dihydro-1,7-naphthyridin-8(5H)-one (Compound IN-9-1)

To a solution of 6,7-dihydro-1,7-naphthyridin-8(5H)-one (1.29 g) in N,N-dimethylformamide (20 mL) was added 55% sodium hydride (0.456 g) under ice temperature, and the mixture was stirred for an hour. Then, allyl iodide (0.949 mL) was added thereto under ice temperature, and the mixture was stirred at room temperature for 3 hours. To the reaction mixture was added water, and the mixture was extracted with chloroform, dried over anhydrous sodium sulfate, filtered, and concentrated. To the residue was added toluene, and the mixture was concentrated. The concentrated residue was purified by silica gel column chromatography (chloroform/methanol) to obtain the titled compound (1.97 g).

$^1$H-NMR (300 MHz, CDCl$_3$) δ: 3.03 (2H, t, J=6.6 Hz), 3.56 (2H, t, J=6.6 Hz), 4.23-4.29 (2H, m), 5.20-5.32 (2H, m), 5.80-5.95 (1H, m), 7.34 (1H, dd, J=7.7, 4.6 Hz), 7.56 (1H, d, J=7.7 Hz), 8.71 (1H, d, J=4.6 Hz).

b) Preparation of 7-(2-hydroxy-2-methoxyethyl)-6,7-dihydro-1,7-naphthyridin-8(5H)-one (Reference Example 22)

To a mixture of Compound IN-9-1 (1.69 g), tetrahydrofuran (44 mL), and water (22 mL) were added sodium periodate (4.80 g) and osmium tetroxide (0.183 g) under ice temperature. After stirring under ice temperature for 6 hours, the reaction mixture was filtered through Celite, and washed with chloroform/methanol (4/1). To the filtrate was added saturated aqueous sodium thiosulfate, and the mixture was extracted with chloroform/methanol (4/1, 50 mL×12), dried over anhydrous sodium sulfate, filtered, and concentrated. The residue was purified by silica gel column chromatography (chloroform/methanol) to obtain the titled compound (1.65 g).

$^1$H-NMR (300 MHz, CDCl$_3$) δ: 3.02-3.11 (2H, m), 3.43 (3H, s), 3.68 (2H, dd, J=13.8, 5.1 Hz), 3.75-3.89 (2H, m), 4.61-4.72 (1H, m), 4.80-4.88 (1H, m), 7.36 (1H, dd, J=7.7, 4.8 Hz), 7.55-7.60 (1H, m), 8.68-8.72 (1H, m).

Reference Examples 23 to 25

According to the method of Reference example 22, the compounds of Reference examples 23 to 25 were prepared from the corresponding starting materials.

| Reference example | Cheminal structure | Instrumental analyses data |
|---|---|---|
| 23 | (structure) | $^1$H-NMR (400 MHz, CDCl$_3$) δ: 1.87-2.04 (1H, m), 2.14-2.25 (1H, m), 2.49-2.62 (1H, m), 2.89-2.97 (1H, m), 3.10-3.26 (3H, m), 7.33 (1H, dd, J = 8.0, 4.4 Hz), 7.58-7.61 (1H, m), 8.64 (1H, d, J = 4.4 Hz), 9.84 (1H, t, J = 0.8 Hz). |
| 24 | (structure) | $^1$H-NMR (400 MHz, CDCl$_3$) δ: 1.90-2.05 (1H, m), 2.26-2.35 (1H, m), 2.50 (1H, dd, J = 17.9, 6.9 Hz), 2.87-2.91 (2H, m), 2.98-3.06 (1H, m), 3.18 (1H, dd, J = 17.9, 5.5 Hz), 3.82 (3H, s), 7.86 (1H, s), 9.90 (1H, s). |
| 25 | (structure) | $^1$H-NMR (400 MHz, CDCl$_3$) δ: 1.68-1.80 (1H, m), 1.96-2.27 (3H, m), 2.52 (1H, ddd, J = 17.4, 5.5, 0.9 Hz), 2.83-3.00 (2H, m), 3.03-3.11 (1H, m), 3.17-3.25 (1H, m), 3.81 (3H, s), 7.90 (1H, s), 9.85 (1H, t, J = 1.4 Hz). |

Reference Example 26

2-Methyl-6,7-dihydro[1,3]oxazolo[5,4-c]pyridin-4(5H)-one

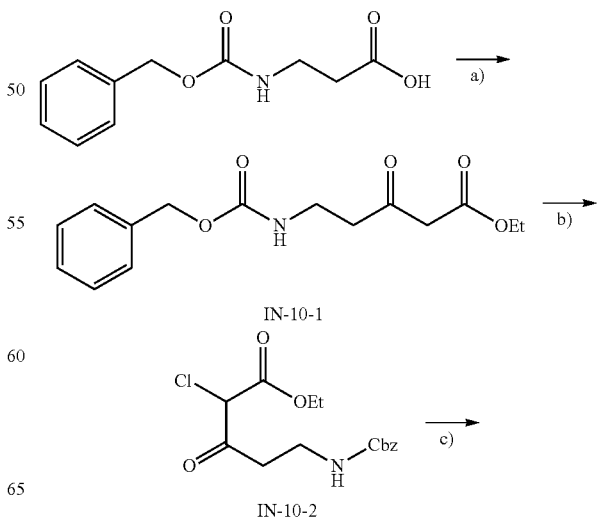

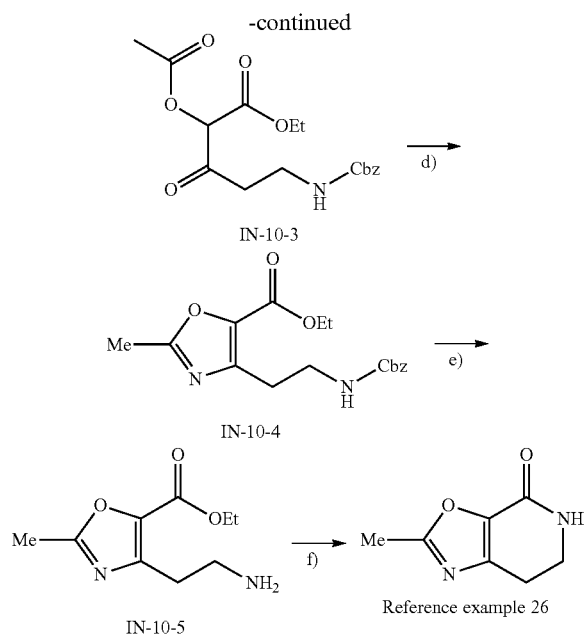

a) Preparation of ethyl 5-{[(benzyloxy)carbonyl]amino}-3-oxopentanoate (Compound IN-10-1)

3-([(Benzyloxy)carbonyl]amino)propionic acid (10.0 g) was dissolved in tetrahydrofuran (180 mL), and carbonyl-1,1'-diimidazole (7.99 g) was added thereto. After stirring at room temperature for 1.5 hours, potassium ethyl malonate (9.91 g) was added, and then magnesium chloride (5.54 g) was slowly added. After stirring for 15 minutes, the mixture was stirred under heat at 50° C. for 1.5 hours. After cooled to room temperature, to the reaction mixture was added water, and the mixture was extracted with ethyl acetate. The combined organic layer was dried over anhydrous sodium sulfate, filtered, and concentrated. The residue was purified by silica gel column chromatography (hexane/ethyl acetate) to obtain the titled compound (8.58 g).
$^1$H-NMR (400 MHz, CDCl$_3$) δ: 1.14 (3H, t, J=7.1 Hz), 2.08-2.20 (2H, m), 3.22-3.34 (2H, m), 3.98 (2H, q, J=6.9 Hz), 4.72 (1H, s), 5.00 (2H, s), 5.25 (1H, brs), 7.27-7.37 (5H, m).

b) Preparation of ethyl 5-{[(benzyloxy)carbonyl]amino}-2-chloro-3-oxopentanoate (Compound IN-10-2)

Compound IN-10-1 (8.58 g) was dissolved in methylene chloride (150 mL), and sulfuryl chloride (2.38 mL) was added dropwise at 0° C. After stirring at 0° C. for 2 hours, to the reaction mixture was added saturated aqueous sodium bicarbonate. The mixture was extracted with methylene chloride, and the combined organic layer was dried over anhydrous sodium sulfate, filtered, and concentrated to obtain the titled compound (9.47 g).
$^1$H-NMR (400 MHz, CDCl$_3$) δ: 1.29 (3H, t, J=7.1 Hz), 2.96-3.03 (2H, m), 3.46-3.53 (2H, m), 4.27 (2H, q, J=7.3 Hz), 4.77 (1H, s), 5.09 (2H, s), 5.16 (1H, brs), 7.29-7.43 (5H, m).

c) Preparation of ethyl 2-(acetyloxy)-5-{[(benzyloxy)carbonyl]amino}-3-oxopentanoate (Compound IN-10-3)

Compound IN-10-2 (1.50 g) was dissolved in acetonitrile (5.0 mL), and acetic acid (0.786 mL) and triethylamine (3.19 mL) were added thereto, and the mixture was stirred at room temperature overnight. Then, to the reaction mixture was added water, and the mixture was extracted with ethyl acetate. The combined organic layer was dried over anhydrous sodium sulfate, filtered, and concentrated to obtain the titled compound (1.57 g).
$^1$H-NMR (300 MHz, CDCl$_3$) δ: 1.29 (3H, t, J=7.2 Hz), 2.22 (3H, s), 2.89-2.97 (2H, m), 3.45-3.53 (2H, m), 4.26 (2H, q, J=7.2 Hz), 5.08 (2H, s), 5.18 (1H, brs), 5.47 (1H, s), 7.30-7.37 (5H, m).

d) Preparation of ethyl 4-(2-{[(benzyloxy)carbonyl]amino}ethyl)-2-methyl-1,3-oxazole-5-carboxylate (Compound IN-10-4)

Compound IN-10-3 (9.11 g) and ammonium acetate (4.00 g) were dissolved in acetic acid (40 mL), and the mixture was heated at 120° C. for an hour. After cooled to room temperature, to the reaction mixture was added water. The mixture was extracted with ethyl acetate, and the combined organic layer was dried over anhydrous sodium sulfate, filtered, and concentrated to obtain the titled compound (8.74 g).
$^1$H-NMR (300 MHz, CDCl$_3$) δ: 1.34 (3H, t, J=7.0 Hz), 2.47 (3H, s), 3.02 (2H, t, J=6.2 Hz), 3.53 (2H, td, J=6.1, 6.1 Hz), 4.33 (2H, q, J=7.1 Hz), 5.06 (2H, s), 5.30 (1H, s), 7.26-7.36 (5H, m).

e) Preparation of ethyl 4-(2-aminoethyl)-2-methyl-1,3-oxazole-5-carboxylate (Compound IN-10-5)

Compound IN-10-4 (3.44 g) and 5% Pd—C (2.00 g) were dissolved in ethanol (25 mL). Then, the mixture was stirred under hydrogen atmosphere at room temperature for 20 hours, and filtered through Celite. The filtrate was concentrated under reduced pressure to obtain the titled compound (1.78 g).
$^1$H-NMR (400 MHz, CDCl$_3$) δ: 1.39 (3H, t, J=7.1 Hz), 2.22 (3H, s), 2.51 (3H, s), 2.99 (2H, dd, J=10.1, 3.7 Hz), 3.05-3.08 (2H, m), 4.38 (2H, q, J=7.2 Hz).

f) Preparation of 2-methyl-6,7-dihydro[1,3]oxazolo[5,4-c]pyridin-4(5H)-one (Reference Example 26)

A mixture of Compound IN-10-5 (0.749 g), potassium carbonate (0.627 g), dimethoxyethane (1.0 mL), and water (1.0 mL) was stirred at room temperature for 3 days, and the solvent was removed. Then, the residue was purified by silica gel column chromatography (chloroform/methanol) to obtain the titled compound (0.322 g).
$^1$H-NMR (400 MHz, CDCl$_3$) δ: 2.55 (3H, s), 2.90 (2H, t, J=7.1 Hz), 3.65 (2H, td, J=7.1, 2.3 Hz), 5.96 (1H, s).

Reference Examples 27 to 30

According to the method of Reference example 26, the compounds of Reference examples 27 to 30 were prepared from the corresponding starting materials.

| Reference example | Chemical structure | Instrumental analyses data |
|---|---|---|
| 27 | ![structure] | $^1$H-NMR (400 MHz, CDCl$_3$) δ: 1.38 (3H, t, J = 7.6 Hz), 2.88 (2H, q, J = 7.6 Hz), 2.91 (2H, t, J = 7.1 Hz), 3.65 (2H, td, J = 7.1, 2.6 Hz), 5.68 (1H, brs). |

-continued

| Reference example | Chemical structure | Instrumental analyses data |
|---|---|---|
| 28 | Me-oxazolo-pyridinone with CH(Me)₂ substituent | ¹H-NMR (400 MHz, CDCl₃) δ: 1.40 (6H, d, J = 6.9 Hz), 2.92 (2H, t, J = 7.1 Hz), 3.12-3.22 (1H, m), 3.65 (2H, td, J = 7.2, 2.6 Hz), 5.50 (1H, brs). |
| 29 | cyclopropyl-oxazolo-pyridinone | ¹H-NMR (400 MHz, CDCl₃) δ: 1.10-1.24 (4H, m), 2.10-2.18 (1H, m), 2.87 (2H, t, J = 7.1 Hz), 3.63 (2H, td, J = 7.12.4 Hz), 5.32 (1H, brs). |
| 30 | Me-oxazolo-azepinone | ¹H-NMR (400 MHz, CDCl₃) δ: 2.04-2.10 (2H, m), 2.49 (3H, s), 2.86 (2H, t, J = 6.6 Hz), 3.38 (2H, dd, J = 9.6, 5.5 Hz), 6.43 (1H, s). |

Reference Example 31

2-Methyl-6,7-dihydro[1,3]oxazolo[4,5-c]pyridin-4(5H)-one

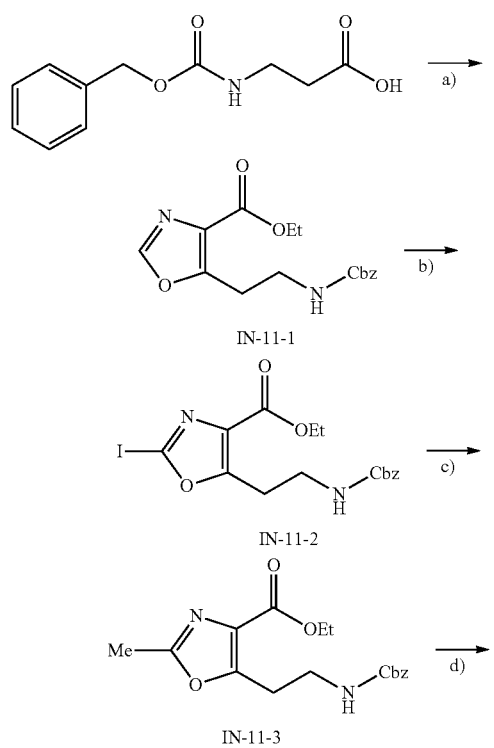

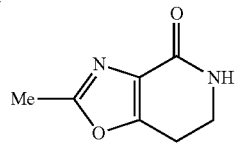

Reference example 31 a) Preparation of ethyl 5-(2-{[(benzyloxy)carbonyl]amino}ethyl)-1,3-oxazole-4-carboxylate (Compound IN-11-1)

To a solution of 3-([(benzyloxy)carbonyl]amino)propionic acid (5.00 g) in tetrahydrofuran (50 mL) was added carbonyl-1,1'-diimidazole (4.00 g) at room temperature. After stirring at room temperature for 1.5 hours, triethylamine (4.06 mL) and isocyanoethyl acetate (3.20 mL) were added thereto. After stirring at 65° C. for 24 hours, to the reaction mixture was added saturated aqueous ammonium chloride, and the mixture was extracted with ethyl acetate. The organic layer was dried over sodium sulfate, filtered, and concentrated under reduced pressure. The residue was purified by silica gel column chromatography (hexane/ethyl acetate) to obtain the titled compound (3.99 g).

¹H-NMR (400 MHz, CDCl₃) δ: 1.36 (3H, t, J=7.1 Hz), 3.27 (2H, t, J=6.4 Hz), 3.53 (2H, dd, J=6.4, 6.4 Hz), 4.35 (2H, q, J=7.1 Hz), 5.00 (1H, brs), 5.05 (2H, s), 7.29-7.33 (5H, m), 7.74 (1H, s).

b) Preparation of ethyl 5-(2-{[(benzyloxy)carbonyl]amino}ethyl)-2-iodo-1,3-oxazole-4-carboxylate (Compound IN-11-2)

To a solution of Compound IN-11-1 (446 mg) in tetrahydrofuran (2.1 mL) was added 1.0 mol/L lithium bis(trimethylsilyl)amide-tetrahydrofuran solution (3.08 mL) at −40° C. After stirring at −40° C. for 15 minutes, 0.5 mol/L zinc chloride-tetrahydrofuran solution (6.17 mL) was added thereto, and the mixture was warmed to 0° C. for 45 minutes, and iodine (462 mg) was added. After stirring at room temperature for an hour, to the reaction mixture was added saturated aqueous sodium thiosulfate, and the mixture was extracted with ethyl acetate. The organic layer was dried over sodium sulfate, filtered, and concentrated under reduced pressure. The residue was purified by silica gel column chromatography (hexane/ethyl acetate) to obtain the titled compound (510 mg).

¹H-NMR (400 MHz, CDCl₃) δ: 1.35 (3H, t, J=7.1 Hz), 3.27 (2H, t, J=6.4 Hz), 3.52 (2H, dd, J=6.4, 6.4 Hz), 4.34 (2H, q, J=7.1 Hz), 5.00 (1H, brs), 5.07 (2H, s), 7.32 (5H, dd, J=10.1, 8.3 Hz).

c) Preparation of ethyl 5-(2-{[(benzyloxy)carbonyl]amino}ethyl)-2-methyl-1,3-oxazole-4-carboxylate (Compound IN-11-3)

To a solution of Compound IN-11-2 (265 mg) in N,N-dimethylformamide (1.5 mL) were added potassium carbonate (247 mg), trimethylboroxine (97.0 mg), and tetrakis(triphenylphosphine)palladium (68.9 mg) at room temperature. After reacted at 120° C. for 1.5 hours under microwave irradiation, the reaction mixture was filtered through Celite, and the filtrate was concentrated under reduced pressure. The residue was purified by silica gel column chromatography (hexane/ethyl acetate) to obtain the titled compound (100 mg).

¹H-NMR (400 MHz, CDCl₃) δ: 1.30 (3H, t, J=7.2 Hz), 2.38 (3H, s), 3.16 (2H, t, J=6.6 Hz), 3.46 (2H, dd, J=6.3, 6.3 Hz), 4.28 (2H, q, J=7.2 Hz), 5.01 (2H, s), 5.00-5.03 (1H, br s) 7.27-7.35 (5H, m).

d) Preparation of 2-methyl-6,7-dihydro[1,3]oxazolo[4,5-c]pyridin-4(5H)-one (Reference Example 31)

To a solution of Compound IN-11-3 (710 mg) in ethanol (11 mL) was added palladium on carbon (227 mg) under room temperature. After stirring under hydrogen atmosphere at room temperature for 15 hours, the reaction mixture was filtered through Celite, and the filtrate was concentrated under reduced pressure.

To a solution of the resulting residue (423 mg) in 1,2-dimethoxyethane/water (1/1, 1.9 mL) was added potassium carbonate (384 mg) under room temperature. After stirring at room temperature for 2 days, the reaction mixture was concentrated under reduced pressure. The residue was purified by silica gel column chromatography (chloroform/methanol) to obtain the titled compound (209 mg).

¹H-NMR (400 MHz, CDCl₃) δ: 2.48 (3H, s), 2.99 (2H, t, J=7.1 Hz), 3.64 (2H, td, J=7.1, 2.5 Hz), 5.40 (1H, brs).

Reference Example 32

2-Methyl-5,6,7,8-tetrahydro-4H-[1,3]oxazolo[4,5-c]azepin-4-one

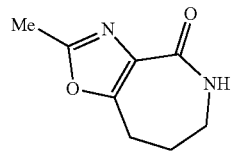

According to a similar method to Reference example 31, the titled compound was prepared from 4-([(benzyloxy)carbonyl]amino)butanoic acid.

¹H-NMR (400 MHz, CDCl₃) δ: 2.07-2.13 (2H, m), 2.44 (3H, s), 2.94 (2H, t, J=6.7 Hz), 3.37 (2H, dd, J=9.8, 5.4 Hz), 6.12 (1H, brs).

Reference Example 33

1-Methyl-4,5,6,7-tetrahydropyrazolo[3,4-c]azepin-8(1H)-one

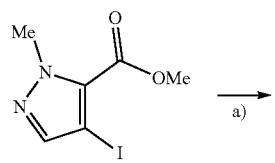

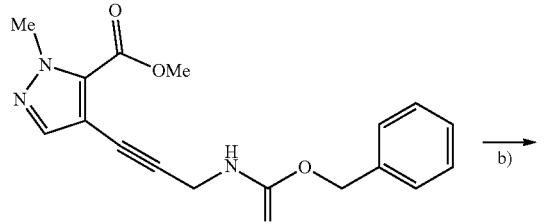

IN-12-1

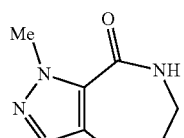

Reference example 33 a) Preparation of methyl 4-(3-{[(benzyloxy)carbonyl]amino}prop-1-yn-1-yl)-1-methyl-1H-pyrazole-5-carboxylate (Compound IN-12-1)

To a solution of methyl 4-iodo-1-methyl-1H-pyrazole-5-carboxylate (600 mg) in N,N-dimethylformamide (5.0 mL) were added benzyl prop-2-yn-1-ylcarbamate (640 mg), triethylamine (2.20 mL), bis(triphenylphosphine)palladium(II) dichloride (158 mg), and copper(I) iodide (43.0 mg), and the mixture was stirred at 90° C. for 3 hours. After that, water (50 mL) was added to the reaction mixture, and the mixture was extracted with ethyl acetate/toluene (1/1), dried over anhydrous sodium sulfate, filtered, and concentrated. The residue was purified by silica gel column chromatography (hexane/ethyl acetate) to obtain the titled compound (610 mg).

¹H-NMR (300 MHz, CDCl₃) δ: 3.89 (3H, s), 4.15 (3H, s), 4.24 (2H, d, J=5.3 Hz), 4.99 (1H, brs), 5.15 (2H, s), 7.29-7.43 (5H, m), 7.54 (1H, s).

b) Preparation of 1-methyl-4,5,6,7-tetrahydropyrazolo[3,4-c]azepin-8(1H)-one (Reference Example 33)

To a solution of Compound IN-12-1 (610 mg) in methanol (10 mL) was added 10% palladium-carbon (600 mg), and the mixture was stirred under hydrogen atmosphere (0.3 MPa) for 6 hours. The reaction mixture was filtered through Celite, and concentrated. To a solution of the resulting residue in ethanol (10 mL) was added triethylamine (0.519 mL), and the mixture was heated under reflux for 140 hours. The reaction mixture was concentrated, and the residue was purified by silica gel column chromatography (chloroform/methanol) to obtain the titled compound (130 mg).

¹H-NMR (400 MHz, CDCl₃) δ: 1.99-2.07 (2H, m), 2.86 (2H, t, J=7.1 Hz), 3.28-3.34 (2H, m), 4.14 (3H, s), 5.93 (1H, brs), 7.31 (1H, s).

Reference Example 34

2-Methyl-4,5,6,7-tetrahydropyrazolo[3,4-c]azepin-8(2H)-one

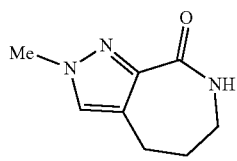 [SMILES: Cn1cc2c(n1)C(=O)NCCC2]

According to a similar method to Reference example 33, the titled compound was obtained from methyl 4-iodo-1-methyl-1H-pyrazole-3-carboxylate.

$^1$H-NMR (400 MHz, CDCl$_3$) δ: 2.00-2.09 (2H, m), 2.83 (2H, t, J=6.8 Hz), 3.33-3.40 (2H, m), 3.95 (3H, s), 6.11 (1H, brs), 7.23 (1H, s).

Reference Example 35

3-Methyl-5,6,7,8-tetrahydroimidazo[4,5-c]azepin-4(3H)-one

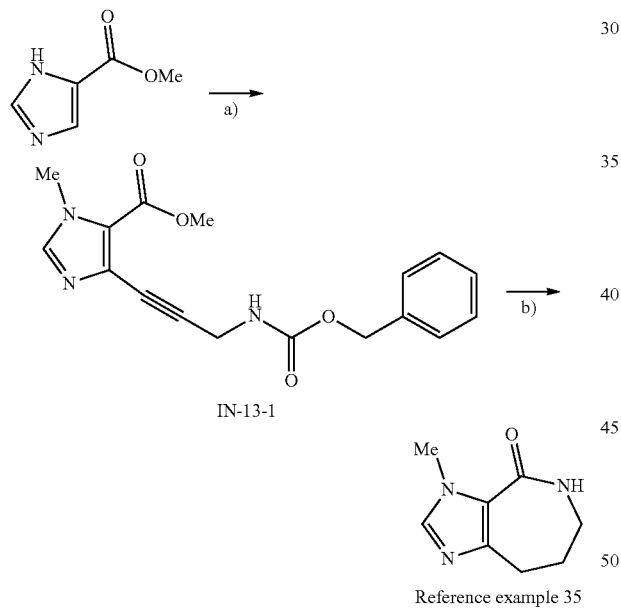

Reference example 35 a) Preparation of methyl 4-(3-{[(benzyloxy)carbonyl]amino}prop-1-yn-1-yl)-1-methyl-1H-imidazole-5-carboxylate (Compound IN-13-1)

A mixture of methyl 4-imidazolecarboxylate (375 mg), N-bromosuccinimide (529 mg), and acetonitrile (15 mL) was stirred at room temperature for 5 hours. The reaction mixture was concentrated, and the residue was purified by silica gel column chromatography (chloroform/methanol). To a solution of the resulting purified product (0.267 g) in N,N-dimethylformamide (6.5 mL) was added 55% sodium hydride (0.0680 g) under ice temperature. After stirring under ice temperature for 30 minutes, methyl iodide (0.277 g) was added thereto, and the mixture was stirred at room temperature for 4 hours. To the reaction mixture was added methanol, and the mixture was concentrated. The residue was purified by silica gel column chromatography (chloroform/methanol). A mixture of the resulting purified product (176 mg), N-(tert-butoxycarbonyl)propargylamine (228 mg), copper(I) iodide (15.3 mg), triethylamine (0.569 g), bis(triphenylphosphine)palladium(II) dichloride (56.4 mg), and N,N-dimethylformamide (15 mL) was stirred at 100° C. for 1.5 hours under microwave irradiation. Then, the reaction mixture was filtered, and the filtrate was concentrated under reduced pressure. The residue was purified by silica gel column chromatography (hexane/ethyl acetate) to obtain the titled compound (101 mg).

$^1$H-NMR (400 MHz, CDCl$_3$) δ: 3.79-3.91 (5H, m), 4.27 (2H, d, J=5.1 Hz), 5.13 (3H, s), 7.28-7.42 (5H, m), 7.49-7.61 (1H, m).

b) Preparation of 3-methyl-5,6,7,8-tetrahydroimidazo[4,5-c]azepin-4(3H)-one (Reference Example 35)

A mixture of Compound IN-13-1 (101 mg), 20% palladium hydroxide on carbon (0.173 g), and methanol (1.7 mL) was stirred under hydrogen atmosphere at room temperature for 1.5 hours. Then, the reaction mixture was filtered, and concentrated. A mixture of the resulting residue (60.9 mg), triethylamine (125 mg), and ethanol (1.6 mL) was stirred at 100° C. for 72 hours. The reaction mixture was concentrated, and the residue was purified by silica gel column chromatography (chloroform/methanol) to obtain the titled compound (6.6 mg).

$^1$H-NMR (400 MHz, CD$_3$OD) δ: 1.97-2.08 (2H, m), 2.91-3.00 (2H, m), 3.26-3.36 (2H, m), 3.87 (3H, s), 7.71 (1H, s).

Reference Example 36

1-Methyl-1,5,6,7-tetrahydro-4H-pyrrolo[3,2-c]pyridin-4-one

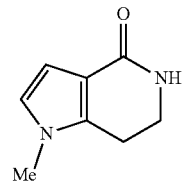

A mixture of 2,4-piperadinedione (200 mg), methylaminoacetaldehyde dimethyl acetal (253 mg), p-toluenesulfonic acid monohydrate (33.6 mg), and toluene (8.8 mL) was stirred with Dean-Stark apparatus at 140° C. for an hour. Then, the reaction mixture was concentrated under reduced pressure, and trifluoroacetic acid (1.6 mL) was added thereto at room temperature. After stirring at room temperature for 24 hours, toluene was added, and the solvent was azeotropically removed. The residue was purified by amino silica gel column chromatography (chloroform/methanol) to obtain the titled compound (194 mg).

$^1$H-NMR (400 MHz, CDCl$_3$) δ: 2.81 (2H, t, J=6.9 Hz), 3.55-3.62 (5H, m), 5.34 (1H, brs), 6.54 (1H, d, J=5.0 Hz), 6.55 (1H, d, J=4.6 Hz).

Reference Example 37

1,7-Dimethyl-1,5,6,7-tetrahydro-4H-pyrrolo[3,2-c]pyridin-4-one

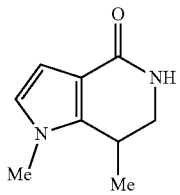

According to a similar method to Reference example 36, the titled compound was prepared by 5-methyl-2,4-piperidinedione.
¹H-NMR (400 MHz, CDCl₃) δ: 1.25 (3H, d, J=7.3 Hz), 3.01-3.09 (1H, m), 3.39-3.46 (1H, m), 3.62 (3H, s), 3.82 (1H, dd, J=13.1, 5.3 Hz), 6.52 (1H, d, J=3.2 Hz), 6.57 (1H, d, J=3.2 Hz), 8.82 (1H, brs).

Reference Example 38

2,3-Dimethyl-2,5,6,7-tetrahydro-4H-pyrazolo[4,3-c]pyridin-4-one

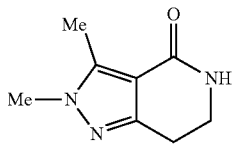 [SMILES: Cc1c2c(nn1C)CCNC2=O]

To a solution of piperidin-2,4-dione (10.0 g, 88.0 mmol) in N,N-dimethylformamide (44 mL) was added methylhydrazine (4.70 mL, 88.0 mmol) under ice temperature. After stirring at room temperature for an hour, to the reaction mixture was added N,N-dimethylacetamide dimethyl acetal (65.4 mL, 442 mmol). After stirring at 130° C. for 3 hours, the reaction mixture was concentrated under reduced pressure. The residue was purified by silica gel column chromatography (chloroform:methanol) to obtain the titled compound (11.2 g).
¹H-NMR (400 MHz, CDCl₃) δ: 2.51 (3H, s), 2.84 (2H, t, J=6.6 Hz), 3.51 (2H, td, J=6.6, 2.8 Hz), 3.74 (3H, s), 5.34 (1H, s).

Reference Examples 39 and 40

3-Bromo-1-methyl-1,5,6,7-tetrahydro-4H-pyrazolo[4,3-c]pyridin-4-one (Reference Example 39)

3-Bromo-2-methyl-2,5,6,7-tetrahydro-4H-pyrazolo[4,3-c]pyridin-4-one (Reference Example 40)

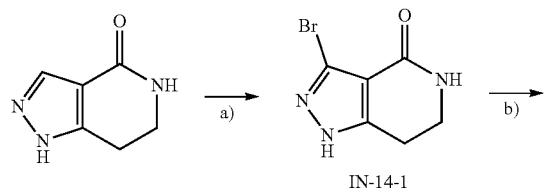

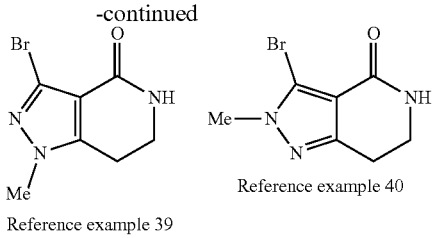

a) Preparation of 3-bromo-1,5,6,7-tetrahydro-4H-pyrazolo[4,3-c]pyridin-4-one (Compound IN-14-1)

To a mixture of 1,5,6,7-tetrahydro-4H-pyrazolo[4,3-c]pyridin-4-one (600 mg), sodium acetate (1.44 g), ethanol (21 mL), and water (14 mL) was added bromine (0.451 mL) under ice temperature. After stirring under ice temperature for 2 hours, additional sodium acetate (1.44 g) and bromine (0.451 mL) were added thereto. After stirring under ice temperature for additional 2 hours, to the reaction mixture was added saturated aqueous sodium thiosulfate. The mixture was filtered through Celite, and concentrated under reduced pressure. The residue was dissolved in methanol, and insolubles were filtered out, and the filtrate was concentrated under reduced pressure. The resulting residue was purified by silica gel column chromatography (chloroform/methanol) to obtain the titled compound (1.02 g).
¹H-NMR (400 MHz, CD₃OD) δ: 2.96 (2H, t, J=6.9 Hz), 3.54 (2H, t, J=6.9 Hz).

b) Preparation of 3-bromo-1-methyl-1,5,6,7-tetrahydro-4H-pyrazolo[4,3-c]pyridin-4-one (Reference Example 39) and 3-bromo-2-methyl-2,5,6,7-tetrahydro-4H-pyrazolo[4,3-c]pyridin-4-one (Reference Example 40)

To a solution of Compound IN-14-1 (1.02 g) in N,N-dimethylformamide (10 mL) were added potassium carbonate (1.31 g), and methyl iodide (0.354 mL) at room temperature. After stirring at room temperature for 2 hours, the reaction mixture was concentrated under reduced pressure. The residue was purified by silica gel column chromatography (chloroform/methanol) to obtain Reference example 39 (341 mg) and Reference example 40 (205 mg).
Reference example 39: ¹H-NMR (400 MHz, DMSO-D₆) δ: 2.88 (2H, t, J=6.9 Hz), 3.37 (2H, td, J=6.9, 2.6 Hz), 3.73 (3H, s), 7.34 (1H, brs).
Reference example 40: ¹H-NMR (400 MHz, DMSO-D₆) δ: 2.73 (2H, t, J=6.6 Hz), 3.34 (2H, td, J=6.6, 3.1 Hz), 3.78 (3H, s), 7.47 (1H, brs).

Reference Example 41

2-Methyl-3-(trifluoromethyl)-2,5,6,7-tetrahydro-4H-pyrazolo[4,3-c]pyridin-4-one

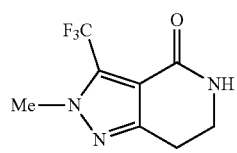 [SMILES: Cn1nc2c(c1C(F)(F)F)C(=O)NCC2]

To a mixture of the compound of Reference example 13 (100 mg), bis(((trifluoromethyl)sulfinyl)oxy)zinc (439 mg), dichloromethane (3.0 mL), and water (1.2 mL) was added dropwise 70% aqueous 2-hydroperoxide-2-methylpropane (0.362 mL) under ice temperature. After stirring at room temperature for 16 hours, aqueous 10% sodium thiosulfate was added to the reaction mixture. The mixture was extracted with chloroform, dried over anhydrous sodium sulfate, filtered, and concentrated. The residue was purified by silica gel column chromatography (chloroform/methanol) to obtain the titled compound (0.0400 g).

$^1$H-NMR (400 MHz, CDCl$_3$) δ: 2.92 (2H, t, J=6.6 Hz), 3.56 (2H, td, J=6.6, 3.2 Hz), 4.04 (3H, q, J=1.4 Hz), 5.79 (1H, brs).

Reference Example 42

2-Methyl-7,8-dihydropyrido[4,3-d]pyrimidin-5(6H)-one

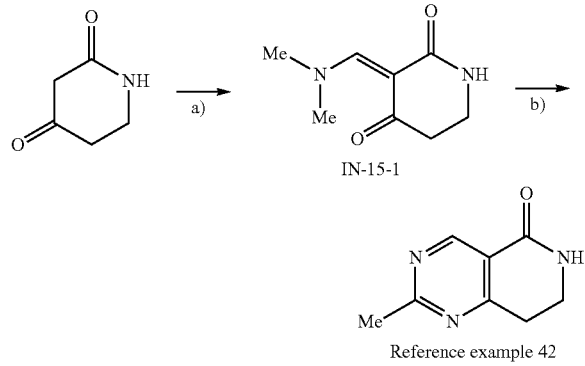

Reference example 42 a) Preparation of (3E)-3-[(dimethylamino)methylidyne]piperidin-2,4-dione (Compound IN-15-1)

To a solution of piperidin-2,4-dione (2.50 g) in N,N-dimethylformamide (50 mL) was added N,N-dimethylformamide dimethyl acetal (3.52 mL), and the mixture was stirred at 90° C. for 4 hours. Then, the reaction mixture was concentrated to obtain the titled compound (3.72 g).

$^1$H-NMR (400 MHz, DMSO-D$_6$) δ: 2.28 (2H, t, J=6.5 Hz), 3.05 (3H, s), 3.12-3.18 (2H, m), 3.28 (3H, s), 7.12 (1H, brs), 7.82 (1H, s).

b) Preparation of 2-methyl-7,8-dihydropyrido[4,3-d]pyrimidin-5(6H)-one (Reference Example 42)

A mixture of Compound IN-15-1 (150 mg), N,N-diisopropylethylamine (300 mg), acetamidine monohydrate (101 mg), and ethanol (4.5 mL) was stirred at 100° C. for 2 hours. Then, the reaction mixture was concentrated under reduced pressure, and the residue was purified by silica gel column chromatography (chloroform/methanol) to obtain the titled compound (87.9 mg).

$^1$H-NMR (400 MHz, CDCl$_3$) δ: 2.78 (3H, s), 3.13 (2H, t, J=6.6 Hz), 3.68 (2H, td, J=6.6, 2.8 Hz), 5.97 (1H, s), 9.15 (1H, s).

Reference Examples 43 to 44

According to the method of Reference example 42, the compounds of Reference examples 43 to 44 were prepared using the corresponding reagents.

| Reference example | Chemical structure | Instrumental analyses data |
|---|---|---|
| 43 | ![structure] | $^1$H-NMR (400 MHz, CDCl$_3$) δ: 1.39 (3H, t, J = 7.6 Hz), 3.02 (2H, q, J = 7.6 Hz), 3.14 (2H, t, J = 6.6 Hz), 3.68 (2H, td, J = 6.6, 2.8 Hz), 6.05 (1H, brs), 9.17 (1H, s). |
| 44 | ![structure] | $^1$H-NMR (400 MHz, CDCl$_3$) δ: 1.10-1.20 (2H, m), 1.20-1.28 (2H, m), 2.23-2.34 (1H, m), 3.08 (2H, t, J = 6.8 Hz), 3.65 (2H, td, 3 = 6.6, 2.6 Hz), 6.39 (1H, brs), 9.05 (1H, s). |

Reference Example 45

2-[4-(1,2-Benzoisoxazol-3-yl)piperidin-1-yl]ethane-1-amine dihydrochloride

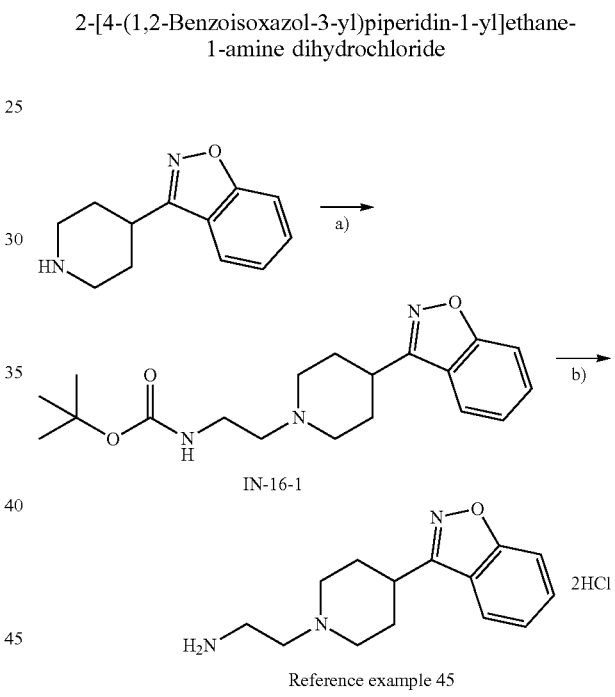

Reference example 45 a) Preparation of tert-butyl {2-[4-(1,2-benzoisoxazol-3-yl)piperidin-1-yl]ethyl}carbamate (Compound IN-16-1)

To a mixture of 3-(piperidin-4-yl)benzo[d]isoxazole (3.00 g), tetrahydrofuran (56 mL), and water (18 mL) were added tert-butyl (2-bromoethyl)carbamate (6.65 g), tetrabutylammonium bromide (0.956 g), and potassium carbonate (10.3 g), and the mixture was stirred at room temperature for 3 days. To the reaction mixture was added water, and the mixture was extracted with ethyl acetate. The combined organic layer was washed with water and brine, dried over anhydrous sodium sulfate, filtered, and concentrated. The resulting residue was purified by silica gel column chromatography (ethyl acetate/methanol) to obtain the titled compound (5.70 g).

$^1$H-NMR (400 MHz, CDCl$_3$) δ: 1.47 (9H, s), 2.05-2.13 (4H, m), 2.13-2.25 (2H, m), 2.52 (2H, t, J=6.0 Hz), 3.00-

3.16 (3H, m), 3.21-3.33 (2H, m), 5.05 (1H, brs), 7.28-7.33 (1H, m), 7.51-7.60 (2H, m), 7.75 (1H, d, J=7.8 Hz).

b) Preparation of 2-[4-(1,2-benzoisoxazol-3-yl)piperidin-1-yl]ethane-1-amine dihydrochloride (Reference Example 45)

According to a similar method to Reference example 8, the titled compound was prepared from Compound IN-16-1.
$^1$H-NMR (400 MHz, DMSO-D$_6$) δ: 2.16-2.32 (2H, m), 2.33-2.46 (2H, m), 3.15-3.29 (1H, m), 3.30-3.44 (4H, m), 3.45-3.59 (2H, m), 3.63-3.78 (2H, m), 7.41 (1H, dd, J=7.4, 7.4 Hz), 7.66 (1H, dd, J=7.7, 7.7 Hz), 7.75 (1H, d, J=8.5 Hz), 8.14 (1H, d, J=8.0 Hz), 8.46 (3H, brs), 11.35 (1H, brs).

Reference Example 46

Methyl 1-methyl-4-(2-oxoethyl)-1H-pyrazole-5-carboxylate

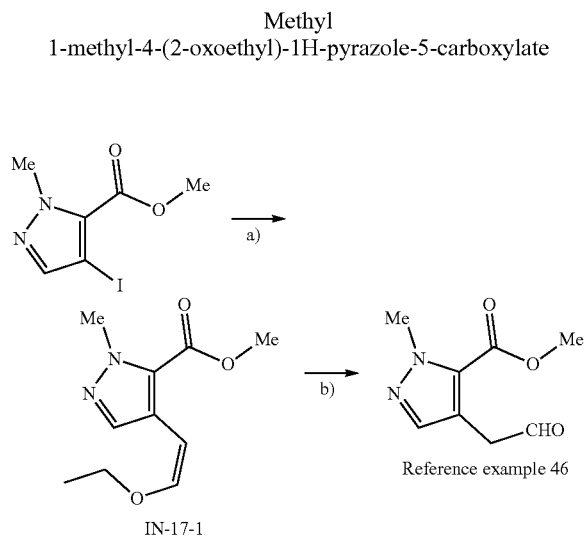

Reference example 46 a) Preparation of methyl 4-[(Z)-2-ethoxyethenyl]-1-methyl-1H-pyrazole-5-carboxylate (Compound IN-17-1)

According to a similar method to Compound IN-12-1, the titled compound was prepared from methyl 4-iodo-1-methyl-1H-pyrazole-5-carboxylate.
$^1$H-NMR (400 MHz, CDCl$_3$) δ: 1.36 (3H, t, J=7.1 Hz), 3.91 (3H, s), 3.99 (2H, q, J=7.1 Hz), 4.13 (3H, s), 5.79 (1H, d, J=6.6 Hz), 6.24 (1H, d, J=6.8 Hz), 8.02 (1H, s).

b) Preparation of methyl 1-methyl-4-(2-oxoethyl)-1H-pyrazole-5-carboxylate (Reference Example 46)

To a solution of Compound IN-17-1 (95.8 mg) in tetrahydrofuran (1.1 mL) was added 1 mol/L hydrochloric acid (1.1 mL) under ice temperature, and the mixture was stirred at 40° C. for 3 hours. To the reaction mixture was added saturated aqueous sodium bicarbonate, and the mixture was extracted with ethyl acetate, dried over anhydrous sodium sulfate, filtered, and concentrated to obtain the titled compound (79.2 mg).
$^1$H-NMR (400 MHz, CDCl$_3$) δ: 3.78 (2H, d, J=1.4 Hz), 3.88 (3H, s), 4.19 (3H, s), 7.42 (1H, s), 9.68 (1H, t, J=1.6 Hz).

Reference Example 47

1-{2-[4-(1,2-Benzoisoxazol-3-yl)piperidin-1-yl]ethyl}azepan-2,4-dione

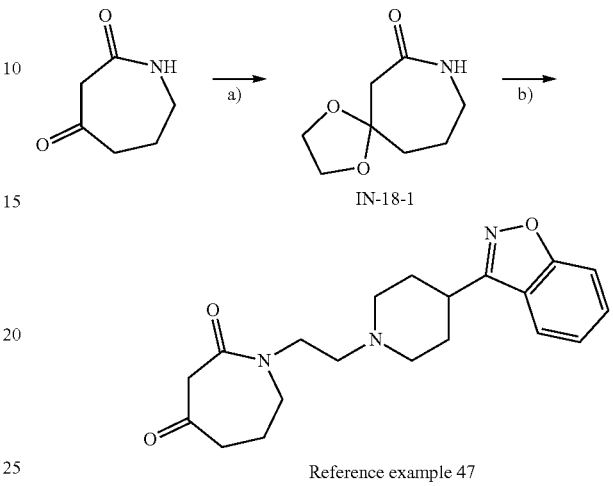

Reference example 47 a) Preparation of 1,4-dioxa-8-azaspiro[4.6]undecan-7-one (Compound IN-18-1)

To a solution of azepan-2,4-dione (1.07 g) in toluene (15 mL) were added ethan-1,2-diol (0.570 mL) and methanesulfonic acid (0.0270 mL), and the mixture was heated under reflux with Dean-Stark apparatus for 4 hours. The reaction mixture was cooled to room temperature, hexane (15 mL) was added thereto. After stirring at room temperature for 30 minutes, the precipitated solid was collected by filtration, washed with toluene/hexane=1/1 (2.0 mL) to obtain the titled compound (1.37 g).
$^1$H-NMR (400 MHz, CDCl$_3$) δ: 1.82-1.90 (2H, m), 1.93-1.99 (2H, m), 2.83 (2H, s), 3.24-3.31 (2H, m), 3.93-4.11 (4H, m), 5.95 (1H, brs).

b) Preparation of 1-{2-[4-(1,2-benzoisoxazol-3-yl)piperidin-1-yl]ethyl}azepan-2,4-dione (Reference Example 47)

To a solution of Compound IN-18-1 (375 mg) in N,N-dimethylformamide (4.4 mL) was added 55% sodium hydride (96.0 mg) under ice temperature. After stirring under ice temperature for 20 minutes, the compound of Reference example 3 (580 mg) and potassium iodide (109 mg) were added, and the mixture was stirred at 50° C. for 4 hours. To the reaction mixture was added water, and the mixture was extracted with chloroform, dried over anhydrous sodium sulfate, filtered, and concentrated. In order to remove the remaining N,N-dimethylformamide, toluene was added to the residue and concentrated, and these procedures were repeated twice. To the resulting concentrated residue were added tetrahydrofuran (7.3 mL) and 6 mol/L hydrochloric acid (7.30 mL), and the mixture was stirred at 60° C. for an hour. Then, to the reaction mixture was added 2 mol/L aqueous sodium hydroxide, and pH was adjusted to 7 or more. The mixture was extracted with chloroform, dried over anhydrous sodium sulfate, filtered, and concentrated.

The residue was purified by silica gel column chromatography (chloroform/methanol) to obtain the titled compound (630 mg).

¹H-NMR (400 MHz, CDCl₃) δ: 1.96-2.15 (6H, m), 2.17-2.29 (2H, m), 2.54-2.63 (2H, m), 2.67 (2H, t, J=7.3 Hz), 3.02-3.14 (3H, m), 3.55 (2H, s), 3.62 (4H, t, J=5.8 Hz), 7.25-7.30 (1H, m), 7.48-7.57 (2H, m), 7.70 (1H, d, J=7.9 Hz).

Reference Example 48

8-{2-[4-(1,2-Benzoisoxazol-3-yl)piperidin-1-yl]ethyl}-1,4-dioxa-8-azaspiro[4.5]decan-7-one

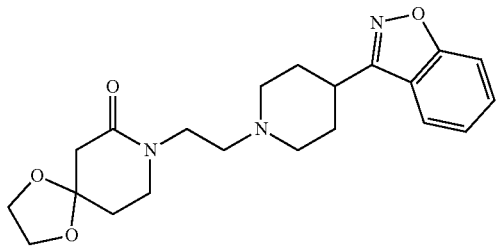 [SMILES: O=C1CC2(CCN1CCN1CCC(c3noc4ccccc34)CC1)OCCO2]

According to a similar method to Example 47, the titled compound was prepared using piperidin-2,4-dione.

¹H-NMR (400 MHz, CDCl₃) δ: 1.89-1.97 (2H, m), 2.01-2.08 (4H, m), 2.18-2.25 (2H, m), 2.55-2.60 (2H, m), 2.59 (2H, s), 3.04-3.08 (3H, m), 3.45 (2H, t, J=6.4 Hz), 3.52 (2H, t, J=6.4 Hz), 3.92-4.00 (4H, m), 7.24-7.28 (2H, m), 7.48-7.55 (2H, m), 7.69-7.73 (1H, m).

Reference Example 49

1-{2-[4-(1,2-Benzoisoxazol-3-yl)piperazin-1-yl]ethyl}azepan-2,4-dione

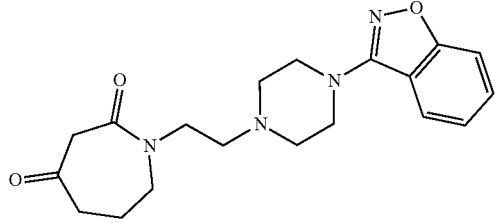 [SMILES: O=C1CCCN(CCN2CCN(c3noc4ccccc34)CC2)C(=O)C1]

To a solution of Compound IN-18-1 (1.20 g) in N,N-dimethylformamide (20 mL) was added 55% sodium hydride (0.421 g) under ice temperature. After stirring under ice temperature for 30 minutes, the compound of Reference example 1 (1.86 g) and potassium iodide (0.582 g) were added thereto, and the mixture was stirred at 60° C. for 4 hours. Then, to the reaction mixture was added 2 mol/L hydrochloric acid, and the mixture was stirred at 90° C. for an hour. Then, to the reaction mixture was added 4 mol/L sodium hydroxide to adjust pH to 9 or more. The mixture was extracted with chloroform, and the combined organic layer was dried over anhydrous sodium sulfate, filtered, and concentrated. The residue was purified by silica gel column chromatography (chloroform/methanol) to obtain the titled compound (1.17 g).

¹H-NMR (400 MHz, CDCl₃) δ: 2.06-2.11 (1H, m), 2.62-2.73 (7H, m), 3.54 (4H, t, J=10.3 Hz), 3.64 (4H, tt, J=8.3, 4.8 Hz), 4.81 (4H, s), 7.22 (1H, ddd, J=8.3, 8.0, 0.9 Hz), 7.44-7.51 (2H, m), 7.68 (1H, dd, J=8.3, 0.9 Hz).

Reference Example 50

Methyl 4-[2-({2-[4-(1,2-benzoisoxazol-3-yl)piperidin-1-yl]ethyl}amino)ethyl]-1-[(4-methoxyphenyl)methyl]-1H-pyrazole-3-carboxylate

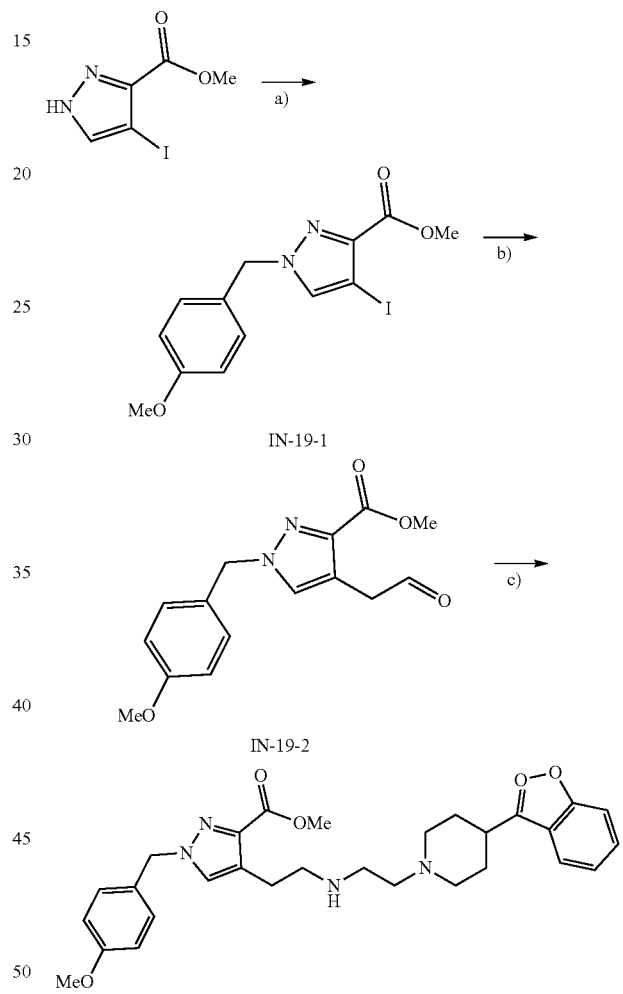

Reference example 50 a) Preparation of methyl 4-iodo-1-[(4-methoxyphenyl)methyl]-1H-pyrazole-3-carboxylate (Compound IN-19-1)

To a mixture of methyl 4-iodo-1H-pyrazole-5-carboxylate (413 mg) and acetonitrile (8.2 mL) were added potassium carbonate (339 mg) and 4-methoxybenzyl chloride (0.268 mL), and the mixture was stirred at 50° C. for 2 hours. To the reaction mixture was added water, and the mixture was extracted with ethyl acetate, dried over anhydrous sodium sulfate, filtered, and concentrated. The concentrated residue was purified by silica gel column chromatography (hexane/ethyl acetate) to obtain the titled compound (467 mg).

$^1$H-NMR (400 MHz, CDCl$_3$) δ: 3.81 (3H, s), 3.95 (3H, s), 5.30 (2H, s), 6.90 (2H, d, J=9.2 Hz), 7.22 (2H, d, J=8.7 Hz), 7.38 (1H, s).

b) Preparation of methyl 1-[(4-methoxyphenyl)methyl]-4-(2-oxoethyl)-1H-pyrazole-3-carboxylate (Compound IN-19-2)

According to a similar method to Reference example 46, the titled compound was prepared from Compound IN-19-1.
$^1$H-NMR (400 MHz, CDCl$_3$) δ: 3.81 (3H, s), 3.86 (2H, d, J=0.9 Hz), 3.93 (3H, s), 5.30 (2H, s), 6.89 (2H, d, J=8.7 Hz), 7.23 (2H, d, J=8.7 Hz), 7.33 (1H, s), 9.72 (1H, t, J=1.4 Hz).

c) Preparation of methyl 4-[2-({2-[4-(1,2-benzo-isoxazol-3-yl)piperidin-1-yl]ethyl}amino)ethyl]-1-[(4-methoxyphenyl)methyl]-1H-pyrazole-3-carboxylate (Reference Example 50)

To a solution of the compound of Reference example 45 (105 mg) in dichloromethane (1.7 mL) was added N,N-diisopropylethylamine (0.144 mL), and the mixture was stirred at room temperature for 5 minutes. Then, Compound IN-19-2 (47.6 mg) and acetic acid (0.0283 mL) were added thereto, and the mixture was stirred at room temperature for 10 minutes. Then, sodium triacetoxyborohydride (70.0 mg) was added thereto, and the mixture was stirred at room temperature for 12 hours. To the reaction mixture was added saturated aqueous sodium bicarbonate, and the mixture was extracted with chloroform, dried over anhydrous sodium sulfate, filtered, and concentrated. The residue was purified by silica gel column chromatography (chloroform/methanol) to obtain the titled compound (26.2 mg).
$^1$H-NMR (400 MHz, CDCl$_3$) δ: 1.99-2.23 (6H, m), 2.52 (2H, t, J=6.2 Hz), 2.75 (2H, t, J=10.0 Hz), 2.84 (2H, t, J=6.9 Hz), 2.93 (2H, t, J=6.6 Hz), 2.98-3.12 (3H, m), 3.79 (3H, s), 3.92 (3H, s), 5.27 (2H, s), 6.87 (2H, d, J=8.3 Hz), 7.20 (2H, d, J=7.8 Hz), 7.27-7.32 (1H, m), 7.50-7.59 (3H, m), 7.75 (1H, d, J=8.3 Hz).

Reference Example 51

Methyl 4-(3-{[(benzyloxy)carbonyl]amino}prop-1-yn-1-yl)-1-{[2-(trimethylsilyl)ethoxy]methyl}-1H-imidazole-5-carboxylate

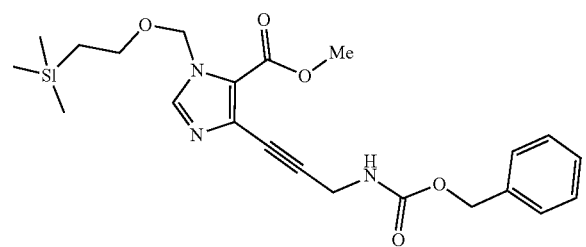

A mixture of methyl 4-bromo-1H-imidazole-5-carboxylate (450 mg), 2-(trimethylsilyl)ethoxymethyl chloride (5.49 g), triethylamine (3.33 g), and acetonitrile (11 mL) was stirred at room temperature for 3 hours. Then, the reaction mixture was concentrated under reduced pressure, and the residue was purified by silica gel column chromatography (hexane/ethyl acetate). A mixture of the resulting purified product (528 mg), N-(benzyloxycarbonyl)propargylamine (596 mg), copper(I) iodide (60.0 mg), triethylamine (1.59 g), bis(triphenylphosphine)palladium(II) dichloride (221 mg), and N,N-dimethylformamide (7.9 mL) was stirred at 130° C. for 1.5 hours under microwave irradiation. Then, the reaction mixture was filtered, and the filtrate was concentrated under reduced pressure. The residue was purified by silica gel column chromatography (hexane/ethyl acetate) to obtain the titled compound (401 mg).
$^1$H-NMR (400 MHz, CDCl$_3$) δ: −0.08-0.01 (9H, m), 0.81-0.99 (2H, m), 1.99-2.08 (3H, m), 3.42-3.65 (2H, m), 3.77-3.96 (2H, m), 4.04-4.18 (2H, m), 4.96-5.22 (2H, m), 7.28-7.42 (5H, m), 7.72 (1H, s).

Reference Example 52

[4-(1,2-Benzoisothiazol-3-yl)piperazin-1-yl]acetaldehyde

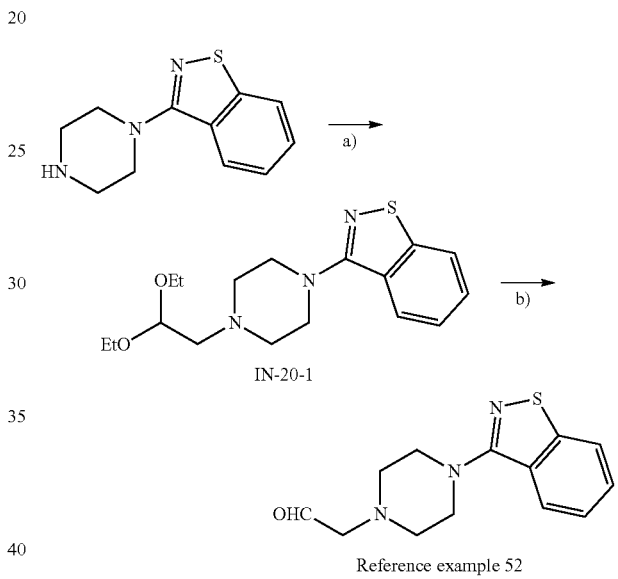

Reference example 52 a) Preparation of 3-[4-(2,2-diethoxyethyl)piperazin-1-yl]-1,2-benzoisothiazole (Compound IN-20-1)

To a solution of 3-(piperazin-1-yl)benzo[d]isothiazole (2.00 g) in acetonitrile (9.1 mL) were added 2-bromo-1,1-diethoxyethane (2.16 g), potassium carbonate (2.52 g), and potassium iodide (0.151 g). After heating under reflux for 13 hours, ethyl acetate (30 mL) was added to the reaction mixture, and the mixture was filtered and concentrated. The residue was purified by silica gel column chromatography (hexane/ethyl acetate) to obtain the titled compound (3.04 g).
$^1$H-NMR (400 MHz, CDCl$_3$) δ: 1.22 (6H, t, J=6.9 Hz), 2.63 (2H, d, J=5.0 Hz), 2.77 (4H, t, J=4.8 Hz), 3.50-3.61 (6H, m), 3.65-3.74 (2H, m), 4.69 (1H, t, J=5.3 Hz), 7.30-7.35 (1H, m), 7.42-7.47 (1H, m), 7.79 (1H, d, J=7.8 Hz), 7.89 (1H, d, J=8.3 Hz).

b) Preparation of [4-(1,2-benzoisothiazol-3-yl)piperazin-1-yl]acetaldehyde (Reference Example 52)

To Compound IN-20-1 (3.04 g) was added 47% hydrobromic acid (15.0 mL) at room temperature for an hour. Then, the reaction mixture was poured into iced water (40 mL), and 20% aqueous sodium hydroxide (27 mL) was added thereto, and the mixture was extracted with chloroform. The organic layer was dried over anhydrous sodium sulfate, filtered, and concentrated to obtain the titled compound (2.48 g).

$^1$H-NMR (400 MHz, CDCl$_3$) δ: 2.77 (4H, t, J=5.0 Hz), 3.27 (2H, d, J=1.4 Hz), 3.61 (4H, t, J=5.0 Hz), 7.32-7.37 (1H, m), 7.43-7.48 (1H, m), 7.80 (1H, d, J=8.3 Hz), 7.87 (1H, d, J=8.3 Hz), 9.75 (1H, t, J=1.4 Hz).

Reference Example 53

Methyl 4-(2-aminoethyl)-6-(trifluoromethyl)pyridine-3-carboxylate monohydrochloride

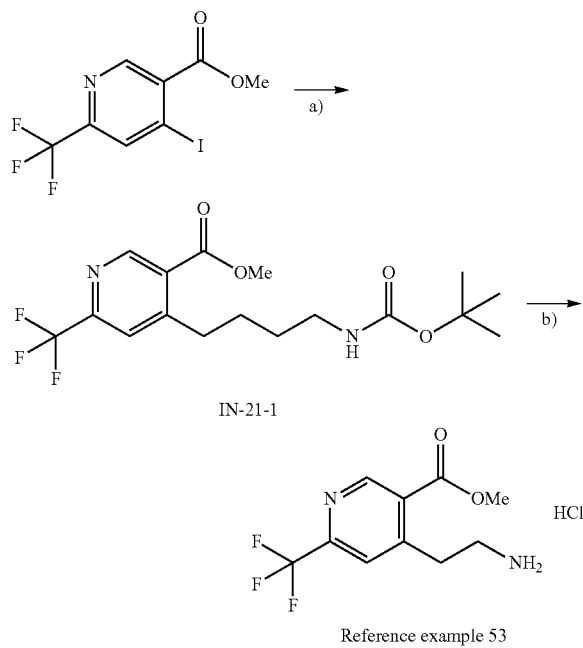

Reference example 53

Reference Example 53 a) Preparation of methyl 4-{2-[(tert-butoxycarbonyl)amino]ethyl}-6-(trifluoromethyl)pyridine-3-carboxylate (Compound IN-21-1)

According to a similar method to Compound IN-7-2, the titled compound was obtained from methyl 4-iodo-6-trifluoromethylpyridine-3-carboxylate.

LC-MS: R.T.=1.693 min ObsMS=249 [M+1]

b) Preparation of methyl 4-(2-aminoethyl)-6-(trifluoromethyl)pyridine-3-carboxylate monohydrochloride (Reference Example 53)

To a mixture of Compound IN-21-1 (1.13 g), ethyl acetate (3.0 mL), and methanol (6.0 mL) was added 4 mol/L hydrochloric acid-ethyl acetate (20 mL), and the mixture was stirred at room temperature for an hour. Then, the reaction mixture was concentrated to obtain the titled compound (0.942 g).

LC-MS: R.T.=1.002 min ObsMS=249 [M+1]

Reference Example 54

5-{2-[4-(1,2-Benzoisoxazol-3-yl)piperidin-1-yl]ethyl}-2-(triphenylmethyl)-2,5,6,7-tetrahydro-4H-pyrazolo[4,3-c]pyridin-4-one

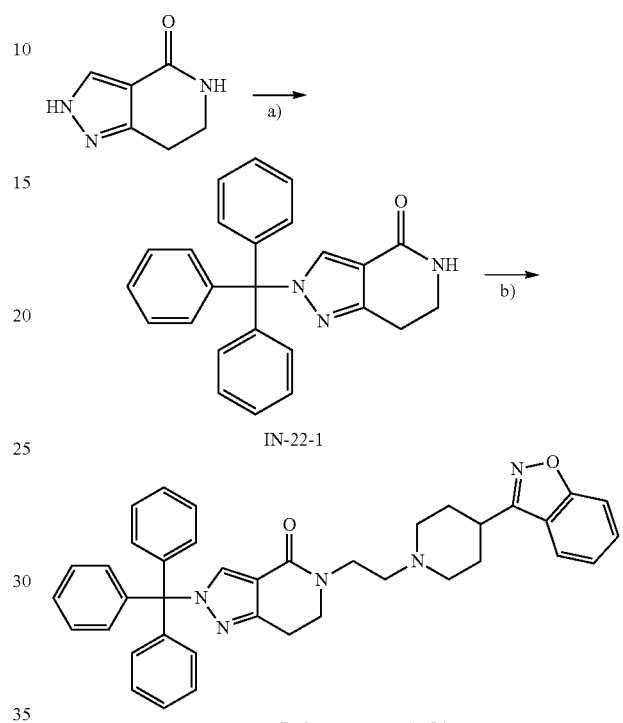

Reference example 54 a) Preparation of 2-(triphenylmethyl)-2,5,6,7-tetrahydro-4H-pyrazolo[4,3-c]pyridin-4-one (Compound IN-22-1)

To a solution of 6,7-dihydro-1H-pyrazolo[4,3-c]pyridin-4(5H)-one (0.500 g) in triethylamine (0.762 mL) were added triethylamine (0.762 mL), and trityl chloride (1.02 g). After stirring at room temperature for 18 hour, to the reaction mixture were added water and hexane. The precipitated solid was collected by filtration to obtain the titled compound (0.796 g).

$^1$H-NMR (400 MHz, DMSO-D$_6$) δ: 2.77 (2H, t, J=6.6 Hz), 3.36-3.41 (2H, m), 7.03-7.09 (6H, m), 7.33-7.41 (9H, m), 7.46-7.50 (2H, m).

b) Preparation of 5-{2-[4-(1,2-benzoisoxazol-3-yl)piperidin-1-yl]ethyl}-2-(triphenylmethyl)-2,5,6,7-tetrahydro-4H-pyrazolo[4,3-c]pyridin-4-one (Reference Example 54)

According to a similar method to Reference example 3, the titled compound was obtained from the compound of Reference example 3 and Compound IN-21-1.

$^1$H-NMR (400 MHz, DMSO-D$_6$) δ: 1.76-1.88 (2H, m), 1.98-2.05 (2H, m), 2.12-2.21 (2H, m), 2.50-2.54 (2H, m), 2.87 (2H, t, J=6.6 Hz), 2.99-3.06 (2H, m), 3.08-3.18 (1H, m), 3.52 (2H, t, J=6.8 Hz), 3.65 (2H, t, J=6.8 Hz), 7.04-7.10 (6H, m), 7.32-7.41 (10H, m), 7.49 (1H, s), 7.59-7.64 (1H, m), 7.70 (1H, d, J=8.3 Hz), 7.92 (1H, d, J=7.8 Hz).

Test 1: Evaluation of Binding Activity for Human 5-$HT_{1A}$ Receptor, Human 5-$HT_{2A}$ Receptor, and Human $D_2$ Receptor Binding affinity of the present compound for human 5-$HT_{1A}$ receptor, human 5-$HT_{2A}$ receptor, and human $D_2$ receptor was measured by the following procedures.

CHO cell membrane fraction in which human 5-$HT_{1A}$ receptor, human 5-$HT_{2A}$ receptor, and human $D_2$ receptor were expressed was purchased from PerkinElmer, Inc. In a test for evaluating binding affinity, a test compound dissolved in dimethylsulfoxide (DMSO) and each receptor membrane sample diluted in buffer were mixed with [$^3$H] 8-OH-DPAT, [$^3$H]Ketanserin, or [3H]Spiperone (all purchased from PerkinElmer, Inc.) for 5-$HT_{1A}$ receptor, 5-$HT_{2A}$ receptor, and $D_2$ receptor, respectively. Each mixture was incubated at room temperature for 60 minutes. Then, the mixture was added quickly on a glassfiber filter plate (Multiscreen FB, Millipore, Inc.) coated with 0.3% aqueous polyethylenimine, and vacuum-filtered. Radioactivity remaining on the filter was measured with a liquid scintillation counter (PerkinElmer, Inc.). Binding inhibition rate was calculated from the following formula.

Binding inhibition rate for 5−$HT_{1A}$ receptor (%)=100−100×{(Binding amount of [$^3$H]8-OH-DPAT in the presence of test compound)}−(Binding amount of [$^3$H]8-OH-DPAT in the presence of 10 μmol/L 8-OH-DPAT)}/{(Binding amount of [$^3$H]8-OH-DPAT in the absence of test compound)}−(Binding amount of [$^3$H]8-OH-DPAT in the presence of 10 μmol/L 8-OH-DPAT)}

Binding inhibition rate for 5-$HT_{2A}$ receptor (%)=100−100×{(Binding amount of [$^3$H]Ketanserin in the presence of test compound))−(Binding amount of [$^3$H]Ketanserin in the presence of 10 μmol/L Mianserin)}/{(Binding amount of [$^3$H]Ketanserin in the absence of test compound)}−(Binding amount of [$^3$H]Ketanserin in the presence of 10 μmol/L Mianserin)}

Binding inhibition rate for $D_2$ receptor (%)=100−100×{(Binding amount of [$^3$H]Spiperone in the presence of test compound)}−(Binding amount of [$^3$H]Spiperone in the presence of 10 μmol/L Spiperone)}/{(Binding amount of [$^3$H]Spiperone in the absence of test compound)}−(Binding amount of [$^3$H]Spiperone in the presence of 10 μmol/L Spiperone)}

$IC_{50}$ value was calculated by Hill analysis (Physiology, 1910, 40, 190-200). Ki of each compound was calculated from the following formula.

Binding inhibition constant $(Ki) = IC_{50}/(1+S/Kd)$ wherein S is concentration of ligand; Kd is a binding dissociation constant of ligand to membrane, which is calculated from a saturated binding experiment conducted with the same cell membrane. A small Ki value means strong binding ability to a receptor.

| Example | 5-$HT_{1A}$ Ki (nmol/L) | 5-$HT_{2A}$ Ki (nmol/L) | $D_2$ Ki (nmol/L) | $D_2$ Ki/ 5-$HT_{1A}$ Ki | $D_2$ Ki/ 5-$HT_{2A}$ Ki |
|---|---|---|---|---|---|
| 1 | 21.49 | 49.00 | 4958 | 231 | 101 |
| 2 | 0.03 | 0.46 | 128 | 3765 | 278 |
| 3 | 2.70 | 2.30 | 1262 | 467 | 549 |
| 4 | 9.82 | 2.40 | 481 | 49 | 200 |
| 5 | 5.78 | 52.00 | 7834 | 1355 | 151 |
| 6 | 2.58 | 68.00 | 8390 | 3258 | 123 |
| 7 | 1.46 | 2.63 | 265 | 181 | 101 |
| 8 | 1.66 | 1.65 | 461 | 277 | 279 |
| 9 | 18.40 | 2.24 | 591 | 32 | 264 |
| 10 | 19.99 | 0.49 | 442 | 22 | 910 |
| 11 | 2.95 | 1.29 | 316 | 107 | 245 |
| 12 | 7.03 | 2.80 | 311 | 44 | 111 |
| 13 | 13.10 | 8.40 | 483 | 37 | 58 |
| 14 | 0.15 | 1.68 | 136 | 899 | 81 |
| 15 | 0.51 | 12.00 | 1556 | 3071 | 130 |
| 16 | 18.60 | 14.00 | 34023 | 1829 | 2430 |
| 17 | 3.46 | 3.44 | 689 | 199 | 200 |
| 18 | 10.58 | 3.70 | 1289 | 122 | 348 |
| 19 | 0.75 | 1.40 | 690 | 916 | 493 |
| 20 | 0.77 | 2.40 | 1889 | 2451 | 787 |
| 21 | 8.62 | 2.20 | 2122 | 246 | 965 |
| 22 | 4.10 | 4.40 | 2600 | 634 | 591 |
| 23 | 9.14 | 6.00 | 878 | 96 | 146 |
| 24 | 13.23 | 3.55 | 230 | 17 | 65 |
| 25 | 0.19 | 3.01 | 207 | 1070 | 69 |
| 26 | 1.52 | 1.92 | 223 | 147 | 116 |
| 27 | 6.04 | 3.00 | 230 | 38 | 77 |
| 28 | 13.76 | 1.40 | 148 | 11 | 106 |
| 29 | 0.68 | 0.23 | 143 | 210 | 613 |
| 30 | 1.76 | 0.76 | 103 | 58 | 136 |
| 31 | 0.08 | 0.47 | 99 | 1194 | 209 |
| 32 | 123.91 | 60.00 | 48923 | 395 | 815 |
| 33 | 9.35 | 8.00 | 1008 | 108 | 126 |
| 34 | 6.99 | 0.70 | 1398 | 200 | 1997 |
| 35 | 3.30 | 9.30 | 1290 | 391 | 139 |
| 36 | 0.45 | 0.62 | 903 | 2007 | 1456 |
| 37 | 2.68 | 0.37 | 267 | 100 | 715 |
| 38 | 13.46 | 4.44 | 425 | 32 | 96 |
| 39 | 0.84 | 3.82 | 1861 | 2211 | 488 |
| 40 | 8.47 | 4.86 | 376 | 44 | 77 |
| 41 | 10.94 | 2.12 | 131 | 12 | 62 |
| 42 | 2.19 | 3.39 | 119 | 54 | 35 |
| 43 | 1.30 | 0.93 | 222 | 171 | 239 |
| 44 | 0.22 | 0.33 | 121 | 558 | 367 |
| 45 | 1.27 | 3.10 | 598 | 472 | 193 |
| 46 | 4.78 | 2.80 | 715 | 150 | 255 |
| 47 | 16.91 | 17.86 | 130 | 8 | 7 |
| 48 | 4.76 | 5.00 | 574 | 121 | 115 |
| 49 | 1.47 | 1.80 | 690 | 470 | 383 |
| 50 | 1.25 | 3.92 | 825 | 662 | 210 |
| 51 | 0.23 | 4.20 | 993 | 4283 | 236 |
| 52 | 0.74 | 4.70 | 479 | 643 | 102 |
| 53 | 6.69 | 4.02 | 1081 | 162 | 269 |
| 54 | 2.75 | 6.50 | 1683 | 612 | 259 |
| 55 | 13.63 | 1.30 | 697 | 51 | 536 |
| 56 | 77.98 | 0.11 | 494 | 6 | 4323 |
| 57 | 60.90 | 7.60 | 973 | 16 | 128 |
| 58 | 6.90 | 2.60 | 780 | 113 | 300 |
| 59 | 1.99 | 0.45 | 125 | 63 | 278 |
| 60 | 13.67 | 1.10 | 260 | 19 | 236 |
| 61 | 1.70 | 0.23 | 134 | 79 | 583 |
| 62 | 0.10 | 0.92 | 222 | 2241 | 241 |
| 63 | 6.50 | 0.69 | 791 | 122 | 1146 |
| 64 | 17.42 | 1.20 | 430 | 25 | 358 |
| 65 | 0.90 | 0.15 | 222 | 245 | 1480 |
| 66 | 8.68 | 2.60 | 841 | 97 | 323 |
| 67 | 1.17 | 1.50 | 1050 | 896 | 700 |
| 68 | 4.11 | 4.00 | 853 | 208 | 213 |
| 69 | 10.37 | 1.00 | 360 | 35 | 360 |
| 70 | 14.08 | 1.50 | 867 | 62 | 578 |
| 71 | 2.64 | 2.50 | 305 | 115 | 122 |
| 72 | 9.47 | 7.80 | 1034 | 109 | 133 |
| 73 | 0.97 | 0.54 | 234 | 242 | 433 |
| 74 | 3.48 | 0.38 | 210 | 60 | 549 |
| 75 | 2.39 | 1.10 | 210 | 88 | 191 |
| 76 | 6.48 | 2.80 | 472 | 73 | 169 |
| 77 | 0.24 | 0.96 | 605 | 2540 | 630 |
| 78 | 0.46 | 0.52 | 343 | 750 | 660 |
| 79 | 0.19 | 0.81 | 239 | 1244 | 295 |
| 80 | 4.50 | 2.80 | 1136 | 252 | 406 |
| 81 | 27.90 | 10.00 | 9302 | 333 | 930 |
| 82 | 0.61 | 0.87 | 361 | 593 | 415 |
| 83 | 11.30 | 4.00 | 2782 | 246 | 696 |
| 84 | 4.63 | 4.50 | 954 | 206 | 212 |

| Example | 5-HT$_{1A}$ Ki (nmol/L) | 5-HT$_{2A}$ Ki (nmol/L) | D$_2$ Ki (nmol/L) | D$_2$ Ki/ 5-HT$_{1A}$ Ki | D$_2$ Ki/ 5-HT$_{2A}$ Ki |
|---|---|---|---|---|---|
| 85 | 100.55 | 5.30 | 1071 | 11 | 202 |
| 86 | 9.90 | 3.30 | 1211 | 122 | 367 |
| 87 | 0.12 | 1.60 | 94 | 767 | 59 |
| 88 | 6.30 | 10.00 | 916 | 145 | 92 |
| 89 | 3.44 | 8.00 | 2250 | 654 | 281 |
| 90 | 6.77 | 8.40 | 1074 | 159 | 128 |
| 91 | 0.57 | 1.59 | 103 | 181 | 65 |
| 92 | 5.19 | 2.45 | 738 | 142 | 301 |
| 93 | 9.36 | 1.30 | 826 | 88 | 635 |
| 94 | 5.24 | 1.20 | 236 | 45 | 197 |
| 95 | 7.91 | 5.80 | 2582 | 326 | 445 |
| 96 | 11.84 | 7.25 | 103 | 9 | 14 |
| 97 | 17.55 | 2.69 | 136 | 8 | 51 |
| 98 | 11.60 | 1.77 | 312 | 27 | 176 |
| 99 | 21.49 | 1.57 | 280 | 13 | 178 |
| 100 | 6.35 | 5.30 | 6945 | 1094 | 1310 |
| 101 | 60.12 | 1.90 | 1022 | 17 | 538 |
| 102 | 0.25 | 2.00 | 852 | 3408 | 426 |
| 103 | 0.47 | 0.80 | 129 | 274 | 161 |
| 104 | 0.41 | 0.69 | 93 | 226 | 135 |
| 105 | 6.00 | 1.10 | 194 | 32 | 176 |
| 106 | 1.63 | 0.46 | 804 | 492 | 1748 |
| 107 | 0.08 | 0.40 | 244 | 3185 | 607 |
| 108 | 0.16 | 0.75 | 163 | 1009 | 217 |
| 109 | 4.30 | 4.20 | 601 | 140 | 143 |
| 110 | 1.63 | 2.60 | 1015 | 623 | 390 |
| 111 | 0.91 | 1.90 | 1007 | 1105 | 530 |
| 112 | 1.58 | 1.30 | 169 | 107 | 130 |
| 113 | 14.42 | 3.70 | 5402 | 375 | 1460 |
| 114 | 11.30 | 2.20 | 309 | 27 | 140 |
| 115 | 1062.88 | 1.07 | >10000 | >9.4 | >9352.5 |
| 116 | 127.78 | 26.00 | >10000 | >78.3 | >384.6 |
| 117 | 36.56 | 19.00 | 1743 | 47.7 | 91.7 |
| 118 | 73.08 | 10.00 | 276 | 3.8 | 27.6 |
| 119 | 3.90 | 0.48 | 105 | 26.9 | 217.0 |
| 120 | 339.61 | 91.00 | >10000 | >29.4 | >109.9 |
| 121 | 60.88 | 105.00 | 54 | 0.9 | 0.5 |
| 122 | 24.03 | 8.00 | 537 | 22.4 | 67.2 |
| 123 | 161.91 | 1.43 | 1704 | 10.5 | 1195.9 |
| 124 | 1039.30 | 77.00 | >10000 | >9.6 | >129.9 |
| 125 | 13.93 | 0.27 | 87 | 6.3 | 323.0 |
| 126 | 15.88 | 0.45 | 93 | 5.9 | 206.3 |
| 127 | 35.74 | 1.01 | 203 | 5.7 | 200.0 |
| 128 | 83.18 | 2.14 | 625 | 7.5 | 292.0 |
| 129 | 51.43 | 20.00 | 1220 | 23.7 | 61.0 |
| 130 | 23.79 | 5.96 | 541 | 22.7 | 90.8 |
| 131 | 279.43 | 12.00 | >10000 | >35.8 | >833.3 |
| 132 | 16.01 | 9.82 | 750 | 46.8 | 76.4 |
| 133 | 327.32 | 0.95 | 914 | 2.8 | 960.1 |
| 134 | 65.30 | 4.21 | 310 | 4.7 | 73.5 |
| 135 | 1.40 | 1.00 | 62 | 44.5 | 62.5 |
| 136 | 75.85 | 3.20 | 2303 | 30.4 | 719.6 |
| 137 | 186.32 | 11.23 | 1082 | 5.8 | 96.4 |
| 138 | 27.59 | 1.61 | 76 | 2.8 | 47.1 |
| 139 | 20.32 | 2.30 | 635 | 31.3 | 276.1 |
| 140 | 167.93 | 118.00 | >10000 | >59.5 | >84.7 |
| 141 | 4.16 | 173.00 | >10000 | >2405.7 | >57.8 |
| 142 | 1.83 | 164.00 | >10000 | >5452.0 | >61.0 |
| 143 | 26.48 | 15.00 | 402 | 15.2 | 26.8 |
| 144 | 127.02 | 27.00 | >10000 | >78.7 | >370.4 |
| 145 | 38.08 | 1.15 | 335 | 8.8 | 291.1 |
| 146 | 3.02 | 10.67 | 772 | 255.8 | 72.4 |
| 147 | 124.21 | 124.00 | >10000 | >80.5 | >80.6 |
| 148 | 156.36 | 43.19 | >10000 | >64.0 | >231.5 |
| 149 | 184.32 | 217.12 | >10000 | >54.3 | >46.1 |
| 150 | 5.36 | 3.09 | 188 | 35.1 | 60.8 |
| 151 | 1.16 | 2.77 | 3706 | 3192.0 | 1340.3 |
| 152 | 0.38 | 11.43 | 2311 | 6051.2 | 202.2 |
| 153 | 578.00 | 12.00 | >10000 | >17.3 | >833.3 |
| 154 | 20.19 | 13.08 | 718 | 35.6 | 54.9 |
| 155 | 14.04 | 4.01 | 114 | 8.1 | 28.4 |
| 156 | 5.17 | 8.59 | 743 | 143.6 | 86.5 |
| 157 | 2.12 | 14.51 | 641 | 302.1 | 44.2 |
| 158 | 216.60 | 0.84 | 327 | 1.5 | 388.7 |
| 159 | 254.92 | 5.83 | 373 | 1.5 | 64.0 |
| 160 | 20.19 | 0.71 | 170 | 8.4 | 240.3 |
| 161 | 202.67 | 1.68 | 216 | 1.1 | 128.4 |
| 162 | 13.82 | 1.13 | 508 | 36.7 | 448.1 |
| 163 | 2.40 | 1.05 | 766 | 319.5 | 728.5 |
| 164 | 11.67 | 6.47 | 819 | 70.2 | 126.7 |
| 165 | 0.74 | 1.20 | 76 | 103.4 | 63.3 |
| 166 | 0.17 | 2.31 | 139 | 820.1 | 60.2 |
| 167 | 0.14 | 0.87 | 71 | 525.2 | 81.5 |
| 168 | 1.02 | 0.18 | 145 | 141.4 | 786.3 |
| 169 | 44.24 | 0.60 | 1920 | 43.4 | 3177.2 |
| 170 | 35.16 | 2.45 | 1681 | 47.8 | 686.1 |
| 171 | 16.00 | 2.60 | 1405 | 87.8 | 540.5 |
| 172 | 3.33 | 2.44 | 384 | 115.1 | 157.1 |
| 173 | 38.59 | 22.83 | >10000 | >259.1 | >438.0 |
| 174 | 78.09 | 71.68 | >10000 | >128.0 | >139.5 |
| 175 | 17.80 | 13.83 | 3475 | 195.2 | 251.4 |
| 176 | 5.10 | 8.45 | 248 | 48.6 | 29.3 |
| 177 | 5.63 | 4.86 | 237 | 42.1 | 48.7 |
| 178 | 530.03 | 179.18 | >10000 | >18.9 | >55.8 |
| 179 | 283.45 | 22.85 | >10000 | >35.3 | >437.6 |
| 180 | 32.18 | 4.28 | 1555 | 48.3 | 363.5 |
| 181 | 48.62 | 5.96 | 3690 | 75.9 | 619.2 |
| 182 | 10.92 | 1.58 | 1398 | 128.1 | 883.1 |
| 183 | 21.86 | 85.00 | >10000 | >457.5 | >117.6 |
| 184 | 2.69 | 26.99 | 1497 | 555.9 | 55.5 |
| 185 | 3.26 | 28.28 | 1170 | 358.6 | 41.4 |
| 186 | 16.53 | 95.00 | 1276 | 77.2 | 13.4 |
| 187 | 1.59 | 14.47 | 772 | 485.6 | 53.3 |
| 188 | 7.85 | 15.00 | 703 | 89.6 | 46.9 |
| 189 | 98.41 | 0.59 | 307 | 3.1 | 523.8 |
| 190 | 49.95 | 51.36 | 2461 | 49.3 | 47.9 |
| 191 | 817.07 | 0.34 | 286 | 0.4 | 848.4 |
| 192 | 200.15 | 0.41 | 219 | 1.1 | 532.3 |
| 193 | 386.90 | 122.33 | >10000 | >25.8 | >81.7 |
| 194 | 8.49 | 7.64 | 1565 | 184.4 | 204.8 |

Test 2: Evaluation of Agonist Activity for Human 5-HT$_{1A}$ Receptor

CHO cell membrane fraction in which human 5-HT$_{1A}$ receptor was expressed as used in Test 1 was purchased. To a buffer containing guanosine diphosphate were added a test compound dissolved in DMSO, each receptor membrane sample diluted with buffer, and [$^{35}$S] Guanosine 5'-O-[gamma-thio]triphosphate (GTPγS). The mixture was incubated at room temperature for 60 minutes. Then, the mixture was added quickly on a glassfiber filter plate (Multiscreen FB, Millipore, Inc.), and vacuum-filtered. Radioactivity remaining on the receptor was measured with a liquid scintillation counter. Agonist activity was calculated from the following formula.

Agonist activity for 5-HT$_{1A}$ receptor (%)=100×{ (Binding amount of [$^{35}$S] GTPγS in the presence of test compound)−(Binding amount of [$^{35}$S] GTPγS in the presence of 20 μmol/L GTPγS)}/{(Binding amount of [$^{35}$S] GTPγS in the presence of 100 μmol/L 5-HT)−(Binding amount of [$^{35}$S] GTPγS in the presence of 20 μmol/L GTPγS)}

The agonist activity in the presence of 10 μM of each compound is shown as the maximum activity (E$_{max}$) of each compound, and the concentration at which half the activity of E$_{max}$ was obtained was calculated as EC$_{50}$.

| | 5-HT$_{1A}$ agonist activity | |
|---|---|---|
| Example | EC$_{50}$ (nmol/L) | Emax (%) |
| 1 | 94.67 | 50 |
| 2 | 0.18 | 69 |

-continued

| Example | 5-HT$_{1A}$ agonist activity | |
|---|---|---|
| | EC$_{50}$ (nmol/L) | Emax (%) |
| 3 | 10.10 | 69 |
| 4 | 20.78 | 52 |
| 5 | 91.56 | 60 |
| 6 | 28.27 | 31 |
| 7 | 40.43 | 55 |
| 8 | 11.83 | 50 |
| 9 | 95.19 | 43 |
| 10 | 118.68 | 44 |
| 11 | 45.80 | 55 |
| 12 | 96.05 | 32 |
| 13 | 225.99 | 56 |
| 14 | 2.87 | 42 |
| 15 | 7.32 | 57 |
| 16 | 299.71 | 40 |
| 17 | 47.14 | 52 |
| 18 | 18.00 | 90 |
| 19 | 6.70 | 68 |
| 20 | 4.72 | 52 |
| 21 | 18.00 | 59 |
| 22 | 37.98 | 52 |
| 23 | 74.57 | 55 |
| 24 | 63.24 | 31 |
| 25 | 5.85 | 57 |
| 26 | 30.41 | 50 |
| 27 | 55.37 | 58 |
| 28 | 7.59 | 94 |
| 29 | 64.47 | 42 |
| 30 | 5.57 | 42 |
| 31 | 1.32 | 40 |
| 32 | 644.24 | 39 |
| 33 | 463.34 | 49 |
| 34 | 50.29 | 54 |
| 35 | 72.00 | 68 |
| 36 | 2.70 | 78 |
| 37 | 35.00 | 71 |
| 38 | 395.49 | 56 |
| 39 | 9.06 | 61 |
| 40 | 66.01 | 60 |
| 41 | 79.30 | 45 |
| 42 | 23.53 | 57 |
| 43 | 8.50 | 73 |
| 44 | 1.80 | 76 |
| 45 | 25.70 | 65 |
| 46 | 55.33 | 58 |
| 47 | 92.17 | 65 |
| 48 | 19.27 | 37 |
| 49 | 14.84 | 64 |
| 50 | 5.14 | 59 |
| 51 | 2.08 | 61 |
| 52 | 6.61 | 77 |
| 53 | 37.09 | 72 |
| 54 | 38.38 | 55 |
| 55 | 4.30 | 50 |
| 56 | 66.61 | 58 |
| 57 | 836.42 | 61 |
| 58 | 42.11 | 51 |
| 59 | 8.00 | 61 |
| 60 | 43.00 | 54 |
| 61 | 9.80 | 63 |
| 62 | 1.01 | 62 |
| 63 | 16.00 | 73 |
| 64 | 191.23 | 69 |
| 65 | 2.10 | 72 |
| 66 | 78.15 | 67 |
| 67 | 3.19 | 65 |
| 68 | 49.26 | 38 |
| 69 | 33.85 | 45 |
| 70 | 79.34 | 50 |
| 71 | 7.34 | 67 |
| 72 | 90.53 | 57 |
| 73 | 7.05 | 62 |
| 74 | 4.42 | 51 |
| 75 | 7.13 | 56 |
| 76 | 4.13 | 35 |
| 77 | 1.30 | 78 |
| 78 | 0.77 | 66 |
| 79 | 6.21 | 63 |
| 80 | 10.70 | 63 |
| 81 | 67.56 | 60 |
| 82 | 8.59 | 61 |
| 83 | 9.61 | 61 |
| 84 | 6.39 | 59 |
| 85 | 41.11 | 35 |
| 86 | 16.00 | 51 |
| 87 | 7.47 | 76 |
| 88 | 37.00 | 49 |
| 89 | 53.79 | 39 |
| 90 | 57.73 | 65 |
| 91 | 8.74 | 46 |
| 92 | 76.24 | 43 |
| 93 | 15.14 | 41 |
| 94 | 79.39 | 53 |
| 95 | 77.86 | 62 |
| 96 | 65.51 | 33 |
| 97 | 446.67 | 42 |
| 98 | 754.56 | 43 |
| 99 | 184.59 | 40 |
| 100 | 86.48 | 58 |
| 101 | 612.38 | 47 |
| 102 | 1.10 | 74 |
| 103 | 5.80 | 62 |
| 104 | 1.99 | 64 |
| 105 | 14.00 | 74 |
| 106 | 38.37 | 74 |
| 107 | 7.67 | 64 |
| 108 | 0.69 | 71 |
| 109 | 17.10 | 60 |
| 110 | 8.22 | 65 |
| 111 | 4.58 | 51 |
| 112 | 9.44 | 64 |
| 113 | 16.00 | 67 |
| 114 | 43.78 | 64 |
| 115 | 2504.50 | 37 |
| 116 | 881.94 | 60 |
| 117 | 570.00 | 40 |
| 118 | 550.00 | 5 |
| 119 | 63.85 | 35 |
| 120 | 630.46 | 7 |
| 121 | 79.44 | 48 |
| 122 | 121.49 | 23 |
| 123 | 186.05 | 71 |
| 124 | 4978.64 | 27 |
| 125 | 41.86 | 34 |
| 126 | 67.17 | 60 |
| 127 | 56.89 | 48 |
| 128 | 35.94 | 33 |
| 129 | 369.74 | 31 |
| 130 | 840.68 | 44 |
| 131 | 404.73 | 48 |
| 132 | 74.52 | 59 |
| 133 | 290.23 | 26 |
| 134 | 220.86 | 41 |
| 135 | 6.14 | 54 |
| 136 | 562.08 | 30 |
| 137 | 4656.25 | 19 |
| 138 | 100.00 | 32 |
| 139 | 72.69 | 48 |
| 140 | 2296.39 | 27 |
| 141 | 30.00 | 44 |
| 142 | 8.80 | 54 |
| 143 | 1036.39 | 31 |
| 144 | 749.41 | 53 |
| 145 | 55.14 | 58 |
| 146 | 6.07 | 55 |
| 147 | 436.35 | 34 |
| 148 | 944.17 | 53 |
| 149 | 718.75 | 16 |
| 150 | 36.88 | 54 |

-continued

| Example | 5-HT$_{1A}$ agonist activity EC$_{50}$ (nmol/L) | Emax (%) |
|---|---|---|
| 151 | 58.87 | 48 |
| 152 | 3.31 | 56 |
| 153 | 658.75 | 16 |
| 154 | 45.09 | 58 |
| 155 | 74.23 | 63 |
| 156 | 31.03 | 46 |
| 157 | 52.69 | 47 |
| 158 | 921.07 | 12 |
| 159 | 853.80 | 18 |
| 160 | 843.57 | 43 |
| 161 | 6181.05 | 17 |
| 162 | 55.03 | 61 |
| 163 | 10.95 | 67 |
| 164 | 69.48 | 48 |
| 165 | 74.45 | 44 |
| 166 | 6.22 | 57 |
| 167 | 0.84 | 60 |
| 168 | 100.00 | 52 |
| 169 | 62.93 | 44 |
| 170 | 822.56 | 42 |
| 171 | 38.70 | 56 |
| 172 | 8.20 | 72 |
| 173 | 40.80 | 50 |
| 174 | 193.09 | 50 |
| 175 | 666.82 | 36 |
| 176 | 30.63 | 40 |
| 177 | 65.73 | 36 |
| 178 | 352.59 | 63 |
| 179 | 546.64 | 7 |
| 180 | 1260.66 | 37 |
| 181 | 78.99 | 53 |
| 182 | 7.85 | 40 |
| 183 | 307.69 | 44 |
| 184 | 4.26 | 59 |
| 185 | 95.32 | 52 |
| 186 | 96.96 | 39 |
| 187 | 38.24 | 55 |
| 188 | 82.59 | 53 |
| 189 | 689.72 | 49 |
| 190 | 7208.86 | 11 |
| 191 | 4260.78 | 14 |
| 192 | 7672.04 | 11 |
| 193 | 755.52 | 27 |
| 194 | 46.48 | 40 |

Test 3: Evaluation of Antagonist Activity for Human 5-HT$_{2A}$ Receptor

Aequorin, Gα16 protein, and each receptor were transiently expressed in CHO-K1 cells (Chinese hamster ovary). The cells were cultured in a CO$_2$ incubator at 37° C. overnight, seeded into a 384-well plate, and stood at room temperature for 2 or more hours. Each compound dissolved in DMSO was added thereto, and changes in luminescence were measured by FDSS/μCELL functional drug screening system (Hamamatsu Photonics K.K.). Antagonist activity was calculated from the following formula.

Antagonist activity (%)=100×{(Luminescence of well in the presence of 1 nmol/L 5-HT−Luminescence of well containing solvent)−(Luminescence of well in the presence of test compound and 1 nmol/L 5-HT−Luminescence of well containing solvent)}/(Luminescence of well in the presence of 1 nmol/L 5-HT−Luminescence of well containing solvent)

The concentration of test compound in which 50% of antagonist activity was obtained was calculated as IC$_{50}$. The results are shown below.

| Example | 5-HT$_{2A}$ antagonist activity IC$_{50}$ (nmol/L) |
|---|---|
| 1 | 44.61 |
| 2 | 2.00 |
| 3 | 8.60 |
| 4 | 9.95 |
| 5 | 676.00 |
| 6 | 651.00 |
| 7 | 7.83 |
| 8 | 5.31 |
| 9 | 2.64 |
| 10 | 0.71 |
| 11 | 2.51 |
| 12 | 3.96 |
| 13 | 71.00 |
| 14 | 5.56 |
| 15 | 11.32 |
| 16 | 132.00 |
| 17 | 21.00 |
| 18 | 36.00 |
| 19 | 54.00 |
| 20 | 33.00 |
| 21 | 30.00 |
| 22 | 94.00 |
| 23 | 7.29 |
| 24 | 33.00 |
| 25 | 5.54 |
| 26 | 4.49 |
| 27 | 4.11 |
| 28 | 9.80 |
| 29 | 3.70 |
| 30 | 43.00 |
| 31 | 2.71 |
| 32 | 95.00 |
| 33 | 68.00 |
| 34 | 8.00 |
| 35 | 74.00 |
| 36 | 6.00 |
| 37 | 5.60 |
| 38 | 24.00 |
| 39 | 84.00 |
| 40 | 8.70 |
| 41 | 34.00 |
| 42 | 5.87 |
| 43 | 6.52 |
| 44 | 4.11 |
| 45 | 27.00 |
| 46 | 52.00 |
| 47 | 4.96 |
| 48 | 76.00 |
| 49 | 7.02 |
| 50 | 8.37 |
| 51 | 19.56 |
| 52 | 12.00 |
| 53 | 8.03 |
| 54 | 13.00 |
| 55 | 9.00 |
| 56 | 6.00 |
| 57 | 76.75 |
| 58 | 97.00 |
| 59 | 9.00 |
| 60 | 3.91 |
| 61 | 22.00 |
| 62 | 7.11 |
| 63 | 8.00 |
| 64 | 9.00 |
| 65 | 6.00 |
| 66 | 48.00 |
| 67 | 23.00 |
| 68 | 44.00 |
| 69 | 7.10 |
| 70 | 9.30 |
| 71 | 67.00 |
| 72 | 72.00 |
| 73 | 6.30 |
| 74 | 7.00 |
| 75 | 6.80 |
| 76 | 30.00 |
| 77 | 7.20 |
| 78 | 7.70 |

-continued

| Example | 5-HT$_{2A}$ antagonist activity IC$_{50}$ (nmol/L) |
|---|---|
| 79 | 8.70 |
| 80 | 55.00 |
| 81 | 83.00 |
| 82 | 46.00 |
| 83 | 49.00 |
| 84 | 73.40 |
| 85 | 6.90 |
| 86 | 1.80 |
| 87 | 34.00 |
| 88 | 52.00 |
| 89 | 96.00 |
| 90 | 45.00 |
| 91 | 6.25 |
| 92 | 4.36 |
| 93 | 46.00 |
| 94 | 41.00 |
| 95 | 66.00 |
| 96 | 20.00 |
| 97 | 6.47 |
| 98 | 53.00 |
| 99 | 2.07 |
| 100 | 48.00 |
| 101 | 46.00 |
| 102 | 50.00 |
| 103 | 10.00 |
| 104 | 6.40 |
| 105 | 5.50 |
| 106 | 8.10 |
| 107 | 8.30 |
| 108 | 7.50 |
| 109 | 73.00 |
| 110 | 42.38 |
| 111 | 17.00 |
| 112 | 32.00 |
| 113 | 8.63 |
| 114 | 3.60 |

| Example | 5-HT$_{2A}$ antagonist activity IC$_{50}$ (nmol/L) |
|---|---|
| 115 | 4.28 |
| 116 | 49.66 |
| 117 | 51.30 |
| 118 | 83.58 |
| 119 | 7.00 |
| 120 | 911.86 |
| 121 | 57.36 |
| 122 | 170.26 |
| 123 | 22.89 |
| 124 | 119.70 |
| 125 | 7.15 |
| 126 | 8.28 |
| 127 | 25.10 |
| 128 | 14.27 |
| 129 | 61.82 |
| 130 | 23.17 |
| 131 | 9.53 |
| 132 | 31.75 |
| 133 | 8.16 |
| 134 | 65.63 |
| 135 | 6.09 |
| 136 | 7.44 |
| 137 | 2.40 |
| 138 | 6.81 |
| 139 | 35.01 |
| 140 | 372.72 |
| 141 | 976.29 |
| 142 | 3914.57 |
| 143 | 7.47 |
| 144 | 355.91 |
| 145 | 19.03 |
| 146 | 198.87 |
| 147 | 414.93 |

-continued

| Example | 5-HT$_{2A}$ antagonist activity IC$_{50}$ (nmol/L) |
|---|---|
| 148 | 45% at 10 μM |
| 149 | 267.19 |
| 150 | 31.27 |
| 151 | 23.56 |
| 152 | 82.72 |
| 153 | 65.92 |
| 154 | 315.92 |
| 155 | 37.15 |
| 156 | 50.97 |
| 157 | 114.75 |
| 158 | 24.77 |
| 159 | 9.67 |
| 160 | 6.70 |
| 161 | 30.88 |
| 162 | 7.67 |
| 163 | 7.22 |
| 164 | 85.45 |
| 165 | 15.38 |
| 166 | 47.15 |
| 167 | 37.85 |
| 168 | 6.38 |
| 169 | 5.90 |
| 170 | 54.91 |
| 171 | 45.87 |
| 172 | 99.54 |
| 173 | 183.99 |
| 174 | 722.66 |
| 175 | 306.62 |
| 176 | 61.71 |
| 177 | 24.83 |
| 178 | 2021.03 |
| 179 | 70.75 |
| 180 | 72.69 |
| 181 | 96.85 |
| 182 | 73.50 |
| 183 | 383.70 |
| 184 | 95.50 |
| 185 | 68.66 |
| 186 | 91.51 |
| 187 | 89.72 |
| 188 | 67.71 |
| 189 | 1.56 |
| 190 | 236.72 |
| 191 | 3.37 |
| 192 | 6.25 |
| 193 | 143.11 |
| 194 | 47.68 |

Test 4: Metabolic Stability Test in Human Hepatic Microsome

The stability of the present compound in human hepatic microsome metabolism was evaluated as mentioned below. Human hepatic microsome was obtained from Xenontech. Human hepatic microsome, NADPH, and each test compound were mixed in 25 mmol/L phosphate buffer solution (pH 7.4) to reach the following concentrations as shown below, and the mixture was incubated at 37° C. for 30 minutes.

Human hepatic microsome: 0.1 mg/mL

NAPDH: 3.2 mmol/L

Test compound: 0.1 μmol/L

The residual ratio of the test compound in each sample after 30 minutes was measured by LC-MS, and the metabolic stability in human hepatic microsome was calculated from the following formula.

Metabolic stability in human hepatic microsome (mL/min/mg protein)=$-LN$ (residual ratio)/30/ 0.1

The results are shown in the following table.

| Example | Metabolic stability in human hepatic microsome (mL/min/mg protein) |
|---|---|
| 1 | <0.01 |
| 2 | 0.22 |
| 3 | <0.01 |
| 4 | 0.011 |
| 5 | <0.01 |
| 6 | 0.061 |
| 7 | 0.041 |
| 8 | 0.064 |
| 9 | 0.100 |
| 11 | 0.245 |
| 12 | 0.02 |
| 13 | <0.01 |
| 14 | <0.01 |
| 15 | 0.055 |
| 16 | <0.01 |
| 17 | <0.01 |
| 18 | 0.124 |
| 19 | 0.378 |
| 20 | 0.091 |
| 21 | 0.323 |
| 22 | 0.039 |
| 23 | 0.109 |
| 24 | 0.018 |
| 25 | 0.398 |
| 26 | <0.01 |
| 27 | 0.048 |
| 28 | 0.017 |
| 29 | 0.063 |
| 30 | 0.065 |
| 31 | 0.305 |
| 32 | <0.01 |
| 33 | 0.074 |
| 34 | 0.124 |
| 35 | <0.01 |
| 36 | 0.085 |
| 37 | 0.017 |
| 38 | 0.136 |
| 39 | 0.016 |
| 40 | 0.278 |
| 41 | <0.01 |
| 42 | 0.100 |
| 43 | <0.01 |
| 44 | 0.04 |
| 45 | 0.032 |
| 46 | 0.018 |
| 47 | 0.418 |
| 48 | <0.01 |
| 49 | 0.063 |
| 50 | 0.038 |
| 51 | 0.074 |
| 52 | 0.043 |
| 53 | 0.436 |
| 54 | <0.01 |
| 55 | 0.161 |
| 56 | 0.195 |
| 57 | 0.013 |
| 58 | 0.092 |
| 59 | 0.173 |
| 60 | 0.018 |
| 61 | 0.056 |
| 62 | 0.505 |
| 63 | <0.01 |
| 64 | 0.064 |
| 65 | 0.126 |
| 66 | 0.357 |
| 67 | 0.269 |
| 68 | 0.056 |
| 75 | 0.174 |
| 76 | 0.018 |
| 77 | 0.119 |
| 78 | 0.459 |
| 79 | 0.409 |
| 80 | 0.012 |
| 81 | <0.01 |
| 82 | 0.072 |
| 83 | 0.135 |
| 85 | 0.046 |
| 87 | 0.458 |
| 88 | <0.01 |
| 89 | 0.050 |
| 90 | 0.070 |
| 91 | <0.05 |
| 92 | 0.065 |
| 93 | 0.149 |
| 94 | 0.368 |
| 95 | 0.143 |
| 96 | 0.019 |
| 97 | <0.01 |
| 98 | 0.013 |
| 99 | <0.01 |
| 102 | 0.194 |
| 103 | <0.01 |
| 104 | 0.358 |
| 105 | 0.101 |
| 106 | 0.244 |
| 107 | 0.210 |
| 108 | 0.119 |
| 109 | <0.01 |
| 110 | 0.353 |
| 111 | 0.254 |
| 112 | 0.459 |
| 113 | 0.079 |
| 114 | 0.102 |
| 115 | <0.05 |

| Example | Metabolic stability in human hepatic microsome (mL/min/mg protein) |
|---|---|
| 116 | 0.1 |
| 117 | <0.05 |
| 121 | <0.05 |
| 122 | <0.05 |
| 123 | <0.05 |
| 125 | <0.05 |
| 126 | 0.135 |
| 127 | <0.05 |
| 128 | <0.05 |
| 129 | 0.084 |
| 130 | <0.05 |
| 131 | <0.05 |
| 132 | 0.148 |
| 133 | <0.05 |
| 134 | <0.05 |
| 135 | <0.05 |
| 136 | 0.598 |
| 137 | <0.05 |
| 138 | 0.083 |
| 139 | <0.05 |
| 144 | <0.05 |
| 145 | 0.302 |
| 146 | <0.05 |
| 150 | <0.05 |
| 153 | <0.05 |
| 154 | <0.05 |
| 155 | 0.121 |
| 156 | <0.05 |
| 157 | <0.05 |
| 158 | 0.113 |
| 159 | <0.05 |
| 160 | 0.13 |
| 161 | <0.05 |
| 162 | 0.196 |
| 163 | 0.118 |
| 164 | 0.097 |
| 165 | 0.265 |
| 166 | <0.05 |
| 167 | 0.413 |
| 168 | 0.924 |

-continued

| Example | Metabolic stability in human hepatic microsome (mL/min/mg protein) |
|---|---|
| 170 | <0.05 |
| 171 | <0.05 |
| 175 | 0.125 |
| 176 | <0.05 |
| 177 | 0.095 |
| 179 | <0.05 |
| 180 | 0.469 |
| 181 | 0.791 |
| 182 | 0.726 |
| 183 | <0.05 |
| 184 | <0.05 |
| 185 | <0.05 |
| 186 | 0.095 |
| 187 | <0.05 |
| 188 | <0.05 |
| 189 | <0.05 |
| 190 | <0.05 |
| 191 | <0.05 |
| 192 | <0.05 |
| 194 | <0.05 |

Test 5: Predictive Test of Human Half-Life

The disappearance half life of the present compound in human was predicted in a manner mentioned below.

The present compound was intravenously administered to cynomolgus monkey as an aqueous solution in 0.01 mol/L hydrochloric acid. Blood was collected on 5 minutes, 15 minutes, 30 minutes, 1 hour, 2 hours, 4 hours, 6 hours, and 24 hours after the administration. Plasma was obtained from the collected blood, the drug concentration in the plasma was measured by LC-MS, and the distribution volume of monkey was calculated from the transition of the concentration.

The unbound fraction rate of the present compound in human or monkey serum was measured by equilibrium dialysis method.

The half-life in human was calculated according to the following formula using the results of the distribution volume of monkey, the unbound fraction rate in human or monkey serum, and the metabolic stability in human hepatic microsome obtained in Test 3.

Distribution volume of human=Distribution volume of monkey×Unbound fraction rate in human serum/Unbound fraction rate in monkey serum Human hepatic clearance=(Hepatic blood flow of human×Unbound fraction rate in human serum× 56.7×Metabolic stability in human hepatic microsome)/(Hepatic blood flow of human+ Unbound fraction rate in human serum×56.7× Metabolic stability in human hepatic microsome)

Half-life in human=0.693×Distribution volume of human/Human hepatic clearance

The results are shown in the following table.

| Example | Half-life in human(h) |
|---|---|
| 3 | >30 |
| 37 | 8 |
| 80 | 10 |
| 88 | >23 |
| 103 | >45 |

Test 6-1: Evaluation of Inhibitory Activity for hERG Channel

Inhibitory activity of the present compound for hERG channel was measured by whole cell patch clamp method with an auto patch clamp system using CHO cells in which hERG channel involved in human rapidly activating delayed rectifier potassium current ($I_{Kr}$) was forcibly expressed.

(Preparation of Cell Suspension)

hERG-CHO cells purchased from ChanTest Cop. were cultured in a $CO_2$ incubator at 37° C., and dissociated from a flask with trypsin shortly before the measurement of hERG current, to prepare a cell suspension.

(Preparation of Solution)

Extracellular and intracellular fluid used in the measurement were prepared as follows.

Extracellular fluid: 2 mmol/L $CaCl_2$, 1 mmol/L $MgCl_2$, 10 mmol/L HEPES, 4 mmol/L KCl, 145 mmol/L NaCl, 10 mmol/L Glucose Intracellular fluid: 5.4 mmol/L $CaCl_2$, 1.8 mmol/L $MgCl_2$, 10 mmol/L HEPES, 31 mmol/L KOH, 10 mmol/L EGTA, 120 mmol/L KCl, 4 mmol/L $Na_2$-ATP Test compound solution: Test compound was dissolved in DMSO to reach the concentration of 2 mmol/L or 20 mmol/L, in order to prepare a test compound solution. The test compound solution was further diluted by 200-fold with extracellular fluid, and serial-diluted with the extracellular fluid to prepare a test compound solution in each concentration which is necessary to calculate $IC_{50}$ value of hERG inhibition.

(Measurement of Current Value and Data Analysis)

The cell suspension, the extracellular fluid, the intracellular fluid, and the measurement plate were set in the auto patch clamp system, and hERG current was measured by whole cell patch clamp method. The voltage-protocol was as follows: the holding potential was adjusted to −80 mV, the depolarizing pulse was provided at −50 mV to +20 mV for 5 seconds, the repolarizing pulse was provided at −50 mV for 5 seconds, then the potential was returned to the holding potential. Each pulse interval was 15 seconds. The data analysis was carried out with Qpatch Assay Software (Biolin Scientific). The test was carried out by applying incrementally 4 concentrations of each test compound, and the average of the maximum peak tail currents which were obtained from the last 3 stimulations in each concentration was determined as the evaluated data. Based on the current inhibition rate for a pre-applied current at each concentration of each test compound, $IC_{50}$ value was calculated by Hill equation with the software. Results are shown below.

| Example | hERG inhibition $IC_{50}$ (µmol/L) | hERG inhibition $IC_{50}$ (nmol/L)/ 5-$HT_{1A}$ Ki (nmol/L) | hERG inhibition $IC_{50}$ (nmol/L)/ 5-$HT_{2A}$ Ki (nmol/L) |
|---|---|---|---|
| 1 | >10 | >465 | >204 |
| 2 | 2.5 | 74968 | 5541 |
| 3 | 7.9 | 2944 | 3456 |
| 4 | 0.4 | 45 | 184 |
| 5 | 2.4 | 413 | 46 |
| 6 | 2.2 | 842 | 32 |
| 7 | 5.2 | 3567 | 1981 |
| 8 | 2.0 | 1201 | 1207 |
| 9 | 2.3 | 125 | 1027 |
| 11 | 2.6 | 894 | 2044 |
| 12 | 0.3 | 43 | 107 |
| 13 | 1.1 | 87 | 136 |
| 14 | 0.8 | 5568 | 500 |
| 15 | 1.6 | 3244 | 137 |
| 16 | >10 | 538 | 714 |

| Example | hERG inhibition IC$_{50}$ (µmol/L) | hERG inhibition IC$_{50}$ (nmol/L)/ 5-HT$_{1A}$ Ki (nmol/L) | hERG inhibition IC$_{50}$ (nmol/L)/ 5-HT$_{2A}$ Ki (nmol/L) |
| --- | --- | --- | --- |
| 17 | 1.0 | 288 | 289 |
| 18 | 5.9 | 559 | 1598 |
| 19 | 5.2 | 6868 | 3694 |
| 20 | 5.4 | 6964 | 2237 |
| 21 | 8.0 | 930 | 3642 |
| 22 | 1.9 | 458 | 427 |
| 23 | 1.9 | 207 | 316 |
| 24 | 0.4 | 31 | 115 |
| 25 | 0.4 | 2152 | 138 |
| 26 | 0.8 | 519 | 411 |
| 27 | 1.3 | 222 | 448 |
| 28 | 1.4 | 101 | 992 |
| 29 | 2.3 | 3393 | 9903 |
| 30 | 0.9 | 530 | 1229 |
| 31 | 1.2 | 15055 | 2641 |
| 32 | 5.5 | 45 | 92 |
| 33 | 0.6 | 61 | 72 |
| 34 | 2.5 | 356 | 3551 |
| 35 | 1.5 | 453 | 161 |
| 36 | 3.2 | 7112 | 5162 |
| 37 | 1.0 | 364 | 2615 |
| 38 | 0.5 | 41 | 124 |
| 39 | 1.8 | 2165 | 478 |
| 40 | 1.8 | 207 | 361 |
| 41 | 0.5 | 42 | 217 |
| 42 | 2.4 | 1084 | 701 |
| 43 | 2.1 | 1630 | 2274 |
| 44 | 7.7 | 35615 | 23390 |
| 45 | 7.0 | 5494 | 2244 |
| 46 | 3.7 | 783 | 1336 |
| 47 | 4.0 | 239 | 226 |
| 48 | 1.2 | 250 | 238 |
| 49 | 5.9 | 3997 | 3259 |
| 50 | 8.5 | 6839 | 2175 |
| 51 | 5.1 | 22043 | 1217 |
| 52 | 4.9 | 6587 | 1044 |
| 53 | 5.8 | 875 | 1456 |
| 54 | >10 | >3637 | >1538 |
| 55 | >10 | >734 | >7692 |
| 56 | 7.6 | 97 | 66474 |
| 57 | 2.2 | 35 | 283 |
| 58 | 6.0 | 865 | 2298 |
| 60 | 0.7 | 51 | 640 |
| 61 | >10 | >5882 | >43478 |
| 62 | 1.5 | 15540 | 1673 |
| 63 | 7.8 | 1193 | 11235 |
| 64 | 7.7 | 440 | 6380 |
| 65 | 4.4 | 4916 | 29636 |
| 66 | 2.1 | 238 | 794 |
| 67 | 1.6 | 1344 | 1049 |
| 68 | <0.27 | <66 | <68 |
| 75 | 1.2 | 491 | 1068 |
| 76 | <0.27 | <42 | <96 |
| 77 | 4.6 | 19331 | 4796 |
| 78 | 5.5 | 11955 | 10510 |
| 79 | 4.5 | 23167 | 5496 |
| 80 | 15.4 | 3423 | 5502 |
| 81 | >10 | >358 | >1000 |
| 82 | 1.9 | 3139 | 2195 |
| 83 | 8.0 | 712 | 2011 |
| 85 | >10 | >99 | >1887 |
| 87 | 0.5 | 4201 | 322 |
| 88 | 5.6 | 896 | 564 |
| 89 | 1.3 | 375 | 161 |
| 90 | >10 | >1477 | >1190 |
| 93 | 6.6 | 709 | 5102 |
| 94 | 2.3 | 447 | 1951 |
| 96 | 1.2 | 97 | 159 |
| 97 | 2.6 | 148 | 969 |
| 98 | 1.1 | 98 | 644 |
| 99 | 2.9 | 134 | 1835 |
| 101 | 4.1 | 68 | 2165 |
| 102 | 1.0 | 4120 | 515 |
| 103 | 1.4 | 3045 | 1790 |
| 104 | 0.7 | 1637 | 977 |
| 105 | 7.9 | 1312 | 7154 |
| 106 | 4.8 | 2936 | 10424 |
| 107 | 1.7 | 22493 | 4285 |
| 108 | 2.8 | 17530 | 3776 |
| 109 | 11.3 | 2639 | 2702 |
| 110 | 2.4 | 1474 | 924 |
| 111 | 1.9 | 2052 | 984 |
| 112 | 2.2 | 1369 | 1663 |
| 113 | 7.0 | 487 | 1897 |
| 114 | 2.7 | 235 | 1207 |
| 115 | 5.0 | 5 | 4676 |
| 116 | 5.3 | 41 | 204 |
| 117 | 4.4 | 120 | 232 |
| 121 | <0.3 | <5 | <3 |
| 123 | 3.9 | 24 | 2737 |
| 125 | <0.3 | <22 | <1111 |
| 126 | <0.3 | <19 | <665 |
| 127 | 0.6 | 17 | 591 |
| 130 | 1.6 | 67 | 268 |
| 131 | >3.0 | >11 | >250 |
| 132 | 0.7 | 44 | 71 |
| 133 | 4.7 | 14 | 4935 |
| 134 | 3.5 | 54 | 831 |
| 135 | 0.7 | 499 | 700 |
| 136 | 6.0 | 79 | 1875 |
| 137 | 7.7 | 41 | 686 |
| 138 | 1.2 | 43 | 744 |
| 139 | 3.8 | 187 | 1652 |
| 143 | 0.8 | 30 | 53 |
| 145 | >3.0 | >79 | >2607 |
| 146 | 0.3 | 99 | 28 |
| 150 | 1.2 | 224 | 388 |
| 153 | 7.1 | 12 | 592 |
| 154 | 0.7 | 35 | 54 |
| 155 | 0.7 | 50 | 175 |
| 156 | 2.1 | 406 | 245 |
| 157 | 1.6 | 754 | 110 |
| 162 | 1.2 | 87 | 1059 |
| 163 | 1.4 | 584 | 1332 |
| 164 | 1.0 | 86 | 155 |
| 165 | 7.9 | 10736 | 6579 |
| 166 | 1.0 | 5890 | 433 |
| 167 | 1.8 | 13297 | 2064 |
| 168 | <0.3 | <293 | <1628 |
| 170 | 7.4 | 210 | 3020 |
| 171 | 6.6 | 413 | 2538 |
| 175 | 3.5 | 197 | 253 |
| 176 | 1.0 | 196 | 118 |
| 177 | 3.7 | 657 | 761 |
| 179 | >10 | >35 | >438 |
| 183 | >3.0 | >137 | >35 |
| 184 | 0.8 | 297 | 30 |
| 185 | 0.7 | 214 | 25 |
| 186 | 2.0 | 121 | 21 |
| 187 | 0.3 | 189 | 21 |
| 188 | 1.9 | 242 | 127 |
| 189 | 1.8 | 18 | 3067 |
| 190 | 1.6 | 32 | 31 |
| 191 | 2.6 | 3 | 7713 |
| 192 | 0.7 | 3 | 1700 |
| 194 | 4.9 | 577 | 641 |

Test 6-2: Evaluation of Inhibitory Activity for hERG Channel

The inhibitory activity of the present compound for hERG channel was measured by whole cell patch clamp method with an auto patch clamp system using CHO cells in which hERG channel involved in human rapidly activating delayed rectifier potassium current was ($I_{Kr}$) forcibly expressed.

(Preparation of Cell Suspension)

hERG-CHO cells obtained from ChanTest were incubated in a $CO_2$ incubator at 37° C., and dissociated from a flask with trypsin shortly before the measurement of hERG current, to prepare a cell suspension.
(Preparation of Solution)
The extracellular and intracellular fluids which were used in the measurement were prepared as follows:
Extracellular fluid: 2 mmol/L $CaCl_2$, 1 mmol/L $MgCl_2$, 10 mmol/L HEPES, 4 mmol/L KCl, 145 mmol/L NaCl, 10 mmol/L Glucose
Intracellular fluid: 10 mmol/L HEPES, 10 mmol/L EGTA, 20 mmol/L KCl, 130 mmol/L KF
Test compound solution: Test compounds were dissolved in DMSO to reach the concentration of 2 mmol/L or 20 mmol/L, in order to prepare each test compound solution. The test compound solutions were further diluted by 200-fold with the extracellular fluid, and serial-diluted with the extracellular fluid to prepare a test compound solution in each concentration which is necessary to calculate $IC_{50}$ value of hERG inhibition.
(Measurement of Current Value and Data Analysis)
The cell suspension, the extracellular fluid, the intracellular fluid, and the measurement plate were set in the auto patch clamp system, and hERG current was measured by whole cell patch clamp method. The voltage-protocol was as follows: the holding potential was adjusted to −80 mV, the depolarizing pulse was provided at −50 mV to +20 mV for 5 seconds, the repolarizing pulse was provided at −50 mV for 5 seconds, then the potential was returned to the holding potential. Each pulse interval was 15 seconds. The data analysis was carried out with Analysis Software for Qube (Sophion Sophion). The test was carried out by applying incrementally 4 concentrations of each test compound, and the average of the maximum peak tail currents which were obtained from the last 3 stimulations in each concentration was determined as the evaluated data. Based on the current inhibition rate for a pre-applied current at each concentration of each test compound, $IC_{50}$ value was calculated by Hill equation with the software.
The results are shown in the following table.

| Example | hERG inhibition $IC_{50}$ (µmol/L) | hERG inhibition $IC_{50}$ (nmol/L)/ $5\text{-}HT_{1A}$ Ki (nmol/L) | hERG inhibition $IC_{50}$ (nmol/L)/ $5\text{-}HT_{2A}$ Ki (nmol/L) |
|---|---|---|---|
| 91 | 1.8 | 3171 | 1129 |
| 92 | >10 | >1926 | >4076 |

Test 7: Evaluation of MK-801 Induced Hyperactivity Suppression
7-Week-old SD male rats were used. Administration liquids of test compounds were prepared by suspending them in a solvent of 0.5% methyl cellulose, and administration liquid of MK-801 was prepared by dissolving it in a solvent of saline.
MK-801 induced hyperactivity suppression test was carried out as follows with Supermex, data collecting program CompACT AMS, and a transparent plastic cage from Muromachi Kikai Co., Ltd.
Animals were housed in the cage, and the amount of exercise was started to be measured. After 45 minutes, the cage with rats was gently taken, and the administration liquids of compounds (a solvent or test compound suspension) or the administration liquid of MK-801 (a solvent or MK-801 solution) were orally or subcutaneously administered, respectively. The cage was backed to a measurement place. The measurement of the amount of exercise was completed in 2 hours and 30 minutes after the measurement was started. Data which were obtained from 90 minutes between 1 hour (15 minutes after the administration of compounds or MK-801) and 2 hours and 30 minutes after the measurement was started were used as the test results to sum up the amount of exercise for 90 minutes of each individual.
Analysis of test results was carried out as follows.
Parametric Dunnett's multiple comparison (significance level: two-side 5%) was carried out for a group to which test compounds were administered and a group to which the solvent was administered. When the group to which a test compound was administered showed a significant decrease in the amount of exercise compared with the group to which the solvent was administered, the compound was determined to have antipsychotic activity. Results of the above test were shown in FIGS. 1 and 2.
Test 8: Evaluation of Binding Activity for Side-Effect-Related Receptor
Binding affinity of the present compounds for side-effect-related receptor (e.g., adrenergic α receptor, histamine receptor, and muscarine receptor) can be measured by the following method.
Evaluation test for binding was carried out as follows with the CHO cell membrane fraction in which human target receptor was expressed. A test compound dissolved in dimethylsulfoxide (DMSO), each receptor membrane sample diluted with buffer, and [3H]-labelled ligand which has strong binding affinity to each target receptor were mixed. Each mixture was incubated at room temperature, added quickly on a glassfiber filter plate (Multiscreen FB, Millipore, Inc.), and vacuum-filtered. Radioactivity remaining on the filter was measured with a liquid scintillation counter (PerkinElmer, Inc.). Binding inhibition rate was calculated from the following formula. A control compound which has strong binding affinity to target receptor was used to calculate the non-specific binding amount to the receptor membrane sample, instead of a test compound.

Binding inhibition rate to target receptor (%)=100−100×{(Binding amount of [$^3$H]-labelled ligand in the presence of test compound)}−(Binding amount of [$^3$H]-labelled ligand in the presence of 10 µmol/L control compound)}/{(Binding amount of [$^3$H]-labelled ligand in the absence of test compound)}−(Binding amount of [$^3$H]-labelled ligand in the presence of 10 µmol/L control compound)}

Test 9: Evaluation of P-gp Substrate Property
NFR (Net Flux Ratio), which is an index of P-gp substrate property, can be calculated as follows. MDCKII (Madin-Darby canine kidney strain II) cells and MDR1-MDCKII cells in which MDR1 (multidrug resistance protein 1) was overexpressed were used to measure an apparent permeability coefficient (Papp A-B) from lumen (A) to basement membrane (B) and an apparent permeability coefficient (Papp B-A) from basement membrane (B) to lumen (A) of both MDCKII cells and MDR1-MDCKII cells. NFR (Net Flux Ratio) was calculated from the ratio between Ratio (Papp B-A/Papp A-B) of an apparent permeability coefficient of MDR1-MDCKII cells and Ratio of an apparent permeability coefficient of MDCKII cells.
Results of Test 9 are shown in the following table.

| Example | NFR |
|---|---|
| 1 | 3.7 |
| 2 | 1.2 |

| Example | NFR |
|---|---|
| 3 | 1.1 |
| 4 | 2.9 |
| 7 | 2.0 |
| 11 | 1.1 |
| 12 | 1.8 |
| 13 | 0.9 |
| 15 | 3.8 |
| 18 | 1.6 |
| 20 | 0.9 |
| 22 | 2.4 |
| 23 | 1.1 |
| 25 | 1.5 |
| 29 | 1.5 |
| 36 | 1.8 |
| 37 | 1.4 |
| 38 | 1.1 |
| 43 | 2.2 |
| 44 | 1.7 |
| 45 | 1.3 |
| 46 | 1.5 |
| 48 | 4.2 |
| 49 | 2.6 |
| 50 | 2.1 |
| 51 | 2.9 |
| 52 | 3.0 |
| 54 | 6.6 |
| 55 | 2.0 |
| 56 | 1.3 |
| 57 | 0.8 |
| 58 | 1.4 |
| 59 | 1.1 |
| 60 | 1.5 |
| 61 | 1.5 |
| 62 | 1.3 |
| 63 | 2.3 |
| 64 | 2.2 |
| 65 | 1.3 |
| 67 | 1.4 |
| 68 | 1.0 |
| 77 | 1.9 |
| 78 | 1.5 |
| 79 | 1.1 |
| 80 | 1.8 |
| 82 | 1.3 |
| 90 | 1.2 |
| 102 | 1.2 |
| 103 | 1.4 |
| 105 | 1.5 |
| 107 | 1.5 |
| 108 | 1.5 |
| 109 | 1.3 |
| 130 | 3.0 |
| 146 | 2.3 |
| 156 | 3.6 |
| 162 | 1.8 |
| 165 | 1.6 |
| 166 | 1.5 |
| 167 | 1.7 |
| 171 | 1.4 |
| 177 | 1.0 |
| 185 | 2.4 |
| 187 | 1.6 |
| 189 | 5.2 |
| 191 | 2.6 |

Test 10: Evaluation of Intracerebral Transferability (Test for Intracerebral Transferability of Rats)

In this test, intracerebral transferability of the present compounds was evaluated by the following method. The present compounds were subcutaneously administered as a solution in saline, or orally administered as a suspension in methyl cellulose to 7-week-old SD or WKY rats. Plasma and brain were collected on 0.5 hours, 1 hour, or 2 hours after the administration to measure the drug concentrations in plasma and brain by LC-MS.

Binding rates of the present compound to plasma and brain protein were measured by equilibrium dialysis method.

$Kp,uu,brain$ (unbound drug concentration ratio between brain/plasma) can be calculated by applying the compound concentrations in plasma and brain and the binding rates to plasma and brain protein obtained from the above test into the following formula.

$Kp,uu$,brain=(Compound concentration in brain×(100−Binding rate to brain protein (%))/100)/(Compound concentration in plasma×(100−Binding rate to plasma protein (%))/100)

Results of Test 10 are shown in the following table.

| Example | Kp, uu, brain |
|---|---|
| 2 | 1.27 |
| 3 | 0.44 |
| 35 | 1.44 |
| 36 | 0.08 |
| 37 | 0.91 |
| 43 | 0.18 |
| 44 | 0.02 |
| 45 | 0.21 |
| 46 | 0.06 |
| 51 | 0.06 |
| 61 | 0.98 |
| 63 | 0.04 |
| 65 | 0.50 |
| 80 | 0.09 |
| 88 | 1.02 |
| 103 | 3.62 |
| 109 | 0.44 |
| 171 | 0.28 |

Test 11: Evaluation of Hepatotoxic Risk (Dansyl Glutathione (dGSH) Trapping Assay)

The present compound was metabolized in hepatic microsome, and reactive metabolite which reacts with dansyl glutathione (dGSH) was detected and quantified from the resulting metabolite. Measurement was carried out with a screening robot (Tecan) for metabolic reaction, and with a fluorescence detection UPLC system (Waters) for metabolite-dGSH binding concentration.

(Preparation of Solution)

The present compound was dissolved in DMSO to prepare 10 mmol/L test compound solution. 7.6 mL of potassium phosphate buffer (500 mmol/L, pH 7.4), 1.9 mL of human hepatic microsome (Xenotech, 20 mg protein/mL), and 1.27 mL of pure water were mixed to prepare a microsome solution. To 3.78 mL of the microsome solution was added 0.67 mL of pure water to prepare a microsome (dGSH(−)) solution. To 6.48 mL of the microsome solution was added 1.14 mL of the dGSH solution (20 mmol/L) to prepare a microsome (dGSH(+)) solution. 80.9 mg of NADPH was dissolved in 30 mL of pure water to prepare a cofactor solution. 33 mg of tris(2-carboxyethyl)phosphine (TECP) was dissolved in 115 mL of methanol to prepare a reaction stop solution.

(Reaction)

12 μL of the test compound solution was mixed with 388 μL of pure water, and the mixture was dispensed in 50 μL each into 6 wells of a 96-well plate. The 6 wells were divided into 3 groups of 2 wells, and each was named as "reaction group", "unreacted group", and "dGSH-free group". To the "reaction group" and "unreacted group" was added the microsome (dGSH(+)) solution, and to the "dGSH-free group" was added the microsome (dGSH(−)) solution in 50 μL each. To the "reaction group" and "dGSH-free group" was added the cofactor solution, and to the "unreacted group" was added pure water in 50 μL each. After incubated at 37° C. for 60 minutes, the reaction stop solution was added in 450 μL each to stop the reaction. To the "reaction group" and "dGSH-free group" was added pure water, and to the "unreacted group" was added the cofactor solution in 50 μL each. The plate was cooled at −20° C. for 1 hour, and the solutions were centrifuged (4000 rpm, 10 minutes). Supernatants were collected into another plate and subjected to analysis.

(Analysis)

Metabolite-dGSH binding concentration was measured by the following method, using a fluorescence detection UPLC system (Waters).

Column: Waters ACQUITY UPLC BEHC18 1.7 μm 2.1×10 mm

Eluent: A, 0.2% aqueous formic acid; B, 0.2% formic acid/acetonitrile

Gradient: B, 20% (0 min)→70% (9.33 min)→90% (10.63 min)→20% (11 min)→20% (14 min)

Fluorescence intensity was corrected with the composition of organic solvent at the time of elution because fluorescence intensity changes depending on the composition of organic solvent.

Results of Test 11 are shown in the following table.

| Example | Metabolite-dGSH binding concentration (μM) |
|---|---|
| 1 | 0.052 |
| 2 | N.D. |
| 3 | N.D. |
| 4 | 0.116 |
| 5 | N.D. |
| 6 | 0.262 |
| 7 | N.D. |
| 8 | N.D. |
| 9 | 0.141 |
| 11 | N.D. |
| 12 | 0.146 |
| 13 | N.D. |
| 14 | N.D. |
| 15 | N.D. |
| 16 | 0.18 |
| 17 | N.D. |
| 19 | 0.337 |
| 20 | 0.188 |
| 21 | N.D. |
| 22 | 0.089 |
| 23 | 0.727 |
| 24 | 0.31 |
| 25 | N.D. |
| 26 | N.D. |
| 27 | N.D. |
| 28 | N.D. |
| 29 | 0.181 |
| 30 | N.D. |
| 31 | 0.201 |
| 32 | 0.553 |
| 33 | 0.214 |
| 34 | N.D. |
| 35 | N.D. |
| 36 | N.D. |
| 37 | N.D. |
| 38 | N.D. |
| 39 | N.D. |
| 40 | N.D. |
| 41 | N.D. |
| 42 | N.D. |
| 43 | N.D. |
| 44 | N.D. |
| 45 | N.D. |
| 46 | N.D. |
| 47 | N.D. |
| 48 | 0.166 |
| 49 | 0.125 |
| 50 | N.D. |
| 51 | N.D. |
| 52 | N.D. |
| 53 | N.D. |
| 55 | N.D. |
| 56 | N.D. |
| 57 | 0.12 |
| 58 | N.D. |
| 59 | N.D. |
| 60 | N.D. |
| 61 | N.D. |
| 62 | 0.162 |
| 63 | N.D. |
| 64 | N.D. |
| 65 | N.D. |
| 66 | N.D. |
| 67 | N.D. |
| 68 | 0.294 |
| 75 | N.D. |
| 76 | N.D. |
| 77 | N.D. |
| 78 | N.D. |
| 79 | N.D. |
| 80 | 0.166 |
| 81 | N.D. |
| 82 | 0.391 |
| 83 | 1.705 |
| 85 | 0.509 |
| 87 | 0.75 |
| 88 | N.D. |
| 89 | 0.122 |
| 90 | N.D. |
| 91 | 0.149 |
| 92 | 0.34 |
| 93 | N.D. |
| 94 | N.D. |
| 95 | N.D. |
| 96 | 0.174 |
| 97 | N.D. |
| 100 | N.D. |
| 102 | N.D. |
| 103 | N.D. |
| 104 | N.D. |
| 105 | 0.187 |
| 106 | N.D. |
| 107 | N.D. |
| 108 | N.D. |
| 109 | 0.056 |
| 111 | 0.14 |
| 112 | 10.23 |
| 113 | N.D. |
| 114 | N.D. |
| 115 | 1.116 |
| 116 | 0.658 |
| 117 | 0.285 |
| 121 | 0.568 |
| 122 | 0.14 |
| 123 | N.D. |
| 125 | 0.131 |
| 126 | 5.351 |
| 127 | 4.685 |
| 128 | 0.963 |
| 129 | N.D. |
| 130 | N.D. |
| 131 | N.D. |
| 132 | 2.207 |
| 133 | N.D. |

(N.D. means below detection limit.)

| Example | Metabolite-dGSH binding concentration (μM) |
|---|---|
| 135 | N.D. |
| 136 | 0.166 |
| 137 | N.D. |
| 138 | N.D. |
| 139 | N.D. |
| 143 | 0.833 |
| 144 | 0.215 |
| 145 | 0.228 |
| 146 | N.D. |
| 150 | N.D. |
| 153 | 7.646 |
| 154 | N.D. |
| 155 | N.D. |
| 156 | N.D. |
| 157 | 0.146 |
| 162 | N.D. |
| 163 | N.D. |
| 164 | 0.334 |
| 165 | 0.155 |
| 166 | 5.684 |
| 167 | 2.909 |
| 168 | N.D. |
| 170 | 0.658 |
| 171 | 0.11 |
| 175 | N.D. |
| 176 | N.D. |
| 177 | N.D. |
| 179 | N.D. |
| 180 | N.D. |
| 181 | N.D. |
| 182 | N.D. |
| 183 | 0.334 |
| 184 | 0.342 |
| 185 | N.D. |
| 186 | 0.283 |
| 187 | N.D. |
| 188 | 0.101 |
| 189 | N.D. |
| 190 | N.D. |
| 191 | 9.709 |
| 192 | N.D. |
| 194 | N.D. |

(N.D. means below detection limit.)

Test 12: Evaluation of Enzyme Induction Activity

The enzyme induction activity of the present compound was measured by the following method.

Preparation of Induction Medium

A DMSO solution of test compound (10 mmol/L) was diluted with HepaRG serum-free Induction Medium to prepare 1 μmol/L or 10 μmol/L induction medium (containing 0.1% DMSO).

Cell Culture

After HepaRG cells were thawed, cells were diluted to $1.25 \times 10^6$ viable cells/mL with HepaRG Thawing Medium, and plated to each well of collagen I-coated 96-well plate at $1.0 \times 10^5$ cells/well. Cells were incubated under 5% $CO_2$ at 37° C. for 6 hours. After confirming cell adhesion, the medium were exchanged with fresh HepaRG Thawing Medium, and cells were incubated under 5% $CO_2$ condition at 37° C. for 3 days. Then, HepaRG Thawing Medium was removed, and induction media containing test compounds at each concentration were added thereto, and cells were incubated for 48 hours. The induction media were exchanged every 24 hours.

Analysis for mRNA Expression Variation

RNA was purified with RNeasy 96, and cDNA was synthesized with SuperScript IV VILO Master Mix. Measurement of mRNA expression was carried out by real-time PCR, using TaqMan Gene Expression Assays and TaqMan Fast Advanced Master Mix.

Calculation of Fold Induction

Fold induction of each CYP molecule was calculated as follows.

$$\text{Fold induction} = 2^{(-\Delta\Delta Ct)}$$

$$\Delta\Delta Ct = \Delta Ct(\text{Test compound treatment}) - \Delta Ct(\text{Solvent control treatment})$$

$$\Delta Ct = CL(\text{Target gene}) - Ct(\text{Endogenous control gene})$$

Ct: Cycles at certain fluorescence intensity (Threshold Cycle)

Results of Test 12 are shown in the following table.

| | Concentration | Fold induction (mRNA) | | |
|---|---|---|---|---|
| Example | (μmol/L) | CYP1A2 | CYP2B6 | CYP3A4 |
| 37 | 1 | 0.994 | 1.32 | 1.43 |
| | 10 | 1.59 | 1.58 | 4.14 |
| 103 | 1 | 1.09 | 2.03 | 5.24 |
| | 10 | 0.875 | 2.24 | 18.0 |

INDUSTRIAL APPLICABILITY

The present compound shows antagonist activity for serotonin 5-$HT_{2A}$ receptor and agonist activity for serotonin 5-$HT_{1A}$ receptor, and therefore, the present compound is useful as a medicament for treating neuropsychiatric disorders.

The invention claimed is:

1. A compound which is represented by any one of the following formulae:

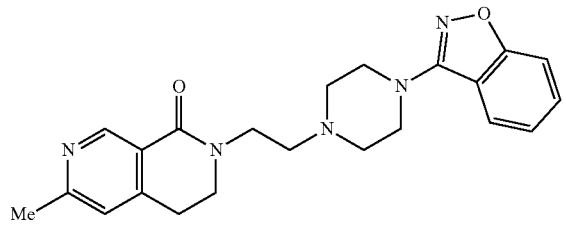

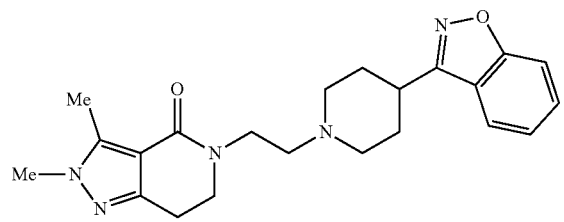

-continued

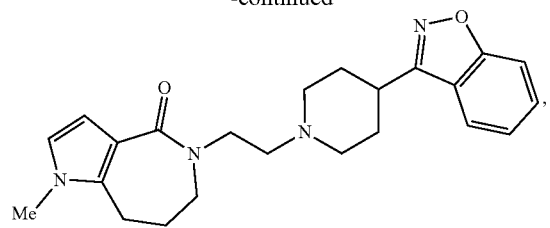

or a pharmaceutically acceptable salt thereof.

2. The compound according to claim 1, which is represented by the following formula:

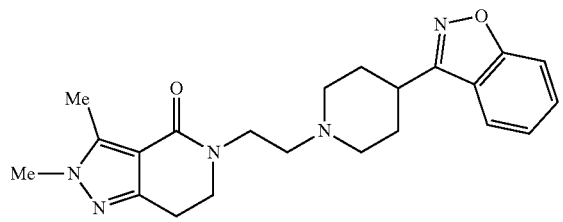

or a pharmaceutically acceptable salt thereof.

3. The compound according to claim 1, which is represented by the following formula:

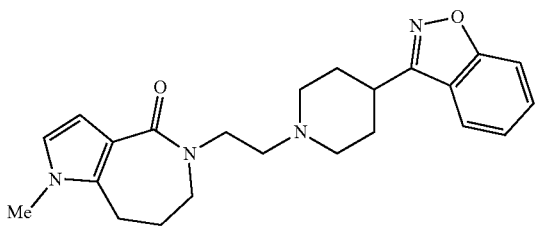

or a pharmaceutically acceptable salt thereof.

4. The compound according to claim 1, which is represented by the following formula:

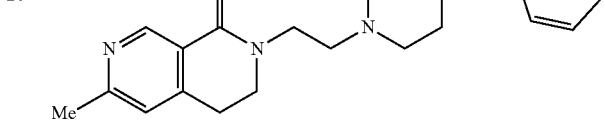

or a pharmaceutically acceptable salt thereof.

* * * * *